US008778963B2

(12) United States Patent
Krepski et al.

(10) Patent No.: US 8,778,963 B2
(45) **Date of Patent: *Jul. 15, 2014**

(54) HYDROXYLAMINE AND OXIME SUBSTITUTED IMIDAZOQUINOLINES, IMIDAZOPYRIDINES, AND IMIDAZONAPHTHYRIDINES

(75) Inventors: Larry R. Krepski, White Bear Lake, MN (US); Joseph F. Dellaria, Jr., Woodbury, MN (US); Gregory J. Marszalek, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 1787 days.

This patent is subject to a terminal disclaimer.

(21) Appl. No.: 10/595,895

(22) PCT Filed: Nov. 24, 2004

(86) PCT No.: PCT/US2004/039673

§ 371 (c)(1), (2), (4) Date: May 18, 2006

(87) PCT Pub. No.: WO2005/051324

PCT Pub. Date: Jun. 9, 2005

(65) Prior Publication Data

US 2007/0099901 A1 May 3, 2007

Related U.S. Application Data

(60) Provisional application No. 60/524,961, filed on Nov. 25, 2003, provisional application No. 60/580,139, filed on Jun. 16, 2004, provisional application No. 60/581,293, filed on Jun. 18, 2004.

(51) Int. Cl.
*C07D 487/06* (2006.01)
*C07D 471/06* (2006.01)
*A61K 31/437* (2006.01)

(52) U.S. Cl.
USPC .......... 514/293; 546/83

(58) Field of Classification Search
USPC .......... 546/83; 514/293
See application file for complete search history.

(56) References Cited

U.S. PATENT DOCUMENTS

| | | | |
|---|---|---|---|
| 3,314,941 | A | 4/1967 | Littell et al. |
| 4,689,338 | A | 8/1987 | Gerster |
| 4,698,348 | A | 10/1987 | Gerster |
| 4,929,624 | A | 5/1990 | Gerster et al. |
| 4,988,815 | A | 1/1991 | Andre et al. |
| 5,037,986 | A | 8/1991 | Gerster |
| 5,175,296 | A | 12/1992 | Gerster |
| 5,238,944 | A | 8/1993 | Wick et al. |
| 5,266,575 | A | 11/1993 | Gerster |
| 5,268,376 | A | 12/1993 | Gester |
| 5,346,905 | A | 9/1994 | Gerster |
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,446,153 | A | 8/1995 | Lindstrom et al. |
| 5,482,936 | A | 1/1996 | Lindstrom |
| 5,693,811 | A | 12/1997 | Lindstrom |
| 5,741,908 | A | 4/1998 | Gerster et al. |
| 5,756,747 | A | 5/1998 | Gerster et al. |
| 5,939,090 | A | 8/1999 | Beaurline et al. |
| 6,039,969 | A | 3/2000 | Tomai et al. |
| 6,069,149 | A | 5/2000 | Nanba et al. |
| 6,083,505 | A | 7/2000 | Miller et al. |
| 6,110,929 | A | 8/2000 | Gerster et al. |
| 6,194,425 | B1 | 2/2001 | Gerster et al. |
| 6,245,776 | B1 | 6/2001 | Skwierczynski et al. |
| 6,331,539 | B1 | 12/2001 | Crooks et al. |
| 6,376,669 | B1 | 4/2002 | Rice et al. |
| 6,451,810 | B1 | 9/2002 | Coleman et al. |
| 6,518,265 | B1 | 2/2003 | Kato et al. |
| 6,518,280 | B2 | 2/2003 | Gerster et al. |
| 6,525,064 | B1 | 2/2003 | Dellaria et al. |
| 6,541,485 | B1 | 4/2003 | Crooks et al. |
| 6,545,016 | B1 | 4/2003 | Dellaria et al. |
| 6,545,017 | B1 | 4/2003 | Dellaria et al. |
| 6,558,951 | B1 | 5/2003 | Tomai et al. |
| 6,573,273 | B1 | 6/2003 | Crooks et al. |
| 6,656,938 | B2 | 12/2003 | Crooks et al. |
| 6,660,735 | B2 | 12/2003 | Crooks et al. |
| 6,660,747 | B2 | 12/2003 | Crooks et al. |
| 6,664,260 | B2 | 12/2003 | Charles et al. |
| 6,664,264 | B2 | 12/2003 | Dellaria et al. |
| 6,664,265 | B2 | 12/2003 | Crooks et al. |

(Continued)

FOREIGN PATENT DOCUMENTS

| | | |
|---|---|---|
| EP | 0 394 026 | 10/1990 |
| EP | 1 104 764 | 6/2001 |

(Continued)

OTHER PUBLICATIONS van de Kerkhof, CA 141:16579, abstract only, 2001.*

Dorwald F. A. Side Reactions in Organic Synthesis, 2005, Wiley: VCH, Weinheim p. IX of Preface.*

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, Jun./Jul. 78, 1983.

Testerman et al., "Cytokine Induction by the Immunomodulators Imiquimod and S-27609.", *Journal of Leukocyte Biology*, vol. 58, pp. 365-372, Sep. 1995.

(Continued)

*Primary Examiner* — Rita Desai

(57) ABSTRACT

Imidazo-quinoline, -pyridine, and -naphthyridine ring systems substituted at the 1-position, pharmaceutical compositions containing the compounds, intermediates, and methods of use of these compounds as immunomodulators, for inducing cytokine biosynthesis in animals and in the treatment of diseases including viral and neoplastic diseases are disclosed.

13 Claims, No Drawings

(56) References Cited

U.S. PATENT DOCUMENTS

| | | | |
|---|---|---|---|
| 6,667,312 | B2 | 12/2003 | Bonk et al. |
| 6,670,372 | B2 | 12/2003 | Charles et al. |
| 6,677,347 | B2 | 1/2004 | Crooks et al. |
| 6,677,348 | B2 | 1/2004 | Heppner et al. |
| 6,677,349 | B1 | 1/2004 | Griesgraber |
| 6,683,088 | B2 | 1/2004 | Crooks et al. |
| 6,696,465 | B2 | 2/2004 | Dellaria et al. |
| 6,706,728 | B2 | 3/2004 | Hedenstrom et al. |
| 6,743,920 | B2 | 6/2004 | Lindstrom et al. |
| 6,756,382 | B2 | 6/2004 | Coleman et al. |
| 6,797,718 | B2 | 9/2004 | Dellaria et al. |
| 6,818,650 | B2 | 11/2004 | Griesgraber |
| 6,841,678 | B2 | 1/2005 | Merli et al. |
| 6,852,861 | B2 | 2/2005 | Merli et al. |
| 2002/0016332 | A1 | 2/2002 | Slade |
| 2002/0055517 | A1 | 5/2002 | Smith |
| 2002/0058674 | A1 | 5/2002 | Hedenstrom et al. |
| 2002/0107262 | A1 | 8/2002 | Lindstrom |
| 2002/0110840 | A1 | 8/2002 | Tomai et al. |
| 2003/0096835 | A1 | 5/2003 | Crooks et al. |
| 2003/0130299 | A1 | 7/2003 | Crooks et al. |
| 2003/0133913 | A1 | 7/2003 | Tomai et al. |
| 2003/0139364 | A1 | 7/2003 | Krieg et al. |
| 2003/0144286 | A1 | 7/2003 | Frenkel et al. |
| 2003/0161797 | A1 | 8/2003 | Miller et al. |
| 2003/0199538 | A1 | 10/2003 | Skwierczynski et al. |
| 2004/0014779 | A1 | 1/2004 | Gorden et al. |
| 2004/0091491 | A1 | 5/2004 | Kedl et al. |
| 2004/0132079 | A1 | 7/2004 | Gupta et al. |
| 2004/0141950 | A1 | 7/2004 | Noelle et al. |
| 2004/0147543 | A1 | 7/2004 | Hays et al. |
| 2004/0162309 | A1 | 8/2004 | Gorden et al. |
| 2004/0171086 | A1 | 9/2004 | Fink et al. |
| 2004/0175336 | A1 | 9/2004 | Egging et al. |
| 2004/0176367 | A1 | 9/2004 | Griesgraber et al. |
| 2004/0180919 | A1 | 9/2004 | Lee et al. |
| 2004/0181130 | A1 | 9/2004 | Fox et al. |
| 2004/0181211 | A1 | 9/2004 | Elliott et al. |
| 2004/0191833 | A1 | 9/2004 | Fink et al. |
| 2004/0192585 | A1 | 9/2004 | Fox et al. |
| 2004/0197865 | A1 | 10/2004 | Gupta et al. |
| 2004/0202720 | A1 | 10/2004 | Wightman et al. |
| 2004/0214851 | A1 | 10/2004 | Birmachu et al. |
| 2005/0054590 | A1 | 3/2005 | Averett |
| 2005/0085500 | A1 | 4/2005 | Gutman et al. |
| 2005/0165236 | A1 | 7/2005 | Colombo et al. |
| 2005/0245562 | A1 | 11/2005 | Garcia-Echeverria et al. |

FOREIGN PATENT DOCUMENTS

| | | | |
|---|---|---|---|
| JP | 9-208584 | | 8/1997 |
| JP | 11-080156 | A | 3/1999 |
| JP | 11-222432 | | 8/1999 |
| JP | 2000-247884 | | 9/2000 |
| WO | WO 01/51486 | A2 | 7/2001 |
| WO | WO 02/36592 | | 5/2002 |
| WO | WO 2005/018551 | | 3/2005 |
| WO | WO 2005/018555 | | 3/2005 |
| WO | WO 2005/018556 | | 3/2005 |
| WO | WO 2005/020999 | | 3/2005 |
| WO | WO 2005/032484 | | 4/2005 |
| WO | WO 2005/048933 | | 6/2005 |
| WO | WO 2005/048945 | | 6/2005 |
| WO | WO 2005/051317 | | 6/2005 |
| WO | WO 2005/051324 | | 6/2005 |
| WO | WO 2005/054237 | | 6/2005 |
| WO | WO 2005/054238 | | 6/2005 |
| WO | WO 2005/066169 | | 7/2005 |
| WO | WO 2005/066170 | | 7/2005 |
| WO | WO 2005/066172 | | 7/2005 |
| WO | WO 2005/076783 | | 8/2005 |
| WO | WO 2005/079195 | | 9/2005 |
| WO | WO 2005/094531 | | 10/2005 |
| WO | WO 2005/123079 | | 12/2005 |
| WO | WO 2005/123080 | | 12/2005 |
| WO | WO 2006/009826 | | 1/2006 |
| WO | WO 2006/009832 | | 1/2006 |
| WO | WO 2006/026760 | | 3/2006 |
| WO | WO 2006/028451 | | 3/2006 |
| WO | WO 2006/028545 | | 3/2006 |
| WO | WO 2006/028962 | | 3/2006 |
| WO | WO 2006/029115 | | 3/2006 |
| WO | WO 2006/031878 | | 3/2006 |
| WO | WO 2006/038923 | | 4/2006 |
| WO | WO 2006/065280 | | 6/2006 |
| WO | WO 2006/074003 | | 7/2006 |
| WO | WO 2006/004737 | | 8/2006 |
| WO | WO 2006/083400 | | 8/2006 |
| WO | WO 2006/083440 | | 8/2006 |
| WO | WO 2006/086449 | | 8/2006 |
| WO | WO 2006/086633 | | 8/2006 |

OTHER PUBLICATIONS

Bachman et al, "Synthesis of Substituted Quinolylamines. Derivatives of 4-Amino-7-Chloroquinoline.", *J. Org. Chem*, 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-as-triazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

Supplementary Partial European Search Report for EP 04812235.2 mailed Oct. 2, 2009.

International Search Report and Written Opinion for PCT/US2004/039673 mailed Nov. 15, 2005.

International Preliminary Report on Patentability for PCT/US2004/039673 mailed May 29, 2006.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Li et al., An improved protocol for the preparation of 3-pyridyl- and some arylboronic acids. J Org Chem. Jul. 26, 2002;67(15):5394-7.

Park et al., Sodium Dithionite Reduction of Nitroarenes Using Viologen as an Electron Phase-Transfer Catalyst. Tetrahedron Lett. 1993;34(46):7445-46.

Stewart et al., Synthesis of a Carba-analog of *S*-Acetyl Coenzyme A,Acetonyl-dethio Coenzyme A; an Effective Inhibitor of Citrate Synthase. Liebigs Ann Chem. 1978:57-65.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

* cited by examiner

HYDROXYLAMINE AND OXIME SUBSTITUTED IMIDAZOQUINOLINES, IMIDAZOPYRIDINES, AND IMIDAZONAPHTHYRIDINES

CROSS-REFERENCE TO RELATED APPLICATIONS

This application is the National Stage of International Application No. PCT/US2004/039673, filed Nov. 24, 2004, which claims priority to U.S. Provisional Application Ser. No. 60/581,293, filed on Jun. 18, 2004, to U.S. Provisional Application Ser. No. 60/580,139, filed on Jun. 16, 2004, and to U.S. Provisional Application Ser. No. 60/524,961, filed on Nov. 25, 2003, all of which are incorporated by reference herein in their entirety.

BACKGROUND

In the 1950's the 1H-imidazo[4,5-c]quinoline ring system was developed and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridinamine compounds as well as certain analogous thiazolo and oxazolo compounds were synthesized and found to be useful as immune response modifiers (IRMs), rendering them useful in the treatment of a variety of disorders.

There continues to be interest in the imidazoquinoline ring system, as well as other imidazo ring systems, and there is a continuing need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula (I):

I

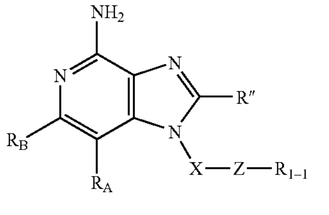

wherein: Z is —C(=N—O—$R_{1-2}$)— or

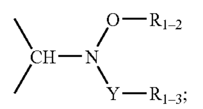

and X, Y, $R_A$, $R_B$, R", $R_{1-1}$, $R_{1-2}$, and $R_{1-3}$ are as defined below.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection and/or treating a neoplastic disease in an animal by administering an effective amount of a compound of Formula I to the animal.

In addition, methods of synthesizing compounds of Formula I useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula (I):

I

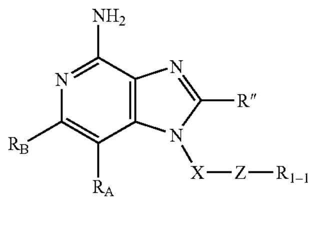

as well as more specific compounds of Formula (I) wherein R" is $R_2$ as defined herein (referred to herein as Formula (II)),

II

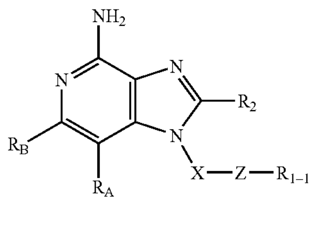

and more specific compounds of the following Formulas (III, IV, V, VI, and VII):

III

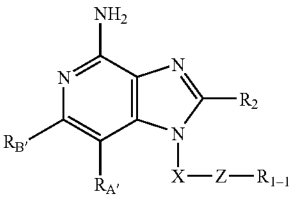

IV

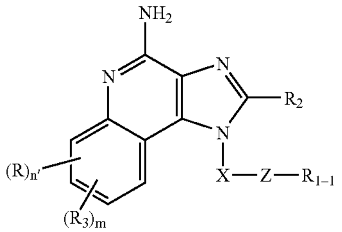

V

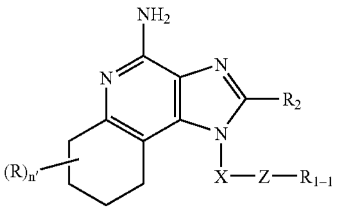

VI

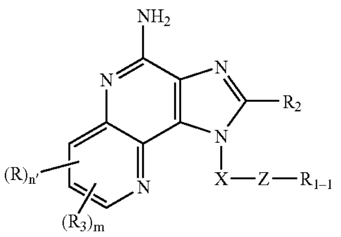

and

VII

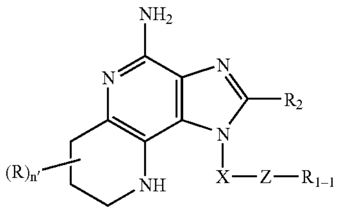

wherein:

Z is $-C(=N-O-R_{1-2})-$ or 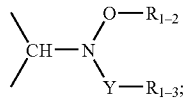

and X, Y, $R_A$, $R_B$, $R_{A'}$, $R_{B'}$, R", R, $R_2$, $R_3$, $R_{1-1}$, $R_{1-2}$, $R_{1-3}$, m, and n' are as defined below;

and pharmaceutically acceptable salts thereof.

In one embodiment, there is provided a compound of the Formula (I):

I

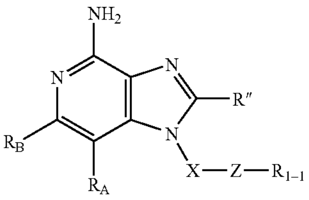

wherein:

Z is $-C(=N-O-R_{1-2})-$ or 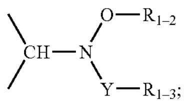

X is selected from the group consisting of:

$-CH(R_9)-$, $-CH(R_9)$-alkylene-, and $-CH(R_9)$-alkenylene-, wherein the alkylene and alkenylene are optionally interrupted by one or more —O— groups;

$R_{1-1}$, is selected from the group consisting of:

hydrogen, alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of:

halogen, cyano (i.e., —CN or nitrile), nitro (i.e., $-NO_2$), alkoxy, dialkylamino, alkylthio, haloalkyl, haloalkoxy, alkyl, $-NH-SO_2-R_{1-4}$, $-NH-C(O)-R_{1-4}$, $-NH-C(O)-NH_2$, $-NH-C(O)-NH-R_{1-4}$, and $-N_3$;

$R_{1-2}$ and $R_{1-3}$ are independently selected from the group consisting of:

hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of:

hydroxy, alkyl, haloalkyl, hydroxyalkyl,
alkoxy,
dialkylamino,
—$S(O)_{0-2}$-alkyl,
—$S(O)_{0-2}$-aryl,
—NH—$S(O)_2$-alkyl,
—NH—$S(O)_2$-aryl,
haloalkoxy,
halogen,
cyano,
nitro,
aryl,
heteroaryl,
heterocyclyl,
aryloxy,
arylalkyleneoxy,
—C(O)—O-alkyl,
—C(O)—$N(R_8)_2$,
—$N(R_8)$—C(O)-alkyl,
—O—(CO)-alkyl, and
—C(O)-alkyl, or the $R_{1-2}$ and $R_{1-3}$ groups can join together to form a ring system selected from the group consisting of:

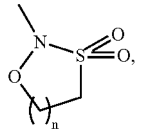 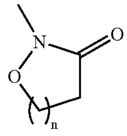 , 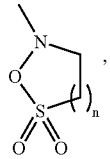 ,

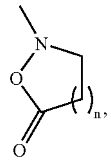 and 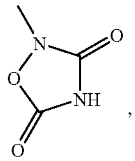 , wherein n 0, 1, 2, or 3;

$R_{1-4}$ is selected from the group consisting of:

alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—$N_3$;

Y is selected from the group consisting of:
a bond,
—C(O)—,
—C(S)—,
—$S(O)_2$—,
—$S(O)_2$—$N(R_8)$—,

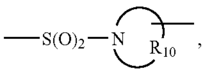 ,

—C(O)—O—,
—C(O)—$N(R_8)$—,
—C(S)—$N(R_8)$—,
—C(O)—$N(R_8)$—$S(O)_2$—,
—C(O)—$N(R_8)$—C(O)—,
—C(S)—$N(R_8)$—C(O)—,

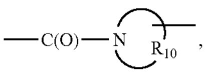 ,

—C(O)—C(O)—,
—C(O)—C(O)—O—, and
—C(=NH)—$N(R_8)$—;

$R_A$ and $R_B$ are each independently selected from the group consisting of:
hydrogen,
halogen,
alkyl,
alkenyl,
alkoxy,
alkylthio, and
—$N(R_9)_2$;

or when taken together, $R_A$ and $R_B$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—$N(R_9)_2$;

R" is hydrogen or a non-interfering substituent;

$R_3$ is selected from the group consisting of:
—Z'—$R_4$,
—Z'—X'—$R_4$,
—Z'—X'—Y'—$R_4$, and
—Z'—X'—$R_5$;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:

—O—, $—S(O)_{0-2}—$, $—S(O)_2—N(R_8)—$, $—C(R_6)—$, $—C(R_6)—O—$, $—O—C(R_6)—$,

—O—C(O)—O—, $—N(R_8)$-Q-, $—C(R_6)—N(R_8)—$, $—O—C(R_6)—N(R_8)—$, $—C(R_6)—N(OR_9)—$,

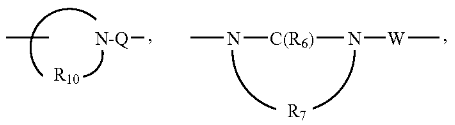

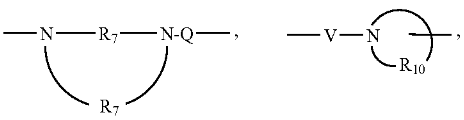
and

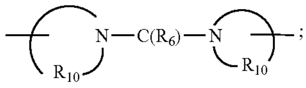
;

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

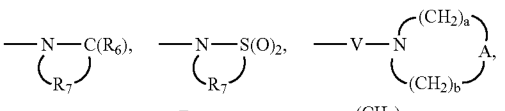
and

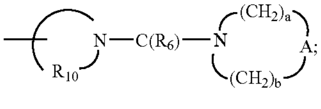

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

A is selected from the group consisting of —O—, —C(O)—, $—S(O)_{0-2}—$, $—CH_2—$, and $—N(R_4)—$;

Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, $—C(R_6)—O—$, $—C(R_6)—S—$, and $—C(R_6)—N(OR_9)—$;

V is selected from the group consisting of $—C(R_6)—$, $—O—C(R_6)—$, $—N(R_8)—C(R_6)—$, and $—S(O)_2—$;

W is selected from the group consisting of a bond, —C(O)—, and $—S(O)_2—$; and a and b are independently integers from 1 to 6 with the proviso that a+b is ≤7;

or a pharmaceutically acceptable salt thereof.

In another embodiment, there is provided a compound of the Formula (II):

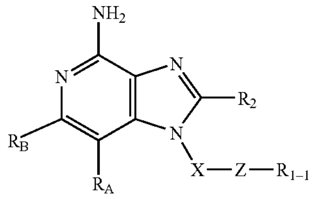
II wherein:

Z is
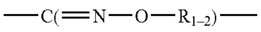
or
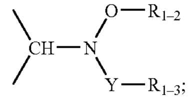

X is selected from the group consisting of:

$—CH(R_9)—$, $—CH(R_9)$-alkylene-, and $—CH(R_9)$-alkenylene-, wherein the alkylene and alkenylene are optionally interrupted by one or more —O— groups;

$R_{1-1}$ is selected from the group consisting of:

hydrogen, alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of:

halogen, cyano, nitro, alkoxy, dialkylamino, alkylthio, haloalkyl, haloalkoxy, alkyl, $—NH—SO_2—R_{1-4}$, $—NH—C(O)—R_{1-4}$, $—NH—C(O)—NH_2$, $—NH—C(O)—NH—R_{1-4}$, and $—N_3$;

$R_{1-2}$ and $R_{1-3}$ are independently selected from the group consisting of:

hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—$S(O)_{0-2}$-alkyl,
—$S(O)_{0-2}$-aryl,
—NH—$S(O)_2$-alkyl,
—NH—$S(O)_2$-aryl,
haloalkoxy,
halogen,
cyano (i.e., nitrile),
nitro,
aryl,
heteroaryl,
heterocyclyl,
aryloxy,
arylalkyleneoxy,
—C(O)—O-alkyl,
—C(O)—$N(R_8)_2$,
—$N(R_8)$—C(O)-alkyl,
—O—(CO)-alkyl, and
—C(O)-alkyl;

or the $R_{1-2}$ and $R_{1-3}$ groups can join together to form a ring system selected from the group consisting of:

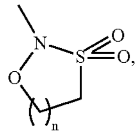
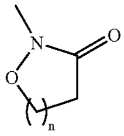
,
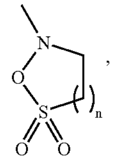
,
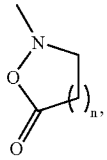
and
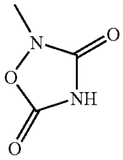
, wherein n 0, 1, 2, or 3;

$R_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:

halogen,
cyano,
nitro,
alkoxy,
dialkylamino,
alkylthio,
haloalkyl,
haloalkoxy,
alkyl, and
—$N_3$;

Y is selected from the group consisting of:
a bond,
—C(O)—,
—C(S)—,
—$S(O)_2$—,
—$S(O)_2$—$N(R_8)$—,

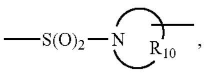
,

—C(O)—O—,
—C(O)—$N(R_8)$—,
—C(S)—$N(R_8)$—,
—C(O)—$N(R_8)$—$S(O)_2$—,
—C(O)—$N(R_8)$—C(O)—,

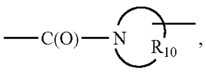
,

—C(O)—C(O)—,
—C(O)—C(O)—O—, and
—C(=NH)—$N(R_8)$—;

$R_A$ and $R_B$ are each independently selected from the group consisting of:
hydrogen,
halogen,
alkyl,
alkenyl,
alkoxy,
alkylthio, and
—$N(R_9)_2$;

or when taken together, $R_A$ and $R_B$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—$N(R_9)_2$;

$R_2$ is selected from the group consisting of:

$-R_4$, $-X'-R_4$, $-X'-Y'-R_4$, and $-X'-R_5$;

$R_3$ is selected from the group consisting of:

$-Z'-R_4$, $-Z'-X'-R_4$, $-Z'-X'-Y'-R_4$, and $-Z'-X'-R_5$;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:

—O—, $-S(O)_{0-2}-$, $-S(O)_2-N(R_8)-$,

—C(R)—, $-C(R_6)-O-$, $-O-C(R_6)-$,

—O—C(O)—O—, $-N(R_8)-Q-$, $-C(R_6)-N(R_8)-$, $-O-C(R_6)-N(R_8)-$, $-C(R_6)-N(OR_9)-$,

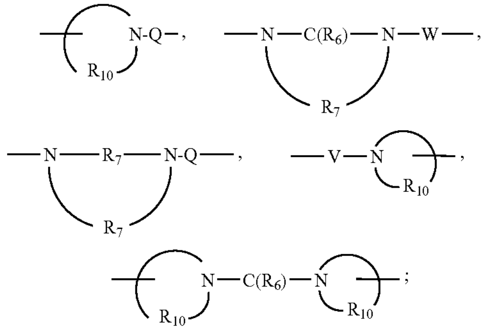

and

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of:

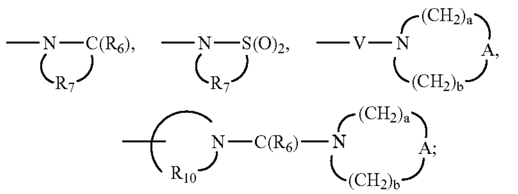

and $R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

A is selected from the group consisting of —O—, —C(O)—, $-S(O)_{0-2}-$, $-CH_2-$, and $-N(R_4)-$;

Q is selected from the group consisting of a bond, $-C(R_4)-$, $-C(R_6)-C(R_6)-$, $-S(O)_2-$, $-C(R_6N(R_8)-W-$, $-S(O)_2-N(R_8)-$, $-C(R_6)-O-$, $-C(R_6)-S-$, and $-C(R_6)-N(OR_9)-$;

V is selected from the group consisting of $-C(R_6)-$, $-O-C(R_6)-$, $-N(R_8)-C(R_6)-$, and $-S(O)_2-$;

W is selected from the group consisting of a bond, —C(O)—, and $-S(O)_2-$; and a and b are independently integers from 1 to 6 with the proviso that a+b is ≤7;

or a pharmaceutically acceptable salt thereof.

In another embodiment, there is provided a compound of the Formula (III):

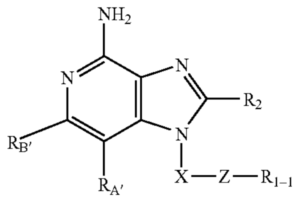

III wherein:

Z is $-C(=N-O-R_{1-2})-$ or

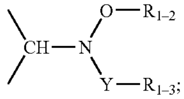

X is selected from the group consisting of:

$-CH(R_9)-$, $-CH(R_9)$-alkylene-, and $-CH(R_9)$-alkenylene-, wherein the alkylene and alkenylene are optionally interrupted by one or more —O— groups;

$R_{1-4}$ is selected from the group consisting of:

hydrogen, alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of:
- halogen,
- cyano,
- nitro,
- alkoxy,
- dialkylamino,
- alkylthio,
- haloalkyl,
- haloalkoxy,
- alkyl,
- —NH—$SO_2$—$R_{1-4}$,
- —NH—C(O)—$R_{1-4}$,
- —NH—C(O)—$NH_2$,
- —NH—C(O)—NH—$R_{1-4}$, and
- —$N_3$;

$R_{1-2}$ and $R_{1-3}$ are independently selected from the group consisting of:
- hydrogen,
- alkyl,
- alkenyl,
- aryl,
- arylalkylenyl,
- heteroaryl,
- heteroarylalkylenyl,
- heterocyclyl,
- heterocyclylalkylenyl, and
- alkyl, alkenyl, aryl, arylalkylenyl, heteroaryl, heteroarylalkylenyl, heterocyclyl, or heterocyclylalkylenyl, substituted by one or more substituents selected from the group consisting of:
  - hydroxy,
  - alkyl,
  - haloalkyl,
  - hydroxyalkyl,
  - alkoxy,
  - dialkylamino,
  - —$S(O)_{0-2}$-alkyl,
  - —$S(O)_{0-2}$-aryl,
  - —NH—$S(O)_2$-alkyl,
  - —NH—$S(O)_2$-aryl,
  - haloalkoxy,
  - halogen,
  - cyano,
  - nitro,
  - aryl,
  - heteroaryl,
  - heterocyclyl,
  - aryloxy,
  - arylalkyleneoxy,
  - —C(O)—O-alkyl,
  - —C(O)—$N(R_8)_2$,
  - —$N(R_9)$—C(O)-alkyl,
  - —O—(CO)-alkyl, and
  - —C(O)-alkyl;

or the $R_{1-2}$ and $R_{1-3}$ groups can join together to form a ring system selected from the group consisting of:

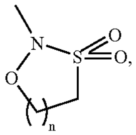

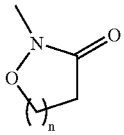
,

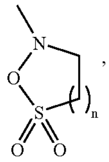
,

-continued

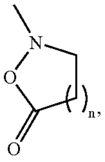

and

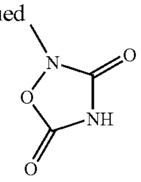
, wherein n=0, 1, 2, or 3;

$R_{1-4}$ is selected from the group consisting of:
- alkyl;
- aryl;
- alkylene-aryl;
- heteroaryl;
- alkylene-heteroaryl; and
- alkyl, aryl, alkylene-aryl, heteroaryl, or alkylene-heteroaryl substituted by one or more substituents selected from the group consisting of:
  - halogen,
  - cyano,
  - nitro,
  - alkoxy,
  - dialkylamino,
  - alkylthio,
  - haloalkyl,
  - haloalkoxy,
  - alkyl, and
  - —$N_3$;

Y is selected from the group consisting of:
- a bond,
- —C(O)—,
- —C(S)—,
- —$S(O)_2$—,
- —$S(O)_2$—$N(R_8)$—,

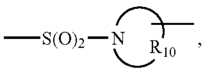

- —C(O)—O—,
- —C(O)—$N(R_8)$—,
- —C(S)—$N(R_8)$—,
- —C(O)—$N(R_8)$—$S(O)_2$—,
- —C(O)—$N(R_8)$—C(O)—,
- —C(S)—$N(R_8)$—C(O)—,

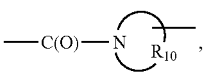

- —C(O)—C(O)—,
- —C(O)—C(O)—O—, and
- —C(=NH)—$N(R_8)$—;

$R_{A'}$ and $R_{B'}$ are each independently selected from the group consisting of:
- hydrogen,
- halogen,
- alkyl,
- alkenyl,
- alkoxy,
- alkylthio, and
- —$N(R_9)_2$;

$R_2$ is selected from the group consisting of:

$—R_4$, $—X'—Y'—R_4$, and $—X'—R_5$;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:

—O—, $—S(O)_{0-2}—$, $—S(O)_2—N(R_8)—$, $—C(R_6)—$, $—C(R_6)—O—$, $—O—C(R_6)—$,

—O—C(O)—O—, $—N(R_8)$-Q-, $—C(R_6)—N(R_8)—$, $—O—C(R_6)—N(R_8)—$, $—C(R_6)N(OR_9)—$,

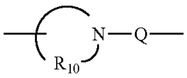, 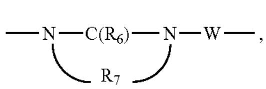,

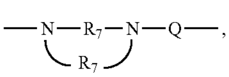, 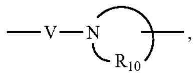, and

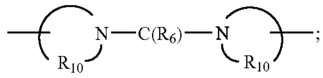;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

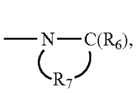, 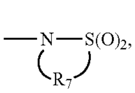, 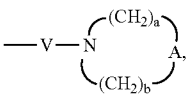, and

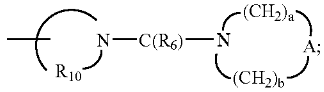;

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

A is selected from the group consisting of —O—, —C(O)—, $—S(O)_{0-2}—$, $—CH_2—$, and $—N(R_4)—$;

Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, $—C(R_6)—O—$, $—C(R_6)—S—$, and $—C(R_6)—N(OR_9)—$;

V is selected from the group consisting of $—C(R_6)—$, $—O—C(R_6)—$, $—N(R_8)—C(R_6)—$, and $—S(O)_2—$;

W is selected from the group consisting of a bond, —C(O)—, and $—S(O)_2—$; and a and b are each independently integers from 1 to 6 with the proviso that a+b is ≤7;

or a pharmaceutically acceptable salt thereof.

In another embodiment, the present invention provides a compound of the Formula (IV):

IV

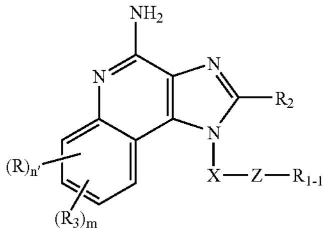

wherein:

Z is 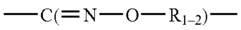 or 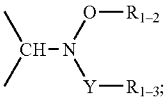;

X is selected from the group consisting of:

$—CH(R_9)—$, $—CH(R_9)$-alkylene-, and $—CH(R_9)$-alkenylene-, wherein the alkylene and alkenylene are optionally interrupted by one or more —O— groups;

$R_{1-1}$ is selected from the group consisting of:

hydrogen, alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of:

halogen, cyano, nitro, alkoxy, dialkylamino, alkylthio, haloalkyl, haloalkoxy, alkyl, $—NH—SO_2—R_{1-4}$, $—NH—C(O)—R_{1-4}$, $—NH—C(O)—NH_2$, —NH—C(O)—NH—$R_{1-4}$, and
—$N_3$;

$R_{1-2}$ and $R_{1-3}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—$S(O)_{0-2}$-alkyl,
—$S(O)_{0-2}$-aryl,
—NH—$S(O)_2$-alkyl,
—NH—$S(O)_2$-aryl,
haloalkoxy,
halogen,
cyano,
nitro,
aryl,
heteroaryl,
heterocyclyl,
aryloxy,
arylalkyleneoxy,
—C(O)—O-alkyl,
—C(O)—$N(R_8)_2$,
—$N(R_9)$C(O)-alkyl,
—O—(CO)-alkyl, and
—C(O)-alkyl;

or the $R_{1-2}$ and $R_{1-3}$ groups can join together to form a ring system selected from the group consisting of:

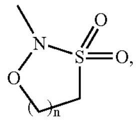
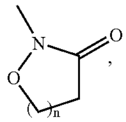
,
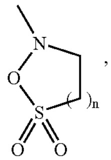
,
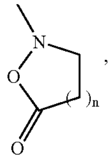
, and
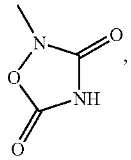
, wherein n=0, 1, 2, or 3;

$R_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—$N_3$;

Y is selected from the group consisting of:
a bond,
—C(O)—,
—C(S)—,
—$S(O)_2$—,
—$S(O)_2$—$N(R_8)$—,

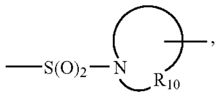
,

—C(O)—O—,
—C(O)—$N(R_9)$—,
—C(S)—$N(R_8)$—,
—C(O)—$N(R_8)$—$S(O)_2$—,
—C(O)—$N(R_8)$—C(O)—,
—C(S)—$N(R_8)$—C(O)—,

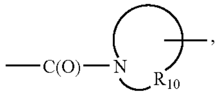
,

—C(O)—C(O)—,
—C(O)—C(O)—O—, and
—C(=NH)—$N(R_8)$—;

R is selected from the group consisting of:
halogen,
hydroxy,
alkyl,
alkenyl,
haloalkyl,
alkoxy,
alkylthio, and
—$N(R_9)_2$;

$R_2$ is selected from the group consisting of:
—$R_4$,
—X'—$R_4$,
—X'—Y'—$R_4$, and
—X'—$R_5$;

$R_3$ is selected from the group consisting of:
—Z'—$R_4$,
—Z'—X'—$R_4$,
—Z'—X'—Y'—$R_4$, and
—Z'—X'—$R_5$;

n' is an integer from 0 to 4;

m is 0 or 1; with the proviso that when m is 1, then n' is 0 or 1;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:

—O—, $—S(O)_{0-2}—$, $—S(O)_2—N(R_8)—$, $—C(R_6)—$, $—C(R_6)—O—$, $—O—C(R_6)—$,

—O—C(O)—O—, $—N(R_8)-Q-$, $—C(R_6)—N(R_8)—$, $—O—C(R_6)—N(R_8)—$, $—C(R_6)—N(OR_9)—$,

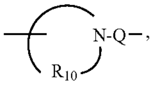, 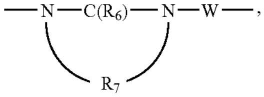,

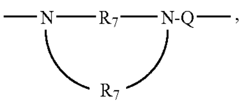, 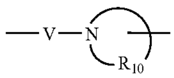, and

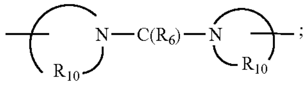;

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

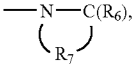, 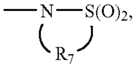,

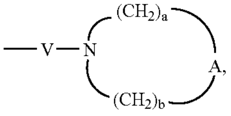, and

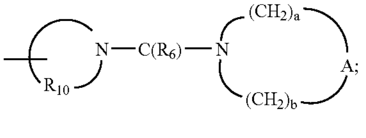;

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

A is selected from the group consisting of —O—, —C(O)—, $—S(O)_{0-2}—$, $—CH_2—$, and $—N(R_4)—$;

Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, $—C(R_6)—O—$, $—C(R_6)—S—$, and $—C(R_6)—N(OR_9)—$;

V is selected from the group consisting of —C(O)—, $—O—C(R_6)—$, $—N(R_8)—C(R_6)—$, and $—S(O)_2—$;

W is selected from the group consisting of a bond, —C(O)—, and $—S(O)_2—$; and a and b are each independently integers from 1 to 6 with the proviso that a+b is ≤7;

or a pharmaceutically acceptable salt thereof.

In another embodiment, there is provided a compound of the Formula (V):

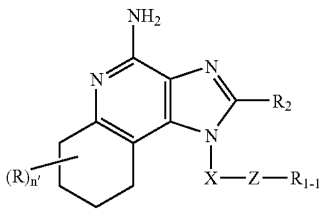

V wherein:

Z is $—C(=N—O—R_{1-2})—$ or

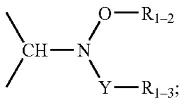;

X is selected from the group consisting of:

$—CH(R_9)—$, $—CH(R_9)$-alkylene-, and $—CH(R_9)$-alkenylene-, wherein the alkylene and alkenylene are optionally interrupted by one or more —O— groups;

$R_{1-1}$ is selected from the group consisting of:

hydrogen, alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of:

halogen, cyano, nitro, alkoxy, dialkylamino, alkylthio, haloalkyl, haloalkoxy,
alkyl,
$—NH—SO_2—R_{1-4}$,
$—NH—C(O)—R_{1-4}$,
$—NH—C(O)—NH_2$,
$—NH—C(O)—NH—R_{1-4}$, and
$—N_3$;

$R_{1-2}$ and $R_{1-3}$ are independently selected from the group consisting of:

hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
$—S(O)_{0-2}$-alkyl,
$—S(O)_{0-2}$-aryl,
$—NH—S(O)_2$-alkyl,
$—NH—S(O)_2$-aryl,
haloalkoxy,
halogen,
cyano,
nitro,
aryl,
heteroaryl,
heterocyclyl,
aryloxy,
arylalkyleneoxy,
—C(O)—O-alkyl,
$—C(O)—N(R_8)_2$,
$—N(R_8)—C(O)$-alkyl,
—O—(CO)-alkyl, and
—C(O)-alkyl;

or the $R_{1-2}$ and $R_{1-3}$ groups can join together to form a ring system selected from the group consisting of:

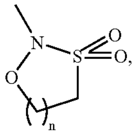
,
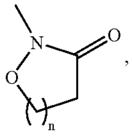
,
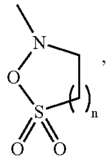
,
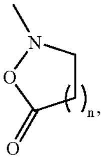
, and
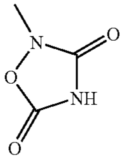
, wherein n=0, 1, 2, or 3;

$R_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
$—N_3$;

Y is selected from the group consisting of:
a bond,
—C(O)—,
—C(S)—,
$—S(O)_2—$,
$—S(O)_2—N(R_8)—$,

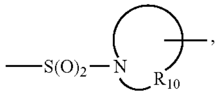
,

—C(O)—O—,
$—C(O)—N(R_8)—$,
$—C(S)—N(R_8)—$,
$—C(O)—N(R_8)—S(O)_2—$,
$—C(O)—N(R_8)—C(O)—$,
$—C(S)—N(R_8)—C(O)—$,

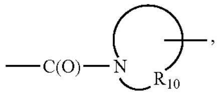
,

—C(O)—C(O)—,
—C(O)—C(O)—O—, and
$—C(=NH)—N(R_8)—$;

R is selected from the group consisting of:
halogen,
hydroxy,
alkyl,
alkenyl,
haloalkyl,
alkoxy,
alkylthio, and
$—N(R_9)_2$;

$R_2$ is selected from the group consisting of:
$—R_4$,
$—X'—R_4$,
$—X'—Y'—R_4$, and
$—X'—R_5$;

n' is an integer from 0 to 4;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—O—,
—$S(O)_{0-2}$—,
—$S(O)_2$—$N(R_8)$—,
—$C(R_6)$—,
—$C(R_6)$—O—,
—O—$C(R_6)$—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—,

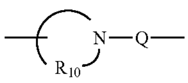,
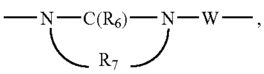,
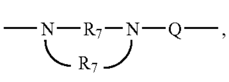,
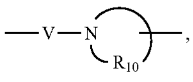, and
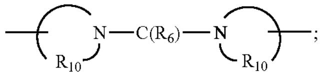;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

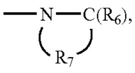,
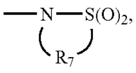,
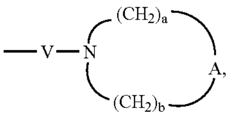, and
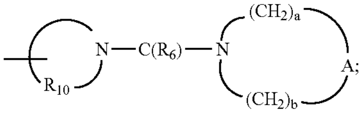;

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

A is selected from the group consisting of —O—, —C(O)—, —$S(O)_{0-2}$—, —$CH_2$—, and —$N(R_4)$—;

Q is selected from the group consisting of a bond, —$C(R_6)$—, —$C(R_6)$—$C(R_6)$—, —$S(O)_2$—, —$C(R_6)$—$N(R_8)$—W—, —$S(O)_2$—$N(R_8)$—, —$C(R_6)$—O—, —$C(R_6)$—S—, and —$C(R_6)$—$N(OR_9)$—;

V is selected from the group consisting of —$C(R_6)$—, —O—$C(R_6)$—, —$N(R_8)$—$C(R_6)$—, and —$S(O)_2$—;

W is selected from the group consisting of a bond, —C(O)—, and —$S(O)_2$—; and a and b are independently integers from 1 to 6 with the proviso that a+b is ≤7;

or a pharmaceutically acceptable salt thereof.

In another embodiment, there is provided a compound of the Formula (VI):

VI

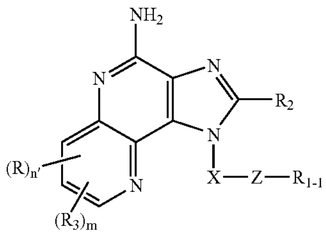

wherein:

Z is —C(=N—O—$R_{1-2}$)— or

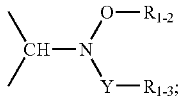

X is selected from the group consisting of:
—$CH(R_9)$—,
—$CH(R_9)$-alkylene-, and
—$CH(R_9)$-alkenylene-,
wherein the alkylene and alkenylene are optionally interrupted by one or more —O— groups;

$R_{1-1}$ is selected from the group consisting of:
hydrogen,
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—$SO_2$—$R_{1-4}$,
—NH—C(O)—$R_{1-4}$,
—NH—C(O)—$NH_2$,
—NH—C(O)—NH—$R_{1-4}$, and
—$N_3$;

$R_{1-2}$ and $R_{1-3}$ are independently selected from the group consisting of:

hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of:

hydroxy, alkyl, haloalkyl, hydroxyalkyl, alkoxy, dialkylamino, $-S(O)_{0-2}$-alkyl, $-S(O)_{0-2}$-aryl, $-NH-S(O)_2$-alkyl, $-NH-S(O)_2$-aryl, haloalkoxy, halogen, cyano, nitro, aryl, heteroaryl, heterocyclyl, aryloxy, arylalkyleneoxy, $-C(O)-O$-alkyl, $-C(O)-N(R_8)_2$, $-N(R_8)-C(O)$-alkyl, $-O-(CO)$-alkyl, and $-C(O)$-alkyl;

or the $R_{1-2}$ and $R_{1-3}$ groups can join together to form a ring system selected from the group consisting of:

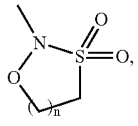

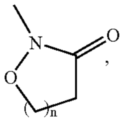
,

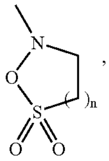
,

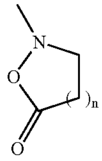
, and

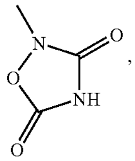
, wherein n=0, 1, 2, or 3;

$R_{1-4}$ is selected from the group consisting of:

alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of:

halogen, cyano, nitro, alkoxy, dialkylamino, alkylthio, haloalkyl, haloalkoxy, alkyl, and $-N_3$;

Y is selected from the group consisting of:

a bond, $-C(O)-$, $-C(S)-$, $-S(O)_2-$, $-S(O)_2-N(R_8)-$,

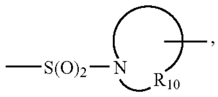
, $-C(O)-O-$, $-C(O)-N(R_8)-$, $-C(S)-N(R_8)-$, $-C(O)-N(R_8)-S(O)_2-$, $-C(O)-N(R_8)-C(O)-$, $-C(S)-N(R_8)-C(O)-$,

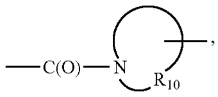
, $-C(O)-C(O)-$, $-C(O)-C(O)-O-$, and $-C(=NH)-N(R_8)-$;

R is selected from the group consisting of:

halogen, hydroxy, alkyl, alkenyl, haloalkyl, alkoxy, alkylthio, and $-N(R_9)_2$;

$R_2$ is selected from the group consisting of:

$-R_4$, $-X'-R_4$, $-X'-Y'-R_4$, and $-X'-R_5$;

$R_3$ is selected from the group consisting of:

$-Z'-R_4$, $-Z'-X'-R_4$, $-Z'-X'-Y'-R_4$, and $-Z'-X'-R_5$;

n' is an integer from 0 to 4;

m is 0 or 1; with the proviso that when m is 1, then n' is 0 or 1;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more $-O-$ groups;

Y' is selected from the group consisting of:

—O—, $—S(O)_{0-2}—$, $—S(O)_2—N(R_8)—$, $—C(R_6)—$, $—C(R_6)—O—$, $—O—C(R_6)—$,

—O—C(O)—O—, $—N(R_8)$-Q-, $—C(R_6)—N(R_8)—$, $—O—C(R_6)—N(R_8)—$, $—C(R_6)—N(OR_9)—$,

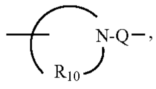,
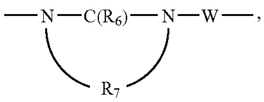,

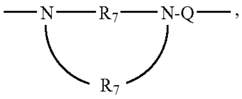,
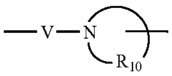, and

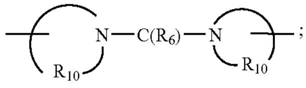;

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of

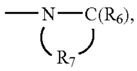,
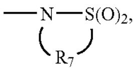,

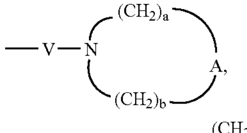 and

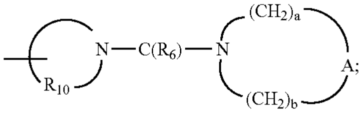;

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

A is selected from the group consisting of —O—, —C(O)—, $—S(O)_{0-2}—$, $—CH_2—$, and $—N(R_4)—$;

Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, —C(R)—O—, $—C(R_6)—S—$, and $—C(R_6)—N(OR_9)—$;

V is selected from the group consisting of $—C(R_6)—$, $—O—C(R_6)—$, $—N(R_8)—C(R_6)—$, and $—S(O)_2—$;

W is selected from the group consisting of a bond, —C(O)—, and $—S(O)_2—$; and a and b are each independently integers from 1 to 6 with the proviso that a+b is ≤7;

or a pharmaceutically acceptable salt thereof.

In another embodiment, there is provided a compound of the Formula (VII):

VII

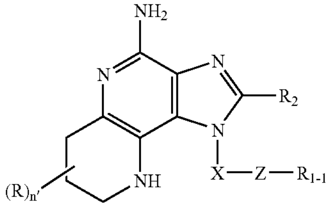

wherein:

Z is $—C(=N—O—R_{1-2})—$ or

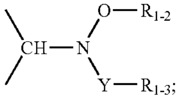

X is selected from the group consisting of:

$—CH(R_9)—$, $—CH(R_9)$-alkylene-, and $—CH(R_9)$-alkenylene-, wherein the alkylene and alkenylene are optionally interrupted by one or more —O— groups;

$R_{1-4}$ is selected from the group consisting of:

hydrogen, alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of:

halogen, cyano, nitro, alkoxy, dialkylamino, alkylthio, haloalkyl, haloalkoxy, alkyl, $—NH—SO_2—R_{1-4}$, $—NH—C(O)—R_{1-4}$, —NH—C(O)—$NH_2$,
—NH—C(O)—NH—$R_{1-4}$, and
—$N_3$;

$R_{1-2}$ and $R_{1-3}$ are independently selected from the group consisting of:

hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—$S(O)_{0-2}$-alkyl,
—$S(O)_{0-2}$-aryl,
—NH—$S(O)_2$-alkyl,
—NH—$S(O)_2$-aryl,
haloalkoxy,
halogen,
cyano,
nitro,
aryl,
heteroaryl,
heterocyclyl,
aryloxy,
arylalkyleneoxy,
—C(O)—O-alkyl,
—C(O)—$N(R_8)_2$,
—$N(R_8)$—C(O)-alkyl,
—O—(CO)-alkyl, and
—C(O)-alkyl;

or the $R_{1-2}$ and $R_{1-3}$ groups can join together to form a ring system selected from the group consisting of:

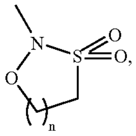 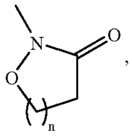 , 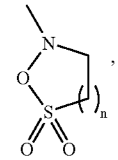 ,

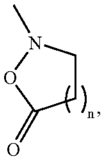 and 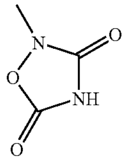 , wherein n=0, 1, 2, or 3;

$R_{1-4}$ is selected from the group consisting of:

aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—$N_3$;

Y is selected from the group consisting of:

a bond,
—C(O)—,
—C(S)—,
—$S(O)_2$—,
—$S(O)_2$—$N(R_8)$—,

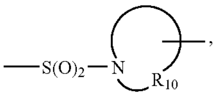

—C(O)—O—,
—C(O)—$N(R_9)$—,
—C(S)—$N(R_8)$—,
—C(O)—$N(R_8)$—$S(O)_2$—,
—C(O)—$N(R_8)$—C(O)—,
—C(S)—$N(R_8)$—C(O)—,

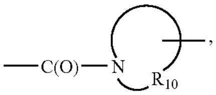

—C(O)—C(O)—,
—C(O)—C(O)—O—, and
—C(=NH)—$N(R_8)$—;

R is selected from the group consisting of:

halogen,
hydroxy,
alkyl,
alkenyl,
haloalkyl,
alkoxy,
alkylthio, and
—$N(R_9)_2$;

$R_2$ is selected from the group consisting of,

—$R_4$,
—X'—$R_4$,
—X'—Y'—$R_4$, and
—X'—$R_5$;

n' is an integer from 0 to 4;

X' is selected from the group consisting of alkylene, alkenylene, alkynylene, arylene, heteroarylene, and heterocyclene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:

—O—,
—$S(O)_{0-2}$—,
—$S(O)_2$—$N(R_8)$—,

—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N($OR_9$)—,

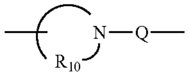,
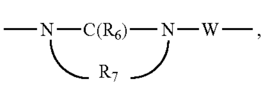,
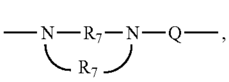,
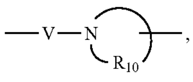, and
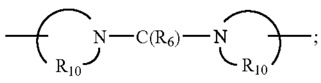;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of

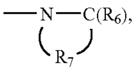,
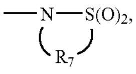,
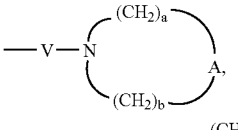 and
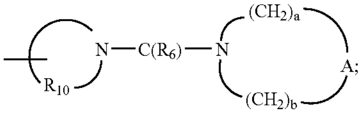;

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, —$CH_2$—, and —N($R_4$)—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N($OR_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are each independently integers from 1 to 6 with the proviso that a+b is ≤7;

or a pharmaceutically acceptable salt thereof.

As used herein, the terms "alkyl", "alkenyl", "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are use when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl (azepanyl), homopiperazinyl (diazepanyl), 1,3-dioxolanyl, aziridinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and the like. When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

Herein, "non-interfering" means that the ability of the compound or salt, which includes a non-interfering substituent, to modulate the biosynthesis of one or more cytokines is not destroyed by the non-interfering substitutent.

When a group (or substituent or variable) is present more than once in any Formula described herein, each group (or substituent or variable) is independently selected, whether explicitly stated or not. For example, for the formula $—C(O)—N(R_8)_2$ each $R_8$ group is independently selected. In another example, when an $R_2$ and an $R_3$ group both contain an $R_4$ group, each $R_4$ group is independently selected. In a further example, when more than one Y' group is present (i.e., $R_2$ and $R_3$ both contain a Y' group) and each Y' group contains one or more $R_7$ groups, then each Y' group is independently selected, and each $R_7$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, each one of the following variables (e.g., X, Y, Y', Z, $R_A$, $R_B$, R", $R_{1-1}$, $R_{1-2}$, $R_{1-3}$, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, A is selected from the group consisting of —O—, —C(O)—, $—S(O)_{0-2}—$, $—CH_2—$, and $—N(R_4)—$.

For certain embodiments, Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, $—C(R_6)—O—$, $—C(R_6)—S—$, and $—C(R_6)—N(OR_9)—$. For certain embodiments, Q is selected from the group consisting of a bond, $—C(R_6)—$, $—C(R_6)—C(R_6)—$, $—S(O)_2—$, $—C(O)—N(R_8)—W—$, $—S(O)_2—N(R_8)—$, $—C(R_6)—O—$, and $—C(R_6)—N(OR_9)—$.

For certain embodiments, V is selected from the group consisting of $—C(R_6)—$, $—O—C(R_6)—$, $—N(R_8)—C(R_6)—$, and $—S(O)_2—$.

For certain embodiments, W is selected from the group consisting of a bond, —C(O)—, and $—S(O)_2—$.

For certain embodiments, X is selected from the group consisting of $—CH(R_9)—$, $—CH(R_9)$-alkylene-, and $—CH(R_9)$-alkenylene-, wherein the alkylene and alkenylene are optionally interrupted by one or more —O— groups.

For certain embodiments, X is selected from the group consisting of $—(CH_2)_{1-6}$, $—CH_2C(CH_3)_2—$, $—CH_2C(CH_3)_2CH_2—$, $—(CH_2)_2OCH_2—$, and $—(CH_2)_3OCH_2—$. For certain embodiments, X is selected from the group consisting of $—(CH_2)_3—$, $—(CH_2)_4—$, $—CH_2C(CH_3)_2—$, $—CH_2C(CH_3)_2CH_2—$, and $—(CH_2)_2OCH_2—$.

For certain embodiments, X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups.

For certain embodiments, Y is selected from the group consisting of a bond, —C(O)—, —C(S)—, $—S(O)_2—$, $—S(O)_2—N(R_9)—$,

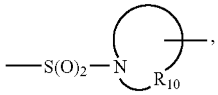,

—C(O)—O—, $—C(O)—N(R_8)—$, $—C(S)—N(R_8)—$, $—C(O)—N(R_8)—S(O)_2—$, $—C(O)—N(R_8)—C(O)—$, $—C(S)—N(R_8)—C(O)—$,

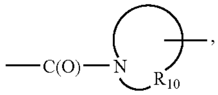,

—C(O)—C(O)—, —C(O)—C(O)—O—, and $—C(=NH)—N(R_8)—$.

For certain embodiments, Y is selected from the group consisting of —C(O)—, —C(S)—, $—S(O)_2—$, $—S(O)_2—N(R_8)—$,

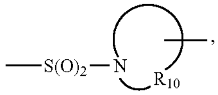,

—C(O)—O—, $—C(O)—N(R_8)—$, $—C(S)—N(R_8)—$, $—C(O)—N(R_8)—S(O)_2—$, $—C(O)—N(R_8)—C(O)—$, $—C(S)—N(R_8)—C(O)—$,

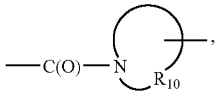,

—C(O)—C(O)—, —C(O)—C(O)—O—, and $—C(=NH)—N(R_8)—$.

For certain embodiments, Y is selected from the group consisting of a bond, —C(O)—, —C(O)—O—, $—S(O)_2—$, $—C(S)—N(R_8)—$ and $—C(O)—N(R_8)—$. For certain embodiments, Y is selected from the group consisting of —C(O)—, —C(O)—O—, $—S(O)_2—$, $—C(S)—N(R_8)—$ and $—C(O)—N(R_8)—$. For certain embodiments, Y is selected from the group consisting of —C(O)—, —C(O)—O—, $—S(O)_2—$, and $—C(O)—N(R_9)—$. For certain embodiments, Y is selected from the group consisting of —C(O)—, $—S(O)_2$, —C(O)—N(H)—, and $—C(O)—N(CH_3)—$.

For certain embodiments, Y' is selected from the group consisting of —O—, $—S(O)_{0-2}—$, $—S(O)_2—N(R_8)—$, $—C(R_6)—$, $—C(R_6)—O—$, $—O—C(R_6)—$, —O—C(O)—O—, $—N(R_9)$-Q-, $—C(R_6)—N(R_8)—$, $—O—C(R_6)—N(R_8)—$, $—C(R_6)—N(OR_9)—$,

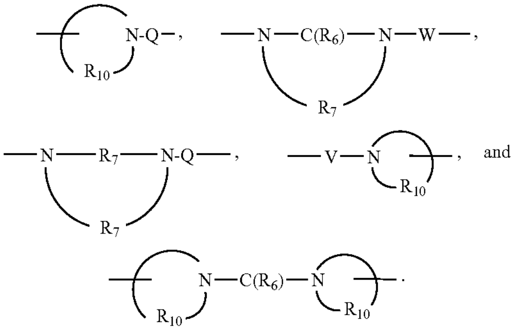

and

For certain embodiments, Y' is selected from the group consisting of —S(O)$_{0-2}$, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

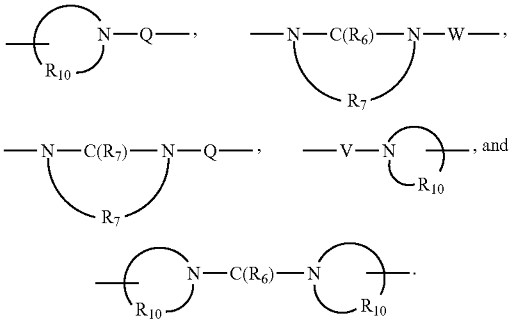

and

For certain embodiments, Y'' is —O— or —S(O)$_{0-2}$—.

For certain embodiments, Z is —C(═N—O—R$_{1-2}$)— or

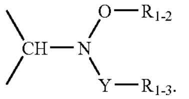

For certain embodiments, Z' is a bond or —O—.

For certain embodiments, R is selected from the group consisting of halogen, hydroxy, alkyl, alkenyl, haloalkyl, alkoxy, alkylthio, and —N(R$_9$)$_2$—.

For certain embodiments, R'' is hydrogen or a non-interfering substituent. Illustrative non-interfering R'' groups include those described above for R$_2$. For certain embodiments, R'' is selected from the group consisting of hydrogen, hydroxymethyl, C$_{1-4}$ alkyl, and C$_{1-4}$ alkyl-O—C$_{1-4}$ alkylenyl.

For certain embodiments, R$_A$ and R$_B$ are each independently selected from the group consisting of hydrogen, halogen, alkyl, alkenyl, alkoxy, alkylthio, and —N(R$_9$)$_2$. For certain embodiments, R$_A$ and R$_B$ are each independently selected from the group consisting of hydrogen and alkyl. For certain embodiments, R$_A$ and R$_B$ are both methyl.

For certain alternative embodiments, when taken together, R$_A$ and R$_B$ form a fused aryl ring or heteroaryl ring containing one heteroatom selected from the group consisting of N and S, wherein the aryl or heteroaryl ring is unsubstituted or substituted by one or more R groups, or substituted by one R$_3$ group, or substituted by one R$_3$ group and one R group. For certain embodiments, R$_A$ and R$_B$ form a fused aryl ring or heteroaryl ring containing one N, wherein the aryl or heteroaryl ring is unsubstituted or substituted by one or more R groups, or substituted by one R$_3$ group, or substituted by one R$_3$ group and one R group.

For certain alternative embodiments, when taken together, R$_A$ and R$_B$ form a fused 5 to 7 membered saturated ring, optionally containing one heteroatom selected from the group consisting of N and S, and unsubstituted or substituted by one or more R groups. For certain embodiments, R$_A$ and R$_B$ form a fused 5 to 7 membered saturated ring, which may optionally contain one N, wherein the saturated ring is unsubstituted or substituted by one or more R groups.

For certain embodiments, R$_{A'}$ and R$_{B'}$ are each independently selected from the group consisting of hydrogen, halogen, alkyl, alkenyl, alkoxy, alkylthio, and —N(R$_9$)$_2$. For certain embodiments, R$_{A'}$ and R$_{B'}$ are each independently selected from the group consisting of hydrogen and alkyl. For certain embodiments, R$_{A'}$ and R$_{B'}$ are both methyl.

For certain embodiments, R$_{1-1}$ is selected from the group consisting of hydrogen, alkyl, aryl, alkylene-aryl, heteroaryl, alkylene-heteroaryl, and alkyl, aryl, alkylene-aryl, heteroaryl, or alkylene-heteroaryl is substituted by one or more substituents selected from the group consisting of halogen, cyano, nitro, alkoxy, dialkylamino, alkylthio, haloalkyl, haloalkoxy, alkyl, —NH—SO$_2$—R$_{1-4}$, —NH—C(O)—R$_{1-4}$, —NH—C(O)—NH$_2$, —NH—C(O)—NH—R$_{1-4}$, and —N$_3$.

For certain embodiments, R$_{1-1}$ is selected from the group consisting of hydrogen, C$_{1-4}$ alkyl, and phenyl. For certain embodiments, R$_{1-1}$ is selected from the group consisting of hydrogen and methyl.

For certain embodiments, R$_{1-2}$ and R$_{1-3}$ are independently selected from the group consisting of hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of hydroxy, alkyl, haloalkyl, hydroxyalkyl, alkoxy, dialkylamino, —S(O)$_{0-2}$-alkyl, —S(O)$_{0-2}$-aryl, —NH—S(O)$_2$-alkyl, —NH—S(O)$_2$-aryl, haloalkoxy, halogen, cyano, nitro, aryl, heteroaryl, heterocyclyl, aryloxy, arylalkyleneoxy, —C(O)—O-alkyl, —C(O)—N(R$_8$)$_2$, —N(R$_8$)—C(O)-alkyl, —O—(CO)-alkyl, and —C(O)-alkyl.

For certain embodiments, the R$_{1-2}$ and R$_{1-3}$ groups can join together to form a ring system selected from the group consisting of:

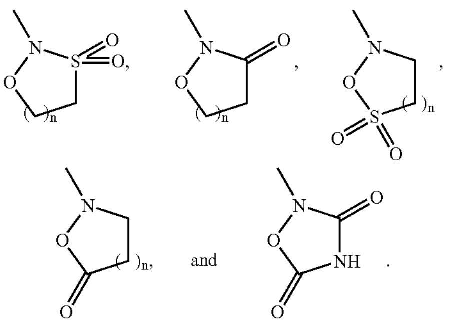

and

For certain embodiments, R$_{1-2}$ is selected from the group consisting of hydrogen, C$_{1-4}$ alkyl, benzyl, and pyridin-2-ylmethyl. For certain embodiments, R$_{1-2}$ is selected from the group consisting of hydrogen and methyl.

For certain embodiments, wherein $R_{1-3}$ is selected from the group consisting of hydrogen, $C_{1-6}$ alkyl, 1-pyrrolidinyl, phenyl, 2-chlorophenyl, 3-chlorophenyl, 4-chlorophenyl, o-tolyl, m-tolyl, p-tolyl, and pyridin-3-yl. For certain embodiments, $R_{1-3}$ is selected from the group consisting of hydrogen, $C_{1-6}$ alkyl, 1-pyrrolidinyl, and phenyl. For certain embodiments, $R_{1-3}$ is selected from the group consisting of methyl, ethyl, isopropyl, and phenyl.

For certain embodiments, the combined group Y—$R_{1-3}$ is —C(O)-phenyl, —C(O)—$C_2H_5$, —C(O)—NH-phenyl, —C(O)—NH—$CH_3$, —C(O)—NH-isopropyl, —C(O)—N$(CH_3)_2$, or —$S(O)_2$—$CH_3$.

For certain embodiments, $R_{1-4}$ is selected from the group consisting of alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of halogen, cyano, nitro, alkoxy, dialkylamino, alkylthio, haloalkyl, haloalkoxy, alkyl, and —$N_3$.

For certain embodiments, $R_2$ is selected from the group consisting of —$R_4$, —X'—$R_4$, —X'—Y'—$R_4$, and —X'—$R_5$.

For certain embodiments, $R_2$ is selected from the group consisting of: hydrogen, alkyl, alkenyl, aryl, heteroaryl, heterocyclyl, alkylene-Y"-alkyl, alkylene-Y"-aryl, and alkyl or alkenyl substituted by one or more substituents selected from the group consisting of: hydroxy, halogen, —$N(R_{11})_2$, —C(O)—$C_{1-10}$ alkyl, —C(O)—O—$C_{1-10}$ alkyl, —$N(R_{11})$—C(O)—$C_{1-10}$ alkyl, aryl, heteroaryl, heterocyclyl, —C(O)-aryl, and —C(O)-heteroaryl. In certain of these embodiments, Y" is —O— or —$S(O)_{0-2}$—; and $R_{11}$ is selected from the group consisting of hydrogen, $C_{1-10}$ alkyl, and $C_{2-10}$ alkenyl.

For certain embodiments, $R_2$ is selected from the group consisting of hydrogen, hydroxymethyl, $C_{1-4}$ alkyl, and $C_{1-4}$ alkyl-O—$C_{1-4}$ alkylenyl. For certain embodiments, $R_2$ is selected from the group consisting of hydrogen, methyl, propyl, ethoxymethyl, and methoxyethyl. For certain embodiments, $R_2$ is hydrogen, methyl, and propyl. For certain embodiments, $R_2$ is selected from the group consisting of hydrogen, methyl, ethyl, propyl, butyl, ethoxymethyl, and 2-methoxyethyl.

For certain embodiments, $R_3$ is selected from the group consisting of —Z'—$R_4$, —Z'—X'—$R_4$, —Z'—X'—Y'—$R_4$, and —Z'—X'—$R_5$. For certain embodiments, $R_3$ is selected from the group consisting of pyridin-3-yl, pyridin-4-yl, 5-(hydroxymethyl)pyridin-3-yl, and 2-ethoxyphenyl.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_5$ is selected from the group consisting of

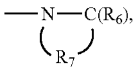,
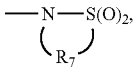,

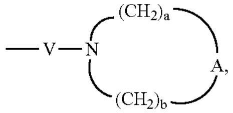, and

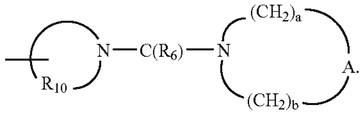.

For certain embodiments, $R_6$ is selected from the group consisting of =O and =S.

For certain embodiments, $R_7$ is $C_{2-7}$ alkylene.

For certain embodiments, $R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl. For certain embodiments, $R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl. For certain embodiments, $R_8$ is H or $CH_3$.

For certain embodiments, $R_9$ is selected from the group consisting of hydrogen and alkyl.

For certain embodiments, $R_{10}$ is $C_{3-8}$ alkylene.

For certain embodiments, $R_{11}$ is selected from the group consisting of hydrogen, $C_{1-10}$ alkyl, and $C_{2-10}$ alkenyl.

For certain embodiments, a and b are independently integers from 1 to 6 with the proviso that a+b is ≤7.

For certain embodiments, m is 0 or 1. For certain embodiments, m is 0. For certain embodiments, m is 1.

For certain embodiments, n is 0, 1, 2, or 3.

For certain embodiments, n' is an integer from 0 to 4 (i.e., n' is 0, 1, 2, 3, or 4). For certain embodiments, n' is 0 or 1. For certain embodiments, n' is 0.

For certain embodiments, m and n' are both 0.

For certain embodiments, m is 0 or 1, with the proviso that when m is 1, then n' is 0 or 1.

Preparation of the Compounds

Compounds of the invention can be prepared according to the routes shown herein where $R_{1-1}$, $R_{1-2}$, $R_{1-3}$, $R_2$, R, Y, X, and n are as defined above and where each $R_{1-6}$ is independently alkyl or the $R_{1-6}$ groups can join together to form a ring system comprising a saturated 5- or 6-membered ring. In Reaction Schemes I, III, V, VII, X, XII, XIII, and XIV, R, $R_{1-1}$, and $R_2$ do not contain substituents that one skilled in the art would recognize as being reactive with Grignard reagents. These substituents include, for example, ketone, ester, hydroxy, and nitrile (i.e., cyano) groups as well as groups containing —NH—.

Compounds of the invention can be prepared according to Reaction Scheme I.

In step (1) of Reaction Scheme I, a 4-chloro-3-nitroquinoline of Formula X is treated with an amino alcohol in the presence of triethylamine in a suitable solvent such as dichloromethane, wherein the amino alcohol is of the general formula $H_2N$—X—$CH_2$—OH and X is as defined herein. Numerous amino alcohols of the formula $H_2N$—X—$CH_2$—OH are commercially available; others can be readily synthesized using well-known methods. Many 4-chloro-3-nitroquinolines of Formula X are known or can be prepared using known synthetic methods, see for example, U.S. Pat. Nos. 4,689,338; 5,175,296; 5,367,076; and 5,389,640; and the references cited therein.

In step (2) of Reaction Scheme I, the resultant compound of Formula XI can be reduced using a variety of methods to provide a quinoline-3,4-diamine of Formula XII. The reaction can be carried out by hydrogenation using a heterogeneous hydrogenation catalyst such as platinum on carbon. The hydrogenation is conveniently carried out in a Parr apparatus in a suitable solvent such as toluene, acetonitrile, or ethanol. The reaction can be carried out at ambient temperature, and the product can be isolated using conventional methods Alternatively step (2) can be carried out using a one- or two-phase sodium dithionite reduction. The reaction is conveniently carried out using the conditions described by Park, K. K.; Oh, C. H.; and Joung, W. K.; *Tetrahedron Lett.*, 34, 7445-7446 (1993) by adding sodium dithionite to a compound of Formula XI in a mixture of dichloromethane and water at ambient temperature in the presence of potassium carbonate and ethyl viologen dibromide. The product can be isolated using conventional methods.

In step (3) of Reaction Scheme I, a quinoline-3,4-diamine of Formula XII is treated with a carboxylic acid equivalent to provide a 1H-imidazo[4,5-c]quinoline of Formula XIII. Suitable carboxylic acid equivalents include orthoesters of Formula $R_2C(O\text{-alkyl})_3$, 1,1-dialkoxyalkyl alkanoates of Formula $R_2C(O\text{-alkyl})_2(O—C(O)\text{-alkyl})$, and acid chlorides of Formula $R_2C(O)Cl$. The selection of the carboxylic acid equivalent is determined by the desired substituent at $R_2$. For example, triethyl orthoformate will provide a compound where $R_2$ is hydrogen, and trimethyl orthovalerate will provide a compound where $R_2$ is a butyl group. The reaction is conveniently carried out by adding the carboxylic acid equivalent to a quinoline-3,4-diamine of Formula XII in a suitable solvent such as toluene or xylenes. Optionally, catalytic pyridine hydrochloride or pyridium p-toluenesulfonate can be added. The reaction is carried out at a temperature high enough to drive off alcohol or water formed during the reaction. Conveniently, a Dean-Stark trap can be used to collect the volatiles.

Optionally, the alcohol group on the compound of Formula XII can be protected with a suitable alcohol protecting group prior to step (2), and this protecting group can be removed prior to step (4). Suitable protecting groups include the tert-butyldimethylsilyl group, which can be introduced and removed using conventional methods.

In step (4) of Reaction Scheme I, the alcohol-substituted 1H-imidazo[4,5-c]quinoline of Formula XIII is oxidized to an aldehyde-substituted 1H-imidazo[4,5-c]quinoline of Formula XIV using conventional methods, for example, Swern conditions. The Swern oxidation is conveniently carried out by adding the compound of Formula XIII followed by triethylamine to a mixture of oxalyl chloride and dimethylsulfoxide in a suitable solvent, such as dichloromethane. The reaction can be carried out at sub-ambient temperatures, such as −78° C., and the product can be isolated using conventional methods.

In step (5) of Reaction Scheme I, the aldehyde-substituted 1H-imidazo[4,5-c]quinoline of Formula XIV is treated with a Grignard reagent. The Grignard reagent is of the formula $R_{1-1}$MgHalide to form a compound of Formula XV. Several of these reagents are commercially available; others can be prepared using known synthetic methods. The reaction is conveniently carried out by adding a solution of the Grignard reagent to a solution of the compound of Formula XIV in a suitable solvent such as tetrahydrofuran. The reaction can be carried out at ambient temperature, and the product can be isolated using conventional methods.

In step (6) of Reaction Scheme I, an alcohol-substituted 1H-imidazo[4,5-c]quinoline of Formula XV is oxidized to a ketone of Formula XVI using conventional methods. The reaction is conveniently carried out under Swern conditions, described in step (4) above.

In step (7) of Reaction Scheme I, a ketone-substituted 1H-imidazo[4,5-c]quinoline of Formula XVI is oxidized to provide an N-oxide of Formula XVII using a conventional oxidizing agent capable of forming such compounds. For example, the reaction can be conveniently carried out by adding 3-chloroperoxybenzoic acid to a solution of a compound of Formula XVI in a solvent, such as chloroform or dichloromethane, at ambient temperature.

In step (8) of Reaction Scheme I, the N-oxide of Formula XVII is animated to provide a ketone-substituted 1H-imidazo[4,5-c]quinolin-4-amine of Formula XVIII. Step (8) involves the activation of an N-oxide of Formula XVII by conversion to an ester and then reacting the ester with an amiuating agent. Suitable activating agents include alkyl- or arylsulfonyl chlorides such as benzenesulfonyl chloride, methanesulfonyl chloride, or p-toluenesulfonyl chloride. Suitable animating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XVII in a suitable solvent, such as dichloromethane or chloroform, and then adding p-toluenesulfonyl chloride. The reaction can be carried out at ambient temperature and the product isolated by conventional methods.

In step (9) of Reaction Scheme I, a ketone-substituted 1H-imidazo[4,5-c]quinolin-4-amine of Formula XVIII is converted to an oxime of Formula IVa. The reaction is conveniently carried out by adding a solution of a hydroxylamine salt of the formula $NH_2OR_{1-2}—HCl$ in water to a compound of Formula XVIII, in a suitable solvent, such as ethanol or methanol, and then adding a base such as aqueous sodium hydroxide. The reaction can be carried out at an elevated temperature such as the reflux temperature of the solvent. Hydroxylamine salts of the formula $NH_2OR_{1-2}.HCl$ can be obtained commercially or they can be prepared using conventional synthetic methods. The product or pharmaceutically acceptable salt thereof is obtained as a mixture of E and Z isomers and can be isolated using conventional methods.

In step (10) of Reaction Scheme I, an oxime substituted 1H-imidazo[4,5-c]quinolin-4-amine of Formula IVa is converted to a hydroxylamine of Formula IVb. The reduction is conveniently carried out by treating an oxime substituted 1H-imidazo[4,5-c]quinolin-4-amine of Formula IVa with excess sodium cyanoborohydride in a suitable solvent or solvent mixture such as a lower alkanol and acetic acid. The reaction can be carried out at ambient temperature. The product or a pharmaceutically acceptable salt thereof can be isolated using conventional methods.

In step (11) of Reaction Scheme I, a hydroxylamine substituted 1H-imidazo[4,5-c]quinolin-4-amine Formula IVb is converted to a hydroxylamine substituted 1H-imidazo[4,5-c]quinolinamine Formula IVc using conventional methods. For example, sulfonamides of Formula IVc (Y is $—S(O)_2—$) can be prepared by reacting a compound of Formula IVb with a sulfonyl chloride of formula $R_{1-3}S(O)_2Cl$. The reaction can be carried out at ambient temperature in an inert solvent such as chloroform or dichloromethane by adding the sulfonyl chloride to a compound of Formula IVb in the presence of a base such as N,N-diisopropylethylamine, triethylamine, or pyridine. The reaction can also be carried out using sulfonic anhydrides in lieu of sulfonyl chlorides.

Sulfamides of Formula IVc (Y is —$S(O)_2$—$N(R_8)$— or

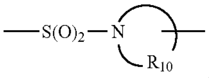

)

can be prepared by reacting a compound of Formula IVb with sulfuryl chloride to generate a sulfamoyl chloride in situ, and then reacting the sulfamoyl chloride with an amine of formula $HN(R_8)R_{1-3}$, or

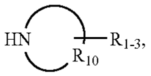

or by reacting a compound of Formula IVb with a sulfamoyl chloride of formula $R_{1-3}(R_8)NS(O)_2Cl$ or

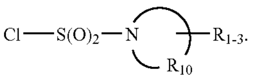

The product or a pharmaceutically acceptable salt thereof can be isolated using conventional methods. Many sulfonyl chlorides of formula $R_{1-3}S(O)_2Cl$, amines of formulas $HN(R_8)R_{1-3}$ and

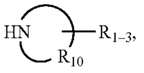

and some sulfamoyl chlorides of formulas $R_{1-3}(R_8)NS(O)_2Cl$ and

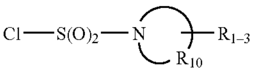

are commercially available; others can be prepared using known synthetic methods.

Amides of Formula IVc (Y is —C(O)—) can be prepared using conventional methods. For example, a compound of Formula IVb can be reacted with an acid chloride of formula $R_{1-3}C(O)Cl$ to provide a compound of Formula IVc. The reaction can be carried out by adding the acid chloride to a solution of a compound of Formula IVb in a suitable solvent such as chloroform, optionally in the presence of a base such as N,N-diisopropylethylamine, triethylamine, or pyridine, at ambient temperature. The product or a pharmaceutically acceptable salt thereof can be isolated using conventional methods. The reaction can also be carried out using an anhydride in lieu of the acid chloride.

Ureas and thioureas of Formula IVc (Y is —C(O)—N($R_8$)—, —C(S)—$N(R_8)$—, —C(O)—$N(R_8)$—$S(O)_2$—, —C(O)—$N(R_8)$—C(O)—, —C(S)—$N(R_8)$—C(O)—, or

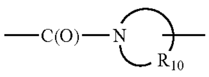

)

can also be prepared using conventional methods. For example, a compound of Formula IVb can be reacted with an isocyanate of formula $R_{1-3}N{=}C{=}O$. The reaction can be carried out by adding the isocyanate to a solution of a compound of Formula IVb in a suitable solvent such as chloroform, optionally in the presence of a base such as N,N-diisopropylethylamine, or triethylamine, at ambient temperature. Alternatively, a compound of Formula IVb can be reacted with a thioisocyanate of formula $R_{1-3}N{=}C{=}S$, a sulfonyl isocyanate of formula $R_{1-3}S(O)_2N{=}C{=}O$ or a carbamoyl chloride of formula $R_{1-3}NC(O)Cl$ or

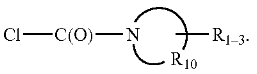

The product or a pharmaceutically acceptable salt thereof can be isolated using conventional methods.

Reaction Scheme I

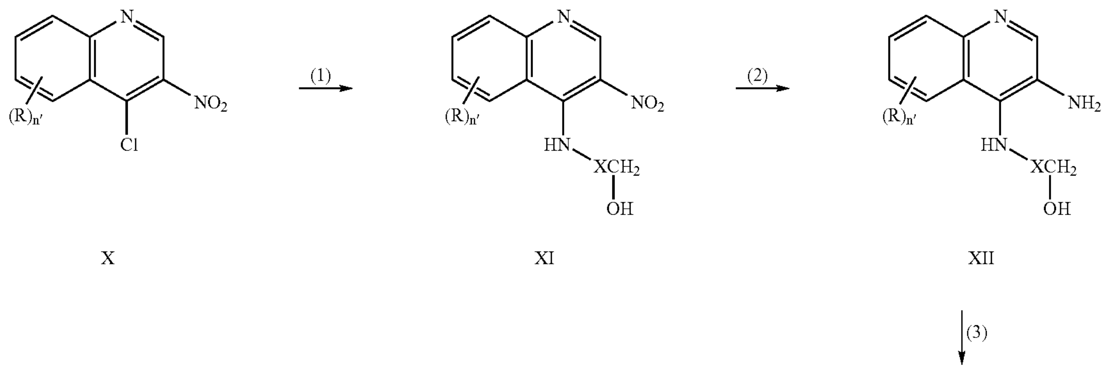

X XI XII

-continued

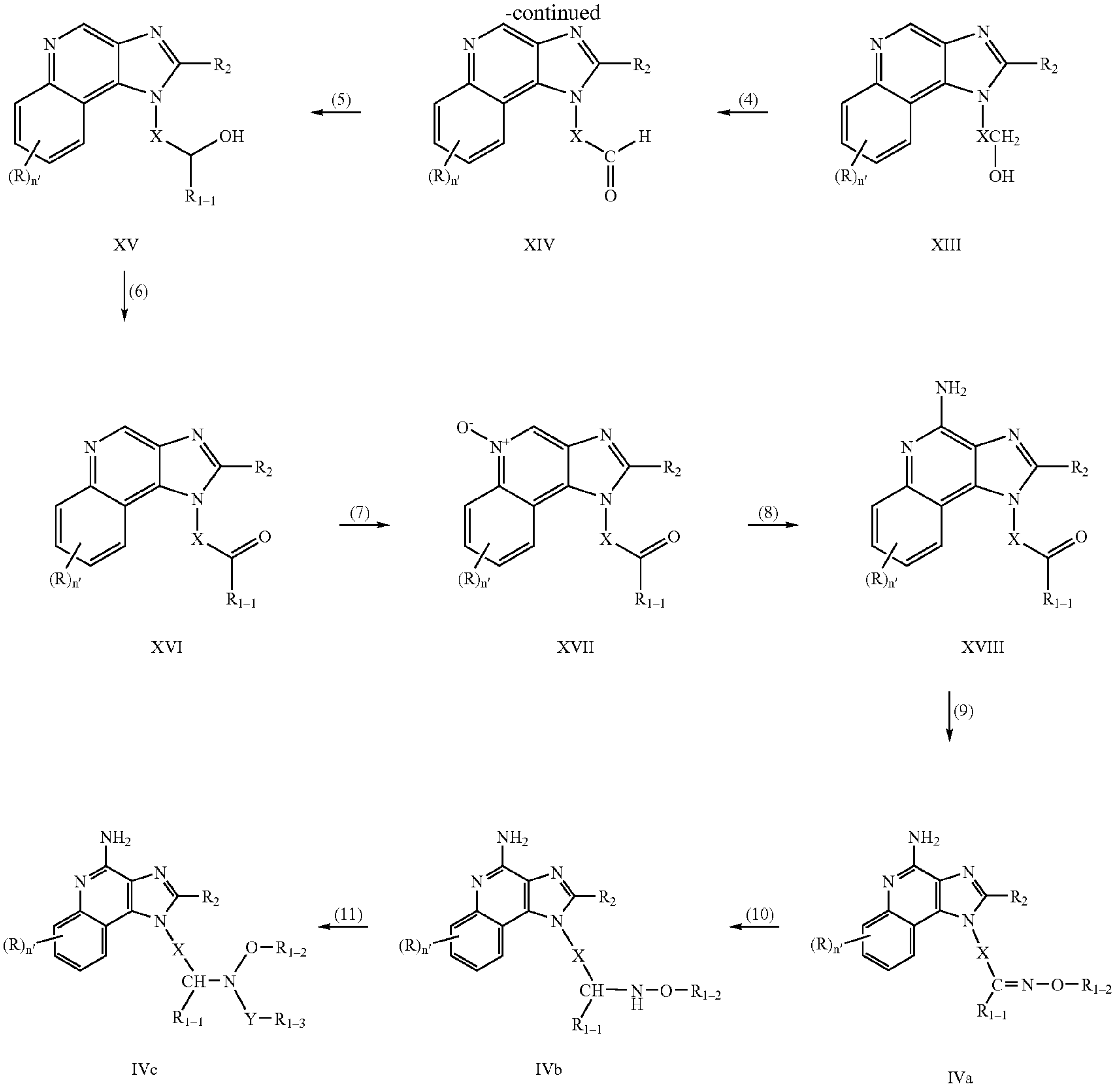

XV XIV XIII

XVI XVII XVIII

IVc IVb IVa

Compounds of the invention can also be prepared according to Reaction Scheme II.

In step (1) of Reaction Scheme II, a 4-chloro-3-nitroquinoline of Formula X is reacted with a compound of the formula $H_2N—X—C(R_{1-1})(O—R_{1-6}—)_2$, such as an amino ketal of this formula, wherein $R_{1-1}$ is methyl and $R_{1-6}$ is ethylene, in the presence of triethylamine in a suitable solvent, such as chloroform or dichloromethane. Compounds of the formula $H_2N—X—C(R_{1-1})(O—R_{1-6})_2$ can be commercially obtained or readily synthesized using conventional methods. For example, see C. J. Stewart et al., *J Liebigs Ann. der Chem.*, 57-65 (1978) and PCT Publication WO 01/51486. Ketals of Formula $H_2NCH_2C(CH_3)_2CH_2C(O—R_{1-6})_2CH_3$ can be prepared according to referenced methods by the reaction of nitro methane and mesityl oxide, conversion of the resulting ketone to a ketal, and reduction of the nitro group to an amine.

In step (2) of Reaction Scheme II, the nitro group on a compound of Formula XIX is reduced to provide a ketal- or acetal-substituted quinoline-3,4-diamine of Formula XX. The reduction can be carried out as described for step (2) of Reaction Scheme I.

In step (3) of Reaction Scheme II, a quinoline-3,4-diamine of Formula XX is treated with a carboxylic acid equivalent to form a ketal- or acetal-substituted 1H-imidazo[4,5-c]quinoline of Formula XX. The reaction can be carried out as described for step (3) of Reaction Scheme I.

In step (4) of Reaction Scheme II, a 1H-imidazo[4,5-c]quinoline of Formula XXI is converted to the N-oxide of Formula XXII using the method described in step (7) of Reaction Scheme I.

In step (5) of Reaction Scheme II, the N-oxide of Formula XXII can be animated to the compound of Formula XXII as described in step (8) of Reaction Scheme I.

In step (6) of Reaction Scheme II, a compound of Formula XXIII is converted to a ketone of Formula XVIII by acid-catalyzed hydrolysis. The reaction is conveniently carried out by adding a strong acid, such as hydrochloric acid, to a ketal of Formula XXIII. The reaction may be carried out at ambient temperature in a suitable solvent such as water.

Steps (7), (8), and (9) are carried out as described for steps (9), (10), and (11) respectively of Reaction Scheme I.

Reaction Scheme II

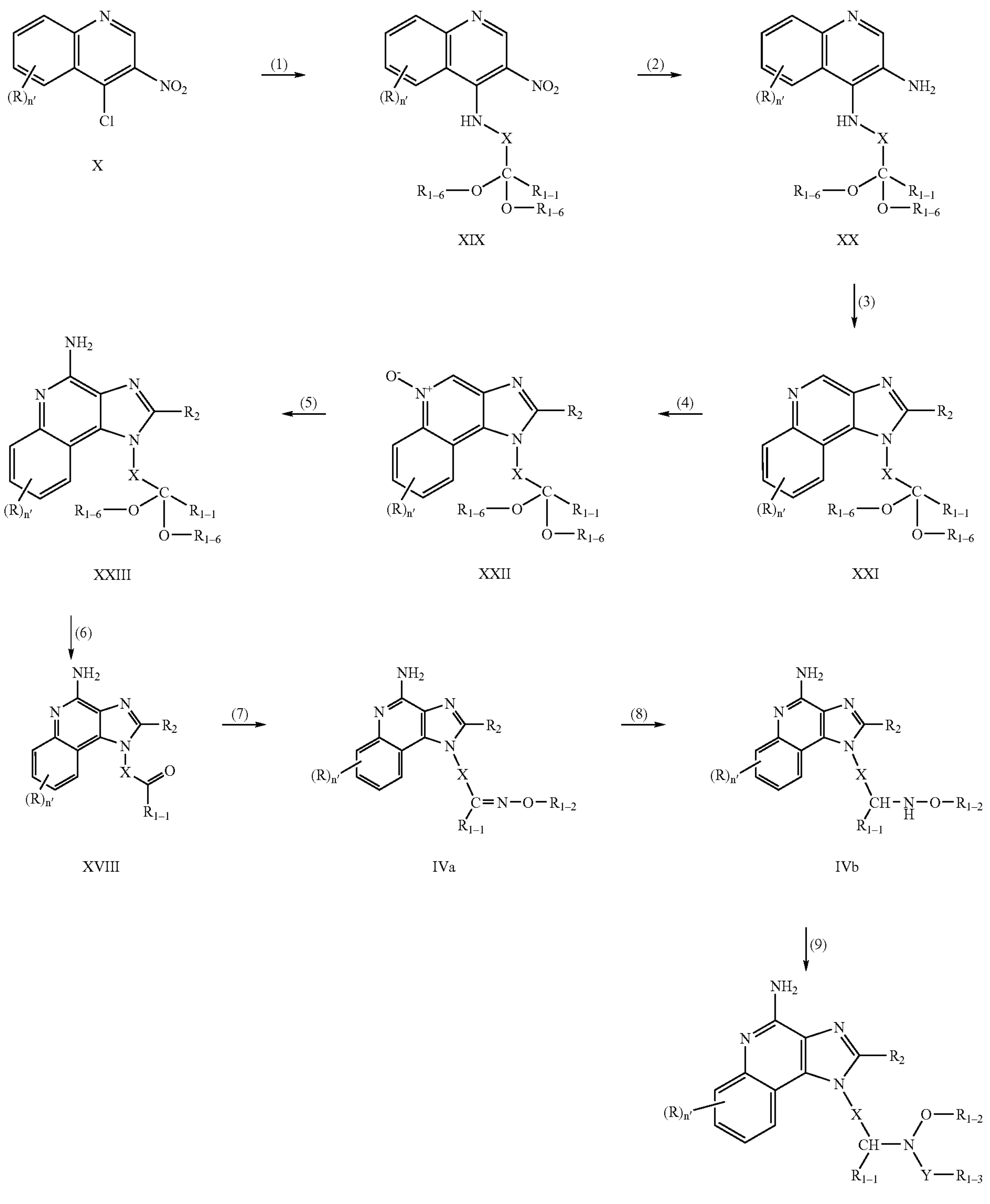

X, XIX, XX, XXI, XXII, XXIII, XVIII, IVa, IVb, IVc

Compounds of the invention can be prepared according to Reaction Scheme III.

In step (1) of Reaction Scheme III, a 4-chloro-3-nitroquinoline of Formula X is reacted with a compound of the formula $H_2N—X—C(O)(O—R_{1-1})$.HCl to form a compound of Formula XXIV. The reaction is conveniently carried out in the presence of triethylamine in a suitable solvent, such as dichloromethane. Compounds of the formula $H_2N—X—C(O)(O—R_{1-1})$.HCl can be commercially obtained or readily synthesized using conventional methods. For example, the amino ester wherein $R_{1-1}$ is ethyl and X is propylene or dodecylene can be synthesized according to the procedure of C. Temple et al., *J Med. Chem.,* 31, 697-700 (1988).

In step (2) of Reaction Scheme III, a compound of Formula XXIV is reduced to form a quinoline-3,4-diamine of Formula XXV. The reaction can be carried out as described in step (2) of Reaction Scheme I.

In step (3) of Reaction Scheme III, a quinoline-3,4-diamine of Formula XXV is reacted with a carboxylic acid equivalent to form a 1H-imidazo[4,5-c]quinoline of Formula XXVI. The reaction can be carried out as described in step (3) of Reaction Scheme I.

In step (4) of Reaction Scheme III, the ester group of a 1H-imidazo[4,5-c]quinoline of Formula XXVI is converted to a Weinreb amide to provide a 1H-imidazo[4,5-c]quinoline of Formula XXVII. The transformation can be carried out by base-promoted hydrolysis of the ester to form a carboxylic acid, conversion to an acid chloride using conventional methods, and finally treating the acid chloride with N,O-dimethylhydroxylamine hydrochloride to form a Weinreb amide of Formula XXVII. The base-promoted hydrolysis is conveniently carried out by adding sodium hydroxide to an ester-substituted 1H-imidazo[4,5-c]quinoline Formula XXVI in a suitable solvent such as ethanol. The reaction can be carried out at ambient temperature, and the product can be isolated using conventional methods. The conversion of the resulting carboxylic acid to an acid chloride is conveniently carried out by slowly adding oxalyl chloride to a solution of the carboxylic acid in a suitable solvent such as dichloromethane. The reaction can be carried out at a sub-ambient temperature, such as 0° C. The resulting acid chloride can then be treated with N,O-dimethylhydroxylamine hydrochloride followed by triethylamine in a suitable solvent such as dichloromethane. The reaction can be run at ambient temperature, and the product of Formula XXVII can be isolated using conventional methods.

Alternatively, step (4) can be carried out in one step by treating an ester-substituted 1H-imidazo[4,5-c]quinoline Formula XXVI with an aluminum reagent made from trimethylaluminum and N,O-dimethylhydroxylamine hydrochloride. The reaction is conveniently carried out by adding a solution of an ester-substituted 1H-imidazo[4,5-c]quinoline of Formula XXVI in a suitable solvent such as dichloromethane to a pre-reacted mixture of trimethylaluminum and N,O-dimethylhydroxylamine hydrochloride in a suitable solvent such as dichloromethane. The reaction can then be heated at an elevated temperature, for example, the reflux temperature of the solvent. The product can be isolated using conventional methods.

In step (5) of Reaction Scheme III, a Weinreb amide of Formula XXVII is treated with a Grignard reagent of Formula $R_{1-1}$MgHalide to form a ketone of Formula XVI. The Grignard reaction can be carried out as described in step (5) of Reaction Scheme I. The product can be isolated using conventional methods.

Steps (6), (7), (8), (9), and (10) of Reaction Scheme III can be carried out as described for steps (7), (8), (9), (10), and (11), respectively, of Reaction Scheme I.

Reaction Scheme III

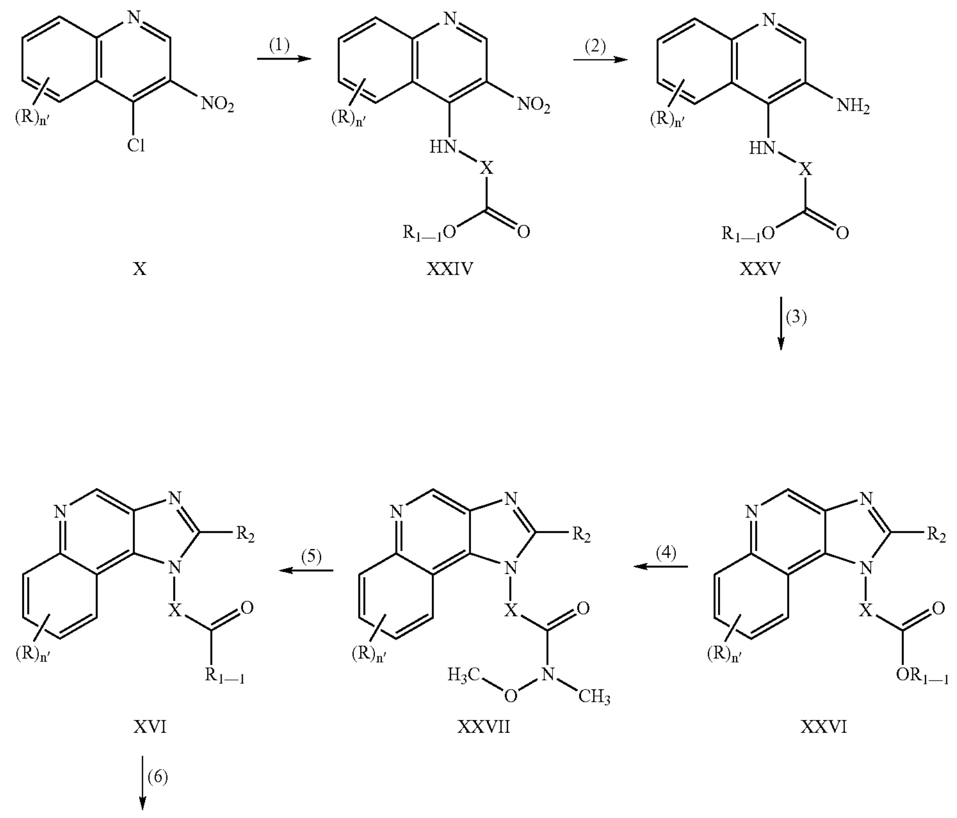

X XXIV XXV

XVI XXVII XXVI

-continued

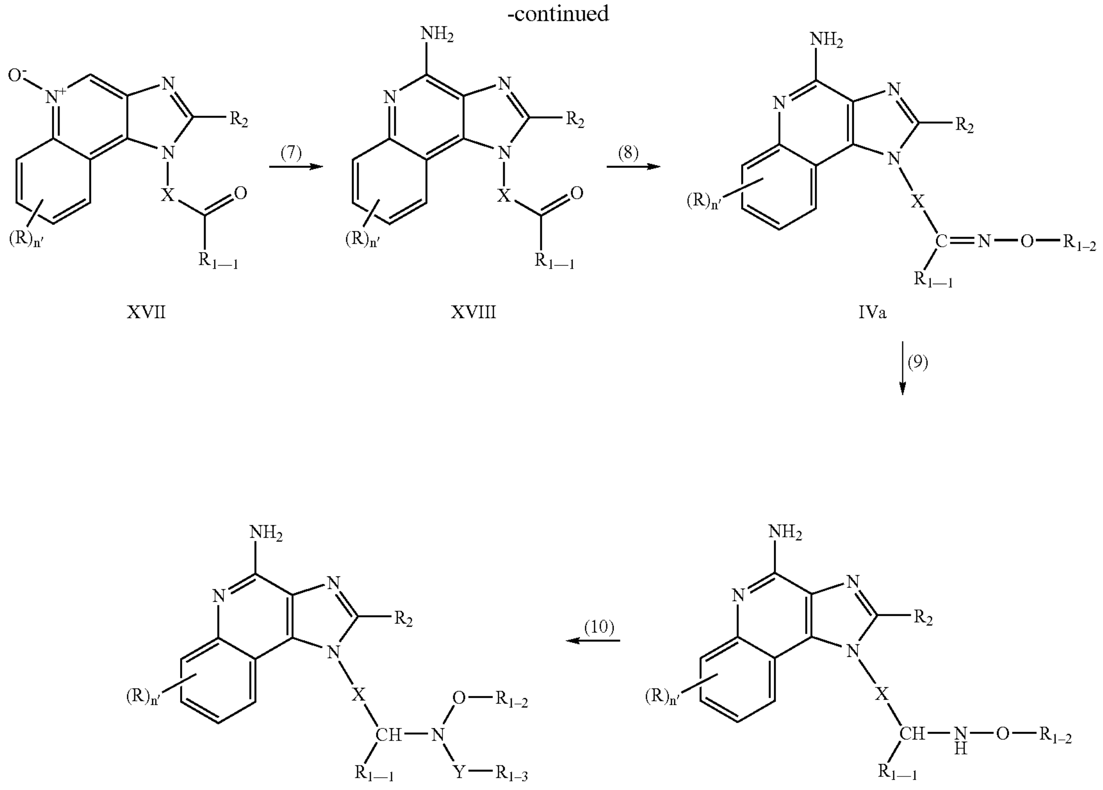

XVII XVIII IVa

IVc IVb

Compounds of the invention can be prepared according to Reaction Scheme IV.

In step (1) of Reaction Scheme IV, an acetal-substituted 1H-imidazo[4,5-c]quinoline of Formula XXIa is hydrolyzed to provide an aldehyde substituted 1H-imidazo[4,5-c]quinoline of Formula XIV. The reaction can be carried out as described in step (6) of Reaction Scheme II.

In step (2) of Reaction Scheme IV, an aldehyde-substituted 1H-imidazo[4,5-c]quinoline of Formula XIV is converted to an oxime substituted 1H-imidazo[4,5-c]quinoline of Formula XXIX. The reaction can be carried out as described in step (9) of Reaction Scheme I.

In step (3) of Reaction Scheme IV, an oxime substituted 1H-imidazo[4,5-c]quinoline of Formula XXIX is oxidized and then animated to provide an oxime substituted 1H-imidazo[4,5-c]quinolin-4-amine of Formula IVd. The oxidation and animation can be carried out as described in steps (7) and (8) respectively of Reaction Scheme I.

Steps (4) and (5) of Reaction Scheme IV are carried out as described for steps (10) and (11), respectively, of Reaction Scheme I.

Reaction Scheme IV

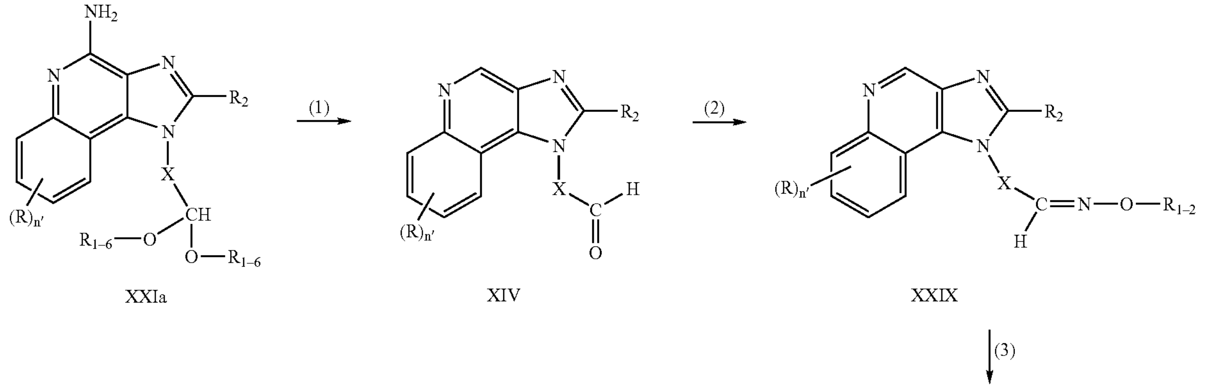

XXIa XIV XXIX

-continued

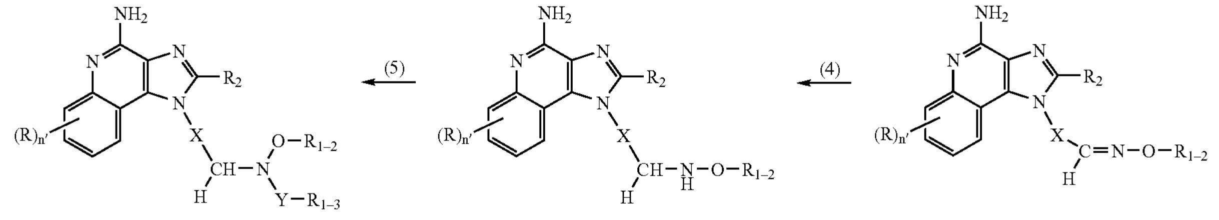

IVf IVe IVd

Compounds of the invention can be prepared according to Reaction Scheme V, where Ph is phenyl and $R_{A'}$ and $R_{B'}$ are independently selected from the group consisting of hydrogen, halogen, alkyl, alkenyl, alkoxy, alkylthio, and $N(R_9)_2$. In step (1) of Reaction Scheme V, a 2,4-dichloro-3-nitropyridine of Formula XXX is reacted with an amino ester of the Formula $H_2N$—X—C(O)—O-alkyl or a hydrochloride salt thereof to form a 2-chloro-3-nitropyridine of Formula XXX. The reaction is conveniently carried out by combining an amino ester of Formula $H_2N$—X—C(O)—O-alkyl.HCl and a 2,4-dichloro-3-nitropyridine of Formula XXX in the presence of a base such as triethylamine in an inert solvent such as N,N-dimethylformamide (DMF). The reaction can be carried out at ambient temperature, and the product can be isolated from the reaction mixture using conventional methods. Many 2,4-dichloro-3-nitropyridines of the Formula XXX are known and can be readily prepared using known synthetic methods. (See, for example, U.S. Pat. No. 6,525,064 (Dellaria et al.) and the references cited therein.)

In step (2) of Reaction Scheme V, a 2-chloro-3-nitropyridine of Formula XXXI is reacted with an alkali metal azide to provide an 8-nitrotetrazolo[1,5-a]pyridin-7-amine of Formula XXXII. The reaction can be carried out by combining the compound of Formula XI with an alkali metal azide, for example, sodium azide, in a suitable solvent such as acetonitrile/water, preferably 90/10 acetonitrile/water, in the presence of cerium III chloride, preferably cerium III chloride heptahydrate. Optionally, the reaction can be carried out with heating, for example, at the reflux temperature. Alternatively, the reaction can be carried out by combining the compound of Formula XXXI with an alkali metal azide, for example, sodium azide, in a suitable solvent such as DMF and heating, for example to about 50-60° C., optionally in the presence of ammonium chloride. The product can be isolated from the reaction mixture using conventional methods.

In step (3) of Reaction Scheme V, an 8-nitrotetrazolo[1,5-a]pyridin-7-amine of Formula XXXII is reduced to provide a tetrazolo[1,5-a]pyridine-7,8-diamine of Formula XXXI. The reduction can be carried out by hydrogenation using a conventional heterogeneous hydrogenation catalyst, for example, platinum on carbon or palladium on carbon. The reaction can conveniently be carried out on a Parr apparatus in a suitable solvent such as acetonitrile or ethyl acetate. The product can be isolated from the reaction mixture using conventional methods. Alternatively, the reduction can be carried out using the one- to two-phase sodium dithionite reduction described in step (2) of Reaction Scheme I.

In step (4) of Reaction Scheme V, a tetrazolo[1,5-a]pyridine-7,8-diamine of Formula XXXII is reacted with a carboxylic acid equivalent to provide a 7H-imidazo[4,5-c]tetrazolo[1,5-a]pyridine of Formula XIV. The reaction can be carried out as described in step (3) of Reaction Scheme I, and the product can be isolated from the reaction mixture using conventional methods.

In step (5) of Reaction Scheme V, the ester group of the 7H-imidazo[4,5-c]tetrazolo[1,5-a]pyridine of Formula XXXIV is converted to a Weinreb amide to provide a 7H-imidazo[4,5-c]tetrazolo[1,5-a]pyridine of Formula XXXV. The conversion can be carried out as described in step (4) of Reaction Scheme III, and the product can be isolated from the reaction mixture using conventional methods.

In step (6) of Reaction Scheme V, the Weinreb amide of Formula XXXV is treated with a Grignard reagent of Formula $R_{1-1}$MgHalide to form a ketone of Formula XXXVI. The Grignard reaction can be carried out as described in step (5) of Reaction Scheme I, and the product can be isolated from the reaction mixture using conventional methods.

In step (7) of Reaction Scheme V, a 7H-imidazo[4,5-c]tetrazolo[1,5-a]pyridine of Formula XVI is reacted with triphenylphosphine to form an N-triphenylphosphinyl intermediate of Formula XXXI. The reaction with triphenylphosphine can be run in a suitable solvent such as toluene or 1,2-dichlorobenzene under an atmosphere of nitrogen with heating, for example at the reflux temperature. The product can be isolated from the reaction mixture using conventional methods.

In step (8) of Reaction Scheme V, an N-triphenylphosphinyl intermediate of Formula XXXVX is hydrolyzed to provide a ketone substituted 1H-imidazo[4,5-c]pyridin-amine of Formula XXXVIII. The hydrolysis can be carried out by general methods well known to those skilled in the art, for example, by heating in a lower alkanol in the presence of an acid. The product can be isolated from the reaction mixture using conventional methods.

Steps (9), (10), and (11) of Reaction Scheme V can be carried out as described for steps (9), (10), and (11), respectively, of Reaction Scheme I.

Reaction Scheme V

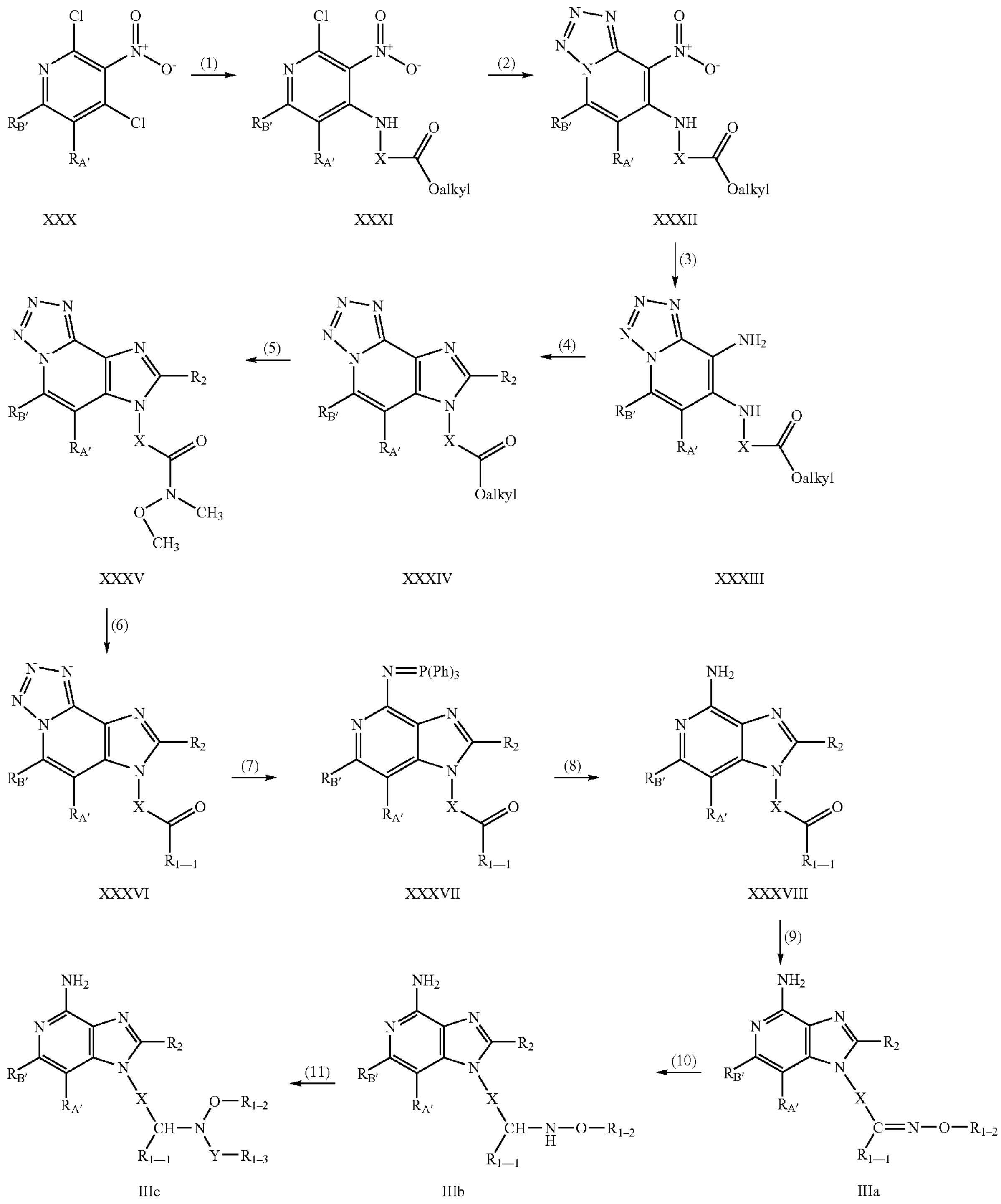

Compounds of the invention can also be prepared according to Reaction Scheme VI where BOC is tert-butoxycarbonyl and $R_{2a}$ is a subset of $R_2$ as defined above that does not include those substituents that one skilled in the art would recognize as being susceptible to reduction under the acidic hydrogenation conditions of step (5) of the reaction. These susceptible groups include, for example, alkenyl, alkynyl, and aryl groups and groups bearing nitro substituents.

In step (1) of Reaction Scheme VI, a 2,4-dichloro-3-nitropyridine of Formula XXX is reacted with an amino alcohol of the formula $H_2N—X—CH_2—OH$ to form a 2-chloro-3-nitropyridine of Formula XXXIX. The reaction can be carried out as described in step (1) of Reaction Scheme V using the amino alcohol in lieu of the amino ester. The product can be isolated using conventional methods.

In step (2) of Reaction Scheme VI, a 2-chloro-3-nitropyridine of Formula XXXIX is reacted with an alkali metal azide to provide an 8-nitrotetrazolo[1,5-a]pyridin-7-amine of Formula XL. The reaction can be carried out as described in step (2) of Reaction Scheme V.

In step (3) of Reaction Scheme VI, an 8-nitrotetrazolo[1,5-a]pyridin-7-amine of Formula XL is reduced to provide a tetrazolo[1,5-a]pyridine-7,8-diamine of Formula XLI. The reduction can be carried out as described in step (3) of Reaction Scheme V.

In step (4) of Reaction Scheme VI, a tetrazolo[1,5-a]pyridine-7,8-diamine of Formula XLI is reacted with a carboxylic acid equivalent to provide a 7H-imidazo[4,5-c]tetrazolo[1,5-a]pyridine of Formula XLII. The reaction can be carried out as described in step (3) of Reaction Scheme I, and the product can be isolated from the reaction mixture using conventional methods.

In step (5) of Reaction Scheme VI, the tetrazolo ring is reductively removed from a 7H-imidazo[4,5-c]tetrazolo[1,5-a]pyridine of the Formula XLII to provide a substituted 1H-imidazo[4,5-c]pyridin-4-amine of the Formula XLIII. The reaction can be carried out by reacting the 7H-imidazo[4,5-c]tetrazolo[1,5-a]pyridine of Formula XLII with hydrogen in the presence of a catalyst and an acid. The hydrogenation can be conveniently run at ambient temperature on a Parr apparatus with a suitable catalyst, such as platinum (I) oxide, and a suitable acid, such as trifluoroacetic acid.

In step (6) of Reaction Scheme VI, the alcohol group of an 1H-imidazo[4,5-c]pyridin-4-amine of the Formula XLIII is converted to a protected hydroxylamine using Mitsunobu conditions. The reaction can be carried out by adding diisopropyl azodicarboxylate to a solution of the 1H-imidazo[4,5-c]pyridamine of the Formula XLIII, triphenylphosphine, and tert-butyl N-(tert-butxoycarbonyloxy)carbamate in a suitable solvent such as DMF. The reaction can be carried out at sub-ambient temperature, such as 0° C., and the product can be isolated using conventional methods.

In step (7) of Reaction Scheme VI, the amine protecting groups of the 1H-imidazo[4,5-c]pyridine of Formula XLIV are removed by acid catalyzed hydrolysis. The reaction can be carried out by adding a solution of hydrochloric acid in dioxane to a solution of the 1H-imidazo[4,5-c]pyridine of Formula XLIV in a suitable solvent such as dichloromethane. The reaction can be carried out at ambient temperature.

Step (8) of Reaction Scheme VI can be carried out as described for step (11) in Reaction Scheme I. The product or a pharmaceutically acceptable salt thereof can be isolated using conventional methods.

Reaction Scheme VI

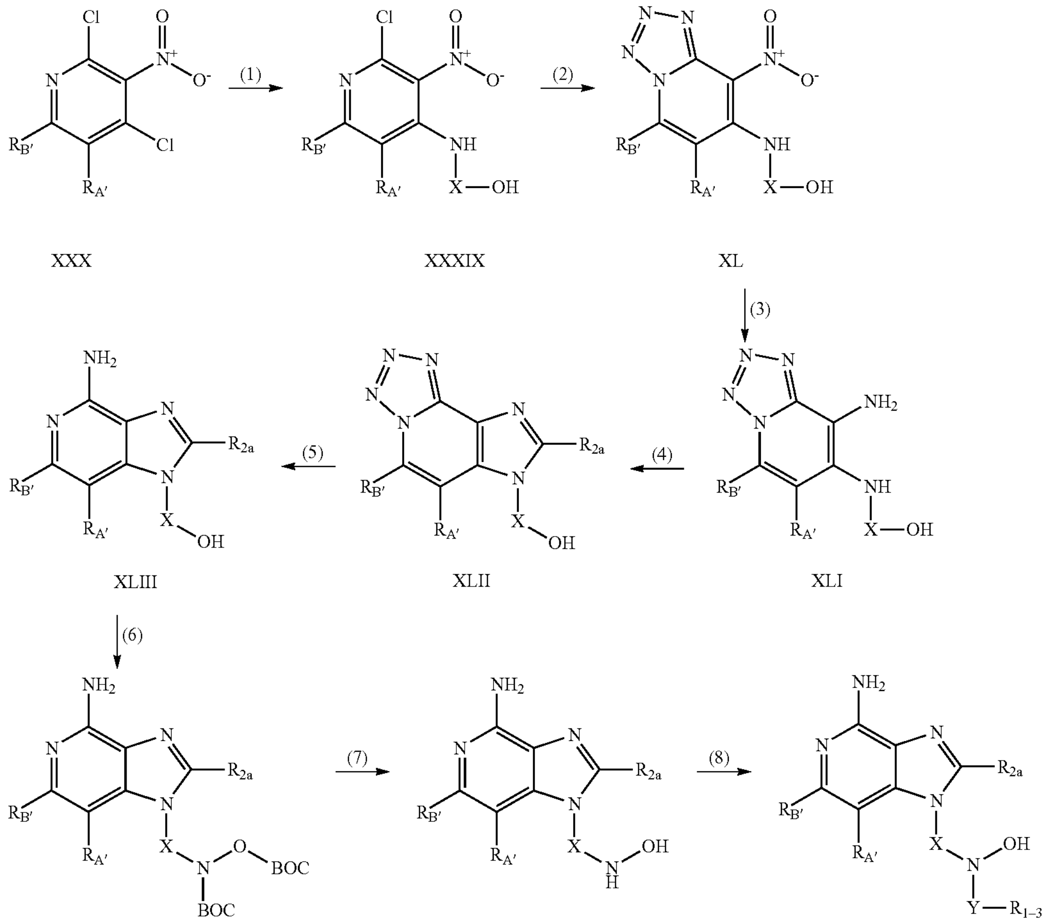

XXX XXXIX XL XLIII XLII XLI XLIV IIId IIIe

Compounds of the invention can be prepared according to Reaction Scheme VII. Reaction Scheme VII begins with a 4-chloro-3-nitro[1,5]naphthyridine of Formula XLV. Compounds of Formula XLV and their preparation are known; see, for example, U.S. Pat. No. 6,194,425 (Gerster) and U.S. Pat. No. 6,518,280 (Gerster). Steps (1) through (10) of Reaction Scheme VII can be carried out as described for the corresponding steps (1) through (10) of Reaction Scheme III to provide 1H-imidazo[4,5-c][1,5]naphthyridin-4-amines of Formulae VIa, VIb, and VIc. The product or pharmaceutically acceptable salt thereof can be isolated by conventional methods.

sponding steps (1) through (3) of Reaction Scheme II; steps (4) through (8) can be carried out as described for steps (1) through (5) respectively of Reaction Scheme IV to provide Reaction Scheme VII

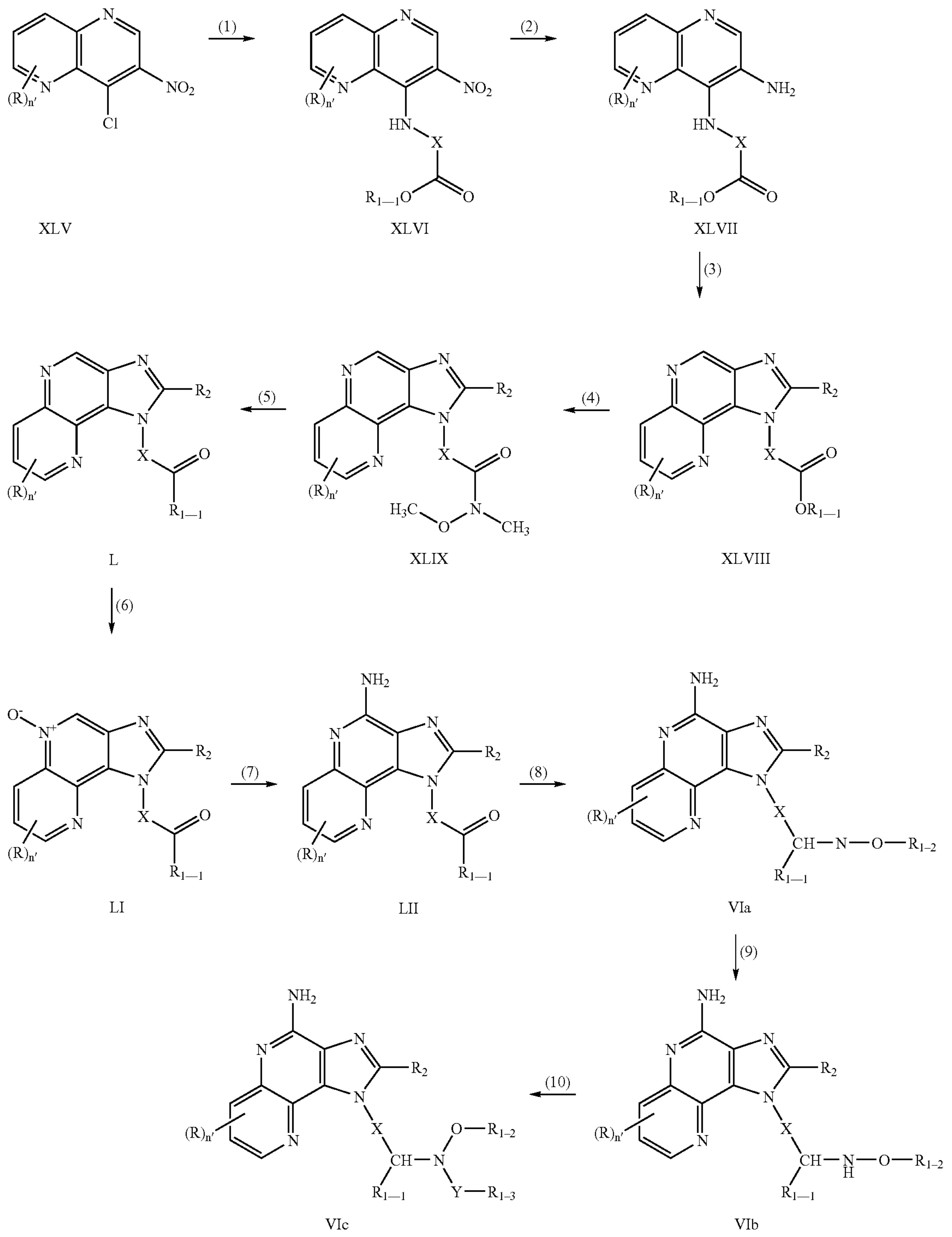

Compounds of the invention can be prepared according to Reaction Scheme VIII. Steps (1) through (3) of Reaction Scheme VIII can be carried out as described for the corresponding steps (1) through (3) of Reaction Scheme II; steps (4) through (8) can be carried out as described for steps (1) through (5) respectively of Reaction Scheme IV to provide 1H-imidazo[4,5-c][1,5]naphthyridin-amines of Formulas VId, VIe, and VIf. The products or pharmaceutically acceptable salts thereof can be isolated by conventional methods.

Reaction Scheme VIII

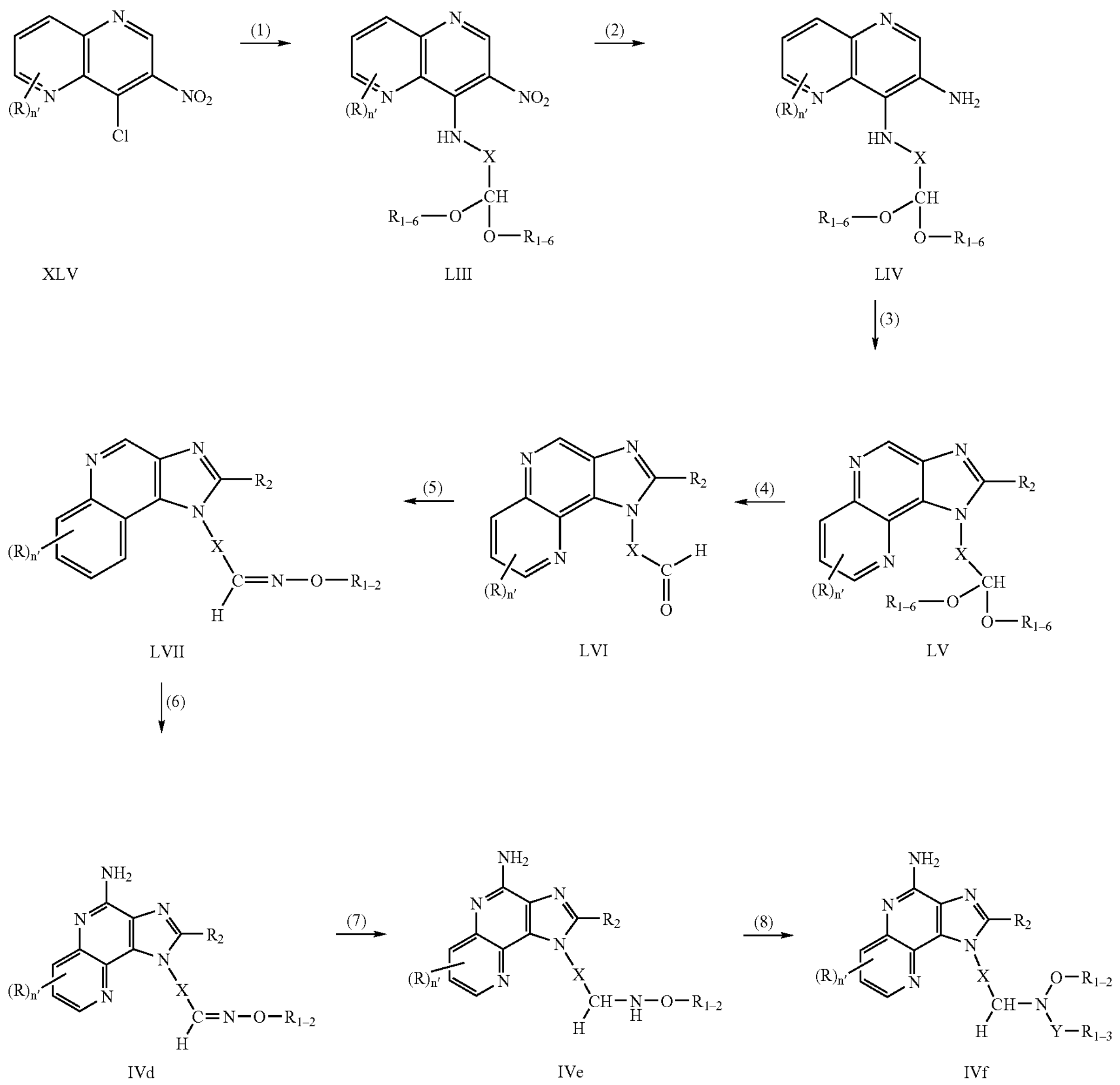

Compounds of the invention can be prepared according to Reaction Scheme IX where $R_{2a}$ and $R_a$ are subsets of $R_2$ and R as defined above that do not include those substituents that one skilled in the art would recognize as being susceptible to reduction under the acidic hydrogenation conditions of step (2) of the reaction. These susceptible groups include, for example, alkenyl, alkynyl, and aryl groups and groups bearing nitro substituents.

In step (1) of Reaction Scheme IX, a 1H-imidazo[4,5-c] quinoline of Formula LVII is oxidized and then animated to provide a 1H-imidazo[4,5-c]quinolin-4-amine of Formula LIX. The reaction can be carried out as described in steps (7) and (8) of Reaction Scheme I. Compounds of Formula LVIII can be prepared as described in steps (1) through (3) of Reaction Scheme I.

In step (2) of Reaction Scheme IX, a 1H-imidazo[4,5-c] quinolin-4-amine of Formula LIX is reduced to provide a 6,7,8,9-tetrahydro-1H-imidazo[4,5-c]quinolin-4-amine of Formula LX. The reaction can be carried out by reacting the compound of Formula LIX with hydrogen in the presence of a catalyst and an acid. The hydrogenation can be conveniently run at ambient temperature on a Parr apparatus with a suitable catalyst, such as platinum (IV) oxide, and a suitable acid, such as trifluoroacetic acid.

Steps (3), (4) and (5) of Reaction Scheme IX can be carried out as described for steps (6), (7), and (8), respectively, of Reaction Scheme VI to provide 6,7,8,9-tetrahydro-1H-imidazo[4,5-c]quinolin-4-amines of Formulas Va and Vb. The products or pharmaceutically acceptable salts thereof can be isolated by conventional methods.

Reaction Scheme IX

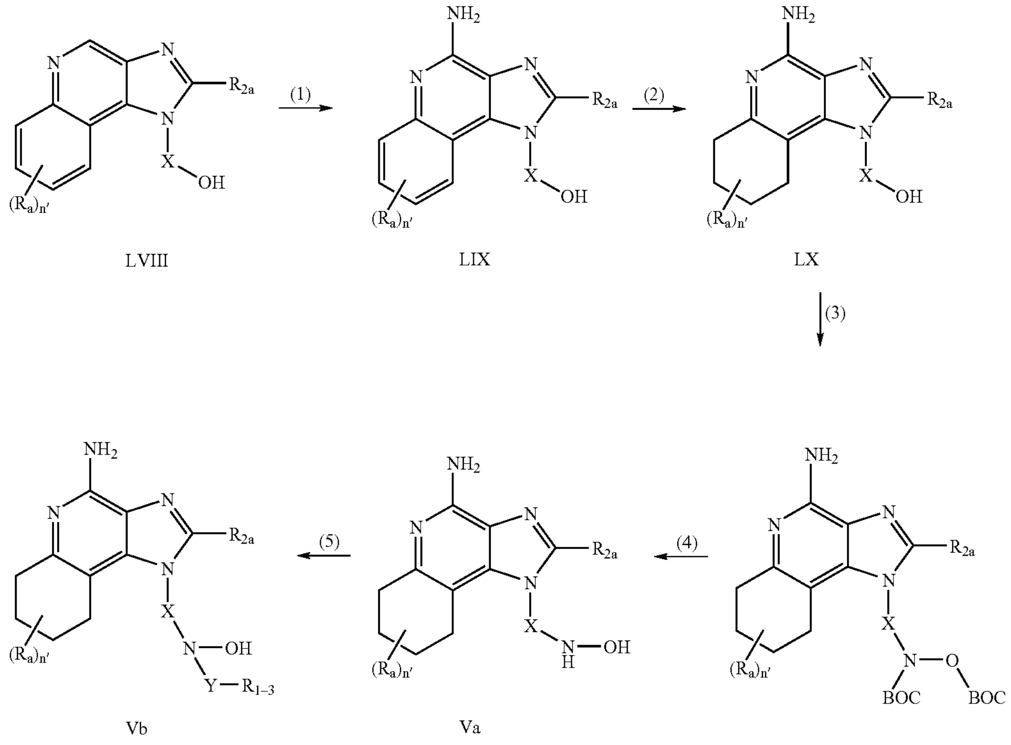

Compounds of the invention can be prepared according to Reaction Scheme X where $R_{3a}$ is —$R_{4a}$, —$X'_a$—$R_{4a}$, or —$X'_b$—Y'—$R_4$, where $R_{4a}$ is aryl, heteroaryl, arylalkylenyl, heteroarylalkylenyl where the aryl, heteroaryl, arylalkylenyl and heteroarylalkylenyl groups can be unsubstituted or substituted as defined in $R_4$ above; $X'_a$ is alkenylene; $X'_b$ is arylene, heteroarylene, alkylene interrupted or terminated on the end distal from the imidazoquinoline ring by arylene or heteroarylene, and alkenylene interrupted or terminated on the end distal from the imidazoquinoline ring by arylene or heteroarylene; and Y' and $R_4$ are as defined above.

Steps (1) through (3) of Reaction Scheme X can be carried out as described in steps (1) through (3) of Reaction Scheme II.

Step (4) of Reaction Scheme X can be carried out as described in step (1) of Reaction Scheme IV.

Step (5) of Reaction Scheme X can be carried out as described in step (5) of Reaction Scheme I.

In step (6) of Reaction Scheme X, the alcohol group of a 1H-imidazo[4,5-c]quinoline of Formula XVa is oxidized using Dess-Martin oxidation conditions to provide a ketone substituted 1H-imidazo[4,5-c]quinoline of Formula XVIa. Triacetoxyperiodinane is added to a solution of the compound of Formula XVa in suitable solvent such as dichloromethane. The product can be isolated using conventional methods.

In step (7) of Reaction Scheme X, a bromo substituted 1H-imidazo[4,5-c]quinoline of Formula XVIa is coupled with a boronic acid of the formula $R_{3a}$—$B(OH)_2$ using Suzuki coupling. A compound of Formula XVIa is combined with a boronic acid of the formula $R_{3a}$—$B(OH)_2$ in the presence of palladium (II) acetate, triphenylphosphine and a base such as sodium carbonate in a suitable solvent such as a mixture of n-propanol and water. The reaction can be carried out at an elevated temperature (e.g., 80-100° C.). Many boronic acids of the formula $R_{3a}$—$B(OH)_2$ are commercially available; others can be readily prepared using known synthetic methods. See for example, Li, W. et al., *J Org. Chem.*, 67, 5394-5397 (2002). The Suzuki coupling reaction can also be carried out using boronic acid esters of the formula $R_{3a}$—$B(O\text{-alkyl})_2$ and anhydrides of boronic acids. The product can be isolated using conventional methods.

In step (8) of Reaction Scheme X, a 1H-imidazo[4,5-c]quinoline of Formula LXI is oxidized and then animated to provide a 1H-imidazo[4,5-c]quinolin-4-amine of Formula LXII. The reaction can be carried out as described in steps (7) and (8) of Reaction Scheme I. The product can be isolated using conventional methods.

Steps (9), (10), and (11) of Reaction Scheme X can be carried out as described in steps (9), (10), and (11) of Reaction Scheme I. The compounds of Formulas IVg, IVh, and IVi or pharmaceutically acceptable salts thereof can be isolated using conventional methods.

Reaction Scheme X

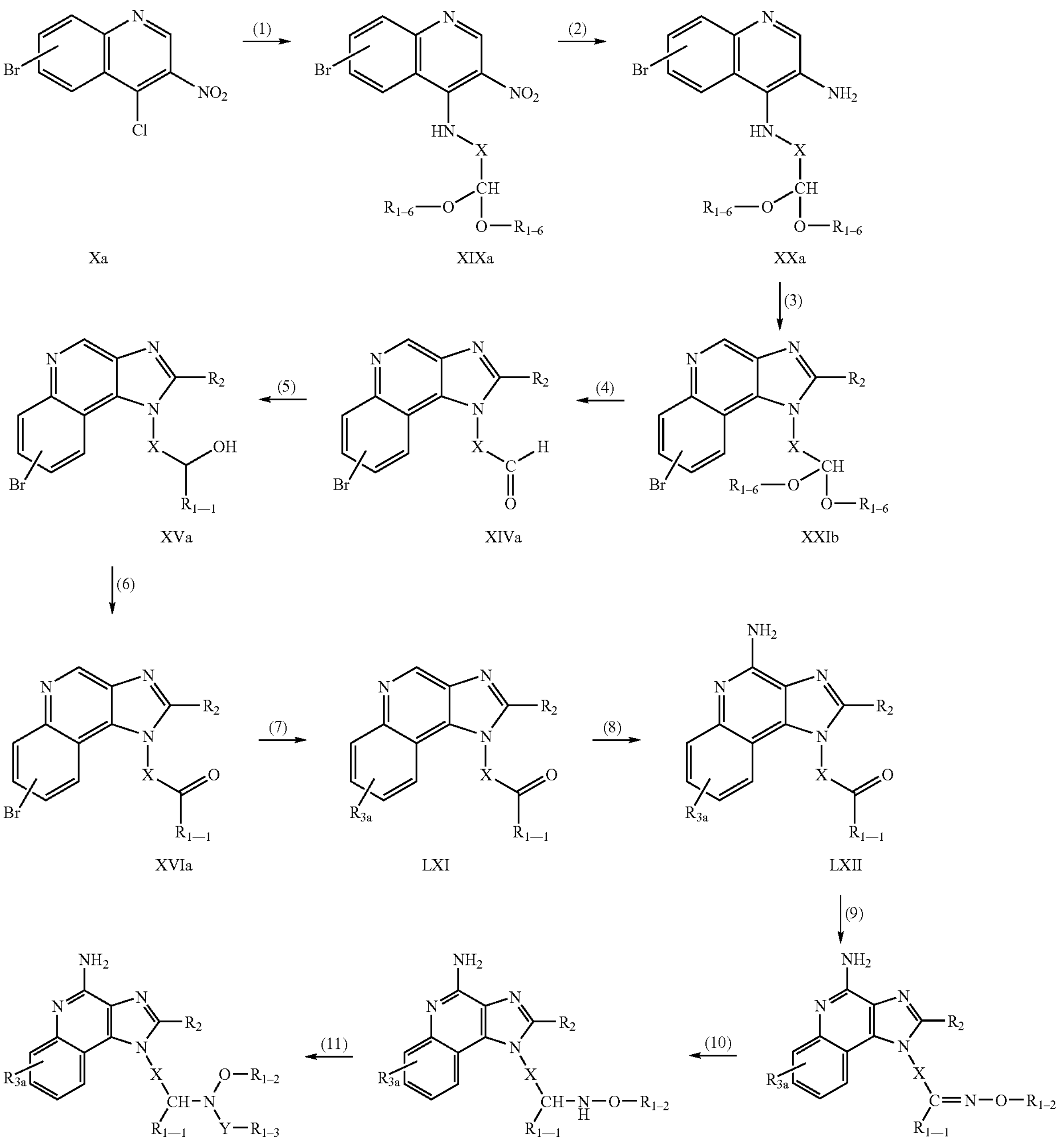

Xa XIXa XXa XXIb XIVa XVa XVIa LXI LXII IVg IVh IVi

Compounds of the invention can be prepared according to Reaction Scheme XI where $R_{2a}$ and $R_a$ are as described above.

In step (1) of Reaction Scheme XI, a 1H-imidazo[4,5-c][1,5]naphthyridine of Formula LXIII is oxidized and then animated to provide a 1H-imidazo[4,5-c][1,5]naphthyridin-4-amine of Formula LXIV. The reaction can be carried out as described in steps (7) and (8) of Reaction Scheme I. Compounds of Formula LXIII can be prepared as described in steps (1) through (3) of Reaction Scheme I using 4-chloro-3-nitro[1,5]naphthyridine in lieu of 4-chloro-3-nitroquinoline.

In step (2) of Reaction Scheme XI, a 1H-imidazo[4,5-c][1,5]naphthyridin-4-amine of Formula LXI is reduced to provide a 6,7,8,9-tetrahydro-1H-imidazo[4,5-c)][1,5]naphthyridin-4-amine of Formula LXV. The reduction can be carried out as described in step (2) of Reaction Scheme IX.

In step (3) of Reaction Scheme XI, the alcohol group of a 6,7,8,9-tetraydro-1H-imidazo[4,5-c][1,5]naphthyridin-4-amine of Formula LXV is oxidized using mild conditions to provide a ketone substituted 6,7,8,9-tetrahydro-1H-imidazo[4,5-c][1,5]naphthyridin-4-amine of Formula LXVI. The reaction can be carried out using Dess-Martin oxidation conditions as described in step (6) of Reaction Scheme X.

Steps (4), (5), and (6) can be carried out as described in steps (9), (10), and (11), respectively, of Reaction Scheme I to provide compounds of Formulas VIIa, VIIb, and VIIc. The products or pharmaceutically acceptable salts thereof can be isolated using conventional methods.

Reaction Scheme XI

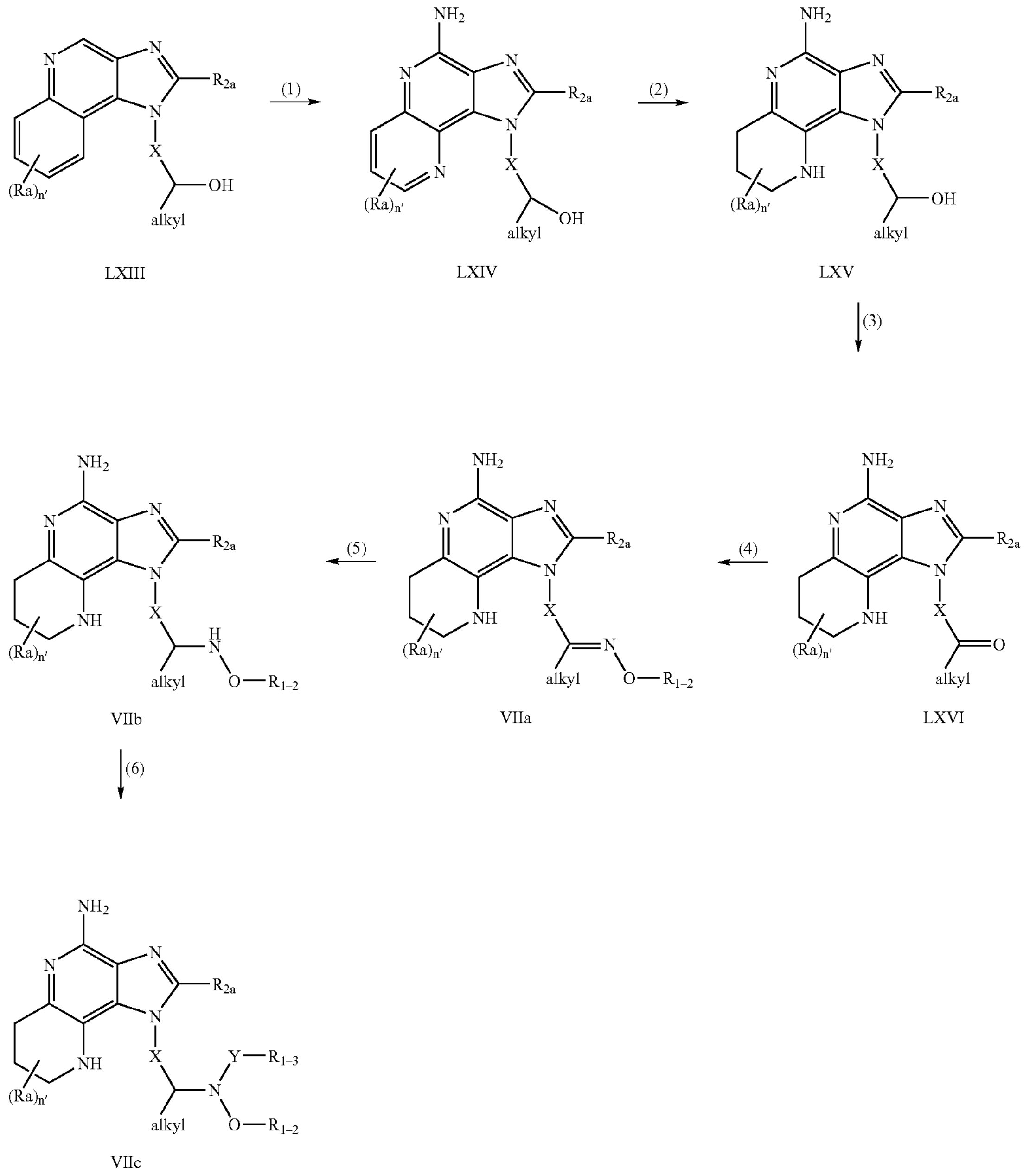

Compounds of the invention can also be prepared according to Reaction Scheme XII.

In step (1) of Reaction Scheme XII, a 5-chloro-4-nitrotetrazolo[1,5-a][1,7]naphthyridine of Formula LXVII is reacted with an amino ester of the Formula $H_2N—X—C(O)—O$-alkyl of a hydrochloride salt thereof to provide an ester substituted 4-nitrotetrazolo[1,5-a][1,7]naphthyridine of Formula LXVIII. The reaction can be carried out as described in step (1) of Reaction Scheme V. Compounds of Formula LXVII can be prepared using the synthetic methods described in U.S. Pat. No. 6,194,425.

In steps 2 through 7 of Reaction Scheme XII, an ester substituted 4-nitrotetrazolo[1,5-a][1,7]naphthyridine of Formula LXVIII is converted to a ketone substituted 1H-imidazo [4,5-c][1,7]naphthyridin-4-amine of Formula LXIX. The reactions can be carried out as described for steps 3 through 8 of Reaction Scheme V.

Steps (8), (9), and (10) of Reaction Scheme XII can be carried out as described for steps (9), (10), and (11) respectively of Reaction Scheme I.

Reaction Scheme XII

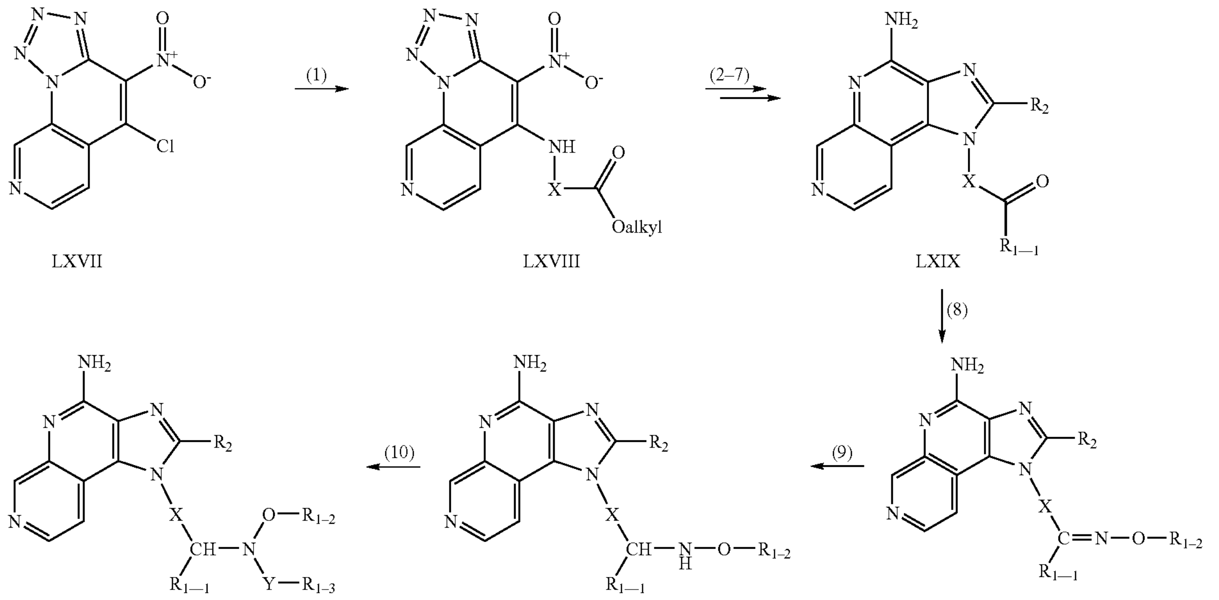

LXVII LXVIII LXIX LXX LXXI LXXII

Compounds of the invention can also be prepared according to Reaction Scheme XIII wherein —OTf is a trifluoromethansulfonate group.

In step (1) of Reaction Scheme XIII, a 4-nitrotetrazolo[1,5-a][1,8]naphthyridine of Formula LXXIII is reacted with an amino ester of the Formula $H_2N—X—C(O)—O$-alkyl or a hydrochloride salt thereof to provide an ester substituted 4-nitrotetrazolo[1,5-a][1,8]naphthyridine of Formula LXXIV. The reaction can be carried out as described in step (1) of Reaction Scheme V. Compounds of Formula LXXIII can be prepared using the synthetic methods described in U.S. Pat. No. 6,194,425.

Steps 2 through 10 of Reaction Scheme XIII can be carried out as described for steps 2 through 10 of Reaction Scheme XII.

Reaction Scheme XIII

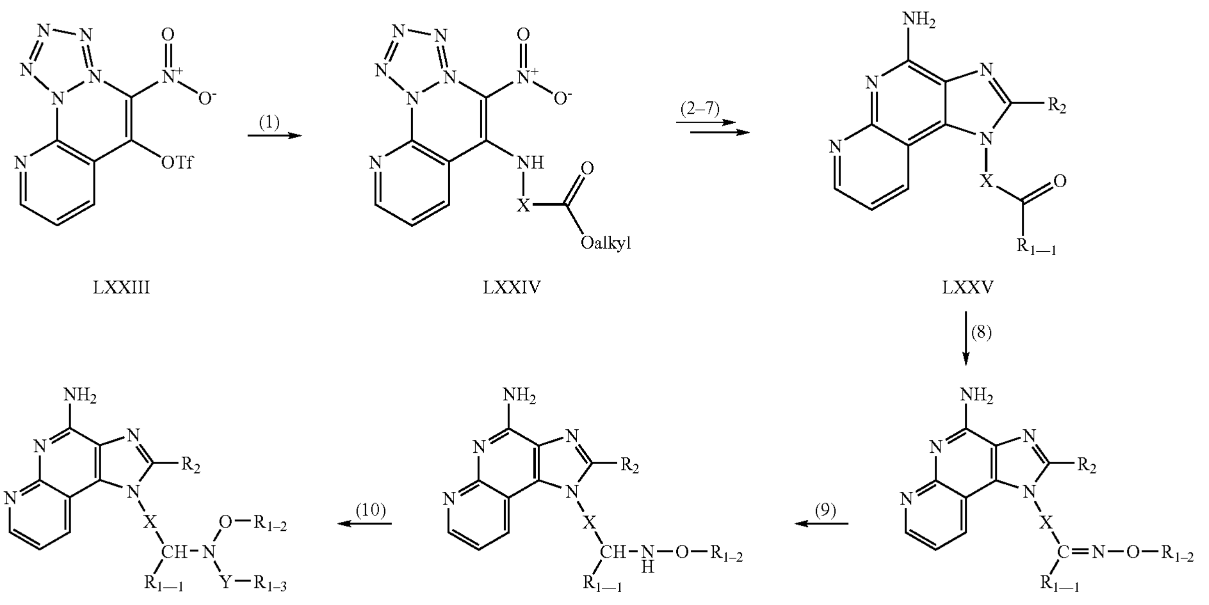

LXXIII LXXIV LXXV LXXVI LXXVII LXXVIII

Compounds of the invention can also be prepared according to Reaction Scheme XIV wherein Bz is benzyl, E' is carbon (imidazoquinoline ring) or nitrogen (imidazonaphthyridine ring), $R_{3b}$ is —O—$R_{4b}$, —O—X'—$R_4$, —O—X'—Y'—$R_4$, or —O—X'—$R_5$; wherein $R_4$, $R_5$, X' and Y' are as defined above, and $R_{4b}$ is aryl or heteroaryl where the aryl or heteroaryl groups can be unsubstituted or substituted as defined in $R_4$ above.

In step (1) of Reaction Scheme XIV, an aniline or aminopyridine of Formula LXXIX is treated with the condensation product generated from 2,2-dimethyl-1,3-dioxane-4,6-dione (Meldrum's acid) and triethyl orthoformate to provide an imine of Formula LXXX. The reaction can be conveniently carried out by adding a solution of an aniline or aminopyridine of Formula LXXIX to a heated mixture of Meldrum's acid and triethyl orthoformate and heating the reaction at an elevated temperature. The product can be isolated using conventional methods. Many anilines and aminopyridines of Formula LXXIX are commercially available; others can be prepared by known synthetic methods. For example, benzyloxypyridines of Formula LXXIX can be prepared using the method of Holladay et al., *Biorg. Med. Chem. Lett.*, 8, pp. 2797-2802, (1998).

In step (2) of Reaction Scheme XIV, an imine of Formula LXXX undergoes thermolysis and cyclization to provide a compound of Formula LXXXI. The reaction is conveniently carried out in a medium such as DOWTHERM A heat transfer fluid at a temperature between 200 and 250° C. The product can be isolated using conventional methods.

In step (3) of Reaction Scheme XIV, a compound of Formula LXXXI is nitrated under conventional nitration conditions to provide a compound of Formula LXXXII. The reaction is conveniently carried out by adding nitric acid to the compound of Formula LXXXI in a suitable solvent such as propionic acid and heating the mixture at an elevated temperature. The product can be isolated using conventional methods.

In step (4) of Reaction Scheme XIV, a 3-nitro[1,5]naphthyridin-4-ol or 3-nitroquinolin-4-ol of Formula LXXI is chlorinated using conventional chlorination chemistry to provide a 4-chloro-3-nitro[1,5]naphthyridine or 4-chloro-3-nitroquinoline of Formula LXXIII. The reaction is conveniently carried out by treating the compound of Formula LXXII with phosphorous oxychloride in a suitable solvent such as N,N-dimethylformamide (DMF). The reaction can be carried out at ambient temperature or at an elevated temperature such as 100° C., and the product can be isolated using conventional methods.

In steps (5) through (12) of Reaction Scheme XIV, a 4-chloro-3-nitro[1,5]naphthyridine or 4-chloro-3-nitroquinoline of Formula LXXIII is converted to a ketone substituted 1H-imidazo[4,5-c]quinolin-4-amine or ketone substituted 1H-imidazo[4,5-c][1,5]naphthyridin-4-amine of Formula LXXXIV. The reactions can be carried out as described for steps (1) through (8) of Reaction Scheme I.

In step (13) of Reaction Scheme XIV, the benzyl group in a benzyloxy-substituted 1H-imidazo[4,5-c][1,5]naphthyridin-4-amine or 1H-imidazo[4,5-c]quinolin-4-amine of Formula LXXXIV is cleaved to provide a hydroxy substituted compound of Formula LXXXV. The cleavage is conveniently carried out on a Parr apparatus under hydrogenolysis conditions using a suitable heterogeneous catalyst such as palladium or platinum on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a compound of Formula LXXXIV in a suitable solvent such as ethanol in the presence of a catalyst such as palladium on carbon. The reaction is carried out at an elevated temperature, for example, the refluxing temperature of the solvent.

In step (14) of Reaction Scheme XIV, a hydroxy-substituted compound of Formula LXXXV is converted to an ether-substituted compound of Formula LXXXVI using a Williamson-type ether synthesis. The reaction is effected by treating a compound of Formula LXXXV with an aryl or alkyl halide of Formula Halide-$R_{4b}$, Halide-alkylene-$R_4$, Halide-alkylene-Y'—$R_4$ or Halide-alkylene-$R_5$ in the presence of a base. Numerous alkyl or aryl halides of these formulas are commercially available, including substituted benzyl bromides and chlorides, substituted or unsubstituted alkyl or arylalkylenyl bromides and chlorides, and substituted fluorobenzenes. Other alkyl or aryl halides of these Formulas can be prepared using conventional synthetic methods. The reaction is conveniently carried out by combining a reagent of Formula Halide-$R_{4b}$, Halide-alkylene-$R_4$, Halide-alkylene-Y'—$R_4$ or Halide-alkylene-$R_5$ with a hydroxy-substituted compound of Formula LXXXV in a solvent such as DMF in the presence of a suitable base such as cesium carbonate. Optionally, catalytic tetrabutylammonium bromide can be added. The reaction can be carried out at ambient temperature or at an elevated temperature, for example 65° C. or 85° C., depending on the reactivity of the aryl or alkyl halide.

Alternatively, step (14) may be carried out using the Ullmann ether synthesis, in which an alkali metal aryloxide of a compound of Formula LXXXV reacts with an aryl halide in the presence of copper salts, to provide a compound of Formula LXXXVI, where $R_{3b}$ is $R_{4b}$, —O—X'—$R_4$, or —O—X'—Y'—$R_4$, wherein X' is an arylene or heteroarylene. Numerous substituted and unsubstituted aryl halides are commercially available; others can be prepared using conventional methods.

Steps (15), (16), and (17) of Reaction Scheme XIV can be carried out as described for steps (9), (10), and (11) respectively of Reaction Scheme I.

Reaction Scheme XIV

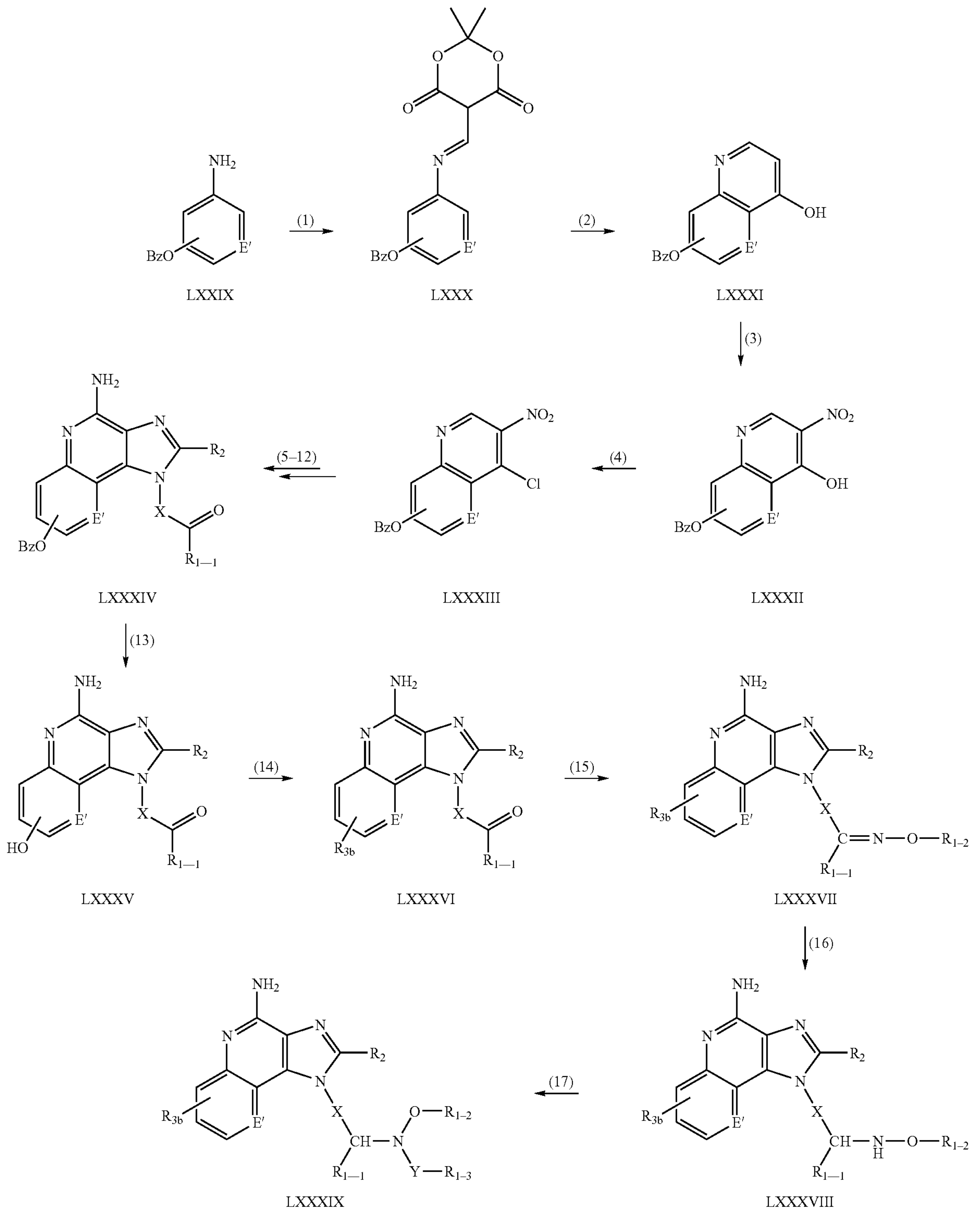

Compounds of the invention can also be prepared using variations of the synthetic routes shown in Reaction Schemes I through XI that would be apparent to one of skill in the art. For example, the synthetic route shown in Reaction Scheme X for the preparation of quinolines having a $R_{3a}$ substituent can be used to prepare [1,5]naphthyridines having a $R_{3a}$ substituent by using a bromo substituted 4-chloro-3-nitro[1,5] naphthyridine in lieu of the bromo substituted 4-chloro-3-nitroquinoline. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce and certain compounds or salts may inhibit the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Other cytokines whose production may be inhibited by the administration of compounds or salts of the invention include tumor necrosis factor-α (TNF-α). Among other effects, inhibition of TNF-α production can provide prophylaxis or therapeutic treatment of TNF-α mediated diseases in animals, making the compounds or salts useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picomavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomavirises, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, compounds or salts of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papirloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

EXAMPLES

Objects and advantages of this invention are further illustrated by the following examples, but the particular materials and amounts thereof recited in these examples, as well as other conditions and details, should not be construed to unduly limit this invention.

Example 1

N-[4-(4-Amino-2-propyl-1H-imidazo[4,5-c]-1,5-naphthyridin-1-yl)butyl]-N-methoxyacetamide

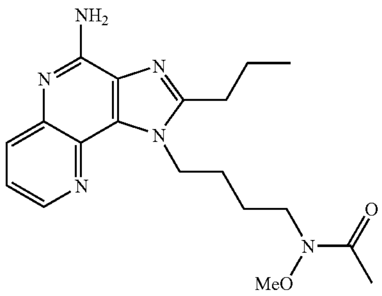 [SMILES: CCCc1nc2c(N)nc3cccnc3c2n1CCCCN(OC)C(C)=O]

Part A

Phosphorus oxychloride (38 mL, 408 mmol) was added dropwise over a period of 70 minutes to a stirred suspension of 4-hydroxy-3-nitro[1,5]naphthyridine (60 g, 313.9 mmol). The orange suspension was stirred at ambient temperature for 5 hours and then poured into ice water (1.9 L) and stirred for 30 minutes. The solid was isolated by filtration, washed with water (3×200 mL), and then dissolved in dichloromethane (1.2 L). The solution was dried over magnesium sulfate, filtered, and concentrated under reduced pressure to provide 61.1 g of 4-chloro-3-nitro[1,5]naphthyridine as an orange solid.

Part B

Triethylamine (3.9 mL, 27.9 mmol, 1.2 eq) was added to a suspension of 4-chloro-3-nitro[1,5]naphthyridine (4.87 g, 23.3 mmol, 1.0 eq) in dichloromethane (100 mL). The resulting solution was cooled to 5° C. and 4,4-diethoxybutylamine (5.36 mL, 27.9 mmol, 1.2 eq) was added dropwise over a period of 5 minutes. The reaction mixture was allowed to stir at ambient temperature for 2 hours and then diluted with saturated aqueous sodium bicarbonate (100 mL). The phases were separated and the aqueous phase was extracted with dichloromethane (2×50 mL). The combined organics were dried over magnesium sulfate, filtered, and then concentrated under reduced pressure to provide 7.93 g of (4,4-diethoxybutyl)(3-nitro[1,5]naphthyridin-4-yl)-amine as a red solid.

Part C

Catalyst (0.78 g of 5% platinum on carbon) was added to a suspension of (4,4-diethoxybutyl)(3-nitro[1,5]naphthyridin- 4-yl)amine (7.8 g, 23.3 mmol) in ethyl acetate (100 mL). The mixture was placed under hydrogen pressure ((30 psi (2.1×$10^5$ Pa)) for 2 hours. The reaction mixture was filtered through a layer of CELITE filter aid and the filter cake was rinsed with ethyl acetate (40 mL). The filtrate was concentrated under reduced pressure to provide $N^4$-(4,4-diethoxybutyl)[1,5]naphthyridine-3,4-diamine as a thick yellow oil which was carried on to the next without further purification.

Part D

Trimethyl orthobutyrate (4.8 mL, 30.3 mmol, 1.3 eq) and pyridine hydrochloride (0.14 g, 1.2 mmol, 0.05 eq) were added sequentially to $N^4$-(4,4-diethoxybutyl)[1,5]naphthyridine-3,4-diamine (7.09 g, 23.3 mmol) in toluene (90 mL) and heated to reflux for 2 hours. The reaction mixture was allowed to cool to ambient temperature and was concentrated under reduced pressure. The residue was dissolved in dichloromethane (120 mL) and washed with saturated aqueous sodium bicarbonate (100 mL). The aqueous wash was extracted with dichloromethane (2×25 mL). The combined organics were dried over magnesium sulfate, filtered, and then concentrated under reduced pressure to provide 8.83 g of $N^4$-(4,4-diethoxybutyl)-2-propyl-1H-imidazo[4,5-c][1,5]naphthyridine as an orange oil.

Part E

At ambient temperature, 6M hydrochloric acid (2 mL) was added to a solution of $N^4$-(4,4-diethoxybutyl)-2-propyl-1H-imidazo[4,5-c][1,5]naphthyridine (7.24 g, 20.3 mmol) in tetrahydrofuran (52.5 mL) and water (17.5 mL) and stirred for 1 hour. Analysis by high performance liquid chromatography (HPLC) indicated the reaction was incomplete. An additional amount of 6M hydrochloric acid (3 mL) was added to the mixture, which was stirred for an additional 2 hours. The reaction mixture was adjusted to a pH of 7 with potassium carbonate and concentrated under reduced pressure. The residue was dissolved in dichloromethane (100 mL) and brine (50 mL) and the phases were separated. The aqueous phase was extracted with dichloromethane (25 mL) and the combined organics were dried over magnesium sulfate, filtered, and concentrated under reduced pressure to afford 6.23 g of 4-(2-propyl-1H-imidazo[4,5-c][1,5]naphthyridin-1-yl)butyraldehyde as a yellow oil.

Part F

Methoxylamine hydrochloride (3.39 g, 40.6 mmol, 2 eq) and 6M sodium hydroxide solution (7.5 mL, 44.7 mmol. 2.2 eq) were added sequentially to a solution of 4-(2-propyl-1H-imidazo[4,5-c][1,5]naphthyridin-1-yl)butyraldehyde (5.73 g, 20.3 mmol, 1 eq) in methanol (80 mL) and stirred overnight. The mixture was concentrated under reduced pressure and the residue was dissolved in dichloromethane (100 mL) and water (60 mL). The pH of the mixture was adjusted to 7 and the layers were separated. The aqueous layer was extracted with dichloromethane (2×20 mL) and the combined organics were washed with brine (75 mL), dried over magnesium sulfate, filtered, and concentrated under reduced pressure to afford 6.45 g of 4-(2-propyl-1H-imidazo[4,5-c][1,5]naphthyridin-1-yl)butyraldehyde O-methyloxime as an orange oil with an E/Z ratio of 77:23. The material was used in subsequent steps without any further purification.

Part G

3-Chloroperoxybenzoic acid (3.43 g of 70%, 19.9 mmol, 2.0 eq) was added to a solution of 4-(2-propyl-1H-imidazo[4,5-c][1,5]naphthyridin-1-yl)butyraldehyde O-methyloxime (3.1 g, 9.96 mmol, 1.0 eq) in chloroform (45 mL). The reaction was stirred at ambient temperature for one hour. Analysis by thin layer chromatography indicated that the reaction was incomplete so additional 3-chloroperoxybenzoic acid (0.70 g) was added. After one additional hour of string, ammonium hydroxide (12 mL of 15M) and p-toluenesulfonyl chloride (2.1 g, 11 mmol, 1.1 eq) were added dropwise. The reaction mixture was stirred for an additional hour, filtered to remove the resulting white solid, and diluted with dichloromethane (60 mL) and saturated aqueous sodium bicarbonate (75 mL). The phases were separated and the aqueous phase was extracted with dichloromethane (2×20 mL). The combined organics were dried over magnesium sulfate, filtered, and then concentrated under reduced pressure to provide a dark orange oil. The material was triturated with acetonitrile to afford 0.94 g of 4-(4-amino-2-propyl-1H-imidazo[4,5-c][1,5]naphthyridin-1-yl)butyraldehyde O-methyloxime as a tan solid material. The filtrate from the trituration was purified by BIOTAGE HORIZON High-Performance Flash Chromatography (HPFC) instrument (eluting with chloroform/methanol/ammonium hydroxide (CMA) (80/18/2):chloroform ranging in ratios from 0:100 to 25:75) to provide an additional 0.84 g of product.

Part H

Sodium cyanoborohydride (0.54 g, 8.64 mmol, 3 eq) and acetic acid (7 mL) were added to a solution of 4-(4-amino-2-propyl-1H-imidazo[4,5-c][1,5]naphthyridin-1-yl)butyraldehyde O-methyloxime (0.94 g, 2.88 mmol, 1 eq) in methanol (7 mL) and stirred at ambient temperature for 20 minutes. The reaction mixture was concentrated under reduced pressure and diluted with dichloromethane (60 mL) and saturated aqueous sodium bicarbonate (40 mL). The phases were separated and the aqueous phase was adjusted to pH ~8 with solid sodium bicarbonate and extracted with dichloromethane (2×20 mL). The combined organics were dried over magnesium sulfate, filtered, and then concentrated under reduced pressure to provide 1.01 g of 1-[4-(methoxyamino)butyl]-2-propyl-1H-imidazo[4,5-c]-1,5-naphthyridin-4-amine as a yellow solid.

Part I

Triethylamine (0.24 mL, 1.69 mmol, 1.2 eq) was added to 1-[4-(methoxyamino)butyl]-2-propyl-1H-imidazo[4,5-c]-1,5-naphthyridin-4-amine (0.46 g, 1.41 mmol, 1.0 eq) in dichloromethane (6 mL) and cooled to 0° C. Acetic anhydride (0.13 mL, 1.41 mmol, 1.0 eq) was added dropwise and the reaction mixture was stirred for 1 hour. The reaction was then diluted with dichloromethane (40 mL) and saturated aqueous sodium bicarbonate (30 mL). The phases were separated and the aqueous phase was extracted with dichloromethane (20 mL). The combined organics were dried over magnesium sulfate, filtered, and concentrated to afford a yellow solid, which was purified by HPFC (silica gel eluting with 0-25% CMA in chloroform) to afford 0.49 g of a pale yellow substance. The material was dissolved in acetonitrile (10 mL), sonicated for 2 minutes, filtered, and dried under vacuum at 100° C. for 24 hours to afford 0.278 g of N-[4-(4-amino-2-propyl-1H-imidazo[4,5-c][1,5]naphthyridin-1-yl)butyl]-N-methoxyacetamide as off-white needles, mp 155-156° C. Anal. calcd for $C_{19}H_{26}N_6O_2$: C, 61.60; H, 7.07; N, 22.69. Found: C, 61.58; H, 7.31; N, 22.64.

Example 2

N-[4-(4-Amino-2-propyl-1H-imidazo[4,5-c][1,5]naphthyridin-1-yl)butyl]-N-methoxybenzamide

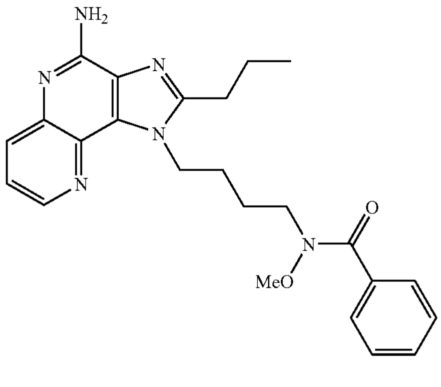 [SMILES: CCCc1nc2c(N)nc3cccnc3c2n1CCCCN(OC)C(=O)c1ccccc1]

Triethylamine (0.32 mL, 2.29 mmol, 1.2 eq) was added to a solution of 1-[4-(methoxyamino)butyl]-2-propyl-1H-imidazo[4,5-c]-1,5-naphthyridin-4-amine (0.626 g, 1.91 mmol, 1.0 eq), prepared as described in Parts A-H of Example 1, in dichloromethane (10 mL) and cooled to −8° C. Benzoyl chloride (0.22 mL, 1.91 mmol, 1.0 eq) was added dropwise and the reaction mixture was stirred for 2 hours. The reaction was then diluted with dichloromethane (80 mL) and saturated aqueous sodium bicarbonate (40 mL). The phases were separated and the aqueous phase was extracted with dichloromethane (30 mL). The combined organics were dried over magnesium sulfate, filtered, concentrated, and purified by HPFC (silica gel eluting with 0-25% CMA in chloroform) to afford 0.47 g of a pale yellow substance. The material was dissolved in acetonitrile, sonicated, filtered, and dried under vacuum at 100° C. for 24 hours to afford 0.225 g of N-[4-(4-amino-2-propyl-1H-imidazo[4,5-c][1,5]naphthyridin-1-yl)butyl]-N-methoxybenzamide as off-white needles, mp 125-127° C. Anal. calcd for $C_{24}H_{28}N_6O_2$: C, 66.65; H, 6.53; N, 19.43. Found: C, 66.43; H, 6.47; N, 19.60.

Example 3

N-[4-(4-Amino-2-propyl-1H-imidazo[4,5-c][1,5]naphthyridin-1-yl)butyl]-N'-isopropyl-N-methoxyurea

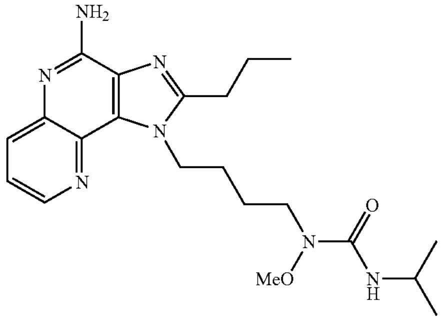 [SMILES: CCCc1nc2c(N)nc3cccnc3c2n1CCCCN(OC)C(=O)NC(C)C]

The general method of Example 2 was followed using isopropyl isocyanate (0.23 mL, 2.38 mmol, 1 eq) in lieu of benzoyl chloride. The reaction was allowed to slowly warm to 10° C. over 3 hours. Purification after HPFC by recrystallization from acetonitrile and subsequent drying at 100° C. under high vacuum afforded 0.504 g of N-[4-(4-amino-2-propyl-1H-imidazo[4,5-c][1,5]naphthyridin-1-yl)butyl]-N'-isopropyl-N-methoxyurea as an off-white powder, mp 161-162° C. Anal. calcd for $C_{21}H_{31}N_7O_2$: C, 61.00; H, 7.56; N, 23.71. Found: C, 60.82; H, 7.78; N, 24.00.

Example 4

5-(4-Amino-2-butyl-1H-imidazo[4,5-c][1,5]naphthyridin-1-yl)-pentan-2-one O-methyloxine

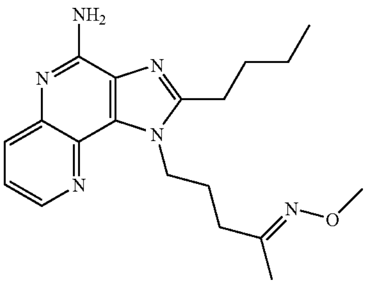 [SMILES: CCCCc1nc2c(N)nc3cccnc3c2n1CCC/C(C)=N/OC]

Part A

The preparation of 4-chloro-3-nitro[1,5]naphthyridine is described in Part A of Example 1. Ethyl 4-aminobutyrate hydrochloride (9.6 g, 57.3 mmol, 1.2 eq) was added to a suspension of 4-chloro-3-nitro[1,5]naphthyridine (10.0 g, 47.7 mmol, 1.0 eq) in dichloromethane (200 mL) and stirred at 5° C. Triethylamine (16.6 mL, 119.3 mmol, 2.5 eq) was added and the reaction mixture was stirred for 2 hours and allowed to warm to ambient temperature. The mixture was diluted with dichloromethane (200 mL) and washed with saturated aqueous sodium bicarbonate (2×150 mL). The phases were separated and the combined aqueous layers were extracted with chloroform (100 mL). The combined organics were dried over magnesium sulfate, filtered, and concentrated under reduced pressure to afford 14.5 g of ethyl 4-[(3-nitro[1,5]naphthyridinyl)amino]butyrate as a yellow solid.

Part B

Ethyl 4-[(3-nitro[1,5]naphthyridin-yl)amino]butyrate (8.47 g, 27.8 mmol, 1 eq) was combined in a pressure vessel with catalyst (0.85 g of 5% platinum on carbon), and ethyl acetate (140 mL). The reaction mixture was placed under hydrogen pressure ((30 psi, ($2.1\times10^5$ Pa)) for 3 hours. The reaction mixture was filtered through a layer of CELITE filter aid and the filter cake was washed with ethyl acetate (80 mL). The filtrate was concentrated under reduced pressure to provide ethyl 4-[(3-amino[1,5]naphthyridin-4-yl)amino]butyrate as a thick, yellow oil.

Part C

Valeryl chloride (1.8 mL, 15.3 mmol, 1.1 eq) was added dropwise to a solution of ethyl 4-[(3-amino[1,5]naphthyridin-4-yl)amino]butyrate (3.8 g, 13.9 mmol, 1 eq) in dichloromethane (55 mL) and stirred for one hour. The reaction mixture was concentrated under reduced pressure and was dissolved in pyridine (55 mL). Pyridine hydrochloride (0.16 g, 1.39 mmol, 0.1 eq) was added and the reaction mixture was heated to reflux for 18 hours. The reaction mixture was concentrated under reduced pressure and diluted with dichloromethane (100 mL) and saturated aqueous sodium bicarbonate (75 mL). The phases were separated and the aqueous phase was extracted with dichloromethane (2×30 mL). The combined organics were dried over magnesium sulfate, stirred over decolorizing charcoal, filtered through CELITE filter aid, concentrated under reduced pressure, and dried at 35° C. under high vacuum to afford 4.18 g of ethyl 4-(2-butyl-1H-imidazo[4,5-c][1,5]naphthyridin-1-yl)butyrate as a brown solid.

Part D

Aqueous sodium hydroxide (6M, 4 mL, 24 mmol, 2 eq) was added to a solution of ethyl 4-(2-butyl-1H-imidazo[4,5-c][1,5]naphthyridin-1-yl)butyrate (4.1 g, 12.0 mmol, 1.0 eq) in ethanol (50 mL) and stirred overnight at ambient temperature. The reaction mixture was concentrated under reduced pressure, dissolved in water (15 mL) and adjusted to a pH of 4. The precipitate was filtered and dried at 65° C. under vacuum to afford 3.53 g of 4-(2-butyl-1H-imidazo[4,5-c][1,5]naphthyridin-1-yl)butyric acid as a tan powder.

Part E

One drop of N,N-dimethylformamide (DMF) was added to a solution of 4-(2-butyl-1H-imidazo[4,5-c][1,5]naphthyridin-1-yl)butyric acid (3.53 g, 11.3 mmol, 1.0 eq) in dichloromethane (55 mL). Oxalyl chloride (3.0 mL, 33.9 mmol, 3.0 eq) was added dropwise over 5 minutes to the reaction mixture, which was subsequently stirred for 2 hours at ambient temperature. The mixture was concentrated under reduced pressure to provide 4-(2-butyl-1H-imidazo[4,5-c][1,5]naphthyridin-1-yl)butyryl chloride.

Part F

The material from Part E (1.0 eq) was dissolved in dichloromethane (55 mL) and cooled to 0° C. N,O-Dimethylhydroxylamine hydrochloride (1.65 g, 16.95 mmol, 1.5 eq) and triethylamine (4.7 mL, 33.9 mmol, 3 eq) were added sequentially to the reaction mixture. The reaction mixture was allowed to warm to ambient temperature and stirred for 3 hours, upon which time the mixture was diluted with dichloromethane (30 mL) and saturated aqueous sodium bicarbonate (50 mL). The aqueous layer was extracted with dichloromethane (25 mL) and the combined organic layers were dried over magnesium sulfate, filtered, and concentrated under reduced pressure to afford 4.58 g of 4-(4-amino-2-butyl-1H-imidazo[4,5-c][1,5]naphthyridin-1-yl)-N-methoxy-N-methylbutanamide as a brown oil.

Part G

Methylmagnesium iodide (3M solution in tetrahydrofuran, 5.6 mL, 16.9 mmol, 1.5 eq) was added dropwise over 10 minutes to a chilled (0°) solution of 4-(4-amino-2-butyl-1H-imidazo[4,5-c][1,5]naphthyridin-1-yl)-N-methoxy-N-methylbutanamide (4.0 g, 11.25 mmol, 1 eq) in tetrahydrofuran (THF) (50 mL). The reaction mixture was stirred at ambient temperature for 4 hours, quenched with 1 M hydrochloric acid, and concentrated under reduced pressure. The residue was diluted with dichloromethane (75 mL) and saturated aqueous sodium bicarbonate (50 mL). The aqueous layer was extracted with dichloromethane (2×30 mL) and the combined organic layers were dried over magnesium sulfate, filtered, and concentrated under reduced pressure to produce 3.12 g of 5-(2-butyl-1H-imidazo[4,5-c][1,5]naphthyridin-1-yl)pentan-2-one as a tan solid.

Part H

3-Chloroperoxybenzoic acid (70% pure, 5.46 g, 22.16 mmol) (mCPBA) was added to a solution of 5-(2-butyl-1H-imidazo[4,5-c][1,5]naphthyridin-1-yl)pentan-2-one (3.44 g, 11.08 mmol, 1 eq) in chloroform (45 mL), and the reaction was stirred for one hour at ambient temperature and then cooled to 5° C. Ammonium hydroxide (10 mL) and p-toluenesulfonyl chloride (2.32 g, 12.19 mmol, 1.1 eq) were sequentially added and the reaction mixture was stirred at 5-10° C. for 1 hour, filtered, and then diluted with dichloromethane (100 mL) and saturated aqueous sodium bicarbonate (75 mL). The aqueous layer was extracted with dichloromethane (2×30 mL) and the combined organic solutions were dried over magnesium sulfate, filtered, and concentrated under reduced pressure to provide a brown oil. The material was triturated with acetonitrile to afford 1.65 g of 5-(4-amino-2-butyl-1H-imidazo[4,5-c][1,5]naphthyridin-1-yl)pentan-2-one. The filtrate from the trituration was purified by BIOTAGE HORIZON High-Performance Flash Chromatography (HPFC) instrument (eluting with chloroform/methanol/ammonium hydroxide (CMA) (80/18/2):chloroform ranging in ratios from 0:100 to 25:75) and subjected to trituration again in acetonitrile to produce an additional 0.240 g of material as an off-white powder, mp 168-169° C. Anal. calcd for $C_{18}H_{23}N_5O$: C, 66.44; H, 7.12; N, 21.52. Found: C, 66.19; H, 7.08; N, 21.22.

Part I

Methoxylamine hydrochloride (0.59 g, 21 mmol, 1.5 eq) was added to a solution of 5-(4-amino-2-butyl-1H-imidazo[4,5-c][1,5]naphthyridin-1-yl)pentan-2-one (1.54 g, 4.73 mmol, 1 eq) in methanol (20 mL) and stirred overnight. The mixture was concentrated under reduced pressure and the residue was dissolved in dichloromethane (100 mL) and saturated aqueous sodium bicarbonate (75 mL). The aqueous layer was extracted with dichloromethane (2×25 mL) and the combined organic layers were dried over magnesium sulfate, filtered, and concentrated under reduced pressure to afford a yellow solid. The material was subjected to HPFC (silica gel, eluting with 0-25% CMA in chloroform), triturated with hot acetonitrile, filtered, and dried at 100° C. under vacuum for 24 hours to afford 1.66 g of 5-(4-amino-2-butyl-1H-imidazo[4,5-c][1,5]naphthyridin-1-yl)pentan-2-one O-methyloxime as a white powder with an E/Z ratio of 80:20, mp 132-134° C. Anal. calcd for $C_{19}H_{26}N_6O$: C, 64.38; H, 7.39; N, 23.71. Found: C, 64.19; H, 7.42; N, 23.76.

Example 5

5-(4-Amino-6,7-dimethyl-2-propyl-1H-imidazo[4,5-c]pyridine-1-yl)pentan-2-one O-methyloxime

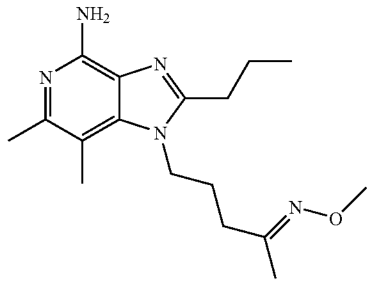

Part A 2,4-Dichloro-5,6-dimethyl-3-nitropyridine (135.0 g, 0.488 mol) and ethyl 4-aminobutyrate hydrochloride (114.0 g, 0.683 mol) were triturated in N,N-dimethylformamide (675 mL) (DMF) at 0° C. Triethylamine (272.6 mL, 1.95 mol) was added to generate a brown slurry. After 15 minutes, the reaction mixture was allowed to warm to ambient temperature and the reaction was stirred overnight. Analysis by $^1$H NMR indicated the reaction was incomplete. An additional amount of triethylamine (102.2 mL, 0.73 mol) and ethyl 4-aminobutyrate hydrochloride (35.28 g, 0.159 mol) in DMF (200 mL) were added to the reaction mixture and allowed to stir over an additional 24 hours. The incomplete reaction mixture was separated into 2 equal sized aliquots. Each aliquot was combined with water (3 L) and stirred for 1 hour. The resulting precipitate in each flask was harvested by filtration and dried under reduced pressure. The crude product was recrystallized from ethyl acetate and filtered to yield 86.20 g of ethyl 4-[(2-chloro-5,6-dimethyl-3-nitropyridin-4-yl)amino]butyrate as a yellow granular solid.

Part B

Ethyl 4-[(2-chloro-5,6-dimethyl-3-nitropyridin-4-yl)amino]butyrate (86.2 g, 0.276 mol), sodium azide (35.49 g, 0.552 mol), and cerium chloride heptahydrate (50.86 g, 0.138 mol) were triturated in a 9:1 mixture of acetonitrile:water (1012 mL). The reaction mixture was stirred and heated to reflux for 18 hours. The reaction was filtered while still hot and the yellow filtrate was concentrated under reduced pressure to yield 90.94 g of crude product. The material was triturated at 95° C. with 360 mL ethyl acetate and filtered. The filtrate produced pale yellow crystals at ambient temperature to afford 64.3 g of ethyl 4-[(5,6-dimethyl-8-nitrotetrazolo[1,5-a]pyridin-7-yl)amino]butyrate as a yellow solid.

Part C

Ethyl 4-[(5,6-dimethyl-8-nitrotetrazolo[1,5-a]pyridin-7-yl)amino]butyrate (64.3 g, 0.198 mol) was mixed with acetonitrile (2 L), and catalytic 10% palladium on carbon was added. The mixture was placed on a hydrogenator for 72 hours and filtered through a layer of CELITE filter aid. The filtrate was concentrated under reduced pressure to yield 58.2 g of ethyl 4-[(8-amino-5,6-dimethyltetrazolo[1,5-a]pyridin-7-yl)amino]butyrate.

Part D

Pyridinium chloride (8.57 g, 74 mmol) and ortho-n-butyric acid trimethyl ester (34.6 mL, 217 mmol) were sequentially added to ethyl 4-[(8-amino-5,6-dimethyltetrazolo[1,5-a]pyridin-7-yl)amino]butyrate (58.2 g, 198 mmol) triturated in toluene (1165 mL) and heated to reflux for 0.5 hour. The reaction mixture was concentrated under reduced pressure and partitioned between dichloromethane and saturated aqueous sodium bicarbonate. The organic layer was isolated, concentrated under reduced pressure, and 70.51 g of ethyl 4-(5,6-dimethyl-8-propyl-1H-imidazo[4,5-c]tetrazolo[1,5-a]pyridin-7-yl)butyrate solid was recrystallized from ethyl acetate and used without additional purification.

Part E

Ethyl 4-(5,6-dimethyl-8-propyl-1H-imidazo[4,5-c]tetrazolo[1,5-a]pyridin-7-yl)butyrate (52.99 g, 0.153 mol) was slurried in ethanol (550 mL) and treated with a 50% sodium hydroxide solution for 0.5 hour. The reaction was concentrated under reduced pressure, maintained overnight, and dissolved in water (250 mL). The pH was adjusted to 5 using concentrated hydrochloric acid and the resulting white precipitate was filtered. The residue was triturated at ambient temperature with methanol (1 L) and concentrated under reduced pressure to afford 4-(5,6-dimethyl-8-propyl-1H-imidazo[4,5-c]tetrazolo[1,5-a]pyridin-7-yl)butyric acid which was used without any further purification.

Part F

Five drops of N,N-dimethylformamide (DMF) were added to 4-(5,6-dimethyl-8-propyl-1H-imidazo[4,5-c]tetrazolo[1,5-a]pyridin-7-yl)butyric acid (36.22 g, 113.8 mmol) and dichloromethane (725 mL). Oxalyl chloride (29.8 mL, 341.3 mmol) was added dropwise to the reaction mixture. After 10 minutes, the reaction mixture was concentrated under reduced pressure to afford 4-(5,6-dimethyl-8-propyl-1H-imidazo[4,5-c]tetrazolo[1,5-a]pyridin-7-yl)butyryl chloride.

Part G 4-(5,6-Dimethyl-8-propyl-1H-imidazo[4,5-c]tetrazolo[1,5-a]pyridin-7-yl)butyryl chloride (38.39 g, 114 mmol) was triturated with chloroform (768 mL) and cooled to 0° C. N,O-Dimethylhydroxylamine hydrochloride (16.68 g, 171 mmol) and triethylanmine (47.7 mL, 342 mmol, dropwise addition) were sequentially added to the reaction mixture and stirred for 0.5 hour. The reaction mixture was stirred for 10 additional minutes after addition of saturated aqueous sodium bicarbonate solution (400 mL). The organic phase was isolated, dried over sodium sulfate, and concentrated under reduced pressure to afford 40.04 g of 4-(5,6-dimethyl-8-propyl-1H-imidazo[4,5-c]tetrazolo[1,5-a]pyridin-7-yl)-N-methoxy-N-methylbutyramide as a yellow oil.

Part H

Methylmagnesium iodide (5.5 mL, 41.5 mmol) was added slowly dropwise to a triturated mixture of 4-(5,6-dimethyl-8-propyl-1H-imidazo[4,5-c]tetrazolo[1,5-a]pyridin-7-yl)-N-methoxy-N-methylbutyramide (10.0 g, 27.7 mmol) and tetrahydrofuran (125 mL) at 0° C. The reaction was warmed to ambient temperature and $^1$H NMR indicated the reaction was incomplete after stirring overnight. An additional amount of methyl magnesium iodide (5.5 mL, 41.5 mmol) was added at 18 and 21.75 hours after the initial addition. A final addition of methyl magnesium iodide (3.6 mL, 27 mmol) was added at 23 hours after the initial addition and allowed to react for one additional hour. Addition of 1N aqueous hydrogen chloride solution (35 mL) followed to generate a yellow-orange slurry and the mixture was concentrated under reduced pressure. The residue was dissolved in dichloromethane (200 mL), washed with saturated aqueous sodium bicarbonate (100 mL), dried over sodium sulfate and concentrated under reduced pressure to afford 8.15 g of 5-(5,6-dimethyl-8-propyl-1H-imidazo[4,5-c]tetrazolo[1,5-a]pyridin-7-yl)pentan-2-one without any further purification.

Part I

Triphenylphosphine (13.5 g, 51.5 mmol) was added to a mixture of 5-(5,6-dimethyl-8-propyl-1H-imidazo[4,5-c]tetrazolo[1,5-a]pyridin-7-yl)pentan-2-one (8.15 g, 25.8 mmol) and 1,2-dichlorobenzene (163 mL) and heated to 133° C. for 13.5 hours. The reaction temperature was incrementally increased to 140° C. over an additional 1.5 hours. Additional triphenylphosphine (3.39 g, 12.9 mmol) was then added and the reaction was heated for one additional hour. The resulting dark brown solution was cooled to ambient temperature and concentrated under reduced pressure. The resulting residue was dissolved in methanol (150 mL) and 1 N aqueous hydrochloric acid (75 mL) was added to create a slurry. The reaction was stirred at 40° C. for an hour, upon which the resulting mixture was filtered, concentrated under reduced pressure, dissolved in dichlorometlane (100 mL) and washed with 1 N aqueous hydrochloric acid. The aqueous layer was adjusted to pH 14 with saturated aqueous sodium bicarbonate and 50% sodium hydroxide solutions and the product was extracted into chloroform (250 mL). The organic layer was dried with sodium sulfate and concentrated under reduced pressure to produce 4.61 g of a brown solid material. The material was recrystallized from acetonitrile to yield 2.53 g of isolated material. A portion of the material (1.22 g) was purified by column chromatography on a BIOTAGE HORIZON High-Performance Flash Chromatography instrument (eluting with chloroform/methanol/ammonium hydroxide (80/18/2):chloroform ranging in ratios from 0:100 to 40:60) and dried overnight at 70° C. to provide 0.81 g of 5-(4-amino-6,7-dimethyl-2-propyl-1H-imidazo[4,5-c]pyridin-1-yl)pentan-2-one as an off-white powder, mp 148.5-149.5° C. $^1$H NMR (300 MHz, DMSO-$d_6$) δ 5.58 (s, 2H), 4.16 (t, J=8.1 Hz, 2H), 2.77 (t, J=8.1 Hz, 2H), 2.58 (t, J=6.9 Hz, 2H), 2.37 (s, 3H), 2.30 (s, 3H), 2.10 (s, 3H), 1.80 (m, J=7.5 Hz, 4H), 1.00 (t, J=7.5 Hz, 3H; MS (APCI) m/z 289 $(M+H)^+$; Anal. calcd for $C_{20}H_{26}N_6O_2$: C, 66.64; H, 8.39; N, 19.43. Found: C, 66.40; H, 8.63; N, 19.44.

Part J

Methoxylamine hydrochloride (0.57 g, 6.8 mmol) was added to a solution of 5-(4-amino-6,7-dimethyl-2-propyl-1H-imidazo[4,5-c]pyridine-1-yl)pentan-2-one (1.31 g, 4.5 mmol) in methanol (30 mL) and stirred for 15 minutes. The reaction mixture was concentrated under reduced pressure, dissolved in dichloromethane (150 mL), washed with saturated aqueous sodium bicarbonate, dried over sodium sulfate and concentrated under reduced pressure to afford 1.33 g of crude material. The crude material was purified by HPFC (silca gel, CMA 0-40% in chloroform) and dried overnight at 70° C. at 28 psi ($1.9\times10^5$ Pa) to afford 0.75 g of 5-(4-amino-6,7-dimethyl-2-propyl-1H-imidazo[4,5-c]pyridine-1-yl)pentan-2-one O-methyloxime as an off-white powder, mp 144.0-145.5° C. $^1$H NMR (300 MHz, DMSO-$d_6$) δ 5.58 (s, 2H), 4.23 (t, J=8.1 Hz, 2H), 3.74 (s, H), 3.71 (s, H), 2.77 (t, J=7.5 Hz, 2H), 2.36 (s, 3H), 2.30 (s, 3H), 2.25 (t, J=7.5 Hz, 2H), 1.80 (m, J=7.5 Hz, 8H), 1.00 (t, J=6.9 Hz, 3H; MS (APCI) m/z 318 $(M+H)^+$; Anal. calcd for $C_{20}H_{26}N_6O_2$: C, 64.32; H, 8.57; N, 22.06. Found: C, 64.19; H, 8.86; N, 22.32.

Example 6

N-[4-(4-Amino-2-propyl-1H-imidazo[4,5-c]quinolin-1-yl)butyl]-N-methoxyacetamide

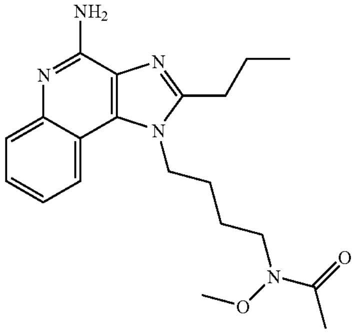 [SMILES: CCCc1nc2c(N)nc3ccccc3c2n1CCCCN(OC)C(C)=O]

Part A

Triethylamine (26.1 mL, 0.187 mmol) was added to a slurry of 4-chloro-3-nitro-quinoline (21.0 g, 0.1 mol) and dichloromethane (100 mL). Aminobutyraldehyde diethylacetal (20.0 g, 0.112 mmol) in dichloromethane (25 mL) was added dropwise over 15 minutes to the reaction mixture, which was then stirred overnight at ambient temperature. The mixture was diluted with dichloromethane (100 mL) and washed with water (2×50 mL). Water (250 mL), sodium dithionate (61.5 g, 300 mmol), ethyl viologen dibromide (0.250 g, 0.67 mmol), and potassium carbonate (55.3 g, 400 mmol) were added to the crude reaction mixture and stirred overnight. Air was bubbled through the blue mixture for 20 minutes and then the reaction mixture was diluted with dichloromethane (100 mL) and water (100 mL). The layers were separated and the organic layer was washed with water (2×100 mL), diluted with methanol, dried over potassium carbonate, filtered, and concentrated under reduced pressure to afford 29.9 g of $N^4$-(4,4-diethoxybutyl)quinoline-2,4 diamine as a brown oil.

Part B

Trimethyl orthobutyrate (17.8 g, 120 mmol) was added to a mixture of $N^4$-(4,4-diethoxybutyl)quinoline-2,4 diamine (29.9 g, 99 mmol) and pyridinium tosylate (0.20 g) in toluene (350 mL) and heated to reflux overnight under a Dean-Stark trap. Analysis by LCMS indicated the reaction was incomplete, so additional trimethyl orthobutyrate (5 g) and pyridinium tosylate (0.20 g) were added to the reaction mixture and it was refluxed for an additional hour. The reaction mixture was cooled to ambient temperature and stirred overnight. The reaction mixture was concentrated under reduced pressure, diluted with dichloromethane (200 mL), washed with saturated aqueous sodium carbonate, filtered, and concentrated under reduced pressure to afford 35.2 g of crude material. The material was purified by flash column chromatography on silica gel (eluting with 0-7% methanol in dichloromethane) to afford 29.8 g of 1-(4,4-diethoxybutyl)-2-propyl-1H-imidazo[4,5-c]quinoline.

Part C 1-(4,4-diethoxybutyl)-2-propyl-1H-imidazo[4,5-c]quinoline (25.3 g, 71.2 mmol) was added to a solution of concentrated hydrochloric acid (35 mL) and water (35 mL) cooled to 0° C. and the reaction mixture was allowed to warm to ambient temperature and was stirred for 30 minutes. The reaction mixture was diluted with water (100 mL) and dichloromethane (200 mL) and the pH of the reaction mixture was slowly made basic with addition of potassium carbonate. The aqueous and organic layers were separated and the organic layer was dried over potassium carbonate, filtered, and concentrated to afford 22.7 g of 4-(2-propyl-1H-imidazo[4,5-c]quinolin-1-yl)butyraldehyde.

Part D

Methoxylamine hydrochloride (3.37 g, 40.3 mmol) was added to a stirred solution of 4-(2-propyl-1H-imidazo[4,5-c]quinolin-1-yl)butyraldehyde (10.0 g, 35.5 mmol) in ethanol (100 mL) cooled to 0° C., followed by addition of 50% sodium hydroxide solution (12.5 M, 3.2 mL, 40 mmol) in water (7 mL). The reaction mixture was allowed to warm to ambient temperature and stirred for 3 days. The reaction mixture was then concentrated under reduce pressure and diluted with dichloromethane (150 mL) and water (50 mL). The layers were separated and the aqueous layer was extracted with dichloromethane (50 mL). The combined organics were dried over potassium carbonate, filtered and concentrated to afford 11.6 g of 4-(2-propyl-1H-imidazo[4,5-c]quinolin-1-yl)-butyraldehyde O-methyloxime as a reddish oil.

Part E

Sodium cyanoborohydride (0.22 g, 3.5 mmol) and acetic acid (2 mL) were added to 4-(2-propyl-1H-imidazo[4,5-c]quinolin-1-yl)butyraldehyde O-methyloxime in ethanol (6 mL) and stirred for 2 hours. The pH of the reaction mixture was made basic with potassium carbonate and the reaction mixture was diluted with water (5 mL) and dichloromethane (50 mL). The layers were separated, and the organic layer was dried over potassium carbonate, filtered, and concentrated under reduced pressure to afford 0.62 g of crude material with a small amount of ethanol present. Silica gel (1 g) was added to the crude material and the mixture was heated for 2.5 hours at 100° C. The mixture was cooled and the material was filtered with a 1:1 mixture of dichloromethane and methanol. The filtrate was concentrated under reduced pressure to afford 0.35 g of O-methyl-N-[4-(2-propyl-1H-imidazo[4,5-c]quinolin-1-yl)butyl]hydroxylamine as an oil.

Part F

Triethylamine (0.167 mL, 1.2 mmol) was added to O-methyl-N-[4-(2-propyl-1H-imidazo[4,5-c]quinolin-1-yl)butyl]hydroxylamine (0.32 g, 1.0 mmol) in dichloromethane (10 mL) and cooled to 0° C. Acetic anhydride (0.103 mL, 1.1 mmol) was added dropwise and the reaction mixture was stirred for 6 hours. The reaction was then diluted with dichloromethane (40 mL) and saturated aqueous sodium bicarbonate (10 mL) and stirred overnight. The phases were separated and the aqueous phase was extracted with dichloromethane (50 mL). The combined organics were dried over potassium carbonate, filtered, and concentrated to afford 0.35 g of N-methoxy-N-[4-(2-propy-1H-imidazo[4,5-c]quinolin-1-yl)butyl]acetamide.

Part G

3-Chloroperoxybenzoic acid (77% pure, 0.44 g, 1.95 mmol) (mCPBA) was added to a solution of N-methoxy-N-[4(2-propyl-1H-imidazo[4,5-c]quinolin-1-yl)butyl]acetamide (1.0 mmol) in dichloromethane (25 mL) cooled to 0° C. and stirred for 10 minutes, and then the reaction was stirred for one hour at ambient temperature. Concentrated ammonium hydroxide (10 mL) and phenylsulfonyl chloride (0.22 mL, 1.75 mmol) were sequentially added and the reaction mixture was stirred for 1 hour and then diluted with dichloromethane (50 mL) and saturated aqueous sodium bicarbonate solution (2×50 mL) containing 5% sodium hydroxide (5 mL). The layers were separated and the aqueous layer was extracted with dichloromethane (2×25 mL) and the combined organic solutions were dried over potassium carbonate, filtered, and concentrated under reduced pressure to provide a brown oil. The material was purified by flash column chromatography on silica gel (eluting with 5% methanol and concentrated ammonium hydroxide (2 mL) in dichloromethane). The resulting crystalline solid was recrystallized twice from acetonitrile and water and dried overnight under vacuum at 70° C. to afford 0.26 g of N-[4-(4-amino-2-propyl-1H-imidazo[4,5-c]quinolin-1-yl)butyl]-N-methoxyacetamide as light yellow needles, mp 138-140° C. MS (APCI) m/z 370 ($M+H^+$); Anal. calcd for $C_{20}H_{27}N_5O_2$: C, 65.02; H, 7.37; N, 18.96. Found: C, 64.97; H, 7.04; N, 18.80.

Example 7

1-[4-(4-Amino-2-propyl-1H-imidazo[4,5-c]quinolin-1-yl)butyl]-1-methoxyurea

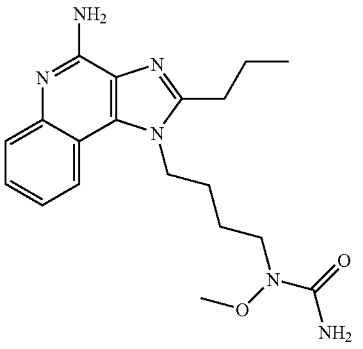 [SMILES: CCCc1nc2c(N)nc3ccccc3c2n1CCCCN(OC)C(N)=O]

Part A

The general method of Part G of Example 6 was followed using 4-(2-propyl-1H-imidazo[4,5-c]quinolin-1-yl)butyraldehyde O-methyloxime (17.5 g, 56.5 mmol), prepared as described in Parts A-D of Example 6, in lieu of N-methoxy-N-[4-(2-propyl-1H-imidazo[4,5-c]quinolin-1-yl)butyl]acetamide. Purification by flash column chromatography on silica gel afforded 11.4 g of 4-(4-amino-2-propyl-1H-imidazo[4,5-c]quinolin-1-yl)butyraldehyde O-methyloxime.

Part B

Sodium cyanoborohydride (5.40 g, 86 mmol) was added to a mixture of 4-(4-amino-2-propyl-1H-imidazo[4,5-c]quinolin-1-yl)butyraldehyde O-methyloxime (5.60 g, 17.2 mmol), acetic acid (30 mL), and ethanol (75 mL) and stirred for 1 hour. The reaction mixture was cooled to 0° C. and the pH was adjusted to 8 with 25% sodium hydroxide solution. The reaction mixture was then concentrated under reduced pressure and diluted with dichloromethane (200 mL) and saturated aqueous sodium bicarbonate solution (75 mL). The layers were separated and the aqueous layer was extracted with dichloromethane (2×75 mL). The combined organics were washed with water (2×50 mL), dried over potassium carbonate, filtered, and concentrated under reduced pressure to afford 5.2 g of N-[4-(4-amino-2-propyl-1H-imidazo[4,5-c]quinolin-1-yl)butyl]-O-methyl-hydroxylamine as a light brown solid.

Part C

Trimethylsilyl isocyanate (0.250 mL, 1.85 mmol) was added dropwise to a solution of N-[4-(4-amino-2-propyl-1H-imidazo[4,5-c]quinolin-1-yl)butyl]-O-methyl-hydroxylamine in dichloromethane (10 mL) cooled to −16° C. The reaction temperature was cooled to −20° C. over 10 minutes. After stirring for 1.5 hours, the reaction was warmed to 0° C. and stirred for an additional hour. A drop of 1,8-diazabicyclo[5.4.0]undec-7-ene (DBU) (0.250 mL, 1.85 mmol) was added to the reaction mixture and stirred for 3 days. The reaction mixture was diluted with dichloromethane (50 mL) and saturated aqueous sodium bicarbonate and stirred for 30 minutes. The layers were separated, and the organic layer was dried over potassium carbonate, filtered, and concentrated under reduced pressure to afford 0.82 g of 1-[4-(4-amino-2-propyl-1H-imidazo[4,5-c]quinolin-1-yl)butyl]-1-methoxyurea as off-white crystals, mp 179-181° C. MS (APCI) m/z 371 ($M+H^+$); Anal. calcd for $C_{19}H_{26}N_6O_2$: C, 61.36; H, 7.09; N, 22.60. Found: C, 61.08; H, 7.41; N, 22.69.

Example 8

N-[4-(4-Amino-2-propyl-1H-imidazo[4,5-c]quinolin-1-yl)butyl]-N-methoxymethanesulfonamide

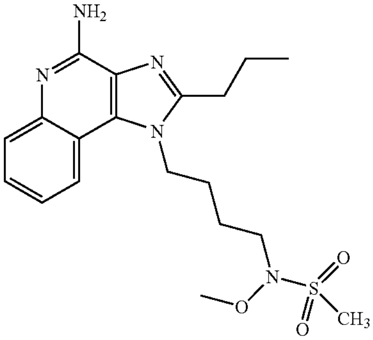 [SMILES: CCCc1nc2c(N)nc3ccccc3c2n1CCCCN(OC)S(C)(=O)=O]

Triethylamine (0.49 mL, 3.5 mmol) and methylsulfonyl anhydride (0.40 g, 2.3 mmol) were sequentially added to a mixture of N-[4-(4-amino-2-propyl-1H-imidazo[4,5-c]quinolin-1-yl)butyl]-O-methylhydroxylamine (0.77 g, 2.3 mmol), prepared as described in Parts A-B of Example 7, in dichloromethane (15 mL) cooled to −18° C. After one hour, an additional amount of the anhydride (50 mg) was added and the reaction was stirred for an additional 2 hours. The reaction mixture was diluted with methanol (10 mL), allowed to warm to ambient temperature and stirred for one hour. The reaction mixture was diluted with dichloromethane (100 mL) and saturated aqueous sodium bicarbonate (25 mL) and the layers were separated. The combined organic layers were dried over potassium carbonate, filtered, and concentrated under reduced pressure to afford 0.93 g of material. The material was purified by flash column chromatography on silica gel (eluting with 5% methanol and concentrated ammonium hydroxide (2 mL/L) in dichloromethane). The resulting crystalline solid was recrystallized from methanol and water and dried overnight under vacuum at 70° C. to afford 0.216 g of N-[4-(4-amino-2-propyl-1H-imidazo[4,5-c]quinolin-1-yl)butyl]-N-methoxymethanesulfonamide as light yellow needles, mp 178-188° C. MS (APCI) m/z 406 (M+H$^+$); Anal. calcd for $C_{19}H_{27}N_5O_3S$: C, 56.28; H. 6.71; N, 17.27. Found: C, 55.99; H, 6.94; N, 17.23.

Example 9

1-[4-(4-Amino-2-propyl-1H-imidazo[4,5-c]quinolin-1-yl-butyl]-1-methoxy-3-phenylurea

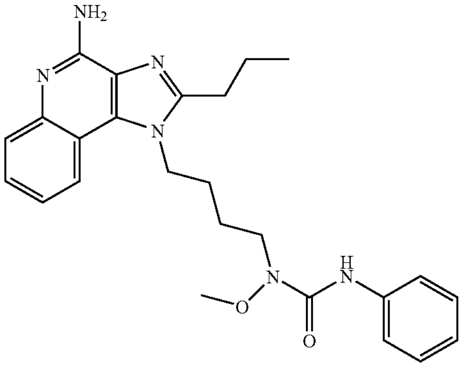 [SMILES: CCCc1nc2c(N)nc3ccccc3c2n1CCCCN(OC)C(=O)Nc1ccccc1]

Phenyl isocyanate (0.340 mL, 3.1 mmol) was added dropwise to a solution of N-[4-(4-Amino-2-propyl-1H-imidazo[4,5-c]quinolin-1-yl)butyl]-O-methylhydroxylamine (1.0 g, 3.05 mmol), prepared as described in Parts A-B of Example 7, in dichloromethane (25 mL) cooled to −78° C. After one hour, 25% sodium hydroxide solution (10 mL) was added and the reaction was allowed to warm to ambient temperature while stirring overnight. The reaction was diluted with dichloromethane (75 mL) and the layers were separated. The combined organic layers were dried over potassium carbonate, filtered, and concentrated under reduced pressure to afford 1.32 g of a dark foam. The crude material was purified by flash column chromatography on silica gel (eluting with 5% methanol and concentrated ammonium hydroxide (2 mL/L) in dichloromethane). The resulting crystalline solid was recrystallized from methanol and water and dried overnight under vacuum at 70° C. to afford 1-[4-(4-amino-2-propyl-1H-imidazo[4,5-c]quinolin-1-yl)butyl]-1-methoxy-3-phenylurea, as light yellow needles, mp 164-166° C. MS (APCI) m/z 447 (M+H$^+$); Anal. calcd for $C_{25}H30N_6O_2.0.28CH_3OH.0.24H_2O$: C, 66.07; H, 6.87; N, 18.29. Found: C, 66.22; H, 6.60; N, 18.11.

Example 10

N-[4-(4-Amino-2-propyl-1H-imidazo[4,5-c]quinolin-1-yl)-1-methylbutyl]-N-methoxy-acetamide

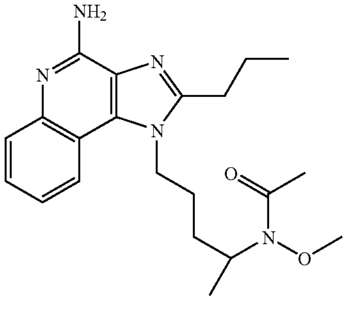 [SMILES: CCCc1nc2c(N)nc3ccccc3c2n1CCCC(C)N(OC)C(C)=O]

Part A

The preparation of 4-(2-propyl-1H-imidazo[4,5-c]quinolin-1-yl)butyraldehyde is described in parts A-C of Example 6. The general procedure of Part G of Example 4 was repeated using 4-(2-propyl-1H-imidazo[4,5-c]quinolin-1-yl)butyraldehyde (6.4 g, 22.74 mmol) in lieu of 4-(4-amino-2-butyl-1H-imidazo[4,5-c][1,5]naphthyridin-1-yl)-N-methoxy-N-methylbutanamide to provide 5.2 g of 5-(2-propyl-1H-imidazo[4,5-c]quinolin-1-yl)pentan-2-ol as a tan oil.

Part B

Oxalyl chloride (4.99 mL, 57.28 mmol) was added to a mixture of methyl sulfoxide (DMSO) (5.54 g, 71.46 mmol) in dichloromethane (50 mL) at −78° C. and stirred for 5 minutes. 5-(2-Propyl-1H-imidazo[4,5-c]quinolin-1-yl)pentan-2-ol (14.2 g, 47.74 mmol) was added dropwise, followed by the addition of triethylamine (19.96 mL, 143.2 mmol). The reaction was allowed to warm to ambient temperature and the reaction was stirred for 2 hours. Saturated aqueous sodium bicarbonate solution was added and the layers were separated. The organic layer was washed with saturated aqueous sodium bicarbonate and brine, filtered over magnesium sulfate, and concentrated under reduced pressure to afford 10.7 g of 5-(2-propyl-1H-imidazo[4,5-c]quinolin-1-yl)pentan-2-one as a brown oil.

Part C

The general procedure of Part I of Example 4 was followed with the following modification. 5-(2-Propyl-1H-imidazo[4,5-c]quinolin-1-yl)pentan-2-one (5.0 g, 16.92 mmol) was used in lieu of 5-(4-amino-2-butyl-1H-imidazo[4,5-c][1,5]naphthyridin-1-yl)-pentan-2-one to afford 4.60 g of 5-(2-propyl-1H-imidazo[4,5-c]quinolin-1-yl)pentan-2-one O-methyl oxime.

Part D

A modification of the general procedure of Part E of Example 6 was followed to treat 5-(2-propyl-1H-imidazo[4,5-c]quinolin-1-yl)pentan-2-one O-methyloxime (4.6 g, 14.17 mmol) in lieu of 4-(2-propyl-1H-imidazo[4,5-c]quinolin-1-yl)butyraldehyde O-methyloxime. Purification with flash column chromatography on silica gel (eluting with 5% methanol in dichloromethane) afforded 2.81 g of O-methyl-N-[1-methyl-4-(2-propyl-1H-imidazo[4,5-c]quinolin-1-yl)butyl]hydroxylamine.

Part E

The general procedure of Part F of Example 6 was followed using O-methyl-N-[1-methyl-4-(2-propyl-1H-imidazo[4,5-c]quinolin-1-yl)butyl]hydroxylamine (0.91 g, 2.78 mmol) in lieu of O-methyl-N-[4-(2-propyl-1H-imidazo[4,5-c]quinolin-1-yl)butyl]hydroxylamine to afford 1.0 g of N-methoxy-N-[1-methyl-4-(2-propyl-1H-imidazo[4,5-c]quinolin-1-yl)butyl]acetamide.

Part F

A modification to the general procedure of Part G of Example 6 was followed using N-methoxy-N-[1-methyl-4-(2-propyl-1H-imidazo-[4,5-c]quinolin-1-yl)butyl]-acetamide (1.0 g, 2.71 mmol) in lieu of N-methoxy-N-[4-(2-propyl-1H-imidazo[4,5-c]quinolin-1-yl)butyl]acetamide. The reaction mixture was cooled to 0° C. before addition of the ammonium hydroxide. Recrystallization from hot acetonitrile following flash column chromatography provided 0.059 g of N-[4-(4-amino-2-propyl-1H-imidazo[4,5-c]quinolin-1-yl)-1-methylbutyl]-N-methoxyacetamide as a tan crystalline solid, mp 140-142° C. MS (APCI) m/z 384.1 (M+H$^+$); Theor. Mass: 384.240 Da Meas. Mass: 384.2406 Da. Mass Dev. 1.6 ppm.

Example 11

1-[4-(4-Amino-2-propyl-1H-imidazo[4,5-c]quinolin-1-yl)-1-methylbutyl]-1-methoxy-3-phenylurea

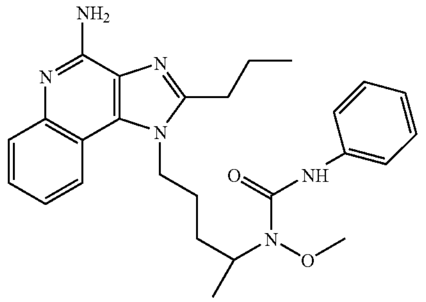 [SMILES: CCCc1nc2c(N)nc3ccccc3c2n1CCCC(C)N(OC)C(=O)Nc1ccccc1]

Part A

The preparation of O-methyl-N-[1-methyl-4-(2-propyl-1H-imidazo-[4,5-c]quinolin-1-yl)butyl]hydroxylamine is described in parts A-D of Example 10. Phenyl isocyanate (0.49 mL, 4.59 mmol) was added to a solution of O-methyl-N-[1-methyl-4-(2-propyl-1H-imidazo[4,5-c]quinolin-1-yl)butyl]hydroxylamine (1.0 g, 3.06 mmol) in tetrahydrofuran (THF) (20 mL) and stirred for 4 hours at ambient temperature. The reaction mixture was concentrated under reduced pressure to afford 1.02 g of 1-[4-(2-propyl-1H-imidazo[4,5-c]quinolin-1-yl)-1-methylbutyl]-1-methoxy-3-phenylurea which was used without any further purification.

Part B

The general procedure of Part F of 10 was repeated using the material from Part A (1.02 g, 2.28 mmol) in lieu of N-methoxy-N-[1-methyl-4-(2-propyl-1H-imidazo[4,5-c]quinolin-1-yl)butyl]acetamide to afford 0.479 g of 1-[4-(4-amino-2-propyl-1H-imidazo[4,5-c]quinolin-1-yl)-1-methylbutyl]-1-methoxy-3-phenylurea as a tan crystalline solid, mp 140-142° C. MS (APCI) m/z 461.2 (M+H$^+$); Anal. calcd for $C_{26}H_{32}N_6O_2$ 0.23 $H_2O$: C, 67.8; H, 7.00; N, 18.25. Found: C, 66.8; H, 6.74; N, 17.75.

Example 12

1-[4-(4-Amino-2-propyl-1H-imidazo[4,5-c]quinolin-1-yl)-1-methylbutyl]-3-ethyl-1-methoxyurea

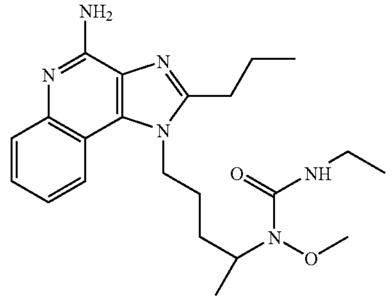 [SMILES: CCCc1nc2c(N)nc3ccccc3c2n1CCCC(C)N(OC)C(=O)NCC]

Part A

Ethyl isocyanate (0.49 mL, 4.59 mmol) was added to a solution of O-methyl-N-[1-methyl-4-(2-propyl-1H-imidazo[4,5-c]quinolin-1-yl)butyl]hydroxylamine (0.600 g, 1.83 mmol) in tetrahydrofuran (THF) (25 mL) at 0° C. and stirred for 1 hour at ambient temperature. Analysis by LC-MS showed the reaction was incomplete and additional ethyl isocyanate (0.19 mL) was added to the reaction mixture. After 1 hour of stirring at ambient temperature, the reaction mixture was concentrated under reduced pressure to afford 0.700 g of 1-[4-(2-propyl-1H-imidazo[4,5-c]quinolin-1-yl)-1-methylbutyl]-3-ethyl-1-methoxyurea.

Part B

The general procedure of Part F of 10 was repeated using 1-[4-(2-propyl-1H-imidazo[4,5-c]quinolin-1-yl)-1-methylbutyl]-3-ethyl-1-methoxyurea (0.700 g, 1.76 mmol) in lieu of N-methoxy-N-[1-methyl-4-(2-propyl-1H-imidazo[4,5-c]quinolin-1-yl)butyl]-acetamide. Purification of the crude material by recrystallization from hot acetonitrile afforded 0.159 g of 1-[4-(4-amino-2-propyl-1H-imidazo[4,5-c]quinolin-1-yl)-1-methylbutyl]-1-methoxy-3-phenylurea as a fluffy white solid, mp 193-194° C. MS (APCI) m/z 383.2 (M+H$^+$); Anal. calcd for $C_{22}H_{32}N_6O_2$ 0.92 $H_2O$: C, 61.59; H, 7.95; N, 19.59. Found: C, 61.41; H, 8.03; N, 19.51.

Example 13

N-[4-(4-Amino-2-ethoxymethyl-1H-imidazo[4,5-c]quinolin-1-yl)-1-methylbutyl]-N-methoxymethanesulfonamide

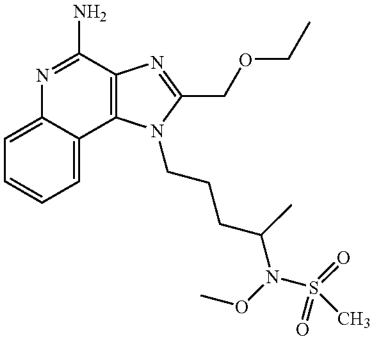 [SMILES: CCOCc1nc2c(N)nc3ccccc3c2n1CCCC(C)N(OC)S(C)(=O)=O]

Part A

Methoxylamine hydrochloride (0.25 g, 3.0 mmol) in water (4 mL) was added to a solution of 5-(4-amino-2-ethoxymethyl-1H-imidazo[4,5-c]quinolin-1-yl)pentan-2-one (0.81 g, 2.5 mmol) in ethanol (25 mL) and stirred at ambient temperature for 3 hours. Addition of acetic acid (20 mL) and sodium cyanoborohydride (2.0 g, 32 mmol) to the reaction mixture followed. After 2.5 hours, the reaction mixture was cooled to 0° C. and the pH was adjusted to ~8 with 25% sodium hydroxide solution. The mixture was concentrated under reduced pressure, diluted with dichloromethane (75 mL) and saturated aqueous sodium bicarbonate and the layers were separated. The combined organic layers were washed with water (25 mL), dried over potassium carbonate, filtered, and concentrated under reduced pressure to afford 0.64 g of N-[4-(4-amino-2-ethoxymethyl-1H-imidazo[4,5-c]quinolin-1-yl)-1-methylbutyl]-O-ethylhydroxylamine.

Part B

Triethylamine (0.56 mL, 4.0 mmol) and mesyl anhydride (0.52 g, 3.0 mmol) were added sequentially to a solution of N-[4-(4-amino-2-ethoxymethyl-1H-imidazo[4,5-c]quinolin-1-yl)-1-methylbutyl]-O-ethylhydroxylamine (2.3 mmol, 1 eq) in dichloromethane (25 mL) cooled to −20° C. The reaction mixture was allowed to warm to ambient temperature and was stirred overnight. The reaction was cooled to 0° C. and additional mesyl anhydride (0.20 g) was introduced to the reaction mixture. After 1.5 hours, the reaction was diluted with 25% sodium hydroxide solution (10 mL), stirred for 10 minutes, warmed to ambient temperature, and the layers were separated. The combined organics were dried over potassium carbonate, filtered, and concentrated under reduced pressure to afford a brown solid. The material was purified by flash column chromatography on silica gel (eluting with 5% methanol in dichloromethane containing ammonium hydroxide (2 mL/L of eluent)) and dried overnight under vacuum at 70° C. to afford 0.754 g of N-[4-(4-amino-2-ethoxymethyl-1H-imidazo[4,5-c]quinolin-1-yl)-1-methylbutyl]-N-methoxymethanesulfonamide as light yellow needles, mp 146-148° C. MS (APCI) m/z 436 ($M+H^+$); Anal. calcd for $C_{20}H_{29}N_5O_4S$: C, 55.15; H, 6.71; N, 16.08. Found: C, 54.87; H, 6.88; N, 15.89.

Example 14

N-[4-(4-Amino-6,7-dimethyl-2-propyl-1H-imidazo[4,5-c]pyridin-1-yl)butyl]-N-[tert-butyl carbamate] hydroxylamine

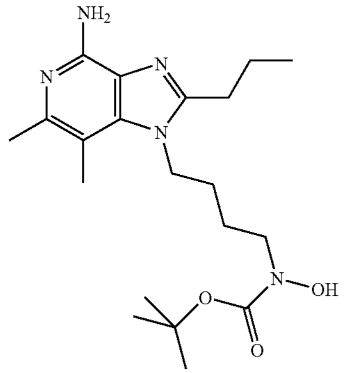 [SMILES: CCCc1nc2c(N)nc(C)c(C)c2n1CCCCN(O)C(=O)OC(C)(C)C]

Part A

Under a nitrogen atmosphere, triethylamine (14.19 mL, 101.8 mmol, 1.5 eq) was added in a single portion to a mixture of 2,4-dichloro-5,6-dimethyl-3-nitropyridine (15.0 g, 67.86 mmol, 1.0 eq) and N,N-dimethylformamide (DMF) (200 mL). The reaction mixture was stirred for 10 minutes, 4-amino-1-butanol (8.76 mL, 95 mmol, 1.4 eq) in DMF (20 mL) was added, and the reaction mixture was stirred overnight. The reaction mixture was concentrated under reduced pressure to provide crude product as an oil. The oil was partitioned between ethyl acetate (300 mL) and water (50 mL). The aqueous layer was back-extracted with ethyl acetate (2×50 mL). The combined organic phases were separated, washed with water (3×30 mL) and brine (30 mL), dried over magnesium sulfate, filtered, and then concentrated under reduced pressure to provide an orange solid. This material was recrystallized from ethyl acetate/hexanes to provide 12.2 g of 4-(2-chloro-5,6-dimethyl-3-nitropyridin-1-yl)butan-1-ol.

Part B

Under a nitrogen atmosphere, a mixture of 4-(2-chloro-5,6-dimethyl-3-nitropyridin-1-yl)butan-1-ol (12.19 g, 44.53 mmol, 1.0 eq), sodium azide (5.8 g, 2.0 eq.), cerium(III) chloride heptahydrate (6.2 g, 0.5 eq), and acetonitrile/water (9:1 180 mL) was heated at reflux overnight. Additional sodium azide (0.3 g) and cerium(III) chloride heptahydrate (0.3 g) were added to the mixture and stirred at reflux for another 2 hours. The reaction mixture was filtered while still hot and the filter cake was rinsed with warm acetonitrile and methanol. The filtrate was concentrated under reduced pressure and then dried under high vacuum to provide 12.5 g of crude 4-[(5,6-dimethyl-8-nitrotetraazolo[1,5-a]pyridin-7-yl)amino]butan-1-ol.

Part C

Crude 4-[(5,6-dimethyl-8-nitrotetraazolo[1,5-a]pyridin-7-yl)amino]butan-1-ol was combined in a pressure vessel with catalyst (1.3 g of 5% platinum on carbon), and acetonitrile (222 mL). The reaction mixture was placed under hydrogen pressure (30 psi, $2.1\times10^5$ Pa) for 3 hours, filtered through a layer of CELITE filter aid, and the filter cake was washed with methanol. The filtrate was concentrated under reduced pressure to provide 11.15 g of 4-[(8-amino-5,6-dimethyl-tetrazolo[1,5-a]pyridin-7-yl)amino]butan-1-ol.

Part D

Under a nitrogen atmosphere, pyridine hydrochloride (1.93 g, 0.375 eq) and trimethyl orthobutyrate (7.8 mL, 1.1. eq) were added sequentially to a suspension of 4-[(8-amino-5,6-dimethyltetrazolo[1,5-a]pyridin-7-yl)amino]butan-1-ol (11.15 g, 44.5 mmol, 1 eq) in toluene (300 mL). The reaction mixture was heated at reflux for 1.5 hours, allowed to stand at ambient temperature overnight, and then concentrated under reduced pressure. The crude material was partitioned between chloroform (300 mL) and saturated aqueous sodium bicarbonate (100 mL). The phases were separated and the combined organics were washed with saturated aqueous sodium bicarbonate (3×25 mL), dried over magnesium sulfate, filtered, and concentrated under reduced pressure. Analysis by $^1H$ NMR indicated presence of starting material. The material was resubjected to the reaction conditions with additional trimethyl orthobutyrate (~2 mL) and heated at reflux for 1 hour and the reaction was worked up as before. Analysis by $^1H$ NMR shows the presence of ester. The crude material was dissolved in ethanol (300 mL) and was stirred overnight at ambient temperature after addition of 6N sodium hydroxide (2 mL). The reaction mixture was concentrated under reduced pressure and partitioned between chloroform (300 mL) and water (25 mL). The phases were separated and the organic layer was washed with saturated sodium bicarbonate solution (30 mL), dried over magnesium sulfate, filtered, and then concentrated under reduced pressure to provide 13.47 g of 4-(5,6-dimethyl-8-propyl-1H-imidazo[4,5-c]tetrazolo[1,5-a]pyridin-7-yl)butan-1-ol as an off white solid.

Part E

Platinum (IV) oxide (200 mg), 4-(5,6-dimethyl-8-propyl-1H-imidazo[4,5-c]tetrazolo[1,5-a]pyridin-7-yl)butan-1-ol (1.0 g, 3.3 mmol), and trifluoroacetic acid (33 mL) were combined in a pressure vessel and placed under hydrogen pressure (50 psi, $3.4\times10^5$ Pa) for 2 days. The reaction mixture was filtered and the filter paper was washed with methanol. The filtrate was concentrated under reduced pressure and the residue was diluted with concentrated hydrochloric acid (7 mL) and then stirred at ambient temperature for 2 hours. The mixture was diluted with chloroform (100 mL) and the pH was adjusted to 14 by adding 6N sodium hydroxide. The pH of the mixture was then adjusted to 8 with 1N hydrochloric acid and the product was then extracted with chloroform (3×50 mL). The combined organics were washed with brine, dried over magnesium sulfate, filtered, concentrated under reduced pressure, and then dried under high vacuum to afford 0.97 g of 4-(4-amino-6,7-dimethyl-2-propyl-1H-imidazo[4,5-c]pyridin-1-yl)butan-1-ol as a white foam.

Part F

Triphenylphosphine (0.845 g, 3.22 mmol, 1.1 eq), 4-(4-amino-6,7-dimethyl-2-propyl-1H-imidazo[4,5-c]pyridin-1-yl)butan-1-ol (0.81 g, 2.93 mmol), and tert-butyl N-(tert-butoxycarbonyloxy)carbamate (0.751 g, 3.22 mmol) were dissolved in DMF and cooled to 0° C. Diisopropyl azodicarboxylate (0.634 mL, 3.22 mmol) was added dropwise over 10 minutes to the reaction mixture and was allowed to warm to ambient temperature and stirred overnight. Analysis by HPLC indicated the reaction was incomplete. An additional amount of reagents (0.5 eq) were added to the reaction mixture (cooled to 0° C. before addition of the diisopropyl azodicarboxylate) and stirred for an additional 2 hours. The reaction mixture was concentrated under reduced pressure, dissolved in ethyl acetate (150 mL), washed with a water and brine mixture (1:1, 4×30 mL), dried over sodium sulfate, filtered, and concentrated under reduced pressure. The residue was purified by column chromatography on a BIOTAGE HORIZON High-Performance Flash Chromatography instrument (silica gel, eluting with 2-30% CMA in chloroform) and concentrated under reduced pressure to provide 1.19 g of tert-butyl 4-(4-amino-6,7-dimethyl-2-propyl-1H-imidazo[4,5-c]pyridin-1-yl)butyl[(tert-butoxycarbonyl)oxy]carbamate.

Part G

Potassium carbonate (62 mg, 0.45 mmol, 1.1 eq) was added to a solution of the material from Part F dissolved in methanol (4 mL) and stirred overnight at ambient temperature. The reaction mixture was concentrated under reduced pressure and diluted with chloroform (20 mL), water (5 mL), and saturated aqueous sodium bicarbonate (5 mL) and the phases were separated. The aqueous phase was back-extracted with chloroform (2×10 mL) and the combined organic phases were washed with saturated aqueous sodium bicarbonate (5 mL), dried over sodium sulfate, filtered, and concentrated under reduced pressure to produce a white foam. The crude material was triturated with acetonitrile and dried under high vacuum at 80° C. for 2 hours to afford N-[(4-amino-6,7-dimethyl-2-propyl-1H-imidazo[4,5-c]pyridin-1-yl)butyl]-N-[tert-butyl carbamate]hydroxylamine as a white powder, mp 157.0-158.5° C. $^{1}$HNMR (300 MHz, DMSO-$d_6$) δ 9.19 (s, 1H), 5.56 (s, 2H), 4.20 (dd, J=7.7, 6.4 Hz, 2H), 3.38 (dd, J=6.1, 5.8 Hz, 2H), 2.75 (dd, J=7.7, 7.4 Hz, 2H), 2.36 (s, 3H), 2.29 (s, 3H), 1.86-1.50 (m, 6H), 1.38 (s, 9H), 0.99 (t, J=7.4 Hz, 3H); MS (APCI) m/z 392 $(M)^+$; Anal. Calcd for $C_{20}H_{33}N_5O_3.0.1H_2O$ C, 61.08; H, 8.51; N, 17.81. Found: C, 60.79; H, 8.71; N, 17.84.

Example 15

N-[4-(4-Amino-6,7-dimethyl-2-propyl-1-imidazo[4,5-c]pyridin-1-yl)butyl]-N-hydroxyacetamide

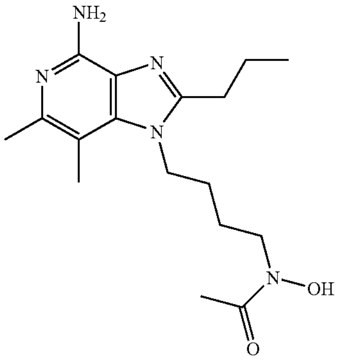 [SMILES: CCCc1nc2c(N)nc(C)c(C)c2n1CCCCN(O)C(C)=O]

The preparation of tert-butyl 4-(4-amino-6,7-dimethyl-2-propyl-1H-imidazo[4,5-c]pyridin-1-yl)butyl[(tert-butoxycarbonyl)oxy]carbamate is described in Parts A-F of Example 14. A solution of 4M hydrochloric acid in dioxane (1.8 mL, 7.2 mmol, 20 eq) is added to a solution of tert-butyl 4-(4-amino-6,7-dimethyl-2-propyl-1H-imidazo[4,5-c]pyridin-1-yl)butyl[(tert-butoxycarbonyl)oxy]carbamate (175 mg, 0.36 mmol, 1.0 eq) in dichloromethane (4 mL) and stirred at ambient temperature for 2 hours. The reaction mixture was concentrated under reduced pressure and the resulting crude material was dissolved in 1-methyl-2-pyrrolidinone (NMP) (4 mL) and cooled to −8° C. Triethylamine (0.500 mL, 10 eq) and acetic anhydride (0.034 mL, 0.36 mmol) were sequentially added dropwise to the reaction mixture and stirred for 1 hour. The crude reaction mixture was concentrated reduced pressure at 70° C. The residue was partitioned between saturated aqueous sodium carbonate and chloroform and the phases were separated. The aqueous phase was back-extracted with chloroform and the combined organics were dried over sodium sulfate, filtered, and concentrated under reduced pressure to afford crude material. The material was purified by column chromatography on a BIOTAGE HORIZON High-Performance Flash Chromatography instrument (silica gel, eluting with 10-50% CMA in chloroform) and trituration with chloroform/ethyl acetate. The resulting material was filtered and washed with ethyl acetate and dried under high vacuum to afford 0.025 g of N-[4-(4-amino-6,7-dimethyl-2-propyl-1H-imidazo[4,5-c]pyridin-1-yl)butyl]-N-hydroxyacetamide as a white powder, mp 164.0-166.0° C. MS (APCI) m/z 334 $(M)^+$; Anal. Calcd for $C_{17}H_{27}N_5O_2.0.05CHCl_3$ C, 60.34; H, 8.03; N, 20.64. Found: C, 60.05; H, 7.97; N, 20.43.

Example 16

1-[4-(4-Amino-2-propyl-1H-imidazo[4,5-c]quinolin-1-yl)-1-methylbutyl]-N-methoxy-3-cyclopentylurea

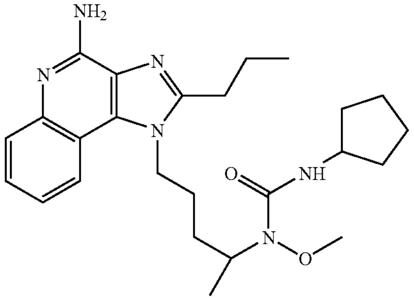 [SMILES: CCCc1nc2c(N)nc3ccccc3c2n1CCCC(C)N(OC)C(=O)NC1CCCC1]

Part A

The preparation of O-methyl-N-[1-methyl-4-(2-propyl-1H-imidazo-[4,5-c]quinolin-1-yl)butyl]hydroxylamine is described in parts A-D of Example 10. Cyclopentyl isocyanate (0.88 mL, 7.8 mmol) was added to a solution of O-methyl-N-[1-methyl-4-(2-propyl-1H-imidazo-[4,5-c]quinolin-1-yl)butyl]hydroxylamine (1.7 g, 5.20 mmol) in tetrahydrofuran (THF) (25 mL) and stirred for 2 hours at ambient temperature. The reaction mixture was concentrated under reduced pressure, diluted in dichloromethane, washed with saturated aqueous sodium bicarbonate, dried over magnesium sulfate, and concentrated under reduced pressure to afford 2.15 g of 1-[4-(4-amino-2-propyl-1H-imidazo[4,5-c]quinolin-1-yl)-1-methylbutyl]-N-methoxy-3-cyclopentylurea.

Part B

The general procedure of Part G of Example 6 was repeated using 1-[4-(2-propyl-1H-imidazo[4,5-c]quinolin-1-yl)-1-methylbutyl]-N-methoxy-3-cyclopentylurea (2.15 g, 4.9 mmol) in the place of N-methoxy-N-[1-methyl-4-(2-propyl-1H-imidazo-[4,5-c]quinolin-1-yl)butyl]acetamide. Chloroform (30 mL), in lieu of dichloromethane, was used as solvent. After purification, the process afforded 0.154 g of 1-[4-(4-amino-2-propyl-1H-imidazo[4,5-c]quinolin-1-yl)-1-methylbutyl]-N-methoxy-3-cyclopentylurea as a tan powder, mp 182-184° C. MS (APCI) m/z 453.3 ($M+H^+$); Anal. calcd for $C_{25}H_{36}N_6O_2$ $0.53H_2O$: C, 64.97; H, 8.08; N, 18.18. Found: C, 64.95; H, 7.78; N, 17.92.

Example 17

5-(4-Amino-7-phenyl-2-propyl-1H-imidazo[4,5-c]quinolin-1-yl)pentan-2-one O-methyloxime

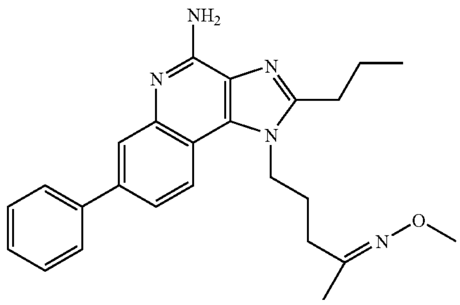 [SMILES: CCCc1nc2c(N)nc3cc(-c4ccccc4)ccc3c2n1CCCC(C)=NOC]

Part A

4-Aminobutyraldehyde dimethylacetal (29.41 g, 208.6 mmol), triethylamine (36.36 mL), and potassium carbonate (24.0 g, 173.9 mmol) were added sequentially to a solution of 7-bromo-4-chloro-3-nitroquinoline (50.1 g, 173.9 mmol) in chloroform (200 mL) cooled to 0° C. The reaction was allowed to warm to ambient temperature and was stirred for 4 hours. The reaction mixture was then diluted with water (100 mL) and the reaction was stirred for 10 minutes and the layers were separated. The organic layer was washed with saturated aqueous sodium bicarbonate and brine, dried over magnesium sulfate, and concentrated under reduced pressure to afford 66.9 g of (7-bromo-3-nitroquinolin-yl)(4,4-dimethoxybutyl)amine as a yellow solid.

Part B

Water (200 mL), sodium hydrosulfite (90.9 g, 522.3 mmol), ethyl viologen dibromide (0.64 g, 1.74 mL mmol) and potassium carbonate (95.0 g, 687 mmol) were sequentially added to a solution of (7-bromo-3-nitroquinolin-4-yl)(4,4-dimethoxybutyl)amine in dichloromethane and stirred overnight at ambient temperature. The layers were separated and the organic layer was washed sequentially with water (5×200 mL), saturated aqueous sodium bicarbonate, and brine, dried over magnesium sulfate, and concentrated under reduced pressure to afford 59.3 g of 7-bromo-$N^4$-(4,4-dimethoxybutyl)quinoline-3,4 diamine as a brown oil.

Part C

A modification of the general method of Part B of Example 6 was followed using 7-bromo-$N^4$-(4,4-dimethoxybutyl) quinoline-3,4 diamine (59.3 g, 167.39 mmol) in lieu of $N^4$-(4,4-diethoxybutyl)quinoline-2,4 diamine. The reaction was incomplete after running overnight. Trimethyl orthobutyrate (5 mL) was added to the reaction mixture and heated to reflux for an additional 2 hours, upon which an additional amount of trimethyl orthobutyrate (5 mL) and pyridinium tosylate (5 mL) were added. After 2 hours of heating to reflux, the mixture was concentrated under reduced pressure, diluted in dichloromethane (300 mL) and methanol (45 mL), washed with saturated aqueous sodium bicarbonate solution, dried over magnesium sulfate, and the mixture was concentrated under reduced pressure to afford 57.0 g of 7-bromo-1-(4,4-dimethoxybutyl)-2-propyl-1H-imidazo[4,5-c]quinoline as a brown solid.

Part D

Concentrated hydrochloric acid (8 mL) was added to a mixture of 7-bromo-1-(4,4-dimethoxybutyl)-2-propyl-1H-imidazo[4,5-c]quinoline (57.0 g, 140.3 mmol) in THF (250 mL) and water (70 mL) and stirred overnight at ambient temperature. Additional concentrated hydrochloric acid (10 mL) was added and the reaction mixture was stirred for 4 hours. The reaction mixture was concentrated under reduced pressure and the residue was diluted with water and neutralized with saturated aqueous sodium bicarbonate solution. The mixture was diluted with 10% methanol in dichloromethane, the phases were separated, and the combined organics were dried over magnesium sulfate and concentrated under reduced pressure to afford 50.3 g of 4-(7-bromo-2-propyl-1H-imidazo[4,5-c]quinolin-1-yl)butyraldehyde.

Part E 4-(7-Bromo-2-propyl-1H-imidazo[4,5-c]quinolin-1-yl) butyraldehyde (2.77 g, 7.68 mmol) was dissolved in THF (75 mL), stirred at ambient temperature for 30 minutes, and cooled to 0° C. Methylmagnesium iodide (3.33 mL, 9.99 mmol, 3 M in diethyl ether) was added over 5 minutes. The reaction mixture was allowed to warm to ambient temperature. After 2 hours, 10% hydrochloric acid was added and the reaction mixture was concentrated under reduced pressure. The residue was neutralized with saturated aqueous sodium bicarbonate, extracted in 10% methanol in dichloromethane, dried over magnesium sulfate and concentrated under reduced pressure to provide 2.6 g of 5-(7-bromo-2-propyl-1H-imidazo[4,5-c]quinolin-1-yl)pentan-2-ol as an orange-brown solid.

Part F

Dess-Martin periodinan (3.51 g, 8.29 mmol) was added to a solution of 5-(7-bromo-2-propyl-1H-imidazo[4,5-c]quinolin-1-yl)pentan-2-ol (2.6 g, 6.9 mmol) in dichloromethane and stirred overnight at ambient temperature. The reaction mixture was diluted with sodium thiosulfite (2×50 mL) and the layers were separated. The organic layer was dried over magnesium sulfate and concentrated under reduced pressure. The residue was dissolved in dichloromethane, washed with saturated aqueous sodium bicarbonate (twice) and brine, dried over magnesium sulfate, and concentrated under reduced pressure to afford 2.50 g of 5-(7-bromo-2-propyl-1H-imidazo[4,5-c]quinolin-1-yl)pentan-2-one.

Part G 5-(7-Bromo-2-propyl-1H-imidazo[4,5-c]quinolin-1-yl) pentan-2-one (2.5 g, 6.68 mmol) was dissolved in propanol (25 mL) and water (5 mL) and degassed with nitrogen for 5 minutes. Phenylboronic acid (1.97 g, 7.35 mmol), palladium (II) acetate (7 mg, 0.03 mmol), triphenylphosphine (0.17 g, 0.06 mmol), and sodium carbonate (0.85 g, 8.01 mmol) were added sequentially to the reaction mixture and heated at 100° C. overnight. The mixture was concentrated under reduced pressure and the residue was diluted with dichloromethane, washed with saturated aqueous sodium bicarbonate solution and brine, dried over magnesium sulfate, and concentrated under reduced pressure. Purification was performed with flash column chromatography on silica gel (eluting with 3% methanol in dichloromethane) to obtain 1.0 g of 5-(7-phenyl-2-propyl-1H-imidazo[4,5-c]quinolin-1-yl)pentan-2-one.

Part H

The general method described in Part G of Example 6 was followed using 5-(7-phenyl-2-propyl-1H-imidazo[4,5-c]quinolin-1-yl)pentan-2-one (1.0 g, 2.69 mmol) in lieu of N-methoxy-N-[4-(2-propyl-1H-imidazo[4,5-c]quinolin-1-yl)butyl]acetamide. Recrystallization from hot methanol and water afforded 0.1815 g of 5-(4-amino-7-phenyl-2-propyl-1H-imidazo[4,5-c]quinolin-1-yl)pentan-2-one as a tan powder, mp 202-204° C. MS (APCI) m/z 387.1 (M+H$^+$); Anal. calcd for $C_{24}H_{26}N_4O$ 0.66$H_2O$: C, 72.36; H, 6.91; N, 14.06. Found: C, 64.95; H, 7.78; N, 17.92.$C_{24}H_{26}N_4O$ 0.66$H_2O$ Exact Mass: Theor. Mass: 387.2185 Da. Meas. Mass: 387.2191 Da. Mass Dev. 1.5 ppm.

Part I

Methoxylamine hydrochloride (0.98 g, 11.79 mmol) was added to a solution of 5-(4-amino-7-phenyl-2-propyl-1H-imidazo[4,5-c]quinolin-1-yl)pentan-2-one (3.8 g, 9.83 mmol) in ethanol (50 mL) and water (10 mL) and stirred at ambient temperature for 3 hours. The mixture was then concentrated under reduced pressure, diluted with dichloromethane, washed with saturated aqueous sodium bicarbonate solution and brine, dried over magnesium sulfate, and concentrated under reduced pressure. The residue was purified by flash column chromatography on silica gel (eluting with 5% methanol in dichloromethane) and recrystallized from methanol and water to afford 3.6 g of 5-(4-amino-7-phenyl-2-propyl-1H-imidazo[4,5-c]quinolin-1-yl)pentan-2-one O-methyloxime as a tan solid, mp 191-192° C. MS (APCI) m/z 416.2 (M+H$^+$); $C_{25}H_{29}N_5O$ Exact Mass: Theor. Mass: 416.2450 Da. Meas. Mass: 416.2448 Da. Mass. Dev. −0.5 ppm.

Example 18

1-[4-(4-Amino-7-phenyl-2-propyl-1H-imidazo[4,5-c]quinolin-1-yl)-1-methylbutyl]-3-isopropyl-1-methoxyurea

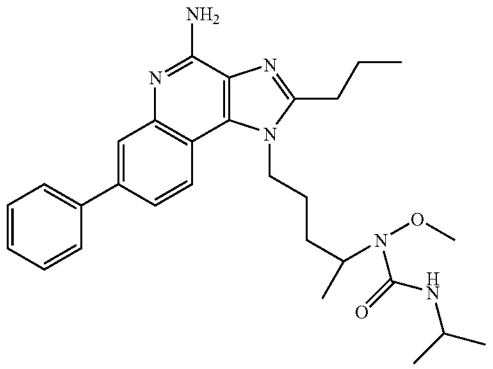 [SMILES: CCCc1nc2c(N)nc3cc(-c4ccccc4)ccc3c2n1CCCC(C)N(OC)C(=O)NC(C)C]

Part A

Sodium cyanoborohydride (2.26 g, 36.1 mmol) was added to a solution of 5-(4-amino-7-phenyl-2-propyl-1H-imidazo[4,5-c]quinolin-1-yl)pentan-2-one O-methyloxime (3.0 g, 7.22 mmol) in ethanol (50 mL) and acetic acid (3 mL) and stirred at ambient temperature overnight. Another portion of sodium cyanoborohydride was added (1.0 g) and the reaction was stirred for an additional 4 hours. The reaction mixture was concentrated under reduced pressure and the residue was diluted in water and neutralized to pH ~8 with 10% sodium hydroxide solution. The product was extracted into dichloromethane, washed with saturated sodium bicarbonate solution and brine, dried over magnesium sulfate, and concentrated under reduced pressure to provide 2.73 g of N-[4-(4-amino-7-phenyl-2-propyl-1H-imidazo[4,5-c]quinolin-1-yl)-1-methylbutyl]-O-methylhydroxylamine.

Part B

Isopropyl isocyanate (0.35 mL, 3.58 mmol) was added to a solution of N-[4-(4-amino-7-phenyl-2-propyl-1H-imidazo[4,5-c]quinolin-1-yl)-1-methylbutyl]-O-methylhydroxylamine (1.25 g, 2.99 mmol) and stirred at ambient temperature for 2 hours. The reaction mixture was concentrated under reduced pressure and purified by flash column chromatography on silica gel (eluting with 5% methanol in dichloromethane) to provide 1-[4-(4-amino-7-phenyl-2-propyl-1H-imidazo[4,5-c]quinolin-1-yl)-1-methylbutyl]-3-isopropyl-1-methoxyurea as a tan powder, mp 101-103° C. MS (APCI) m/z 503.3 (M+H$^+$); Anal. calcd for $C_{29}H_{38}N_6O_2$ 0.85$H_2O$: C, 67.25; H, 7.73; N, 16.22. Found: C, 66.84; H, 7.64; N, 15.89.

Example 19

N-[4-(4-Amino-2-propyl-1H-imidazo[4,5-c][1,5]naphthyridin-1-yl)butyl]-N-methoxy-N'-phenylurea

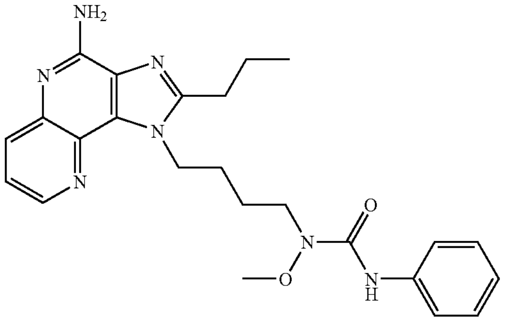 [SMILES: CCCc1nc2c(N)nc3cccnc3c2n1CCCCN(OC)C(=O)Nc1ccccc1]

The preparation of 4-(4-amino-2-propyl-1H-imidazo[4,5-c][1,5]naphthyridin-1-yl)butyl O-methylhydroxylamine is described in Parts A-H of Example 1. Triethylamine (0.23 mL, 1.64 mmol) was added to a solution of 4-(4-amino-2-propyl-1H-imidazo[4,5-c][1,5]naphthyridin-1-yl)butyl O-methylhydroxylamine (0.45 g, 1.37 mmol) in dichloromethane (10 mL) cooled to −10° C. Phenyl isocyanate (0.15 mL, 1.37 mmol) was added to the reaction mixture and it was allowed to warm to 0° C. over 1 hour. The reaction mixture was diluted with dichloromethane (50 mL) and saturated sodium bicarbonate (40 mL) and the phases were separated. The aqueous layer was extracted with dichloromethane (30 mL) and the combined organic layers were dried over magnesium sulfate, filtered, and concentrated under reduced pressure to afford a yellow material. The material was purified by HPFC (0-25% CMA in chloroform) and recrystallized from acetonitrile to afford an off-white solid. The solid was dried at 100° C. under high vacuum to afford 0.388 g of N-[4-(4-amino-2-propyl-1H-imidazo[4,5-c][1,5]naphthyridin-1-yl)butyl]-N-methoxy-N'-phenylurea as an off-white powder, mp 155-156° C. Anal. calcd for $C_{24}H_{29}N_7O_2$: C, 64.41; H, 6.53; N, 21.91. Found: C, 64.20; H, 6.64; N, 21.93.

Example 20

N-[4-(4-amino-2-ethoxymethyl-1H-imidazo[4,5-c][1,5]naphthyridin-1-yl)butyl]-N-Methoxyacetamide

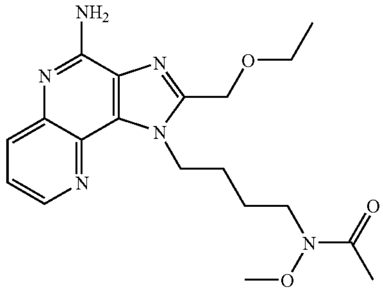 [SMILES: CCOCc1nc2c(N)nc3cccnc3c2n1CCCCN(OC)C(C)=O]

Part A

The general methods of Parts A-C of Example 1 were repeated using 4,4-dimethoxybutylamine (14.4 mL) in lieu of 4,4-diethoxybutylamine in Part B of Example 1 to transform 4-chloro-3-nitro[1,5]naphthyridine into $N^4$-(4,4-dimethoxybutyl)-[1,5]naphthyridine-3,4-diamine.

Part B

Ethoxyacetyl chloride (4.2 mL, 37.4 mmol, 1.1 eq) was added dropwise over 8 minutes to a solution of $N^4$-(4,4-dimethoxybutyl)[1,5]naphthyridine-3,4-diamine (9.50 g, 34.0 mmol) in dichloromethane (140 mL) and stirred at ambient temperature for 2 hours. The reaction mixture was concentrated under reduced pressure and the residue was dissolved in ethanol (140 mL). Sodium hydroxide (6M) solution (8.5 mL, 51 mmol) was added to the reaction mixture, which was then heated for 60° C. for 3 hours. The mixture was cooled to ambient temperature and concentrated under reduced pressure. The residue was dissolved in dichloromethane (150 mL) and water (100 mL). The pH of the mixture was adjusted to 7 and the layers were separated. The aqueous layer was back-extracted with dichloromethane (2×50 mL) and the combined organic layers were dried over magnesium sulfate, filtered, and concentrated under reduced pressure to afford 10.52 g of 1-(4,4-dimethoxybutyl)-2-ethoxymethyl-1H-imidazo[4,5-c][1,5]naphthyridine.

Part C

A modified version of the general methods described in Parts E-H of Example 1 was sequentially followed with 1-(4,4-dimethoxybutyl)-2-ethoxymethyl-1H-imidazo[4,5-c][1,5]naphthyridine (10.5 g, 30.5 mmol) used in lieu of $N^4$-(4,4-diethoxybutyl)-2-propyl-1H-imidazo[4,5-c][1,5]naphthyridine as the substrate. The formation of the O-methyl oxime, analogous to part F of Example 1, was accomplished in the absence of sodium hydroxide solution and the reaction was complete after 2 hours. Isolation after the last step of the sequence afforded 0.55 g of O-methyl-N-[4-(4-amino-2-ethoxymethyl-1H-imidazo[4,5-c][1,5]naphthyridin-1-yl)butyl]hydroxylamine.

Part D

The general method of Part I of Example 1 was followed using O-methyl-N-[4-(4-amino-2-ethoxymethyl-1H-imidazo[4,5-c][1,5]naphthyridin-1-yl)butyl]hydroxylamine (0.24 g, 0.70 mmol, 1.0 eq) in lieu of 4-(4-amino-2-propyl-1H-imidazo[4,5-c][1,5]naphthyridin-1-yl)butyl O-methylhydroxylamine. After purification by HPFC, the isolated material was recrystallized from acetonitrile, filtered, and dried at 140° C. under high vacuum to provide 0.121 g of N-[4-(4-amino-2-ethoxymethyl-1H-imidazo[4,5-c][1,5]naphthyridin-1-yl)butyl]-N-methoxyacetamide as a white powder, mp 180-181° C. Anal. calcd for $C_{19}H_{26}N_6O_3$: C, 58.90; H, 6.76; N, 21.68. Found: C, 58.55; H, 6.71; N, 21.51.

Example 21

1-[4-(4-Amino-2-ethoxymethyl-1H-imidazo[4,5-c][1,5]naphthyridin-1-yl)butyl]-3-isopropyl-1-methoxyurea

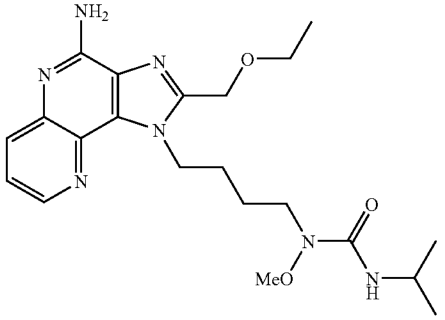 [SMILES: CCOCc1nc2c(N)nc3cccnc3c2n1CCCCN(OC)C(=O)NC(C)C]

The preparation of O-methyl-N-[4-(4-amino-2-ethoxymethyl-1H-imidazo[4,5-c][1,5]naphthyridin-1-yl)butyl]-hydroxylamine is described in Parts A-C of Example 20. Triethylamine (0.14 mL, 1.01 mmol) was added to a solution of O-methyl-N-[4-(4-amino-2-ethoxymethyl-1H-imidazo[4,5-c][1,5]naphthyrdin-1-yl)butyl]hydroxylamine (0.29 g, 0.84 mmol) in dichloromethane (8 mL) and cooled to −8° C. Isopropyl isocyanate (0.08 mL, 0.84 mmol) was added dropwise to the reaction mixture, allowed to warm to ambient temperature and was stirred overnight. The reaction mixture was then diluted with dichloromethane (40 mL) and saturated aqueous sodium bicarbonate (30 mL) and the phases were separated. The aqueous phase was extracted with dichloromethane (20 mL) and the combined organic layers were dried over magnesium sulfate, filtered, and concentrated to afford a yellow solid. The material was then purified by HPFC (eluting with 0-25% CMA in chloroform) and crystallized from acetonitrile, filtered, dried at 80° C. in a vacuum oven over the weekend to afford 0.178 g of 1-[4-(4-amino-2-ethoxymethyl-1H-imidazo[4,5-c][1,5]naphthyridin-1-yl)butyl]-3-isopropyl-1-methoxyurea as a white powder, mp 146-147° C. Anal. calcd for $C_{21}H_{31}N_7O_3$: C, 58.72; H, 7.27; N, 22.83. Found: C, 58.54; H, 7.27; N, 22.78.

Example 22

N-Methoxy-N-[4-(4-amino-2-propyl-1H-imidazo[4,5-c][1,5]naphthyridin-1-yl)1-methyl-butyl]acetamide

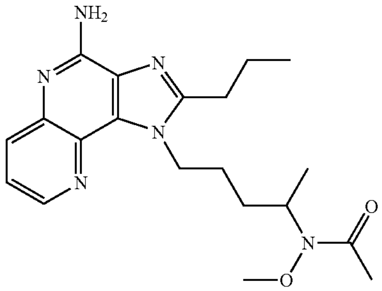 [SMILES: CCCc1nc2c(N)nc3cccnc3c2n1CCCC(C)N(OC)C(C)=O]

Part A

The preparation of ethyl 4-[(3-amino[1,5]naphthyridine-4-yl)amino]butyrate is described in Parts A-B of Example 4. Trimethyl orthobutyrate (9.1 mL, 57.2 mmol) and pyridine hydrochloride (110 mg, 0.95 mmol) were added to a solution of ethyl 4-[(3-amino-[1,5]naphthyridine-4-yl)amino]butyrate (13.08 g, 47.7 mmol) in toluene (190 mL) and heated at reflux for 3 hours. The reaction mixture was cooled to ambient temperature and concentrated under reduced pressure. The residue was dissolved in dichloromethane (200 mL) and washed with saturated aqueous sodium bicarbonate (150 mL). The aqueous layer was extracted with dichloromethane (2×50 mL). The combined organics were dried over magnesium sulfate, filtered, and concentrated under reduced pressure to afford 14.9 g of ethyl 4-(2-propyl-1H-imidazo[4,5-c][1,5]naphthyridin-1-yl)-butyrate as a yellow solid.

Part B

A modified version of the general methods described in Parts D-G of Example 4 was sequentially followed with ethyl 4-(2-propyl-1H-imidazo[4,5-c][1,5]naphthyridin-1-yl)butyrate (6.0 g, 18.4 mmol) used in lieu of ethyl 4-(2-butyl-1H-imidazo[4,5-c][1,5]naphthyridin-1-yl)butyrate as the starting substrate. Isolation after the last step of the sequence afforded 6.06 g of crude 5-(2-propyl-1H-imidazo[4,5-c][1,5]naphthyridin-1-yl)pentan-2-one.

Part C

A modified version of the general methods described in Parts D-G of Example 6 was sequentially followed with 5-(2-propyl-1H-imidazo[4,5-c][1,5]naphthyridin-1-yl)-pentan-2-one (5.27 g, 17.8 mmol) used in lieu of 4-(2-propyl-1H-imidazo[4,5-c]quinolin-1-yl)butyraldehyde as the starting substrate. The formation of the O-methyl oxime, analogous to Part D of Example 6, was performed in the absence of sodium hydroxide and the pH of the reaction mixture was adjusted to ~8 after completion of the reaction. The reduction of the oxime, analogous to Part E of Example 6, was complete after running overnight. Prior to addition of the ammonium hydroxide in the step analogous to Part G of Example 6, the reaction mixture was cooled to 0° C. and para-toluenesulfonyl chloride (1.1 eq) was substituted for phenylsulfonyl chloride. The reaction was incomplete after an hour, and additional para-toluenesulfonyl chloride (0.5 eq) was added. After the final step in the sequence, purification by HPFC (0-30% CMA in chloroform), trituration from acetonitrile, filtration, and drying of the material in a vacuum oven at 80° C. afforded 77 mg of N-[4-(4-amino-2-propyl-1H-imidazo[4,5-c][1,5]naphthyridin-1-yl)1-methyl-butyl]-N-methoxyacetamide as an off-white powder, mp 158-159° C. Anal. calcd for C20H28N6O2: C, 62.48; H, 7.34; N, 21.86. Found: C, 62.19; H, 7.61; N, 22.09.

Example 23

1-[4-(4-Amino-6,7-dimethyl-2-propyl-1H-imidazo[4,5-c]pyridin-1-yl)butyl]-1-hydroxy-3-isopropylurea

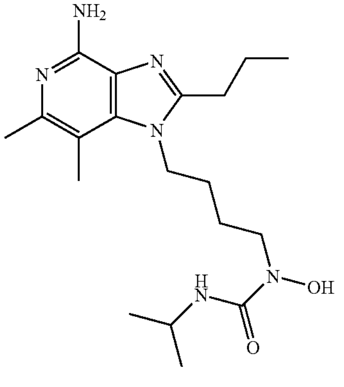 [SMILES: CCCc1nc2c(N)nc(C)c(C)c2n1CCCCN(O)C(=O)NC(C)C]

Part A

The preparation of tert-butyl 4-(4-amino-6,7-dimethyl-2-propyl-1H-imidazo[4,5-c]pyridin-1-yl)butyl[(tert-butoxycarbonyl)oxy]carbamate is described in Parts A-F of Example 14. A mixture of 4M hydrochloric acid in dioxane (2.25 mL, 9.0 mmol, 20 eq) was added to a solution of tert-butyl 4-(4-amino-6,7-dimethyl-2-propyl-1H-imidazo[4,5-c]pyridin-1-yl)butyl[(tert-butoxycarbonyl)oxy]carbamate (0.22 g, 0.45 mmol, 1 eq) in dichloromethane (5 mL) and stirred for 2 hours. The reaction mixture was concentrated under reduced pressure and the resulting white solid was concentrated from chloroform and dried under vacuum to provide N-[4-(4-amino-6,7-dimethyl-2-propyl-1H-imidazo[4,5-c]pyridin-1-yl)butyl]hydroxylamine.

Part B

Triethylamine (0.250 mL, 1.8 mmol) was added to a suspension of the material from Part A in dichloromethane (5 mL). Addition of dichloroethane (2 mL), DMF (0.5 mL), and additional triethylamine (0.250 mL) failed to provide a homogeneous mixture. The reaction mixture was cooled to −10° C. and isopropyl isocyanate (0.045 mL, 0.45 mmol) was added dropwise to the mixture, which was then allowed to slowly warm to between 0-5° C. while stirring over 1 hour. The reaction mixture was diluted with dichloromethane (20 mL) and saturated aqueous sodium bicarbonate (15 mL) and stirred vigorously and the phases were separated. The aqueous layer was extracted with dichloromethane (3×10 mL) and the combined organics were washed with saturated aqueous sodium bicarbonate (10 mL), dried over sodium sulfate, filtered, and concentrated under reduced pressure to produce a white solid. The material was triturated with acetonitrile, dried under high vacuum at 80° C. overnight, recrystallized from acetonitrile, sonicated for 1 minute, filtered, and washed with cold acetonitrile to afford 0.08 g of 1-[4-(4-amino-6,7-dimethyl-2-propyl-1H-imidazo[4,5-c]pyridine-1-yl]butyl-1-hydroxy-3-isopropylurea as a white powder, mp 138.5-140.0° C. Anal. Calcd for $C_{19}H_{32}N_6O_2$ C, 60.61; H, 8.57; N, 22.32. Found: C, 60.49; H, 8.80; N, 22.56.

Example 24

1-[4-(4-Amino-6,7-dimethyl-2-propyl-1H-imidazo[4,5-c]pyridine-1-yl)butyl]-1-hydroxy-3-phenylurea

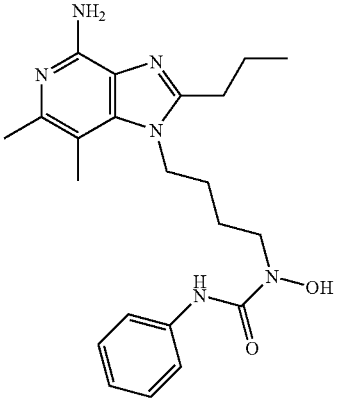 [SMILES: CCCc1nc2c(N)nc(C)c(C)c2n1CCCCN(O)C(=O)Nc1ccccc1]

A solution of 4N hydrochloric acid in dioxane (2.5 mL, 10.2 mmol, 20 eq) was added to a solution of tert-butyl 4-(4-amino-6,7-dimethyl-2-propyl-1H-imidazo[4,5-c]pyridin-1-yl)butyl[(tert-butoxycarbonyl)oxy]carbamate (250 mg, 0.51 mmol), prepared as described in Parts A-F of Example 14, and stirred for 1 hour at ambient temperature. Methanol (2 mL) was added to the reaction mixture, which was stirred overnight. The reaction mixture was concentrated under reduced pressure and the material was concentrated from methanol and chloroform and dried. The material was suspended in dichloromethane (5 mL) and triethylamine (0.71 mL, 5.1 mmol) and cooled to −5° C. Phenyl isocyanate (0.056 mL, 0.51 mmol) was added dropwise and the reaction mixture was slowly allowed to warm to ambient temperature. After two hours, the reaction mixture was diluted with dichloromethane (10 mL) and saturated aqueous sodium bicarbonate (5 mL) and stirred vigorously and the phases were separated. The aqueous layer was extracted with dichloromethane (2×10 mL) and the combined organics were washed with saturated aqueous sodium bicarbonate (10 mL), dried over sodium sulfate, filtered, and concentrated under reduced pressure to produce a white solid. The material was purified by HPFC (eluting with 5-30% CMA in chloroform), recrystallized from acetonitrile, triturated with ethyl acetate and dried at 80° C. under high vacuum to afford 60 mg of 1-[4-(4-amino-6,7-dimethyl-2-propyl-1H-imidazo[4,5-c]pyridine-1-yl)butyl]-1-hydroxy-3-phenyl-urea as a white powder, mp 159.0-160.5° C. Anal. Calcd for $C_{22}H_{30}N_6O_2$ C, 64.37; H, 7.37; N, 20.47. Found: C, 64.01; H, 7.20; N, 20.27.

Example 25

N-Hydroxy-N-[4-(4-amino-6,7-dimethyl-2-propyl-1H-imidazo[4,5-c]pyridin-1-yl)-butyl]benzamide

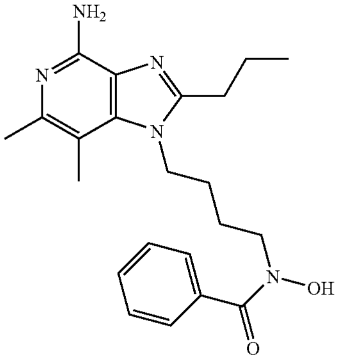 [SMILES: CCCc1nc2c(N)nc(C)c(C)c2n1CCCCN(O)C(=O)c1ccccc1]

The general method of Example 24 was followed with benzoyl chloride (0.059 mL) used in lieu of phenyl isocyanate. After the addition of benzoyl chloride, the reaction mixture was stirred overnight and cooled to −5° C. Additional portions of benzoyl chloride (0.002 and 0.005 mL) were added in one hour increments and after one additional hour, the work-up procedure of Example 24 was followed. Prior to purification, the crude material was dissolved in a potassium carbonate and methanol solution (10 mL, 0.5% weight/volume) and stirred. After 30 minutes, the reaction was diluted with water (5 mL) and the pH of the mixture was adjusted to 9 with 1N hydrochloric acid. The reaction mixture was concentrated under reduced pressure, diluted with chloroform (50 mL), washed with saturated aqueous sodium bicarbonate (2×10 mL), dried over sodium sulfate, filtered and concentrated under reduced pressure. The material was purified by BPFC (5-35% CMA in chloroform) and recrystallization from acetonitrile. The purification by HPFC and recrystallization were repeated to afford 0.043 g of N-hydroxy-N-[4-(4-amino-6,7-dimethyl-2-propyl-1H-imidazo[4,5-c]pyridin- 1-yl)butyl]benzamide as a white powder, mp 132.0-134.0° C. Anal. Calcd for $C_{22}H_{29}N_5O_2.0.5H_2O$ C, 65.32; H, 7.48; N, 17.31. Found: C, 65.45; H, 7.74; N, 17.47.

Example 26

N-[4-(4-Amino-6,7-dimethyl-2-propyl-1H-imidazo[4,5-c]pyridin-1-yl)butyl]-N-[tert-butyl-carbamate]-O-methylhydroxylamine

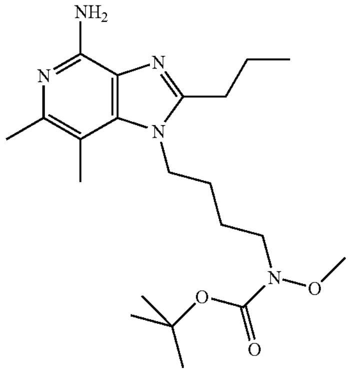

Sodium hydride (0.032 g, 0.81 mmol, 60% dispersion in mineral oil, 1 eq) was added to a solution of N-[(4-amino-6,7-dimethyl-2-propyl-1H-imidazo[4,5-c]pyridine-1-yl)-butyl]-N-[tert-butyl carbamate]hydroxylamnine (0.318 g, 0.81 mmol), prepared as described in Example 14, in DMF (8 mL) cooled to 0° C. The reaction mixture was stirred for 10 minutes and iodomethane (0.061 mL, 0.97 mmol) was added. After one hour of stirring, the reaction mixture was concentrated under reduced pressure and the residue was partitioned between chloroform (20 mL) and saturated aqueous sodium bicarbonate (10 mL). The aqueous layer was extracted with chloroform (2×10 mL) and the combined organics were dried over sodium sulfate, filtered, and concentrated under reduced pressure. The residue was purified by HPFC (2-40% CMA in chloroform), recrystallized from acetonitrile, and then dried under high vacuum at 90° C. for 3 hours to afford 0.258 g of N-[4-(4-amino-6,7-dimethyl-2-propyl-1H-imidazo[4,5-c]pyridin-1-yl)-butyl]-N-[tert-butyl-carbamate]-O-methylhydroxylamine as a white powder, mp 127.0-128.0° C. Anal. Calcd for $C_{21}H_{35}N_5O_3$ C, 62.20; H, 8.70; N, 17.27. Found: C, 62.21; H, 8.82; N, 17.30.

Example 27

N-Methoxy-N-[4-(4-amino-6,7-dimethyl-2-propyl-1H-imidazo[4,5-c]pyridin-1-yl)-butyl]benzamide

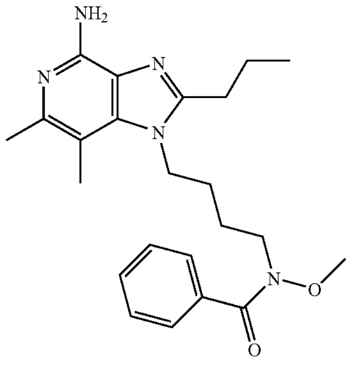

A solution of 4N hydrochloric acid in dioxane (2 mL, 7.8 mmol, 20 eq) was added to a solution of N-[4-(4-amino-6,7-dimethyl-2-propyl-imidazo[4,5-c]pyridin-1-yl)-butyl]-N-[tert-butyl carbamate]-O-methyl-hydroxylamine (160 mg, 0.39 mmol), prepared as described in Example 26, and stirred for 2 hours at ambient temperature. The reaction mixture was concentrated under reduced pressure and the material was washed with methanol and chloroform and concentrated under reduced pressure. The material was suspended in dichloromethane (4 mL) and triethylamine (0.54 mL, 3.9 mmol) and cooled to −5° C. Benzoyl chloride (0.045 mL, 0.39 mmol) was added dropwise and the reaction mixture was slowly allowed to warm to ambient temperature. After two hours, the reaction mixture was diluted with dichloromethane (20 mL) and washed with saturated aqueous sodium bicarbonate (3×5 mL), dried over sodium sulfate, filtered, and concentrated under reduced pressure to produce a white solid. The material was purified by HPFC (eluting with 2-30% CMA in chloroform), recrystallized from ethyl acetate, and dried at 100° C. under high vacuum to afford 32 mg of N-methoxy-N-[4-(4-amino-6,7-dimethyl-2-propyl-1H-imidazo[4,5-c]pyridin-1-yl)butyl]benzamide as a white powder, mp 136.0-137.0° C. Anal. Calcd for $C_{23}H_{31}N_5O_2$.0.25$H_2O$. C, 66.72; H, 7.67; N, 16.91. Found: C, 66.63; H, 7.63; N, 16.90.

Example 28

4-(4-Amino-2-butyl-1H-imidazo[4,5-c]quinolin-1-yl)-1-phenylbutan-1-one oxime

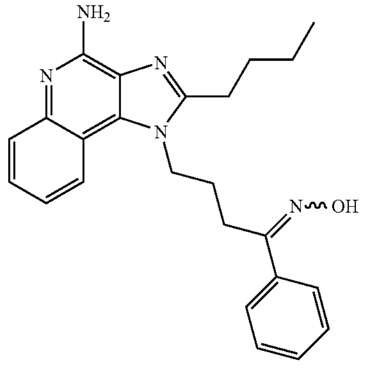 [SMILES: CCCCc1nc2c(N)nc3ccccc3c2n1CCCC(=NO)c1ccccc1]

Part A

To a stirred mixture of 4-chloro-3-nitroquinoline (100.0 g, 479 mmol) and triethylamine (72.8 g, 719 mmol) in dichloromethane (700 mL) was added dropwise 4-amino-1-butanol (42.7 g, 479 mmol). After the addition was complete, water (500 mL) was added to the reaction mixture to cause the product to precipitate. More water (2 L) was added, and the mixture was stirred overnight and then filtered. The organic solution was dried over sodium sulfate, concentrated under reduced pressure, and combined with the product isolated by filtration to provide 4-(3-nitroquinolin-ylamino)butan-1-ol (113 g) as a bright yellow solid.

Part B

To a stirred solution of 4-(3-nitroquinolin-4-ylamino)butan-1-ol (70.0 g, 268 mmol) and triethylamine (54.2 g, 536 mmol) in chloroform (900 mL) was added tert-butyldimethylsilyl chloride (TBDMSCl, 60.6 g, 402 mmol). After 3.5 hours, additional triethylamine (19.0 g, 188 mmol) and TBDMSCl (20.2 g, 134 mmol) were added and the mixture stirred overnight. After the addition of additional TBDMSCl (4.0 g, 27 mmol), the reaction was complete as judged by thin layer chromatography (TLC). Chloroform (900 mL) was added and the mixture washed successively with 360 mL each of a 0.10 N hydrochloric acid solution, a saturated aqueous sodium bicarbonate solution, and brine; dried over sodium sulfate; filtered; and solvent evaporated to leave a mixture of [4-(tert-butyldimethylsilanyloxy)butyl](3-nitro-quinolin-yl)amine and tert-butyldimethylsilanol (117 g total, about 65:35 mol:mol) which was used in the next step without further purification.

Part C

The mixture of [4-(tert-butyldimethylsilanyloxy)butyl](3-nitro-quinolin-4-yl)amine and tert-butyldimethylsilanol (110 g) from the previous step was dissolved in toluene (880 mL) and placed in a Parr hydrogenation vessel along with 5% platinum on carbon catalyst (3.0 g). The vessel was pressurized to 50 psi ($3.4\times10^5$ Pa) hydrogen and shaken on the Parr apparatus for 1.5 hours, occasionally adding additional hydrogen to maintain a pressure of 50 psi ($3.4\times10^5$ Pa). After 3 hours, the reaction mixture was filtered through CELITE filter agent and concentrated under reduced pressure to provide $N^4$-[4-(tert-butyldimethylsilanyloxy)butyl]quinoline-3,4-diamine as a dark oil that was used directly in the next step without further purification.

Part D

A solution of $N^4$-[4-(tert-butyldimethylsilanyloxy)butyl]quinoline-3,4-diamine (62.9 g, 182 mmol) and trimethyl orthovalerate (45.2 g, 278 mmol) in toluene (200 mL) was heated at reflux for 2 hours and then concentrated under reduced pressure to provide 2-butyl-1-[4-(tert-butyldimethylsilanyloxy)butyl]-1H-imidazo[4,5-c]quinoline as an oil that was used directly in the next step without further purification.

Part E

The 2-butyl-1-[4-(tert-butyldimethylsilanyloxy)butyl]-1H-imidazo[4,5-c]quinoline from the previous step and tetrabutylammonium fluoride (142 mL of a 1 M solution in tetrahydrofuran) were dissolved in tetrahydrofuran (THF) (400 mL) and stirred for 1 hour, then concentrated under reduced pressure to provide 4-(2-butyl-1H-imidazo[4,5-c]quinolin-1-yl)butan-1-ol (20.0 g) as a light brown solid after chromatography on silica gel (elution with 10% methanol in dichloromethane).

Part F

A solution of dimethyl sulfoxide (DMSO, 7.88 g, 101 mmol) in dichloromethane (130 mL) was cooled in a dry ice/acetone bath and stirred. Oxalyl chloride (9.40 g, 74 mmol) was added dropwise, followed by a solution of 4-(2-butyl-1H-imidazo[4,5-c]quinolin-1-yl)butan-1-ol (20.0 g, 67.3 mmol) in dichloromethane (320 mL). After five minutes triethylamine (20.42 g, 202 mmol) was added, and the mixture was allowed to warm to room temperature. After the addition of chloroform (500 mL), the mixture was washed successively with a saturated ammonium chloride solution (200 mL) and a saturated aqueous sodium bicarbonate solution (200 mL), dried over sodium sulfate, filtered, and concentrated to a dark solid. This solid was slurried in diethyl ether until a fine solid resulted. The product was filtered and dried to provide 4-(2-butyl-1H-imidazo[4,5-c]quinolin-1-yl)butyraldehyde (17.9 g) as a light brown solid.

Part G

To a stirred solution of 4-(2-butyl-1H-imidazo[4,5-c]quinolin-1-yl)butyraldehyde (8.0 g, 27.1 mmol) in anhydrous THF (270 mL) was added dropwise a solution of phenylmagnesium bromide (27.08 mL of a 1 M solution in THF). After 30 minutes, the solution was quenched with saturated ammonium chloride (100 mL), diluted with ethyl acetate (300 mL), and the layers separated. The organic solution was washed successively with a saturated aqueous sodium bicarbonate solution (100 mL) and brine (100 mL), dried over sodium sulfate, filtered, and concentrated to a light orange oil. Chromatography on silica gel (elution with 5% methanol in dichloromethane) provided 4-(2-butyl-1H-imidazo[4,5-c]quinolin-1-yl)-1-phenylbutan-1-ol (4.3 g) as a light orange, gummy solid.

Part H

A solution of DMSO (1.35 g, 17.3 mmol) in dichloromethane (22 mL) was cooled in a dry ice/acetone bath and stirred. Oxalyl chloride (1.61 g, 12.7 mmol) was added dropwise, followed by a solution of 4-(2-butyl-1H-imidazo[4,5-c]quinolin-1-yl)-1-phenylbutan-1-ol (4.3 g, 11.5 mmol) in dichloromethane (55 mL). After five minutes, triethylamine (3.49 g, 34.5 mmol) was added, and the mixture was allowed to warm to room temperature. After the addition of chloroform (300 mL), the mixture was washed successively with a saturated ammonium chloride solution (100 mL) and a saturated aqueous sodium bicarbonate solution (100 mL), dried over sodium sulfate, filtered, and concentrated to provide 4-(2-butyl-1H-imidazo[4,5-c]quinolin-1-yl)-1-phenylbutan-1-one (4.15 g) as an off-white solid.

Part I

To a stirred solution of 4-(2-butyl-1H-imidazo[4,5-c]quinolin-1-yl)-1-phenylbutan-1-one (4.15 g, 11.2 mmol) in chloroform (56 mL) was added 3-chloroperoxybenzoic acid (m-CPBA, approximately 77% purity, 2.75 g, 12.3 mmol) portionwise over a several minute period. After 1 hour, the reaction was not complete as judged by TLC, so an additional charge of m-CPBA (1.0 g) was added. After stirring for 30 minutes, the mixture was diluted with chloroform (200 mL), washed successively with a saturated aqueous sodium bicarbonate solution (2×100 mL) and brine (100 mL), dried over sodium sulfate, filtered, and concentrated to provide 4-(2-butyl-5-oxido-1H-imidazo[4,5-c]quinolin-1-yl)-1-phenylbutan-1-one as a dark oil that was used directly in the next step without further purification.

Part J

To a vigorously stirred mixture of the 4-(2-butyl-5-oxido-1H-imidazo[4,5-c]quinolin-1-yl)-1-phenylbutan-1-one from the previous step in dichloromethane (49 mL) and ammonium hydroxide (16 mL) was added p-toluenesulfonyl chloride (2.34 g, 12.3 mmol) portionwise over several minutes. After 15 minutes the reaction mixture was diluted with chloroform (200 mL) and saturated aqueous sodium bicarbonate solution (100 mL). The layers were separated and the organic phase was washed again with a saturated aqueous sodium bicarbonate solution (100 mL). The aqueous portions were then back extracted with chloroform (50 mL). The organics were combined, dried over sodium sulfate, filtered, and concentrated to a dark yellow solid. The dark yellow solid was slurried in diethyl ether and filtered to form a fine off-white solid. This solid was recrystallized from N,N-dimethylformamide (DMF) and water to afford 4-(4-amino-2-butyl-1H-imidazo[4,5-c]quinolin-1-yl)-1-phenylbutan-1-one as an off-white fluffy solid, mp 178-180° C.

MS (APCI) m/z 387 M+H)$^+$;

Anal. calcd for $C_{24}H_{26}N_4O$: C, 74.58; H, 6.78; N, 14.50. Found: C, 74.45; H, 6.77; N, 14.47.

Part K

By the general method described in Part F of Example 30, 4-(4-amino-2-butyl-1H-imidazo[4,5-c]quinolin-1-yl)-1-phenylbutan-1-one was reacted with hydroxylamine hydrochloride to provide 4-(4-amino-2-butyl-1H-imidazo[4,5-c]quinolin-1-yl)-1-phenylbutan-1-one oxime in about a 10 to 1 mixture of E and Z isomers as white crystals after recrystallization from methanol, mp 242-244° C.

MS (APCI) m/z 402 (M+H)$^+$;

Anal. calcd for $C_{24}H_{27}N_5O.0.45\ H_2O$: C, 70.39; H, 6.86; N, 17.10. Found: C, 70.18; H, 6.78; N, 16.83.

Example 29

4-(4-Amino-2-butyl-1H-imidazo[4,5-c]quinolin-1-yl)-1-phenylbutan-1-one O-methyloximie

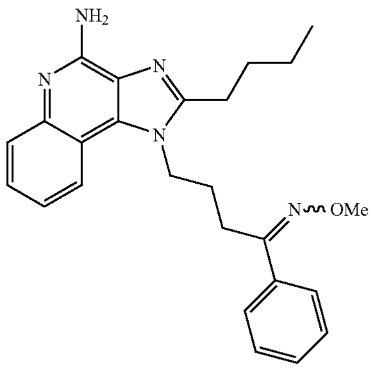 [SMILES: CCCCc1nc2c(N)nc3ccccc3c2n1CCCC(=NOC)c1ccccc1]

By the general method described in Part F of Example 30, 4-(4-amino-2-butyl-1H-imidazo[4,5-c]quinolin-1-yl)-1-phenylbutan-1-one was reacted with O-methylhydroxylamine hydrochloride to provide 4-(4-amino-2-butyl-1H-imidazo[4,5-c]quinolin-1-yl)-1-phenylbutan-1-one O-methyloxime) in about an 8.7 to 1 mixture of E and Z isomers as a yellow solid after recrystallization from methanol, mp 198-200° C.

MS (APCI) m/z 416 (M+H)$^+$;

Anal. calcd for $C_{25}H_{29}N_5O$: C, 72.26; H, 7.03; N, 16.85. Found: C, 72.12; H, 7.11; N, 16.72.

Example 30

5-(4-Amino-2-methyl-1H-imidazo[4,5-c]quinolin-1-yl)pentan-2-one oxime

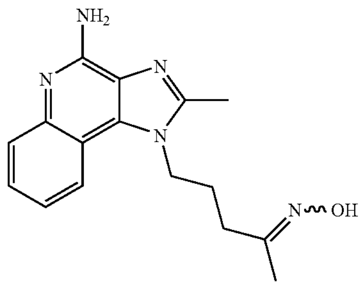 [SMILES: CC(CCCn1c(C)nc2c(N)nc3ccccc3c21)=NO]

Part A

The general method described in Part A of Example 28 was used to react 4-chloro-3-nitroquinoline (45.0 g, 216 mmol), 3-(2-methyl-[1,3]dioxolan-2-yl)propylamine (37.0 g, 255 mmol, prepared as described in PCT Publication WO 01/51486) and triethylamine (37.0 g, 366 mmol) in dichloromethane for 15 hours to provide [3-(2-methyl-[1,3]dioxolan-2-yl)propyl]-(3-nitroquinolin-4-yl)amine (44.1 g) as a yellow solid after recrystallization from a toluene/hexane mixture.

Part B

The product from the previous step, [3-(2-methyl-[1,3]dioxolan-2-yl)propyl](3-nitro-quinolin-4-yl)amine (29.5 g, 93.0 mmol), was stirred with sodium dithionite (67.0 g, approximately 85% pure), potassium carbonate (51.4 g, 372 mmol), and ethyl viologen dibromide (0.37 g, 1 mmol) in a mixture of dichloromethane and water (375 mL each) for 15 hours. The layers were then separated, and the organic phase was washed successively with a saturated aqueous sodium bicarbonate solution and water (250 mL each), dried over potassium carbonate, filtered, and concentrated under reduced pressure to provide $N^4$-[3-(2-methyl-[1,3]dioxolan-2-yl)-propyl]quinoline-3,4-diamine (26.0 g) as a dark solid that was used directly in the next step without further purification.

Part C

A solution of $N^4$-[3-(2-methyl-[1,3]dioxolan-2-yl)propyl]quinoline-3,4-diamine (6.20 g, 21.6 mmol), triethyl orthoacetate (3.10 g, 25.8 mmol) and pyridinium p-toluenesulfonate (0.18 g, 0.71 mmol) in toluene (250 mL) was heated at reflux under a Dean-Stark trap for 2 hours, periodically draining off the distillate and adding fresh toluene to the reaction mixture. The solution was concentrated under reduced pressure, and the residue was taken up in dichloromethane (150 mL), washed successively with a saturated aqueous sodium bicarbonate solution and water (100 mL each), dried over potassium carbonate, filtered, and concentrated under reduced pressure to provide 2-methyl-1-[3-(2-methyl-[1,3]dioxolan-2-yl)propyl]-1H-imidazo[4,5-c]quinoline (6.70 g) as a dark oil that was used directly in the next step without further purification.

Part D

The general method described in Parts I and J of Example 28 was used to aminate 2-methyl-1-[3-(2-methyl-[1,3]dioxolan-2-yl)propyl]-1H-imidazo[4,5-c]quinoline (6.70 g, 21.5 mmol) by reaction with m-CPBA (9.4 g) to provide 2-methyl-1-[3-(2-methyl-[1,3]dioxolan-2-yl)-propyl]-5-oxido-1H-imidazo[4,5-c]quinoline followed by reaction with p-toluenesulfonyl chloride (7.20 g, 37.8 mmol) and ammonium hydroxide solution (100 mL) to provide 2-methyl-1-[3-(2-methyl-[1,3]dioxolan-2-yl)propyl]-1H-imidazo[4,5-c]quinolin-4-amine (3.9 g) as an off-white solid after recrystallization from toluene, mp 193-195° C.

MS (APCI) m/z 327 $(M+H)^+$;

Anal. calcd for $C_{18}H_{22}N_4O_2$: C, 66.24; H, 6.79; N, 17.17. Found: C, 66.07; H, 6.58; N, 16.91.

Part E

Concentrated hydrochloric acid (3 mL) was added to 2-methyl-1-[3-(2-methyl-[1,3]dioxolan-2-yl)propyl]-1H-imidazo[4,5-c]quinolin-4-amine (1.0 g, 2.7 mmol), and the mixture stirred for a few minutes until everything was in solution. Water (5 mL) was then added and the solution stirred for one hour at room temperature. After the addition of dichloromethane (75 mL) and water (25 mL), the solution was made basic by the slow addition of potassium carbonate (10.0 g). The layers were separated, and the organic layer was washed with a saturated aqueous sodium bicarbonate solution (25 mL), dried over potassium carbonate, filtered, and concentrated under reduced pressure to provide 5-(4-amino-2-methyl-1H-imidazo[4,5-c]quinolin-1-yl)pentan-2-one, mp 194-196° C.

MS (APCI) m/z 283 $(M+H)^+$;

Anal. calcd for $C_{16}H_{18}N_4O.0.44\ H_2O$: C, 66.20; H. 6.56; N, 19.30. Found: C, 66.23; H, 6.52; N, 19.35.

Part F

A solution of 5-(4-amino-2-methyl-1H-imidazo[4,5-c]quinolin-1-yl)pentan-2-one, 2.20 g, 7.80 mmol) in ethanol (50 mL) was heated at reflux, and a solution of hydroxylamine hydochloride (1.08 g, 15.6 mmol) in water (10 mL) was added, followed by a solution of sodium hydroxide (0.94 g, 23.5 mmol) in water (10 mL). After 30 minutes, the reaction mixture was cooled in an ice bath to cause crystallization of the product, which was isolated by filtration and recrystallized from aqueous DMSO to provide 5-(4-amino-2-methyl-1H-imidazo[4,5-c]quinolin-1-yl)pentan-2-one oxime in about a 16 to 1 mixture of E and Z isomers as yellow crystals, mp 264-266° C.

MS (APCI) m/z 298 $(M+H)^+$;

Anal. calcd for $C_{16}H_{19}N_5O$: C, 64.63; H, 6.44; N, 23.55. Found: C, 64.39; H, 6.37; N, 23.17.

Example 31

5-(4-Amino-2-methyl-1H-imidazo[4,5-c]quinolin-1-yl)pentan-2-one O-benzyloxime

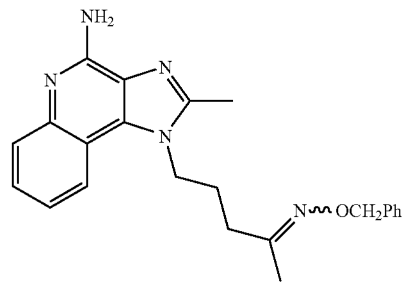

By the general method described in Part F of Example 30, 5-(4-amino-2-methyl-1H-imidazo[4,5-c]quinolin-1-yl)pentan-2-one was reacted with O-benzylhydroxylamine hydrochloride to provide 5-(4-amino-2-methyl-1H-imidazo[4,5-c]quinolin-1-yl)pentan-2-one O-benzyloxime) in about a 3 to 1 mixture of E and Z isomers as white crystals after recrystallization from a mixture of toluene and hexane, mp 146-148° C.

MS (APCI) m/z 388 $(M+H)^+$;

Anal. calcd for $C_{23}H_{25}N_5O$: C, 71.29; H, 6.50; N, 18.07. Found: C, 71.52; H, 6.60; N, 18.01.

Example 32

5-(4-Amino-2-methyl-1H-imidazo[4,5-c]quinolin-1-yl)pentan-2-one O-methyloxime

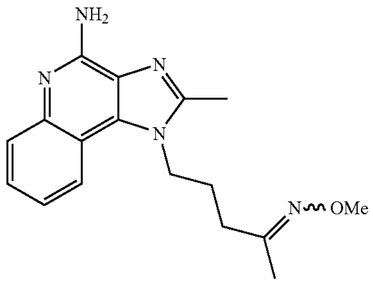 [SMILES: CON=C(C)CCCn1c(C)nc2c(N)nc3ccccc3c21]

By the general method described in Part F of Example 30, 5-(4-amino-2-methyl-1H-imidazo[4,5-c]quinolin-1-yl)pentan-2-one was reacted with O-methylhydroxylamine hydrochloride to provide 5-(4-amino-2-methyl-1H-imidazo[4,5-c]quinolin-1-yl)pentan-2-one O-methyloxime in about a 5.25 to 1 mixture of E and Z isomers as white needles after recrystallization from toluene, mp 158-161° C.

MS (APCI) m/z 312 $(M+H)^+$;

Anal. calcd for $C_{17}H_{21}N_5O$: C, 65.57; H, 6.80; N, 22.49. Found: C, 65.74; H, 6.90; N, 22.44.

Example 33

5-(4-Amino-2-butyl-1H-imidazo[4,5-c]quinolin-1-yl)pentan-2-one O-methyloxime

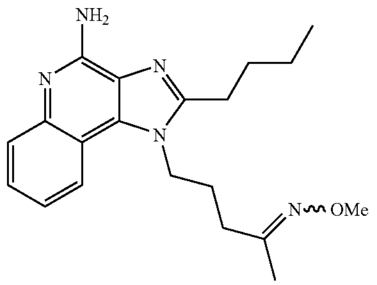 [SMILES: CCCCc1nc2c(N)nc3ccccc3c2n1CCCC(C)=NOC]

Parts A through F were carried out as described above in Example 28.

Part G

The general method described in Part G of Example 28 was used to react 4-(2-butyl-1H-imidazo[4,5-c]quinolin-1-yl)butyraldehyde (8.5 g, 28.8 mmol) with methylmagnesium bromide (20.6 mL of a 1.4 M solution in toluene/THF, 28.8 mmol) to provide 5-(2-butyl-1H-imidazo[4,5-c]quinolin-1-yl)pentan-2-ol (3.54 g) as an off-white solid after chromatography on silica gel (elution with 5% methanol in dichloromethane).

Part H

The general method described in Part H of Example 28 was used to oxidize 5-(2-butyl-1H-imidazo[4,5-c]quinolin-1-yl)pentan-2-ol (3.54 g, 11.4 mmol) with DMSO (1.33 g, 17.1 mmol), oxalyl chloride (1.59 g, 12.5 mmol), and triethylamine (3.45 g, 34.1 mmol) to provide 5-(2-butyl-1H-imidazo[4,5-c]quinolin-1-yl)pentan-2-one (2.15 g) as a dark solid.

Parts I and J

The general method described in Parts I and J of Example 28 was used to aminate 5-(2-butyl-1H-imidazo[4,5-c]quinolin-1-yl)pentan-2-one (2.15 g, 6.95 mmol) by reaction with m-CPBA (1.71 g, 7.64 mmol) to provide 5-(2-butyl-5-oxido-1H-imidazo[4,5-c]quinolin-1-yl)pentan-2-one followed by reaction with p-toluenesulfonyl chloride (1.46 g, 7.64 mmol) and ammonium hydroxide solution (10 mL) to provide 5-(4-amino-2-butyl-1H-imidazo[4,5-c]quinolin-1-yl)pentan-2-one as an off-white solid, mp 173-176° C.

MS (APCI) m/z 325 $(M+H)^+$;

Anal. calcd for $C_{19}H_{24}N_4O$: C, 70.34; H, 7.46; N, 17.27. Found: C, 70.24; H, 7.37; N, 17.25.

Part K

By the general method described in Part F of Example 30, 5-(4-amino-2-butyl-1H-imidazo[4,5-c]quinolin-1-yl)pentan-2-one was reacted with O-methylhydroxylamine hydrochloride to provide 5-(4-amino-2-butyl-1H-imidazo[4,5-c]quinolin-1-yl)pentan-2-one O-methyloxime in about a 7.9 to 1 mixture of E and Z isomers as light brown crystals after recrystallization from aqueous methanol, mp 157-159° C.

MS (APCI) m/z=354 $(M+H)^+$;

Anal. calcd for $C_{20}H_{27}N_5O$: C, 67.96; H, 7.69; N, 19.81. Found C, 67.79; H, 7.59; N, 19.55.

Example 34

5-(4-Amino-2-ethoxymethyl-1H-imidazo[4,5-c]quinolin-1-yl)pentan-2-one oxime

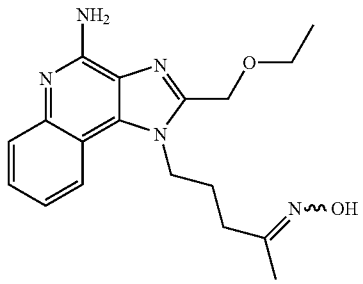 [SMILES: CCOCc1nc2c(N)nc3ccccc3c2n1CCCC(C)=NO]

Part A

By utilizing ethoxyacetyl chloride (1.1 equivalents) and triethylamine (1.1 equivalents) instead of triethyl orthoacetate and pyridinium p-toluenesulfonate in Part C of Example 30, 2-ethoxymethyl-1-[3-(2-methyl-[1,3]dioxolan-2-yl)propyl]-1H-imidazo[4,5-c]quinolin-4-amine was prepared, mp 150-152° C.

MS (APCI) m/z 371 $(M+H)^+$;

Anal. calcd for $C_{20}H_{26}N_4O_3$: C, 64.84; H, 7.07; N, 15.12. Found: C, 64.65; H, 7.13; N, 15.01.

Part B

By the general method described in Part E of Example 30, 2-ethoxymethyl-1-[3-(2-methyl-[1,3]dioxolan-2-yl)propyl]-1H-imidazo[4,5-c]quinolin-4-amine was hydrolyzed to 5-(4-amino-2-ethoxymethyl-1H-imidazo[4,5-c]quinolin-1-yl)pentan-2-one, mp 173-175° C.

MS (APCI) m/z 327 $(M+H)^+$;

Anal. calcd for $C_{18}H_{22}N_4O_2$: C, 66.24; H, 6.79; N, 17.17. Found: C, 66.05; H, 6.94; N, 16.89.

Part C

By the general method described in Part F of Example 30, 5-(4-amino-2-ethoxymethyl-1H-imidazo[4,5-c]quinolin-1-yl)pentan-2-one was reacted with hydroxylamine hydrochloride to provide 5-(4-amino-2-ethoxymethyl-1H-imidazo[4,5-c]quinolin-1-yl)pentan-2-one oxime in about a 3.5 to 1 mixture of E and Z isomers as a white solid after recrystallization from a mixture of toluene and methanol, mp 220-223° C.

MS (APCI) m/z 342 $(M+H)^+$;

Anal. calcd for $C_{18}H_{23}N_5O_2$: C, 63.32; H, 6.79; N, 20.51. Found: C, 63.23; H, 6.91; N, 20.57.

Example 35

5-(4-Amino-2-ethoxymethyl-1H-imidazo[4,5-c]quinolin-1-yl)pentan-2-one O-methyloxime hydrochloride

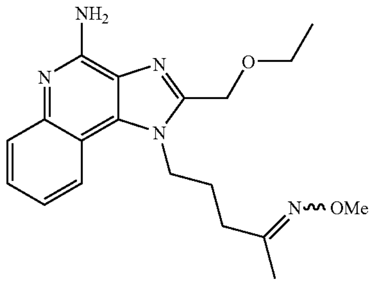 [SMILES: CCOCc1nc2c(N)nc3ccccc3c2n1CCCC(C)=NOC]

By the general method described in Part F of Example 30, 5-(4-amino-2-ethoxymethyl-1H-imidazo[4,5-c]quinolin-1-yl)pentan-2-one was reacted with O-methylhydroxylamine hydrochloride. The product was dissolved a mixture of ethanol and diethyl ether, and a solution of hydrogen chloride (1 equivalent of a 1.0 M solution in diethyl ether) was added. A precipitate formed, and the solvents were removed under reduced pressure. The resulting solid was recrystallized from a mixture of ethanol and diethyl ether to provide 5-(4-amino-2-ethoxymethyl-1H-imidazo[4,5-c]quinolin-1-yl)pentan-2-one O-methyloxime hydrochloride in about a 6.4 to 1 mixture of E and Z isomers as a white solid, mp 189-192° C.

MS (APCI) m/z 356 $(M+H)^+$;

Anal. calcd for $C_{19}H_{25}N_5O_2$.HCl: C, 58.23; H, 6.69; N, 17.87; Cl, 9.05. Found: C, 58.24; H, 6.88; N, 17.84; Cl, 8.88.

Example 36

5-(4-Amino-2-ethoxymethyl-1H-imidazo[4,5-c]quinolin-1-yl)pentan-2-one O-benzyloxime hydrochloride

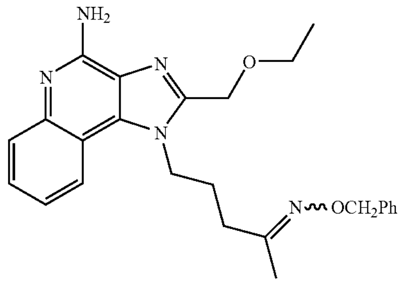

By the general methods described in Example 35, 5-(4-amino-2-ethoxymethyl-1H-imidazo[4,5-c]quinolin-1-yl)pentan-2-one was reacted with O-benzylhydroxylamine hydrochloride to provide 5-(4-amino-2-ethoxymethyl-1H-imidazo[4,5-c]quinolin-1-yl)pentan-2-one O-benzyloxime hydrochloride in about a 16 to 1 mixture of E and Z isomers as a white solid after recrystallization of the hydrochloride salt from a mixture of toluene and methanol, mp 184-186° C.

MS (APCI) m/z 432 $(M+H)^+$;

Anal. calcd for $C_{25}H_{29}N_5O_2$.HCl: C, 64.16; H, 6.46; N, 14.96; Cl, 7.58. Found: C, 64.09; H, 6.26; N, 15.01; Cl, 7.64.

Example 37

1-(4-Amino-2-propyl-1H-imidazo[4,5-c]quinolin-1-yl)-6-methylheptan-4-one oxime

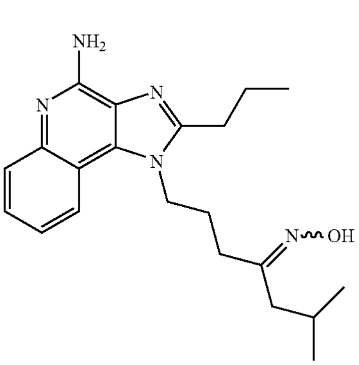 [SMILES: CCCc1nc2c(N)nc3ccccc3c2n1CCCC(CC(C)C)=NO]

Part A

The general method described in Part A of Example 28 was used to react 4-chloro-3-nitroquinoline (49.6 g, 238 mmol), ethyl 4-aminobutyrate hydrochloride (43.8 g, 262 mmol), and triethylamine (36.1 g, 357 mmol) in dichloromethane for 15 hours to provide ethyl 4-(3-nitroquinolin-4-ylamino)butyrate (63.8 g) as a yellow solid that was used directly in the next step without further purification.

Part B

The general method described in Part B of Example 30 was used to reduce ethyl 4-(3-nitroquinolin-4-ylamino)butyrate (37.0 g, 122 mmol) to provide ethyl 4-(3-aminoquinolin-4-ylamino)butyrate (24.9 g) as a dark oil that was used directly in the next step without further purification.

Part C

The general method described in Part C of Example 30 was used to cyclize ethyl 4-(3-aminoquinolin-4-ylamino)butyrate (18.0 g, 65.9 mmol) by reaction with trimethyl orthobutyrate (10.4 g, 70.2 mmol) to provide ethyl 4-(2-propyl-1H-imidazo[4,5-c]quinolin-1-yl)butyrate (14.2 g) as a solid after chromatography on silica gel (elution with 5% methanol in dichloromethane).

Part D

A solution of trimethylaluminum in toluene (80 mL of a 2 M solution, 160 mmol) was added dropwise to a stirred suspension of N,O-dimethylhydroxylamine hydrochloride (15.6 g, 160 mmol) in dichloromethane (150 mL) at 0° C. After 15 minutes, the reaction flask was removed from bath and the solution stirred for 15 minutes at room temperature. The flask was then cooled in ice bath, and a solution of ethyl 4-(2-propyl-1H-imidazo[4,5-c]quinolin-1-yl)butyrate (34.7 g, 107 mmol) in dichloromethane (100 mL) was added rapidly dropwise. After 15 minutes, the ice bath was removed and the solution heated at reflux to cause considerable gas evolution. After 20 hours, a 10% solution of hydrochloric acid in water (15 mL) was added slowly, followed by a saturated solution of sodium bicarbonate in water (50 mL). The layers were separated, and the aqueous mixture was extracted with dichloromethane (2×50 mL). The combined organic solutions were washed successively with a 5% solution of sodium hydroxide in water (2×50 mL) and a saturated solution of sodium bicarbonate in water (1×50 mL), dried over potassium carbonate, filtered, and concentrated under reduced pressure to provide N-methoxy-N-methyl-4-(2-propyl-1H-imidazo[4,5-c]quinolin-1-yl)butyramide (35.9 g) as a dark oil that was used directly in the next step without further purification.

Part E

To a stirred solution of N-methoxy-N-methyl-4-(2-propyl-1H-imidazo[4,5-c]quinolin-1-yl)butyramide (4.80 g, 14.1 mmol) in THF (100 mL) in a dry ice/isopropanol bath was added a solution of isobutylmagnesium chloride (28 mL of a 2 M solution in diethyl ether, 56 mmol) over a period of several minutes. When addition was complete, the reaction flask was removed from the cold bath and the mixture stirred for 4 hours at room temperature. A 10% solution of hydrochloric acid in water (3 mL) was added slowly, followed by a saturated solution of sodium bicarbonate in water (15 mL) and dichloromethane (100 mL). The layers were separated, the aqueous phase extracted with dichloromethane (1×75 mL), and the combined organics dried over potassium carbonate, filtered, and concentrated under reduced pressure. After chromatography on silica gel (elution with 5% methanol in dichloromethane) 6-methyl-1-(2-propyl-1H-imidazo[4,5-c]quinolin-1-yl)heptan-4-one (2.40 g) was obtained as an oil.

Part F

The general method described in Parts I and J of Example 28 was used to aminate 6-methyl-1-(2-propyl-1H-imidazo[4, 5-c]quinolin-1-yl)heptan-4-one (2.40 g, 7.10 mmol) by reaction with m-CPBA (3.9 g) to provide 6-methyl-1-(5-oxido-2-propyl-1H-imidazo[4,5-c]quinolin-1-yl)heptan-4-one followed by reaction with p-toluenesulfonyl chloride (2.0 g, 10.5 mmol) and ammonium hydroxide solution (75 mL) to provide 1-(4-amino-2-propyl-1H-imidazo[4,5-c]quinolin-1-yl)-6-methylheptan-4-one as tan crystals after recrystallization from aqueous methanol, mp 136-138° C.

MS (APCI) m/z 353 $(M+H)^+$;

Anal. calcd for $C_{21}H_{28}N_4O$: C, 71.56; H, 8.01; N, 15.90. Found: C, 71.33; H, 8.09; N. 15.69.

Part G

By the general method described in Part F of Example 30, 1-(4-amino-2-propyl-1H-imidazo[4,5-c]quinolin-1-yl)-6-methylheptan-4-one was reacted with hydroxylamine hydrochloride to provide 1-(4-amino-2-propyl-1H-imidazo[4,5-c]quinolin-1-yl)-6-methylheptan-4-one oxime in about a 5 to 1 mixture of E and Z isomers as a white solid after recrystallization from aqueous methanol, mp 207-209° C.

MS (APCI) m/z 368 $(M+H)^+$;

Anal. calcd for $C_{21}H_{29}N_5O$: C, 68.63; H, 7.95; N, 19.06. Found: C, 68.32; H, 7.72; N, 18.80.

Example 38

1-(4-Amino-2-propyl-1H-imidazo[4,5-c]quinolin-1-yl)decan-4-one oxime

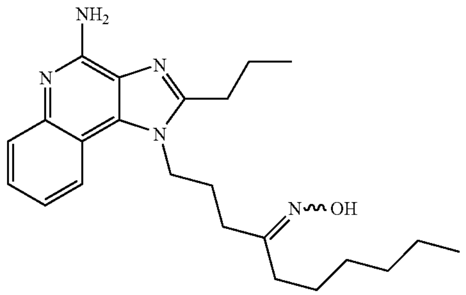 [SMILES: CCCCCCC(CCCn1c(CCC)nc2c(N)nc3ccccc3c21)=NO]

Parts A through D

The general method described in Parts A through D of Example 37 was used to prepare N-methoxy-N-methyl-4-(2-propyl-1H-imidazo[4,5-c]quinolin-1-yl)butyramide.

Part E

The general method described in Part E of Example 37 was used to react N-methoxy-N-methyl-4-(2-propyl-1H-imidazo[4,5-c]quinolin-1-yl)butyramide (6.10 g, 17.9 mmol) with n-hexylmagnesium bromide (13.5 mL of a 2 M solution in diethyl ether, 27 mmol) to provide 1-(2-propyl-1H-imidazo[4,5-c]quinolin-1-yl)decan-4-one (6.10 g) as a yellow oil that was used directly in the next step without further purification.

Part F

The general method described in Parts I and J of Example 28 was used to aminate 1-(2-propyl-1H-imidazo[4,5-c]quinolin-1-yl)decan-4-one (6.10 g, 17.2 mmol) by reaction with m-CPBA (8.50 g) to provide 1-(5-oxido-2-propyl-1H-imidazo[4,5-c]quinolin-1-yl)decan-4-one followed by reaction with p-toluenesulfonyl chloride (4.90 g, 25.8 mmol) and ammonium hydroxide solution (100 mL) to provide 1-(4-amino-2-propyl-1H-imidazo[4,5-c]quinolin-1-yl)decan-4-one) as a white solid after recrystallization from aqueous methanol, mp 111-113° C.

MS (APCI) m/z 381 $(M+M)^+$;

Anal. calcd for $C_{23}H_{32}N_4O$: C, 72.59; H, 8.48; N, 14.72. Found: C, 72.53; H, 8.59; N, 14.63.

Part G

By the general method described in Part F of Example 30, 1-(4-amino-2-propyl-1H-imidazo[4,5-c]quinolin-1-yl)decan-4-one was reacted with hydroxylamine hydrochloride to provide 1-(4-amino-2-propyl-1H-imidazo[4,5-c]quinolin-1-yl)decan-4-one oxime in about a 1 to 1 mixture of E and Z isomers as a white solid after recrystallization from aqueous methanol, mp 113-115° C.

MS (APCI) m/z 396 $(M+H)^+$;

Anal. calcd for $C_{23}H_{33}N_5O$: C, 69.84; H, 8.41; N, 17.71. Found: C, 69.65; H, 8.28; N, 17.42.

Example 39

5-(4-Amino-2-methyl-1H-imidazo[4,5-c]quinolin-1-yl)-4,4-dimethylpentan-2-one O-methyl-oxime

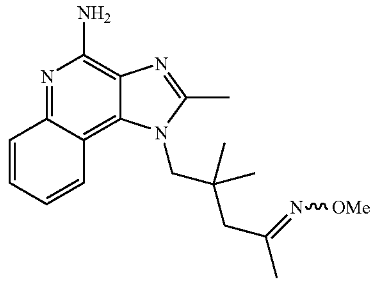 [SMILES: CON=C(C)CC(C)(C)Cn1c(C)nc2c(N)nc3ccccc3c21]

Part A

A mixture of nitro methane (36.3 g, 0.59 mol), mesityl oxide (53.0 g, 0.54 mol), and 1,5-diazabicyclo[5.4.0]undec7-ene (DBU, 1.5 g, 10 mmol) was allowed to stand at room temperature for 14 days. Dichloromethane (150 mL) was then added, and the solution was washed with a 10% hydrochloric acid solution (3×35 mL), dried over potassium carbonate, and filtered. The dichloromethane solution of 4,4-dimethyl-5-nitropentan-2-one was used directly in the next step without further purification.

Part B

A stirred solution of 1,2-bis(trimethylsilyloxy)ethane (26.5 g, 128 mmol) in dichloromethane (50 mL) was cooled in a dry ice/isopropanol bath, and trimethylsilyl trifluoromethanesulfonate (2.2 g, 1.0 mmol) was added, followed by the dichloromethane solution of 4,4-dimethyl-5-nitropentan-2-one (50 mL, 19.0 g, 119 mmol) from the previous step. After 30 minutes, the cooling bath was removed and the solution was allowed to warm to room temperature. The solution was filtered through a plug of potassium carbonate and concentrated under reduced pressure to provide 2-(2,2-dimethyl-3-nitropropyl)-2-methyl-[1,3]dioxolane (23.5 g) as a dark oil that was used directly in the next step without further purification.

Part C

A Parr hydrogenation vessel was charged with 2-(2,2-dimethyl-3-nitropropyl)-2-methyl-[1,3]dioxolane (23.1 g, 113 mmol), 5% platinum on carbon catalyst (3.0 g) and ethanol (250 mL); placed on a Parr shaker; and the system pressurized to 50 psi ($3.4\times10^5$ Pa) hydrogen. After shaking for 24 hours, the reaction mixture was filtered through CELITE filter agent and concentrated under reduced pressure to provide 2,2-dimethyl-3-(2-methyl-[1,3]dioxolan-2-yl)propylamine (19.8 g) as an oil that was used directly in the next step without further purification.

Part D

The general method described in Part A of Example 28 was used to react 4-chloro-3-nitroquinoline (21.8 g, 104 mmol), 2,2-dimethyl-3-(2-methyl-[1,3]dioxolan-2-yl)propylamine (19.8 g, 114 mmol) and triethylamine (15.2 g, 150 mmol) in dichloromethane for 75 hours to provide [2,2-dimethyl-3-(2-methyl-[1,3]dioxolan-2-yl)propyl]-(3-nitroquinolin-4-yl) amine (35.9 g) as a yellow solid that was used directly in the next step without further purification.

Part E

The general method described in Part B of Example 30 was used to reduce [2,2-dimethyl-3-(2-methyl-[1,3]dioxolan-2-yl)propyl]-(3-nitroquinolin-4-yl)amine (35.9 g, 104 mmol) to provide $N^4$-[2,2-dimethyl-3-(2-methyl-[1,3]dioxolan-2-yl)propyl]quinoline-3,4-diamine (25.2 g) as a dark oil that was used directly in the next step without further purification.

Part F

The general method described in Part C of Example 30 was used to cyclize $N^4$-[2,2-dimethyl-3-(2-methyl-[1,3]dioxolan-2-yl)propyl]quinoline-3,4-diamine (8.0 g, 25.4 mmol) by reaction with trimethyl orthoacetate (3.6 g, 30 mmol) to provide 1-[2,2-dimethyl-3-(2-methyl-[1,3]dioxolan-2-yl)propyl]-2-methyl-1H-imidazo[4,5-c]quinoline (5.80 g) as a solid after chromatography on silica gel (elution with a solution of 7% methanol in dichloromethane that contained about 5 mL of ammonium hydroxide solution per liter of eluent).

Part G

The general method described in Parts I and J of Example 28 was used to aminate 1-[2,2-dimethyl-3-(2-methyl-[1,3]dioxolan-2-yl)propyl]-2-methyl-1H-imidazo[4,5-c]quinoline (5.80 g, 17.1 mmol) by reaction with m-CPBA (7.5 g) to provide 1-[2,2-dimethyl-3-(2-methyl-[1,3]dioxolan-2-yl)propyl]-2-methyl-5-oxido-1H-imidazo[4,5-c]quinoline followed by reaction with p-toluenesulfonyl chloride (5.7 g, 30 mmol) and ammonium hydroxide solution (150 mL) to provide 1-[2,2-dimethyl-3-(2-methyl-[1,3]dioxolan-2-yl)propyl]-2-methyl-1H-imidazo[4,5-c]quinolin-4-amine as a light brown solid after recrystallization from a mixture of acetonitrile, methanol, and water, mp 209-211° C.

MS (APCI) m/z 355 $(M+H)^+$;

Anal. calcd for $C_{20}H_{26}N_4O_2$: C, 67.77; H, 7.39; N, 15.81. Found: C, 67.68; H, 7.62; N, 15.87.

Part H

By the general method of Part E of Example 30, 1-[2,2-dimethyl-3-(2-methyl-[1,3]dioxolan-2-yl)propyl]-2-methyl-1H-imidazo[4,5-c]quinolin-4-amine was hydrolyzed with aqueous hydrochloric acid to provide 5-(4-amino-2-methyl-1H-imidazo[4,5-c]quinolin-1-yl)-4,4-dimethylpentan-2-one as a light brown solid after recrystallization from aqueous acetonitrile, mp 223-225° C.

MS (APCI) m/z 311 $(M+H)^+$;

Anal. calcd for $C_{18}H_{22}N_4O$: C, 69.65; H, 7.14; N, 18.05. Found: C, 69.64; H, 7.42; N, 18.04.

Part I

By the general method described in Part F Example 30, 5-(4-amino-2-methyl-1H-imidazo[4,5-c]quinolin-1-yl)-4,4-dimethylpentan-2-one was reacted with O-methylhydroxylamine hydrochloride to provide 5-(4-amino-2-methyl-1H-imidazo[4,5-c]quinolin-1-yl)-4,4-dimethylpentan-2-one O-methyloxime as about a 4.9 to 1 mixture of E and Z isomers as light yellow needles after recrystallization from aqueous methanol, mp 193-195° C.

MS (APCI) m/z 340 $(M+M)^+$;

Anal. calcd for $C_{19}H_{25}N_5O$: C, 67.23; H, 7.42; N, 20.63. Found: C, 66.99; H, 7.64; N, 20.50.

Example 40

5-(4-Amino-2-propyl-1H-imidazo[4,5-c]quinolin-1-yl)-4,4-dimethylpentan-2-one O-methyloxime

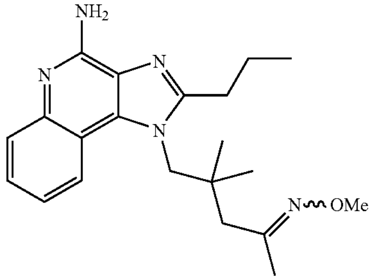 [SMILES: CCCc1nc2c(N)nc3ccccc3c2n1CC(C)(C)CC(C)=NOC]

Parts A through E were the same as described for Example 39.

Part F

The general method described in Part F of Example 39 was used to cyclize $N^4$-[2,2-dimethyl-3-(2-methyl-[1,3]dioxolan-2-yl)propyl]quinoline-3,4-diamine (9.1 g, 28.9 mmol) by reaction with trimethyl orthobutyrate (4.4 g, 30 mmol) to provide 1-[2,2-dimethyl-3-(2-methyl-[1,3]dioxolan-2-yl) propyl]-2-propyl-1H-imidazo[4,5-c]quinoline (3.10 g) as a solid after chromatography on silica gel (elution with a solution of 7% methanol in dichloromethane that contained about 5 mL of ammonium hydroxide solution per liter of eluent).

Part G

The general method described in Parts I and J of Example 28 was used to aminate 1-[2,2-dimethyl-3-(2-methyl-[1,3]dioxolan-2-yl)propyl]-2-propyl-1H-imidazo[4,5-c]quinoline (3.10 g, 8.44 mmol) by reaction with m-CPBA (3.70 g) to provide 1-[2,2-dimethyl-3-(2-methyl-[1,3]dioxolan-2-yl) propyl]-5-oxido-2-propyl-1H-imidazo[4,5-c]quinoline followed by reaction with p-toluenesulfonyl chloride (2.80 g, 14.7 mmol) and ammonium hydroxide solution (100 mL) to provide 1-[2,2-dimethyl-3-(2-methyl-[1,3]dioxolan-2-yl) propyl]-2-propyl-1H-imidazo[4,5-c]quinolin-4-amine as off-white needles after recrystallization from aqueous methanol, mp 186-188° C.

MS (APCI) m/z 383 $(M+H)^+$;

Anal. calcd for $C_{22}H_{30}N_4O_2$: C, 69.08; H, 7.91; N, 14.65. Found: C, 69.03; H, 8.15; N, 14.60.

Part H

By the general method of Part E of Example 30, 1-[2,2-dimethyl-3-(2-methyl-[1,3]dioxolan-2-yl)propyl]-2-propyl-1H-imidazo[4,5-c]quinolin-4-amine was hydrolyzed with aqueous hydrochloric acid to provide 5-(4-amino-2-propyl-1H-imidazo[4,5-c]quinolin-1-yl)-4,4-dimethylpentan-2-one as a light brown solid after recrystallization from aqueous acetonitrile, mp 178-180° C.

MS (APCI) m/z 339 $(M+H)^+$;

Anal. calcd for $C_{20}H_{26}N_4O$: C, 70.97; H, 7.74; N, 16.55. Found: C, 70.80; H, 7.89; N, 16.66.

Part I

By the general method of Part F in Example 30, 5-(4-amino-2-propyl-1H-imidazo[4,5-c]quinolin-1-yl)-4,4-dimethylpentan-2-one was reacted with O-methylhydroxylamine hydrochloride to provide 5-(4-amino-2-propyl-1H-imidazo [4,5-c]quinolin-1-yl)-4,4-dimethylpentan-2-one O-methyloxime as about a 49 to 1 mixture of E and Z isomers as a yellow solid after recrystallization from aqueous methanol, mp 196-198° C. MS (APCI) m/z 368 $(M+H)^+$; Anal. calcd for $C_{21}H_{29}N_5O$: C, 68.63; H, 7.95; N, 19.06. Found: C, 68.69; H, 7.66; N, 19.04.

Example 41

5-(4-Amino-1H-imidazo[4,5-c]quinolin-1-yl)-4,4-dimethylpentan-2-one O-methyloxime

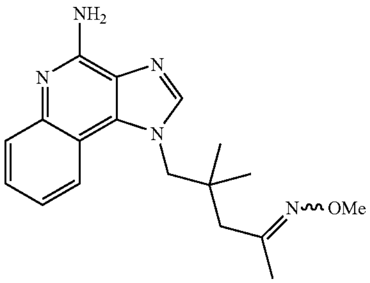 [SMILES: CON=C(C)CC(C)(C)Cn1cnc2c(N)nc3ccccc3c21]

Parts A through E were the same as described for Example 39.

Part F

The general method described in Part C of Example 30 was used to cyclize N-[2,2-dimethyl-3-(2-methyl-[1,3]dioxolan-2-yl)propyl]quinoline-3,4-diamine (8.1 g, 25.7 mmol) by reaction with trimethyl orthoformate (3.3 g, 10 mmol) to provide 1-[2,2-dimethyl-3-(2-methyl[1,3]dioxolan-2-yl)propyl]-1H-imidazo[4,5-c]quinoline (8.8 g) as an oil that was used directly in the next step without further purification.

Part G

The general method described in Parts I and J of Example 28 was used to aminate 1-[2,2-dimethyl-3-(2-methyl[1,3]dioxolan-2-yl)propyl]-1H-imidazo[4,5-c]quinoline (8.8 g, 27 mmol) by reaction with m-CPBA (11.8 g) to provide 1-[2,2-dimethyl-3-(2-methyl-[1,3]dioxolan-2-yl)propyl]-5-oxido-1H-imidazo[4,5-c]quinoline followed by reaction with p-toluenesulfonyl chloride (9.1 g, 48 mmol) and ammonium hydroxide solution (100 mL) to provide 1-[2,2-dimethyl-3-(2-methyl[1,3]dioxolan-2-yl)propyl]-1H-imidazo[4,5-c]quinolin-4-amine as a light brown solid after chromatography on silica gel (elution with a solution of 7% methanol in dichloromethane that contained about 5 mL of ammonium hydroxide solution per liter of eluent) and recrystallization from aqueous methanol, mp 153-155° C.

MS (APCI) m/z 341 $(M+H)^+$;

Anal. calcd for $C_{19}H_{24}N_4O_2$: C, 67.04; H, 7.11; N, 16.46. Found: C, 66.76; H, 7.39; N, 16.41.

Part H

By the general method described in Part F of Example 30, 5-(4-amino-1H-imidazo[4,5-c]quinolin-1-yl)-4,4-dimethylpentan-2-one was reacted with O-methylhydroxylamine hydrochloride to provide 5-(4-amino-1H-imidazo[4,5-c]quinolin-1-yl)-4,4-dimethylpentan-2-one O-methyloxime as about a 2.9 to 1 mixture of E and Z isomers as a tan solid after recrystallization from aqueous methanol, mp 148-150° C.

MS (APCI) m/z 326 $(M+H)^+$;

Anal. calcd for $C_{18}H_{23}N_5O$: C, 66.44; H, 7.12; N, 21.52. Found: C, 66.58; H, 7.12; N, 21.48.

Example 42

(1E,Z)-4-(4-amino-2-butyl-1H-imidazo[4,5-c]quinolin-1-yl)butanal O-methyloxime

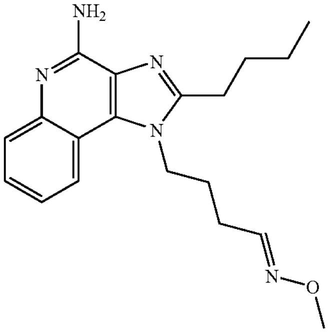 [SMILES: CCCCc1nc2c(N)nc3ccccc3c2n1CCC/C=N/OC]

Under a nitrogen atmosphere, a mixture of 4-(4-amino-2-butyl-1H-imidazo[4,5-c]quinolin-1-yl)butanal (0.6 g, 1.9 mmol, 1.0 eq), methoxylamine hydrochloride (0.33 g, 2.0 eq), pyridine (0.6 g, 4.0 eq), and methanol (25 mL) was refluxed overnight. The reaction mixture was concentrated under reduced pressure. The residue was dissolved in dichloromethane, washed sequentially with 10% aqueous sodium carbonate (×2) and brine, dried and concentrated under reduced pressure. The residue was purified by column chromatography on silica gel followed by recrystallization from ethyl acetate (10 mLs/g) to provide 0.15 g of (1E,Z)-4(4-amino-2-butyl-1H-imidazo[4,5-c]quinolin-1-yl)butanal O-methyloxime, mp 153.0-155.0° C. Analysis by H NMR showed both cis and trans isomers. Anal. calcd for $C_{19}H_{25}N_5O$: C, 67.23; H, 7.42; N, 20.63. Found: C, 66.97; H, 7.38; N, 20.46.

Example 43

N-[4-(4-Amino-2-propyl-1H-imidazo[4,5-c]quinolin-1-yl)butyl]-N-hydroxyacetamide

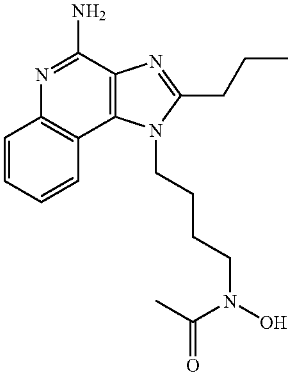 [SMILES: CCCc1nc2c(N)nc3ccccc3c2n1CCCCN(O)C(C)=O]

Part A

Sodium borohydride (2.28 g, 60.4 mmol) was added to a solution of 4-(2-propyl-1H-imidazo[4,5-c]quinolin-1-yl)butyraldehyde (prepared as described in Parts A-C of Example 6, 17.0 g, 60.4 mmol) in ethanol (200 mL). The reaction mixture was stirred for 2 hours, then saturated aqueous sodium bicarbonate was added. The ethanol was removed under reduced pressure and the mixture was extracted with dichloromethane. The organic layer was washed with saturated aqueous sodium bicarbonate and brine, dried over magnesium sulfate, filtered, and concentrated under reduced pressure to yield 15.7 g of 4-(2-propyl-1H-imidazo[4,5-c]quinolin-1-yl)butan-1-ol as a yellow oil.

Part B

Triphenylphosphine (6.67 g, 25.5 mmol), tert-butyl N-(tert-butoxycarbonyloxy)carbamate (5.94 g, 25.5 mmol), and diisopropyl azodicarboxylate (5.00 mL, 25.5 mmol) were added to a solution of 4-(2-propyl-1H-imidazo[4,5-c]quinolin-1-yl)butan-1-ol (6.56 g, 23.2 mmol) in DMF (100 mL). The reaction mixture was stirred overnight at room temperature, then was concentrated under reduced pressure. The residue was partitioned between dichloromethane and saturated aqueous sodium bicarbonate. The organic layer was washed with brine, dried over magnesium sulfate, filtered, and concentrated to provide 9.5 g of N-[(tert-butoxycarbonyl)oxy]-2,2-dimethyl-N-[4-(2-propyl-1H-imidazo[4,5-c]quinolin-1-yl)butyl]propanamide, which was used without purification in the next step.

Part C mCPBA (75% purity, 4.03 g, 17.5 mmol) was added to a solution of N-[(tert-butoxycarbonyl)oxy]-2,2-dimethyl-N-[4-(2-propyl-1H-imidazo[4,5-c]quinolin-1-yl)butyl]propanamide (5.00 g, 10.0 mmol) in chloroform (975 mL). The reaction mixture was stirred at room temperature for 1.5 hours. The mixture was cooled to 0° C. and concentrated ammonium hydroxide (20 mL) was added, followed by benzene sulfonyl chloride (2.49 mL, 19.5 mmol). The reaction mixture was stirred for 2 hours at room temperature, then was transferred to a separatory funnel. The layers were separated and the organic layer was washed with saturated aqueous sodium bicarbonate and brine, dried over magnesium sulfate, filtered, and concentrated under reduced pressure. The crude product was purified by flash chromatography (silica gel, eluted with 5% methanol in dichloromethane) to afford 3.35 g of N-[4-(4-amino-2-propyl-1H-imidazo[4,5-c]quinolin-1-yl)butyl]-N-[(tert-butoxycarbonyl)oxy]-2,2-dimethylpropanamide.

Part D

A mixture of N-[4-(4-amino-2-propyl-1H-imidazo[4,5-c]quinolin-1-yl)butyl]-N-[(tert-butoxycarbonyl)oxy]-2,2-dimethylpropanamide (3.35 g, 6.52 mmol), dichloromethane (50 mL), and 4 M HCl in dioxane (13.0 mL, 52.2 mmol) was stirred at room temperature overnight. The reaction mixture was concentrated under reduced pressure. The residue was concentrated twice from dichloromethane (2×25 mL) to provide 1-[4-(hydroxyamino)butyl]-2-propyl-1H-imidazo[4,5-c]quinolin-4-amine hydrochloride.

Part E

Acetic anhydride (0.490 mL, 5.14 mmol) and triethylamine (2.86 mL, 20.6 mmol) were added to a solution of 1-[4-(hydroxyamino)butyl]-2-propyl-1H-imidazo[4,5-c]quinolin-4-amine hydrochloride (1.80 g, 5.14 mmol) in dichloromethane (50 mL). The reaction mixture was stirred at room temperature for 2 hours, then 10% aqueous sodium hydroxide was added. The mixture was stirred for 1 hour, then was concentrated under reduced pressure. The residue was purified by flash chromatography (silica gel, gradient elution with 10-20% methanol in dichloromethane). The appropriate fractions were combined and concentrated under reduced pressure to afford a solid that was slurried in 1:1 saturated aqueous sodium bicarbonate/water, filtered, washed with water, and dried to yield N-[4-(4-amino-2-propyl-1H-imidazo[4,5-c]quinolin-1-yl)butyl]-N-hydroxyacetamide as brown needles, mp 191-193° C.

MS (APCI) m/z 356.2 $(M+H^+)$;

Anal. calcd for $C_{19}H_{25}N_5O_2.0.61\ H_2O$: C, 62.28; H, 7.21; N, 19.11. Found: C, 61.87; H, 6.49; N, 19.43.

Example 44

N-[4-(4-Amino-2-propyl-1H-imidazo[4,5-c]quinolin-1-yl)butyl]-N-hydroxy-N'-isopropylurea

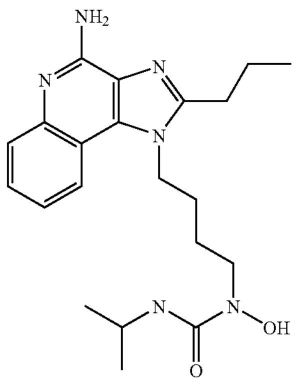 [SMILES: CCCc1nc2c(N)nc3ccccc3c2n1CCCCN(O)C(=O)NC(C)C]

Isopropyl isocyanate (0.67 mL, 6.85 mmol) and triethylamine (2.38 mL, 17.1 mmol) were added to a solution of 1-[4-(hydroxyamino)butyl]-2-propyl-1H-imidazo[4,5-c]quinolin-4-amine hydrochloride (prepared as described in Parts A-D of Example 43, 2.00 g, 5.71 mmol) in dichloromethane (50 mL). The reaction mixture was stirred at room temperature for 2 hours, then 10% aqueous sodium hydroxide (2 equivalents) was added. After the mixture was stirred for 1 hour at room temperature, the layers were separated and the organic layer was washed with saturated aqueous sodium bicarbonate and brine. The organic layer was dried over magnesium sulfate, filtered, and concentrated. The crude product was purified by flash chromatography (silica gel, eluted with 3% methanol in dichloromethane). The appropriate fractions were combined and concentrated under reduced pressure. The resulting solid was slurried in 1:1 saturated aqueous sodium bicarbonate/water and was isolated by filtration, washed with water, and dried overnight in a vacuum oven at 80° C. to provide 0.327 g of N-[4-(4-amino-2-propyl-1H-imidazo[4,5-c]quinolin-1-yl)butyl]-N-hydroxy-N'-isopropylurea as beige needles, mp 158-160° C.

MS (APCI) m/z 399.3 $(M+H^+)$;

Anal. calcd for $C_{21}H_{30}N_6O_2.0.14\ H_2O$: C, 62.90; H, 7.61; N, 20.96. Found: C, 62.51; H, 7.63; N, 20.73.

Example 45

4-(4-Amino-2-methyl-1H-imidazo[4,5-c]quinolin-1-yl)butanal O-methyloxime

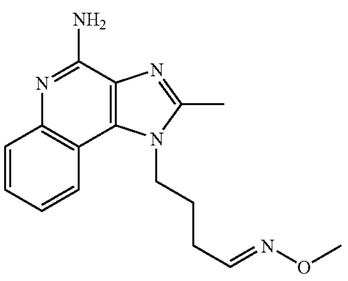 [SMILES: CO/N=C/CCCn1c(C)nc2c(N)nc3ccccc3c21]

Part A

The general procedure used to prepare 1-(4,4-diethoxybutyl)-2-propyl-1H-imidazo[4,5-c]quinoline in Parts A and B of Example 6 was used to prepare 1-(4,4-dimethoxybutyl)-2-methyl-1H-imidazo[4,5-c]quinoline with aminobutyraldehyde dimethylacetal used in lieu of aminobutyraldehyde diethylacetal and trimethyl orthoacetate used in lieu of trimethyl orthobutyrate.

Part B

A modification of the procedure used in Part C of Example 43 was used to convert 1-(4,4-dimethoxybutyl)-2-methyl-1H-imidazo[4,5-c]quinoline with aminobutyraldehyde dimethylacetal (49.2 g, 164 mmol) into 1-(4,4-dimethoxybutyl)-2-methyl-1H-imidazo[4,5-c]quinolin-4-amine. The reaction was worked up by adding 10% aqueous NaOH (150 mL) and transferring the mixture to a separatory funnel, where the organic layer was isolated. The organic layer was washed with saturated aqueous sodium bicarbonate solution and brine, dried over magnesium sulfate, filtered, and concentrated under reduced pressure. The resulting solid was dissolved in dichloromethane and the solution was washed with 1:1 saturated aqueous sodium bicarbonate/water, dried over magnesium sulfate, filtered, and concentrated to afford 49.5 g of crude 1-(4,4-dimethoxybutyl)-2-methyl-1H-imidazo[4,5-c]quinolin-4-amine as a brown oil.

Part C

Methoxylamine hydrochloride (22.8 g, 272 mmol) was added to a solution of 1-(4,4-dimethoxybutyl)-2-methyl-1H-imidazo[4,5-c]quinolin-4-amine (36.6 g, 136 mmol) in ethanol (200 mL). The reaction mixture was stirred at room temperature for two hours, then was concentrated under reduced pressure. The residue was diluted with water and brought to pH 7 with saturated aqueous sodium bicarbonate. The mixture was extracted with 5% methanol/dichloromethane. The organic layers were combined, washed with saturated aqueous sodium bicarbonate and brine, dried over magnesium sulfate, filtered, and concentrated under reduced pressure. The crude product was purified by flash chromatography (silica gel, elution with 5% methanol in dichloromethane) followed by recrystallization from ethyl acetate to yield 4-(4-amino-2-methyl-1H-imidazo[4,5-c]quinolin-1-yl)butanal O-methyloxime as an off-white powder, mp 153-155° C.

MS (APCI) m/z 298.2 (M+H$^+$);

Anal. calcd for $C_{16}H_{19}N_5O_1$.0.03 $C_4H_8O_2$: C, 64.42; H, 6.50; N, 23.07. Found: C, 64.42; H, 6.44; N, 22.73.

Example 46

N-[4-(4-Amino-2-methyl-1H-imidazo[4,5-c]quinolin-1-yl)butyl]-N-methoxyurea

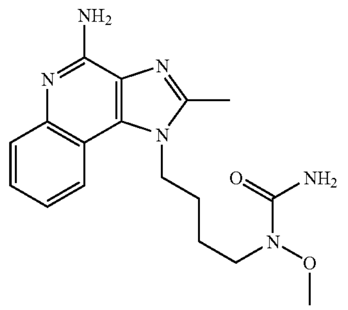 [SMILES: CON(CCCCn1c(C)nc2c(N)nc3ccccc3c21)C(N)=O]

Part A

Sodium cyanoborohydride (16.0 g, 254 mmol) was added to a solution of 4-(4-amino-2-methyl-1H-imidazo[4,5-c]quinolin-1-yl)butanal O-methyloxime (prepared as described in Example 45, 15.1 g, 50.8 mmol) in ethanol (100 mL) and acetic acid (15 mL). The reaction mixture was stirred at room temperature for 2 hours, additional acetic acid (15 mL) was added, and stirring was continued for 1 hour. The reaction mixture was concentrated under reduced pressure. The residue was diluted with water and adjusted to pH 7 with saturated aqueous sodium bicarbonate. The mixture was extracted with dichloromethane. The organic layers were combined, washed with saturated aqueous sodium bicarbonate and brine, dried over magnesium sulfate, filtered, and concentrated to provide 12.1 g of 1-[4-(methoxyamino)butyl]-2-methyl-1H-imidazo[4,5-c]quinolin-4-amine.

Part B

Trimethylsilyl isocyanate (1.62 mL, 12.0 mmol) and 1,8-diazabicyclo[5.4.0]undec-7ene (one drop) were added to a solution of 1-[4-(methoxyamino)butyl]-2-methyl-1H-imidazo[4,5-c]quinolin-4-amine (3.00 g, 10.0 mmol) in dichloromethane (100 mL). The reaction mixture was stirred overnight at room temperature, then concentrated under reduced pressure to afford 4.1 g of crude N-[4-(4-amino-2-methyl-1H-imidazo[4,5-c]quinolin-1-yl)butyl]-N-methoxy-N'-(trimethylsilyl)urea, which was used without purification in the next step.

Part C

To a solution of N-[4-(4-amino-2-methyl-1H-imidazo[4,5-c]quinolin-1-yl)butyl]-N-methoxy-N'-(trimethylsilyl)urea (4.1 g, 9.9 mmol) in tetrahydrofuran (75 mL) was added 10% aqueous HCl (5 mL). The reaction mixture was stirred at room temperature for two hours. The reaction mixture was concentrated under reduced pressure and the residue was neutralized with saturated aqueous sodium bicarbonate. The mixture was extracted with 10% methanol/dichloromethane solution. The organic layer was concentrated under reduced pressure and the crude product was recrystallized twice from methanol. The crystals were dissolved in hot methanol, filtered through a micron filter, and concentrated under reduced pressure to afford a solid that was crystallized from 5% methanol in dichloromethane to yield 0.264 g of N-[4-(4-amino-2-methyl-1H-imidazo[4,5-c]quinolin-1-yl)butyl]-N-methoxyurea as a yellow powder, mp 158-160° C.

MS (APCI) m/z 343.2 (M+H$^+$);

Anal. calcd for $C_{21}H_{30}N_6O_2$.0.14 $H_2O$: C, 62.91; H, 7.71; N, 20.96. Found: C, 62.51; H, 7.63; N, 20.73.

Example 47

N-[4-(4-Amino-2-methyl-1H-imidazo[4,5-c]quinolin-1-yl)butyl]-N-methoxymethanesulfonamide

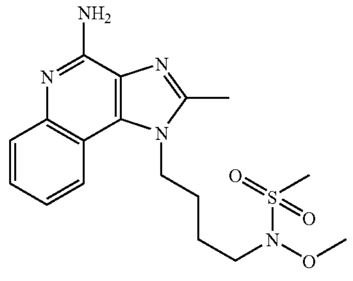 [SMILES: CON(CCCCn1c(C)nc2c(N)nc3ccccc3c21)S(C)(=O)=O]

Part A

Methanesulfonic anhydride (1.75 g, 10.0 mmol) and triethylamine (5.62 mL, 40.1 mmol) were added to a solution of 1-[4-(methoxyamino)butyl]-2-methyl-1H-imidazo[4,5-c]quinolin-4-amine (prepared as described in Part A of Example 46, 3.00 g, 10.0 mmol) in dichloromethane (100 mL). The reaction mixture was stirred for 2 hours at room temperature, then concentrated under reduced pressure to afford 3.36 g of a brown oil, which was used in the next step.

Part B

The brown oil from Part A (3.36 g) was dissolved in methanol (25 mL) and HBr in acetic acid (33%, 20 mL) was added. The reaction mixture was stirred overnight at room temperature, then the volatiles were removed under reduced pressure. The residue was adjusted to pH 7 with saturated aqueous sodium bicarbonate. The mixture was extracted with 5% methanol in chloroform. The organic layer was concentrated under reduced pressure and the residue was purified by flash chromatography (silica gel, eluted with 10% methanol in dichloromethane) followed by crystallization from methanol/dichloromethane to afford N-[4-(4-amino-2-methyl-1H-imidazo[4,5-c]quinolin-1-yl)butyl]-N-methoxymethanesulfonamide as a white powder, mp 201-203° C.

MS (APCI) m/Z 378.2 (M+H$^+$);

Anal. calcd for $C_{17}H_{23}N_5O_3S_1$.0.03 $CH_2Cl_2$.0.04 $H_2O$: C, 53.38; H, 6.12; N, 18.43. Found: C, 53.37; H, 7.16; N, 18.29.

Example 48

1-[4-Amino-2-(ethoxymethyl)-1H-imidazo[4,5-c]quinolin-1-yl]butan-2-one O-methyloxime

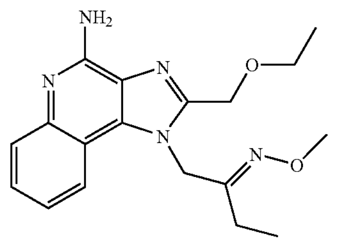 [SMILES: CCOCc1nc2c(N)nc3ccccc3c2n1C/C(CC)=N/OC]

Part A 1-(Aminomethyl)cyclopropanol was prepared using the method of I. L. Lysenko and O. G. Kulinkovich, Russ. *J Org. Chem.,* 37, pp. 1238-1243 (2001). A solution of 4-chloro-3-nitroquinoline (7.28 g, 34.9 mmol) was added dropwise to a 0° C. stirred suspension of 1-(aminomethyl)cyclopropanol (36.7 mmol) and triethylamine (6.30 mL, 45.4 mmol) in dichloromethane (120 mL). The mixture was stirred at room temperature for 3 days, then was concentrated under reduced pressure. The residue was suspended in water (150 mL) and was stirred for 3 hours. The solid was isolated by filtration, washed with water (50 mL), and dried in a vacuum oven at 75° C. to afford 8.99 g of 1-{[(3-nitroquinolin-4-yl)amino]methyl}cyclopropanol as a yellow solid.

Part B

A mixture of 1-{[(3-nitroquinolin-4-yl)amino]methyl}cyclopropanol (4.00 g, 15.4 mmol) and 5% platinum on carbon (400 mg) in ethyl acetate (80 mL) and methanol (8 mL) was hydrogenated on a Pair apparatus at 35 psi ($2.4\times10^5$ Pa) of hydrogen at room temperature for 3 hours. The mixture was filtered through CELITE filter agent, which was rinsed with 10% methanol/ethyl acetate. The filtrate was concentrated to an orange oil that was used directly in the next step.

Part C

The material from Part B was dissolved in dichloromethane (70 mL). The solution was cooled to 0° C. and ethoxyacetyl chloride (1.7 mL, 16.9 mmol) was added dropwise. The reaction mixture was stirred at 0° C. for 1 hour, then the solvent was removed under reduced pressure. The residue was used directly in the next step.

Part D

The material from Part C was dissolved in ethanol (70 mL) and 2 M aqueous sodium hydroxide (15 mL, 30.8 mmol) was added. The reaction mixture was heated at 60° C. for 1 hour, and then was stirred at room temperature overnight. The volatiles were removed under reduced pressure and to the resulting residue was added dichloromethane (70 mL) and water (50 mL). The mixture was adjusted to pH 7 with 1 M HCl. The layers were separated and the aqueous layer was extracted with dichloromethane (25 mL). The organic layers were combined, dried over magnesium sulfate, filtered, and concentrated to afford 4.23 g of crude 1-[2-(ethoxymethyl)-1H-imidazo[4,5-c]quinolin-1-yl]butan-2-one a tan solid.

Part E mCPBA (2.11 g, 8.57 mmol) was added to a solution of 1-[2-(ethoxymethyl)-1H-imidazo[4,5-c]quinolin-1-yl]butan-2-one (1.96 g, 6.59 mmol) in chloroform (30 mL) at room temperature. The reaction mixture was stirred for 1 hour, then was cooled to 0° C. Concentrated ammonium hydroxide (10 mL) and p-toluenesulfonyl chloride (1.38 g, 7.25 mmol) were added. The mixture was stirred at 0° C. for 1 hour, then was filtered. The filtrate was diluted with dichloromethane (50 mL) and saturated aqueous sodium bicarbonate (50 mL). The layers were separated and the aqueous layer was extracted with dichloromethane (25 mL). The organic layers were combined, dried over magnesium sulfate, filtered, and concentrated to yield a brown solid. The solid was purified by chromatography on a HORIZON High-Performance Flash Chromatography (HPFC) instrument (available from Biotage, Inc, Charlottesville, Va., USA) (silica gel, gradient elution with 0-35% of a solution comprised of 80% CHCl3, 18% MeOH, and 2% conc. $NH_4OH$ (CMA) in chloroform) to afford a tan solid that was recrystallized from chloroform/hexanes. The crystals were isolated by filtration and dried in a vacuum oven at 80° C. to afford 0.718 g of 1-[4-amino-2-(ethoxymethyl)-1H-imidazo[4,5-c]quinolin-1-yl]butan-2-one as pale pink needles, mp 187-188° C.

MS (APCI) m/z 313 (M+H)$^+$;

Anal. calcd for $C_{17}H_{20}N_4O_2$: C, 65.37; H, 6.45; N, 17.94. Found: C, 65.22; H, 6.19; N, 17.71.

Part F

Methoxylamine hydrochloride (0.36 g, 4.28 mmol) was added to a solution of 1-[4-amino-2-(ethoxymethyl)-1H-imidazo[4,5-c]quinolin-1-yl]butan-2-one (0.89 g, 2.85 mmol) in methanol (10 mL). The reaction mixture was stirred at room temperature for 48 hours and then concentrated under reduced pressure. The residue was partitioned between dichloromethane (40 mL) and saturated aqueous sodium bicarbonate (30 mL). The layers were separated and the aqueous layer was extracted with dichloromethane (15 mL). The combined organics were dried over magnesium sulfate, filtered, and then concentrated under reduced pressure to afford an orange oil. The oil was purified by chromatography on a HORIZON High-Performance Flash Chromatography (HPFC) instrument (available from Biotage, Inc, Charlottesville, Va., USA) (silica gel, gradient elution with 0-35% of a solution comprised of 80% CHCl3, 18% MeOH, and 2% conc. $NH_4OH$ (CMA) in chloroform) to afford a tan solid. This material was triturated with acetonitrile and then dried in a vacuum oven at 80° C. for 24 hours to afford 0.459 g of 80/20 E/Z 1-[4-amino-2-(ethoxymethyl)-1H-imidazo[4,5-c] quinolin-1-yl]butan-2-one O-methyloxime as tan needles, mp 175-178° C. MS (ESI) m/z 342 $(M+H)^+$; Anal. calcd for $C_{18}H_{23}N_5O_2$: C, 63.32; H, 6.79; N, 20.51. Found: C, 63.49; H, 6.67; N, 20.37.

Example 49

N-{4-[4-Amino-2-(ethoxymethyl)-1H-imidazo[4,5-c][1,5]naphthyridin-1-yl]-1-methylbutyl}-N'-isopropyl-N-methoxyurea

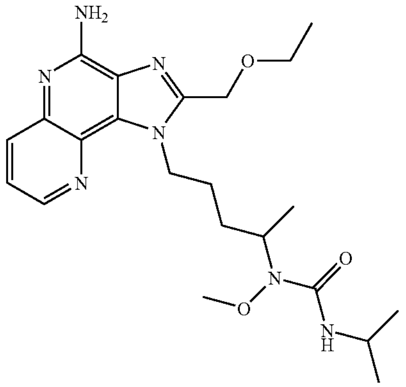 [SMILES: CCOCc1nc2c(N)nc3cccnc3c2n1CCCC(C)N(OC)C(=O)NC(C)C]

Part A

Methoxylamine hydrochloride (2.23 g, 26.7 mmol) was added to a solution of 5-(2-propyl-1H-imidazo[4,5-c][1,5] naphthyridin-1-yl)pentan-2-one (6.06 g of crude material prepared as described in Parts A and B of Example 22) in methanol (80 mL). The reaction mixture was stirred at room temperature for 48 hours and then concentrated under reduced pressure. The residue was dissolved dichloromethane (60 mL) and the pH was adjusted to 8 by the addition of saturated aqueous sodium bicarbonate (40 mL) and then solid sodium bicarbonate. The layers were separated and the aqueous layer was extracted with dichloromethane (30 mL). The combined organics were dried over magnesium sulfate, filtered, and then concentrated under reduced pressure to afford 6.33 g of 5-(2-propyl-1H-imidazo[4,5-c][1,5] naphthyridin-1-yl)pentan-2-one O-methyloxime a yellow oil.

Part B

Sodium cyanoborohydride (2.78 g, 44.2 mmol) and acetic acid (25 mL) were added to a solution of the material from Part A in methanol (25 mL). The reaction mixture was stirred at room temperature for 5 hours and then concentrated under reduced pressure. The residue was dissolved in a mixture dichloromethane (100 mL) and saturated aqueous sodium bicarbonate (75 mL). Solid sodium bicarbonate was added until the solution no longer bubbled and the pH was about 8. The layers were separated and the aqueous layer was extracted with dichloromethane (2×40 mL). The combined organics were dried over magnesium sulfate, filtered, and then concentrated under reduced pressure to afford a yellow oil. This material was absorbed onto silica gel (30 g) and heated at 100° C. with stirring for 8 hours. The mixture was placed in a fritted glass funnel and washed with 5% methanol in chloroform (200 mL). The filtrate was concentrated under reduced pressure to provide 4.70 g O-methyl-N-[1-methyl-(2-propyl-1H-imidazo[4,5-c][1,5]naphthyridin-1-yl)butyl] hydroxylamine as a yellow oil.

Part C

Triethylamine (1.3 mL, 9.17 mmol) and isopropyl isocyanate (0.72 mL, 7.33 mmol) were added to a solution of material from Part B (2.0 g, 6.11 mol) in dichloromethane (20 mL). The reaction mixture was stirred at room temperature for 24 hours. Additional isopropyl isocyanate (0.35 mL) was added. The reaction mixture was stirred for 18 hours and then it was diluted with dichloromethane (50 mL) and saturated aqueous sodium bicarbonate (40 mL). The layers were separated and the aqueous layer was extracted with dichloromethane (20 mL). The combined organics were dried over magnesium sulfate, filtered, and then concentrated under reduced pressure to afford a yellow oil. The oil was purified by chromatography on a HORIZON High-Performance Flash Chromatography (BPFC) instrument (available from Biotage, Inc, Charlottesville, Va., USA) (silica gel, gradient elution with 0-25% of a solution comprised of 80% CHCl3, 18% MeOH, and 2% conc. $NH_4OH$ (CMA) in chloroform) to afford 1.74 g of N-{4-[2-(ethoxymethyl)-1H-imidazo[4,5-c] [1,5]naphthyridin-1-yl]-1-methylbutyl}-N'-isopropyl-N-methoxyurea.

Part D

Using the general method of Example 4 Part H, the material from Part C was oxidized and then animated. The crude product was purified by HPFC (silica gel, gradient elution with 0-30% a solution of CMA in chloroform) to afford a light orange oil. This material was crystallized sequentially from ether/hexanes and acetonitrile and then dried in a vacuum oven at 80° C. overnight to afford 150 mg of N-{4-[4-amino-2-(ethoxymethyl)-1H-imidazo[4,5-c][1,5]naphthyridin-1-yl]-1-methylbutyl}-N'-isopropyl-N-methoxyurea as off-white needles, mp 174-175° C. MS (ESI) m/z 428 $(M+H)^+$; Anal. calcd for $C_{22}H_{33}N_7O_2$: C, 61.80; H. 7.78; N, 22.93. Found: C, 61.46; H, 8.08; N, 22.94.

Example 50

N-[4-(4-Amino-2-propyl-6,7,8,9-tetrahydro-1H-imidazo[4,5-c]quinolin-1-yl)butyl]-N-hydroxy-N'-isopropylurea

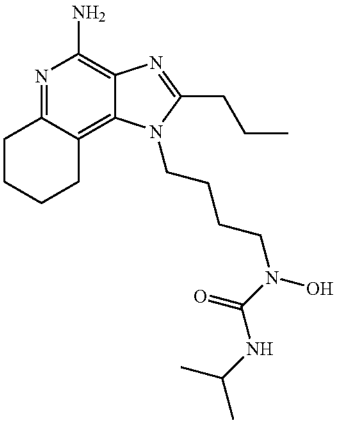 [SMILES: CCCc1nc2c(N)nc3c(c2n1CCCCN(O)C(=O)NC(C)C)CCCC3]

Part A 4-(2-Propyl-1H-imidazo[4,5-c]quinolin-1-yl)butan-1-ol (7.27 g, 25.7 mmol, which can be prepared using the method described in Example 43 Part A) was oxidized and then animated using a modification of the general method described in Example 4 Part H. The oxidation was run in chloroform in lieu of dichloromethane and the crude N-oxide was isolated prior to being dissolved in dichloromethane and treated with ammonium hydroxide and toluene sulfonyl chloride. 3.82 g of 4-(4-amino-2-propyl-1H-imidazo[4,5-c]quinolin-1-yl)butan-1-ol was obtained.

Part B

The material from Part A was dissolved in trifluoroacetic acid (76 mL) and placed in a Parr vessel. Platinum (IV) oxide (1.5 g) was added and the reaction was placed under hydrogen pressure. Additional platinum (IV) oxide (20% w/w) was added after 2 days and again after 4 days from the start of the reaction. After a total of 6 days the reaction mixture was filtered through a layer of CELITE filter aid. The filter cake was rinsed with isopropanol and the filtrate was concentrated under reduced pressure. The residue was combined with 1N hydrochloric acid (10 mL). The pH was adjusted to 14 by the addition of 50% sodium hydroxide. The resulting slurry was partitioned between chloroform (250 mL) and saturated aqueous sodium bicarbonate (200 mL). The layers were separated. Product (lot 1) was isolated from the aqueous layer by filtration. The organic layer was concentrated under reduced pressure. The residue was combined with a minimum amount of chloroform, chilled in an ice bath, and then filtered to provide product (lot 2). The two lots were combined and then dissolved in methanol. The solution was concentrated under reduced pressure to provide 2.43 g of 4-(4-amino-2-propyl-6,7,8,9-tetrahydro-1H-imidazo[4,5-c]quinolin-1-yl)butan-1-ol.

Part C

The alcohol group on the material from Part B was converted to a protected hydroxylamine using the general method of 14 Part F to provide 2.86 g of tert-butyl 4-(4-amino-2-propyl-6,7,8,9-tetrahydro-1H-imidazo[4,5-c] quinolin-1-yl)butyl[(tert-butoxycarbonyl)oxy]carbamate.

Part D

The material was combined with 4M hydrochloric acid in dioxane (32 mL). Chloroform (0.5 mL) was added to improve solubility. The reaction mixture was stirred overnight and then concentrated under reduced pressure to provide 1.79 g of N-[4-(4-amino-2-propyl-6,7,8,9-tetrahydro-1H-imidazo[4,5-c]quinolin-1-yl)butyl]hydroxylamine.

Part E

Isopropyl isocyanate (0.21 mL, 2.2 mmol) was added to a chilled (−10° C.) slurry of material from Part D (0.79 g, 2.0 mmol), triethylamine (0.99 mL, 7.1 mmol) and chloroform (16 mL). The reaction was complete in 5 minutes. The reaction mixture was diluted with chloroform (16 mL) and deionized water (10 mL) and stirred for 10 minutes. The organic phase was isolated, washed with 1% sodium carbonate (25 mL), dried over sodium sulfate, and then concentrated under reduced pressure to provide 0.79 g of a yellow residue. This material was purified by HPFC (silica gel, gradient elution with 0-40% a solution of CMA in chloroform) and then triturated with acetonitrile at 95° C. to provide a white crystalline solid. This material was combined with 1M sodium hydroxide, sonicated for 15 minutes, and then partitioned between chloroform and 1% sodium carbonate. Product was isolated by filtration and then combined with the isolated organic phase. The mixture was concentrated under reduced pressure. The residue was dried in a vacuum oven at 90° C. over the weekend to provide 0.08 g of N-[4-(4-amino-2-propyl-6,7,8,9-tetrahydro-1H-imidazo[4,5-c]quinolin-1-yl) butyl]-N-hydroxy-1N-isopropylurea as a white solid, mp 178-180° C. $^1$H NMR (300 MHz, DMSO-$d_6$) δ 9.18 (s, 1H), 6.50 (d, J=8.3 Hz, 1H), 5.60 (s, 2H), 4.18 (t, J=7.3, 2H), 3.74 (hex, J=6.5, 1H), 3.33 (m, 2H), 2.93 (m, 2H), 2.74 (t, J=7.4 Hz, 2H), 2.65 (m, 2H), 1.76 (m, 6H), 1.59 (m, 4H), 1.06 (d, J=6.6, 6H), 0.99 (t, J=7.4, 3H); MS (APCI) m/z 403 $(M+H)^+$; Anal. calcd for $C_{21}H_{34}N_6O_2$.0.26 mol $H_2O$: C, 61.97; H, 8.54; N, 20.65. Found: C, 61.93; H, 8.64; N, 20.44.

Example 51

N-[3-(4-Amino-2-ethyl-1H-imidazo[4,5-c]quinolin-1-yl)propyl]-O-methylhydroxylamine

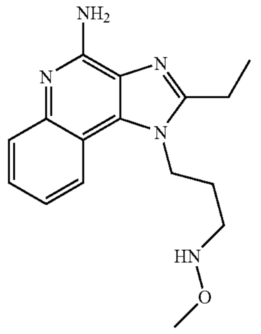 [SMILES: CCc1nc2c(N)nc3ccccc3c2n1CCCNOC]

Part A

Potassium carbonate (19.9 g, 144 mmol) was added to a mixture of 4-chloro-3-nitroquinoline (30 g, 144 mmol) and dichloromethane (150 mL). The reaction mixture was sparged with nitrogen. Triethylamine (21.8 g, 216 mmol) was added dropwise. The reaction mixture was cooled to 0° C. then a solution of 3,3-diethoxypropylamine (25.4 g, 173 mmol) in dichloromethane (50 mL) was added dropwise over a period of 15 minutes. The reaction mixture was stirred at room temperature for 3 hours. Dichloromethane and water (200 mL) were added. The layers were separated. The organic layer was washed with brine (×2). The combined aqueous layers were extracted with dichloromethane. The combined organic layers were dried over magnesium sulfate, filtered, and then concentrated under reduced pressure to provide 45 g of N-(3,3-diethoxypropyl)-3-nitroquinolin-4-amine.

Part B

A solution of the material from Part A in acetonitrile was placed in a Parr vessel. 5% Platinum on carbon (4.5 g) was added and the reaction mixture was placed under hydrogen pressure overnight. Magnesium sulfate was added. The reaction mixture was stirred and then filtered through a layer of CELITE filter aid. The filtrate was concentrated under reduced pressure to provide 39.78 g of $N^4$-(3,3-diethoxypropyl)quinoline-3,4-diamine as a dark green oil.

Part C

Pyridine hydrochloride (1.59 g, 13.9 mmol) was added to a solution of the material from Part B (39.78 g, 138.1 mmol) in toluene (200 mL). The reaction mixture was cooled in an ice bath and sparged with nitrogen. A solution of triethyl orthopropionate (26.77 g, 151.9 mmol) in toluene was added dropwise. After the addition was complete the ice bath was removed and the reaction mixture was heated at reflux for 2 hours. The reaction mixture was concentrated under reduced pressure to provide a green solid. The solid was dissolved in dichloromethane, washed with brine (×2), dried over magnesium sulfate, filtered, and then concentrated under high vacuum to provide 49.94 g of 1-(3,3-diethoxyproyl)-2-ethyl-1H-imidazo[4,5-c]quinoline as a pale green solid.

Part D mCPBA (20.67 g of 77%, 92.20 mmol) was added in a single portion to a chilled (ice bath) solution of material from Part C (15.48 g, 47.28 mmol) in chloroform (100 mL). The ice bath was removed and the reaction mixture was stirred overnight. The reaction mixture was filtered to remove a white precipitate. The filtrate was concentrated under reduced pressure to provide crude 1-(3,3-diethoxyproyl)-2-ethyl-1H-imidazo[4,5-c]quinoline 5-N-oxide as a red oil.

Part E

A solution of the material from Part D in 1,2-dichloroethane (100 mL) was cooled in an ice bath. Concentrated ammonium hydroxide (100 mL) was added followed by the slow addition of toluene sulfonyl chloride (15.77 g, 82.71 mmol). The reaction mixture was stirred vigorously. The ice bath was removed; the reaction was stirred for 4 hours and then concentrated under reduced pressure. The residue was filtered to remove a white solid. The filtrate was diluted with chloroform and brine. The resulting emulsion was broken up using a large quantity of ethyl acetate. The organics were combined, dried over magnesium sulfate, filtered, and then concentrated under reduced pressure to provide about 21 g of crude product as an orange solid. A portion (about 6 g) of this material was purified by column chromatography (150 g of silica gel eluted with a gradient of 0 to 7% methanol in dichloromethane) to provide about 4 g of 1-(3,3-diethoxypropyl)-2-ethyl-1H-imidazo[4,5-c]quinoline-4-amine.

Part F

Water (15 mL) and trifluoroacetic acid (75 mL) were added to a solution of crude material (5.66 g, 16.5 mmol) in chloroform (15 mL). The reaction mixture was stirred at room temperature for 2 hours and then adjusted to pH 5 with 6M sodium hydroxide. Methoxylamine hydrochloride (1.35 g, 16.5 mmol) was added and the reaction mixture was stirred for 2 hours at room temperature. More methoxylamine hydrochloride (1.35 g, 16.5 mmol) was added, the pH was adjusted to 5, and the reaction mixture was stirred for 3 days. The reaction mixture was adjusted to pH 1 with trifluoroacetic acid and then stirred for 2 days. A solution of sodium cyanoborohydride in tetrahydrofuran (33 mL of 1M, 33.04 mmol) was slowly added and the reaction mixture was stirred for 3 days. The reaction mixture was adjusted to pH 9 with 6M sodium hydroxide and then concentrated under reduced pressure to remove the chloroform. The residue was diluted with ethyl acetate, washed with brine (×2), dried over magnesium sulfate, filtered, and concentrated under reduced pressure. The aqueous layer was extracted with ethyl acetate (×3). The material from the combined organics was purified by column chromatography (silica gel eluted with a gradient of 0 to 7.5% methanol in dichloromethane) to provide 750 mg of N-[3-(4-amino-2-ethyl-1H-imidazo[4,5-c]quinolin-1-yl)propyl]-O-methylhydroxylamine as a pale yellow solid, mp 210-213° C.

$^1$H NMR (300 MHz, DMSO-$d_6$) δ 8.1 (d, J=7.4 Hz, 1H), 7.6 (dd, J=1.1 Hz, J=8.3 Hz, 1H), 7.4 (t, J=7.0 Hz, J=8.3 Hz, 1H), 7.2 (t, J=8.2 Hz, J=7.0 Hz, 1H), 6.8 (br s, 1H), 6.6 (br s, 2H), 4.6 (t, J=7.6 Hz, 2H), 3.4 (s, 3H), 3.0 (q, J=7.5 Hz, 2H), 2.9 (m, 2H), 2.0 (m, 2H), 1.3 (t, J=7.4 Hz, 3H);

MS (APCI) m/z 300.1 $(M+H)^+$;

Anal. calcd for $C_{16}H_{21}N_5O.0.53H_2O$: C, 62.21; H, 7.20; N, 22.67. Found: C, 61.88; H, 6.91; N, 22.58.

Examples 52-75

A reagent from the table below (1.1 equivalents) was added to a test tube containing a solution N-[3-(4-amino-2-ethyl-1H-imidazo[4,5-c]quinolin-1-yl)propyl]-O-methylhydroxylamine (prepared as described Example 51, 29 mg, 0.1 mmol) and triethylamine (2.0 eq) in dichloromethane (1 mL). The test tube was capped and placed on a shaker at ambient temperature overnight. The reactions were quenched with water (2 drops), vortexed, and then the solvent was removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

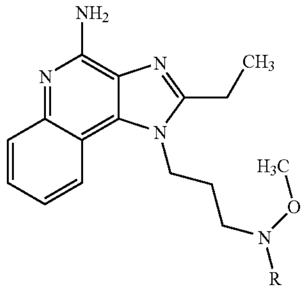

| Example | Reagent | R | Measured Mass (M + H) |
|---|---|---|---|
| 52 | Hexanoyl chloride | 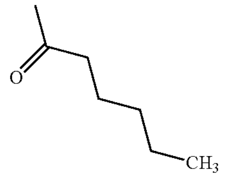 | 398.2554 |
| 53 | Cyclohexanecarbonyl chloride | 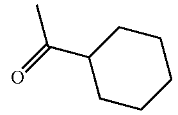 | 410.2526 |
| 54 | o-Toluoyl chloride | 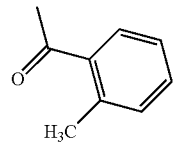 | 418.2209 |
| 55 | p-Toluoyl chloride | 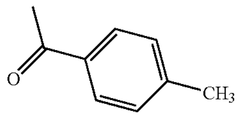 | 418.2216 |
| 56 | 2-Chlorobenzoyl chloride | 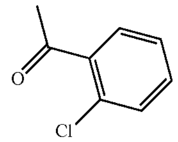 | 438.1670 |

-continued

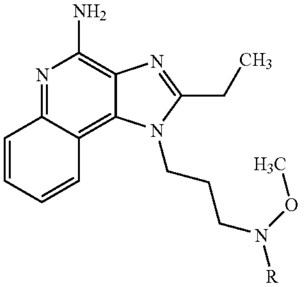

| Example | Reagent | R | Measured Mass (M + H) |
|---|---|---|---|
| 57 | 3-Chlorobenzoyl chloride | 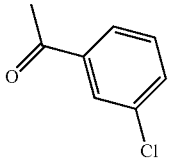 | 438.1660 |
| 58 | 4-Chlorobenzoyl chloride | 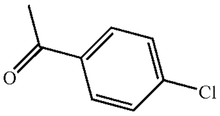 | 438.1683 |
| 59 | Nicontinoyl chloride hydrochloride | 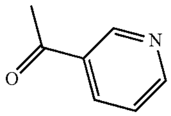 | 405.2031 |
| 60 | Methanesulfonyl chloride | 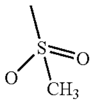 | 378.1590 |
| 61 | 3-Methylbenzene-sulfonyl chloride | 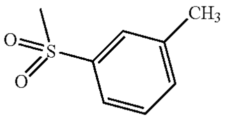 | 454.1884 |
| 62 | o-Toluenesulfonyl chloride | 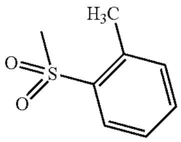 | 454.1894 |
| 63 | p-Toluenesulfonyl chloride | 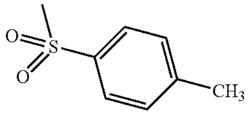 | 454.1911 |
| 64 | 2-Chlorobenzene-sulfonyl chloride | 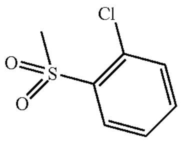 | 474.1404 |
| 65 | 3-Chlorobenzene-sulfonyl chloride | 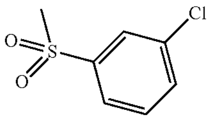 | 474.1352 |

-continued

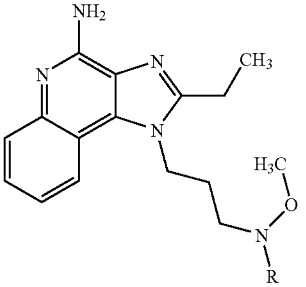

| Example | Reagent | R | Measured Mass (M + H) |
|---|---|---|---|
| 66 | 4-Chlorobenzene-sulfonyl chloride | 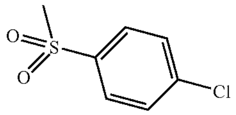 | 474.1355 |
| 67 | 10-Camphorsulfonyl chloride | 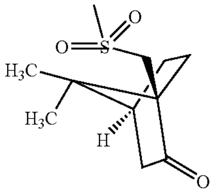 | 514.2455 |
| 68 | Phenyl isocyanate | 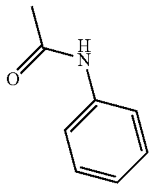 | 419.2177 |
| 69 | Dimethylthio-carbamoyl chloride | 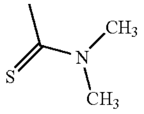 | 387.1939 |
| 70 | Cyclohexyl isocyanate | 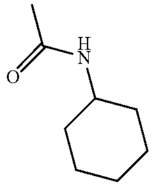 | 425.2623 |
| 71 | m-Tolyl isocyanate | 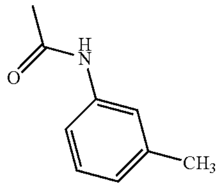 | 433.2336 |
| 72 | o-Tolyl isocyanate | 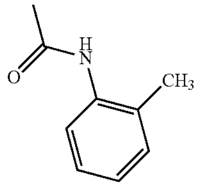 | 433.2310 |

-continued

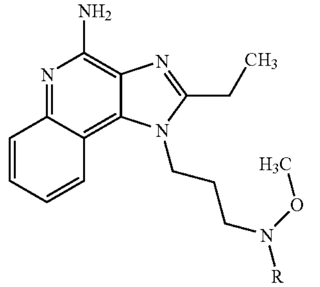

| Example | Reagent | R | Measured Mass (M + H) |
| --- | --- | --- | --- |
| 73 | 3-Pyridyl isothiocyanate | 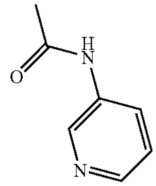 | 436.1878 |
| 74 | 4-Morpholinylcabonyl chloride | 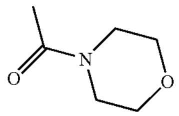 | 413.2276 |
| 75 | N-Methyl-N-Phenylcarbamoyl chloride | 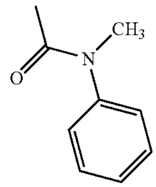 | 433.2338 |

Examples 76-87

Part A

Methoxylamine hydrochloride (11.86 g, 142.1 mmol) was added to a solution of 4-(7-bromo-2-propyl-1H-imidazo[4,5-c]quinolin-1-yl)butyraldehyde (25.6 g, 71.0 mmol, prepared as described in Example 17 Parts A through D) in ethanol (200 mL). The reaction mixture was stirred at room temperature for 2 hours and then concentrated under reduced pressure. The residue was dissolved in water, neutralized with saturated sodium bicarbonate, and then extracted into dichloromethane. The extract was washed sequentially with saturated sodium bicarbonate and brine, dried over magnesium sulfate, and then concentrated under reduced pressure to provide 27.1 g of 4-(7-bromo-2-propyl-1H-imidazo[4,5-c]quinolin-1-yl)butyraldehyde O-methyloxime.

Part B mCPBA (28.03 g of 75%, 122 mmol) was added to a solution of the material from Part A in chloroform (200 mL). The reaction mixture was stirred at room temperature for 2 hours and then cooled to 0° C. in an ice bath. Concentrated ammonium hydroxide (75 mL) and benzenesulfonyl choride were added sequentially. The reaction mixture was warmed to room temperature and then stirred for 2 hours. The reaction mixture was diluted with saturated sodium bicarbonate and stirred for 5 minutes. The layers were separated. The organic layer was washed sequentially with saturated sodium bicarbonate and brine, dried over magnesium sulfate, and then concentrated under reduced pressure to provide 27.5 g of 4-(4-amino7-bromo-2-propyl-1H-imidazo[4,5-c]quinolin-1-yl)butyraldehyde O-methyloxime.

Part C

Acetic acid (30 mL) was added to a solution of the material from Part B in ethanol (200 mL). Sodium cyanoborohydride (21.3 g, 340 mmol) was added over a period of 5 minutes. The reaction mixture was stirred at room temperature for 4 hours and then concentrated under reduced pressure. The residue was diluted with water (100 mL), neutralized with saturated sodium bicarbonate, and then extracted into dichloromethane. The extract was washed sequentially with saturated sodium bicarbonate and brine, dried over magnesium sulfate, and then concentrated under reduced pressure. The crude product was purified by column chromatography (silica gel eluted with 5% methanol in chloroform) to provide 9.12 g of N-[4-(4-amino-7-bromo-2-propyl-1H-imidazo[4,5-c]quinolin-1-yl)butyl]-O-methylhydroxylamine as an orange sticky solid.

Part D

Triethylamine (590 mg, 5.9 mmol) was added to a solution of material from Part D (about 2 g, 4.9 mmol) in chloroform (50 mL). The reaction mixture was stirred for 5 minutes and then acetyl chloride (384 mg, 4.9 mmol) was added. After 30 minutes more triethylamine (1.2 eq) and acetyl chloride (0.4 eq) were added. After a total of 60 minutes the reaction mixture was concentrated under reduced pressure. The residue was dissolved in chloroform (100 mL), washed with water (3×100 mL), dried over magnesium sulfate, and then concentrated under reduced pressure to provide 700 mg of N-[4-(4-amino-7-bromo-2-propyl-1H-imidazo[4,5-c]quinolin-1-yl)butyl]-N-methoxyacetamide as an off white solid.

Part E

A solution of material from Part D (40 mg, 0.10 mmol) in 7:3 volume:volume (v:v) chloroform:methanol (2 mL) was added to a test tube, and the solvent was removed by vacuum centrifugation. The boronic acid (0.11 mmol) indicated in the table below and n-propanol (1.6 mL) were added sequentially, and the test tube was purged with nitrogen. The reaction mixture was sonicated. Palladium (II) acetate (150 μL of a solution prepared by dissolving 60 mg of palladium (II) acetate in 15 L of toluene), 2M aqueous sodium carbonate solution (600 μL), deionized water (113 μL), and a solution of 0.15 M triphenylphosphine in n-propanol (53 μL) were sequentially added. The test tube was purged with nitrogen, capped, and then heated to 80° C. overnight in a sand bath. The solvent was removed from the test tubes by vacuum centrifugation.

The contents of each: test tube were passed through a Waters Oasis Sample Extractions Cartridge MCX (6 cc) according to the following procedure. Hydrochloric acid (1 N) was added to adjust each sample to pH 5, and the resulting solution was passed through the cartridge optionally using light nitrogen pressure. The cartridge was washed with methanol (5 mL) optionally using light nitrogen pressure and transferred to a clean test tube. A solution of 1 N ammonia in methanol (2×5 mL) was then passed through the cartridge optionally using light nitrogen pressure, and the basic solution was collected and concentrated.

The compounds were purified as described in Examples 52-75. The table below shows the boronic acid used for each example, the structure of the resulting compound, and the observed accurate mass for the isolated trifluoroacetate salt.

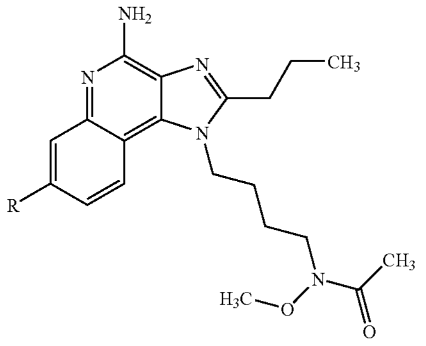

| Example | Reagent | R | Measured Mass (M + H) |
|---|---|---|---|
| 76 | None | 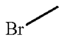 | 448.1339 |
| 77 | Phenylboronic acid | 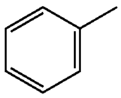 | 446.2587 |
| 78 | Pyridine-3-boronic acid | 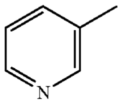 | 447.2555 |
| 79 | Pyridine-4-boronic acid | 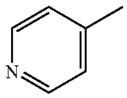 | 447.2528 |
| 80 | 2-Hydroxyphenylboronic acid | 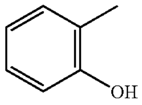 | 462.2502 |
| 81 | 3-Hydroxyphenylboronic acid | 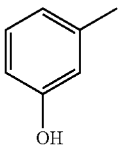 | 462.2493 |
| 82 | (3-Aminocarbonylphenyl)boronic acid | 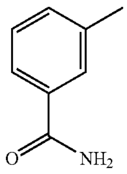 | 489.2644 |
| 83 | 3-(Methylsulfonylamino)phenylboronic acid | 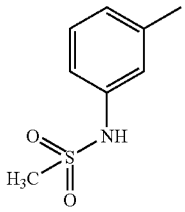 | 539.2392 |

-continued

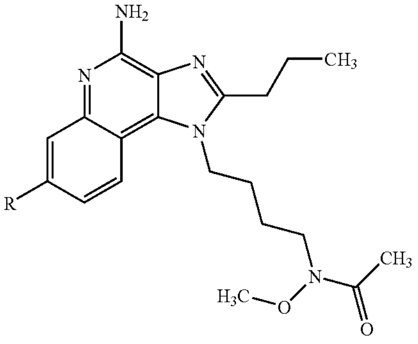

| Example | Reagent | R | Measured Mass (M + H) |
|---|---|---|---|
| 84 | 3-(Isobutylaminocarbonyl)phenylboronic acid | 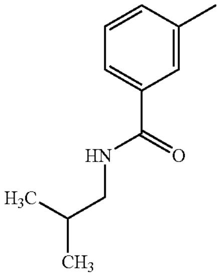 | 545.3268 |
| 85 | 3-(Morpholine-4-carbonyl)phenylboronic acid | 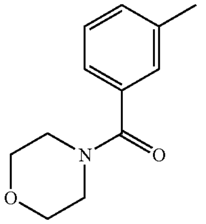 | 559.3039 |
| 86 | 4(Morpholine-4-carbonyl)phenylboronic acid | 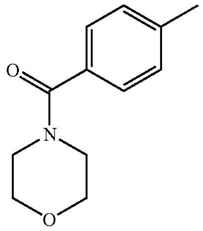 | 559.3040 |
| 87 | 4'-(4,4,5,5-Tetramethyl-1,3,2-dioxaborolan-2-yl)acetanilide | 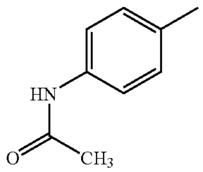 | 503.2769 |

Examples 88-101

Part A

Triethylamine (6.5 mL, 2.0 eq) was added to a solution of N-[4-(4-amino-7-bromo-2-propyl-1H-imidazo[4,5-c]quinolin-1-yl)butyl]-O-methylhydroxylamine (9.15 g prepared as described in Example Parts A through C) in chloroform (225 mL). The reaction mixture was stirred for about 5 minutes, methanesulfonyl chloride (1.74 mL, 1.0 eq) was added dropwise, and the reaction mixture was stirred at room temperature. Analysis by liquid chromatography/mass spectroscopy (LC/MS) after 30 minutes indicated that starting material was still present. Additional methanesulfonyl chloride (0.4 eq) was added and the reaction mixture was heated to 50° C. More methanesulfonyl chloride (1.0 eq) was added at after 1 hour and again after 3 hours. After a total of 4 hours (3.5 at 50° C.) the reaction mixture was diluted with chloroform (400 mL), washed with water (3×350 mL), dried over magnesium sulfate, filtered, and then concentrated under reduced pressure to provide 10.65 g of a yellow solid. This material was purified by BPFC eluting with a gradient of 0 to 3% methanol in dichloromethane containing 5% ammonium hydroxide to provide 1.42 g of N-[4-(4-amino-7-bromo-2-propyl-1H-imidazo[4,5-c]quinolin-1-yl)butyl]-N-methoxymethanesulfonamide as a white solid.

Part B

A solution of material from Part A (49 mg, 0.10 mmol) in 7:3 volume:volume (v:v) chloroform:methanol (2 mL) was added to a test tube, and the solvent was removed by vacuum centrifugation. The boronic acid (0.11 mmol) indicated in the table below, n-propanol (1.6 mL), palladium (II) acetate (150 µL of a solution prepared by dissolving 60 mg of palladium (II) acetate in 15 mL of toluene), 2M aqueous sodium carbonate solution (600 µL), deionized water (113 µL), and a solution of 0.15 M triphenylphosphine in n-propanol (53 µL) were added sequentially. The test tube was purged with nitrogen, capped, and then heated to 80° C. overnight in a sand bath. For Example 91, the solvent was removed by vacuum centrifugation, and glacial acetic acid (3 mL), tetrahydrofuran (1 mL), and deionized water (1 mL) were added to the test tube. The reaction was heated overnight at 60° C. The solvent was removed from the test tubes by vacuum centrifugation.

The contents of each test tube were passed through a, Waters Oasis Sample Extractions Cartridge MCX (6 cc) according to the following procedure. Methanol (3 mL) and hydrochloric acid (3 mL of 1 N) were added, the mixture was vortexed, and the resulting solution was passed through the cartridge optionally using light nitrogen pressure. The cartridge was washed with methanol (5 mL) optionally using light nitrogen pressure and transferred to a clean test tube. A solution of 1 N ammonia in methanol (2×5 mL) was then passed through the cartridge optionally using light nitrogen pressure, and the basic solution was collected and concentrated.

The compounds were purified as described in Examples 52-75. The table below shows the boronic acid used for each example, the structure of the resulting compound, and the observed accurate mass for the isolated trifluoroacetate salt.

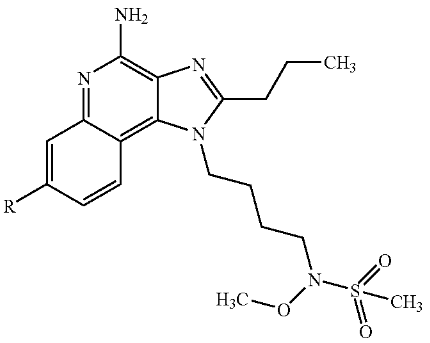

| Example | Reagent | R | Measured Mass (M + H) |
|---|---|---|---|
| 88 | None | 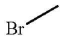 | 484.0980 |
| 89 | Phenylboronic acid | 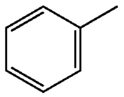 | 482.2234 |
| 90 | Pyridine-3-boronic acid | 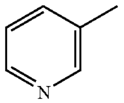 | 483.2148 |
| 91 | 4-Methoxyphenylboronic acid | 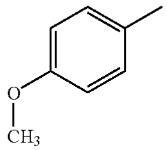 | 512.2299 |
| 92 | 5-(tert-Butyldimethylsilanyloxymethyl)pyridine-3-boronic acid | 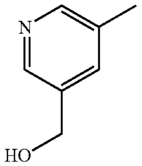 | 513.2307 |

-continued
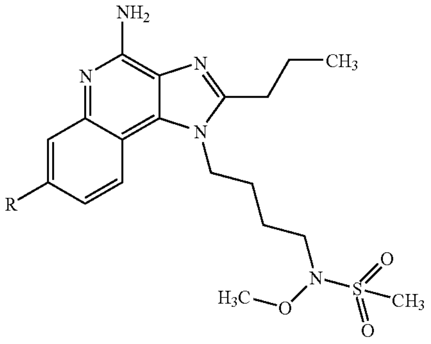
| Example | Reagent | R | Measured Mass (M + H) |
|---|---|---|---|
| 93 | 3-Chlorophenylboronic acid | 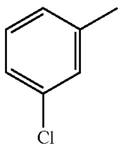 | 516.1818 |
| 94 | 2-Chlorophenylboronic acid | 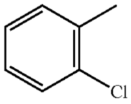 | 516.1788 |
| 95 | (3-Aminocarbonylphenyl)boronic acid | 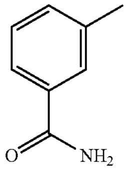 | 525.2325 |
| 96 | 3-(N,N-Dimethylaminocarbonyl)phenylboronic acid | 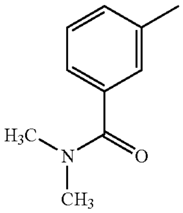 | 553.2610 |
| 97 | 3-(N-Isopropylaminocarbonyl)phenylboronic acid | 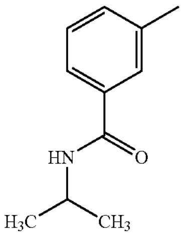 | 567.2809 |

-continued

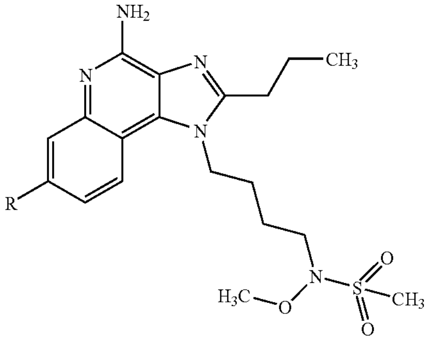

| Example | Reagent | R | Measured Mass (M + H) |
|---|---|---|---|
| 98 | 3-(Isobutylaminocarbonyl)phenylboronic acid | 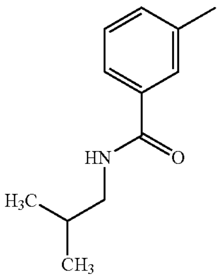 | 581.2923 |
| 99 | 4-(Isobutylaminocarbonyl) phenylboronic acid | 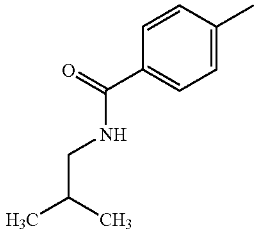 | 581.2943 |
| 100 | 3-(Morpholine-4-carbonyl)phenylboronic acid | 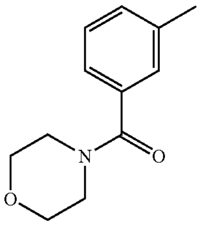 | 595.2739 |
| 101 | 4-(Morpholine-4-carbonyl)phenylboronic acid | 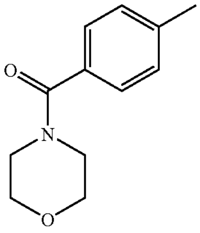 | 595.2744 |

Exemplary Compounds Table 1

Certain exemplary compounds, including some of those described above in the Examples, have the following Formulas (III-1, IV-1, IV-2, IV-3, IV-4, IV-5, V-1, VI-1, and VII-1), wherein X, $R_2$, $R_{1-1}$, $R_{1-2}$, and Y—$R_{1-3}$ are defined immediately below in the table. In this table, for each ring system, each row represents one specific compound.

IV-1
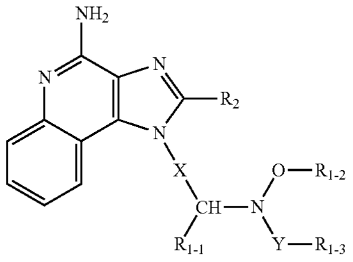
V-1
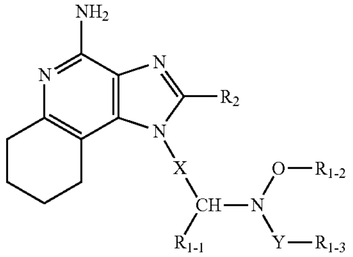
III-1
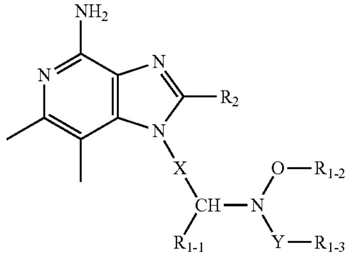
VI-1
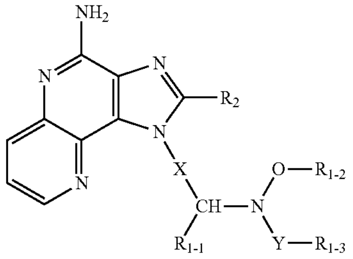
IV-2
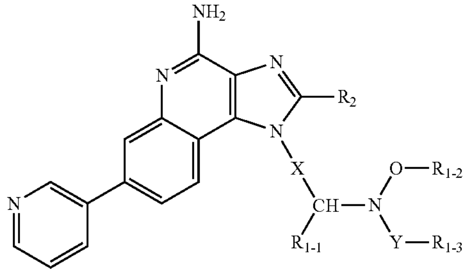

IV-3

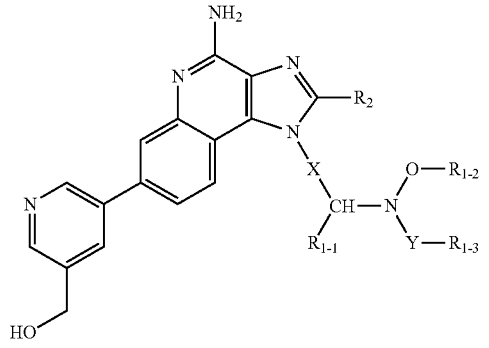

IV-4

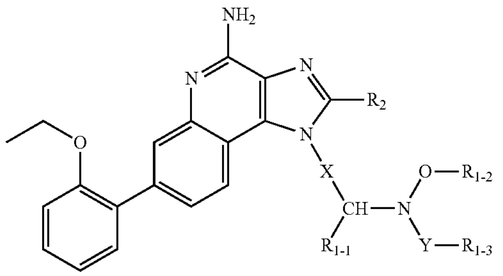

IV-5

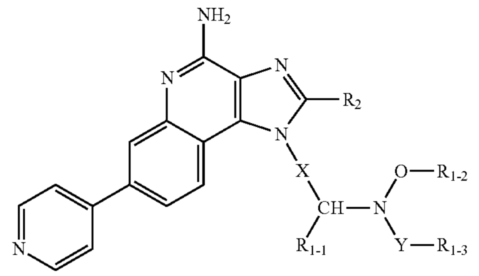

VII-1

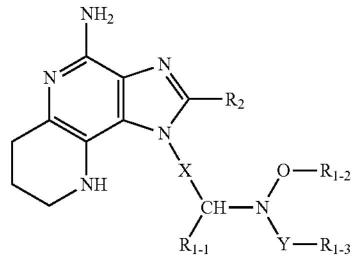

| $R_2$ | X | $R_{1-1}$ | $R_{1-2}$ | $Y-R_{1-3}$ |
|---|---|---|---|---|
| H | $-(CH_2)_3-$ | H | H | —C(O)—phenyl |
| H | $-(CH_2)_3-$ | H | H | $-C(O)-C_2H_5$ |
| H | $-(CH_2)_3-$ | H | H | —C(O)—NH—phenyl |
| H | $-(CH_2)_3-$ | H | H | $-C(O)-NH-CH_3$ |
| H | $-(CH_2)_3-$ | H | H | —C(O)—NH—isopropyl |
| H | $-(CH_2)_3-$ | H | H | $-C(O)-N(CH_3)_2$ |
| H | $-(CH_2)_3-$ | H | H | $-S(O)_2-CH_3$ |
| H | $-(CH_2)_3-$ | H | $-CH_3$ | —C(O)—phenyl |
| H | $-(CH_2)_3-$ | H | $-CH_3$ | $-C(O)-C_2H_5$ |
| H | $-(CH_2)_3-$ | H | $-CH_3$ | —C(O)—NH—phenyl |
| H | $-(CH_2)_3-$ | H | $-CH_3$ | $-C(O)-NH-CH_3$ |
| H | $-(CH_2)_3-$ | H | $-CH_3$ | —C(O)—NH—isopropyl |
| H | $-(CH_2)_3-$ | H | $-CH_3$ | $-C(O)-N(CH_3)_2$ |
| H | $-(CH_2)_3-$ | H | $-CH_3$ | $-S(O)_2-CH_3$ |
| H | $-(CH_2)_3-$ | $-CH_3$ | H | —C(O)—phenyl |
| H | $-(CH_2)_3-$ | $-CH_3$ | H | $-C(O)-C_2H_5$ |
| H | $-(CH_2)_3-$ | $-CH_3$ | H | —C(O)—NH—phenyl |
| H | $-(CH_2)_3-$ | $-CH_3$ | H | $-C(O)-NH-CH_3$ |

| | | | | |
|---|---|---|---|---|
| H | —$(CH_2)_3$— | —$CH_3$ | H | —C(O)—NH—isopropyl |
| H | —$(CH_2)_3$— | —$CH_3$ | H | —C(O)—$N(CH_3)_2$ |
| H | —$(CH_2)_3$— | —$CH_3$ | H | —$S(O)_2$—$CH_3$ |
| H | —$(CH_2)_3$— | —$CH_3$ | —$CH_3$ | —C(O)—phenyl |
| H | —$(CH_2)_3$— | —$CH_3$ | —$CH_3$ | —C(O)—$C_2H_5$ |
| H | —$(CH_2)_3$— | —$CH_3$ | —$CH_3$ | —C(O)—NH—phenyl |
| H | —$(CH_2)_3$— | —$CH_3$ | —$CH_3$ | —C(O)—NH—$CH_3$ |
| H | —$(CH_2)_3$— | —$CH_3$ | —$CH_3$ | —C(O)—NH—isopropyl |
| H | —$(CH_2)_3$— | —$CH_3$ | —$CH_3$ | —C(O)—$N(CH_3)_2$ |
| H | —$(CH_2)_3$— | —$CH_3$ | —$CH_3$ | —$S(O)_2$—$CH_3$ |
| H | —$(CH_2)_4$— | H | H | —C(O)—phenyl |
| H | —$(CH_2)_4$— | H | H | —C(O)—$C_2H_5$ |
| H | —$(CH_2)_4$— | H | H | —C(O)—NH—phenyl |
| H | —$(CH_2)_4$— | H | H | —C(O)—NH—$CH_3$ |
| H | —$(CH_2)_4$— | H | H | —C(O)—NH—isopropyl |
| H | —$(CH_2)_4$— | H | H | —C(O)—$N(CH_3)_2$ |
| H | —$(CH_2)_4$— | H | H | —$S(O)_2$—$CH_3$ |
| H | —$(CH_2)_4$— | H | —$CH_3$ | —C(O)—phenyl |
| H | —$(CH_2)_4$— | H | —$CH_3$ | —C(O)—$C_2H_5$ |
| H | —$(CH_2)_4$— | H | —$CH_3$ | —C(O)—NH—phenyl |
| H | —$(CH_2)_4$— | H | —$CH_3$ | —C(O)—NH—$CH_3$ |
| H | —$(CH_2)_4$— | H | —$CH_3$ | —C(O)—NH—isopropyl |
| H | —$(CH_2)_4$— | H | —$CH_3$ | —C(O)—$N(CH_3)_2$ |
| H | —$(CH_2)_4$— | H | —$CH_3$ | —$S(O)_2$—$CH_3$ |
| H | —$(CH_2)_4$— | —$CH_3$ | H | —C(O)—phenyl |
| H | —$(CH_2)_4$— | —$CH_3$ | H | —C(O)—$C_2H_5$ |
| H | —$(CH_2)_4$— | —$CH_3$ | H | —C(O)—NH—phenyl |
| H | —$(CH_2)_4$— | —$CH_3$ | H | —C(O)—NH—$CH_3$ |
| H | —$(CH_2)_4$— | —$CH_3$ | H | —C(O)—NH—isopropyl |
| H | —$(CH_2)_4$— | —$CH_3$ | H | —C(O)—$N(CH_3)_2$ |
| H | —$(CH_2)_4$— | —$CH_3$ | H | —$S(O)_2$—$CH_3$ |
| H | —$(CH_2)_4$— | —$CH_3$ | —$CH_3$ | —C(O)—phenyl |
| H | —$(CH_2)_4$— | —$CH_3$ | —$CH_3$ | —C(O)—$C_2H_5$ |
| H | —$(CH_2)_4$— | —$CH_3$ | —$CH_3$ | —C(O)—NH—phenyl |
| H | —$(CH_2)_4$— | —$CH_3$ | —$CH_3$ | —C(O)—NH—$CH_3$ |
| H | —$(CH_2)_4$— | —$CH_3$ | —$CH_3$ | —C(O)—NH—isopropyl |
| H | —$(CH_2)_4$— | —$CH_3$ | —$CH_3$ | —C(O)—$N(CH_3)_2$ |
| H | —$(CH_2)_4$— | —$CH_3$ | —$CH_3$ | —$S(O)_2$—$CH_3$ |
| H | —$CH_2C(CH_3)_2$— | H | H | —C(O)—phenyl |
| H | —$CH_2C(CH_3)_2$— | H | H | —C(O)—$C_2H_5$ |
| H | —$CH_2C(CH_3)_2$— | H | H | —C(O)—NH—phenyl |
| H | —$CH_2C(CH_3)_2$— | H | H | —C(O)—NH—$CH_3$ |
| H | —$CH_2C(CH_3)_2$— | H | H | —C(O)—NH—isopropyl |
| H | —$CH_2C(CH_3)_2$— | H | H | —C(O)—$N(CH_3)_2$ |
| H | —$CH_2C(CH_3)_2$— | H | H | —$S(O)_2$—$CH_3$ |
| H | —$CH_2C(CH_3)_2$— | H | —$CH_3$ | —C(O)—phenyl |
| H | —$CH_2C(CH_3)_2$— | H | —$CH_3$ | —C(O)—$C_2H_5$ |
| H | —$CH_2C(CH_3)_2$— | H | —$CH_3$ | —C(O)—NH—phenyl |
| H | —$CH_2C(CH_3)_2$— | H | —$CH_3$ | —C(O)—NH—$CH_3$ |
| H | —$CH_2C(CH_3)_2$— | H | —$CH_3$ | —C(O)—NH—isopropyl |
| H | —$CH_2C(CH_3)_2$— | H | —$CH_3$ | —C(O)—$N(CH_3)_2$ |
| H | —$CH_2C(CH_3)_2$— | H | —$CH_3$ | —$S(O)_2$—$CH_3$ |
| H | —$CH_2C(CH_3)_2$— | —$CH_3$ | H | —C(O)—phenyl |
| H | —$CH_2C(CH_3)_2$— | —$CH_3$ | H | —C(O)—$C_2H_5$ |
| H | —$CH_2C(CH_3)_2$— | —$CH_3$ | H | —C(O)—NH—phenyl |
| H | —$CH_2C(CH_3)_2$— | —$CH_3$ | H | —C(O)—NH—$CH_3$ |
| H | —$CH_2C(CH_3)_2$— | —$CH_3$ | H | —C(O)—NH—isopropyl |
| H | —$CH_2C(CH_3)_2$— | —$CH_3$ | H | —C(O)—$N(CH_3)_2$ |
| H | —$CH_2C(CH_3)_2$— | —$CH_3$ | H | —$S(O)_2$—$CH_3$ |
| H | —$CH_2C(CH_3)_2$— | —$CH_3$ | —$CH_3$ | —C(O)—phenyl |
| H | —$CH_2C(CH_3)_2$— | —$CH_3$ | —$CH_3$ | —C(O)—$C_2H_5$ |
| H | —$CH_2C(CH_3)_2$— | —$CH_3$ | —$CH_3$ | —C(O)—NH—phenyl |
| H | —$CH_2C(CH_3)_2$— | —$CH_3$ | —$CH_3$ | —C(O)—NH—$CH_3$ |
| H | —$CH_2C(CH_3)_2$— | —$CH_3$ | —$CH_3$ | —C(O)—NH—isopropyl |
| H | —$CH_2C(CH_3)_2$— | —$CH_3$ | —$CH_3$ | —C(O)—$N(CH_3)_2$ |
| H | —$CH_2C(CH_3)_2$— | —$CH_3$ | —$CH_3$ | —$S(O)_2$—$CH_3$ |
| H | —$CH_2C(CH_3)_2CH_2$— | H | H | —C(O)—phenyl |
| H | —$CH_2C(CH_3)_2CH_2$— | H | H | —C(O)—$C_2H_5$ |
| H | —$CH_2C(CH_3)_2CH_2$— | H | H | —C(O)—NH—phenyl |
| H | —$CH_2C(CH_3)_2CH_2$— | H | H | —C(O)—NH—$CH_3$ |
| H | —$CH_2C(CH_3)_2CH_2$— | H | H | —C(O)—NH—isopropyl |
| H | —$CH_2C(CH_3)_2CH_2$— | H | H | —C(O)—$N(CH_3)_2$ |
| H | —$CH_2C(CH_3)_2CH_2$— | H | H | —$S(O)_2$—$CH_3$ |
| H | —$CH_2C(CH_3)_2CH_2$— | H | —$CH_3$ | —C(O)—phenyl |
| H | —$CH_2C(CH_3)_2CH_2$— | H | —$CH_3$ | —C(O)—$C_2H_5$ |
| H | —$CH_2C(CH_3)_2CH_2$— | H | —$CH_3$ | —C(O)—NH—phenyl |
| H | —$CH_2C(CH_3)_2CH_2$— | H | —$CH_3$ | —C(O)—NH—$CH_3$ |
| H | —$CH_2C(CH_3)_2CH_2$— | H | —$CH_3$ | —C(O)—NH—isopropyl |
| H | —$CH_2C(CH_3)_2CH_2$— | H | —$CH_3$ | —C(O)—$N(CH_3)_2$ |
| H | —$CH_2C(CH_3)_2CH_2$— | H | —$CH_3$ | —$S(O)_2$—$CH_3$ |
| H | —$CH_2C(CH_3)_2CH_2$— | —$CH_3$ | H | —C(O)—phenyl |
| H | —$CH_2C(CH_3)_2CH_2$— | —$CH_3$ | H | —C(O)—$C_2H_5$ |

| | | | | |
|---|---|---|---|---|
| H | $—CH_2C(CH_3)_2CH_2—$ | $—CH_3$ | H | —C(O)—NH—phenyl |
| H | $—CH_2C(CH_3)_2CH_2—$ | $—CH_3$ | H | $—C(O)—NH—CH_3$ |
| H | $—CH_2C(CH_3)_2CH_2—$ | $—CH_3$ | H | —C(O)—NH—isopropyl |
| H | $—CH_2C(CH_3)_2CH_2—$ | $—CH_3$ | H | $—C(O)—N(CH_3)_2$ |
| H | $—CH_2C(CH_3)_2CH_2—$ | $—CH_3$ | H | $—S(O)_2—CH_3$ |
| H | $—CH_2C(CH_3)_2CH_2—$ | $—CH_3$ | $—CH_3$ | —C(O)—phenyl |
| H | $—CH_2C(CH_3)_2CH_2—$ | $—CH_3$ | $—CH_3$ | $—C(O)—C_2H_5$ |
| H | $—CH_2C(CH_3)_2CH_2—$ | $—CH_3$ | $—CH_3$ | —C(O)—NH—phenyl |
| H | $—CH_2C(CH_3)_2CH_2—$ | $—CH_3$ | $—CH_3$ | $—C(O)—NH—CH_3$ |
| H | $—CH_2C(CH_3)_2CH_2—$ | $—CH_3$ | $—CH_3$ | —C(O)—NH—isopropyl |
| H | $—CH_2C(CH_3)_2CH_2—$ | $—CH_3$ | $—CH_3$ | $—C(O)—N(CH_3)_2$ |
| H | $—CH_2C(CH_3)_2CH_2—$ | $—CH_3$ | $—CH_3$ | $—S(O)_2—CH_3$ |
| H | $—(CH_2)_2OCH_2—$ | H | H | —C(O)—phenyl |
| H | $—(CH_2)_2OCH_2—$ | H | H | $—C(O)—C_2H_5$ |
| H | $—(CH_2)_2OCH_2—$ | H | H | —C(O)—NH—phenyl |
| H | $—(CH_2)_2OCH_2—$ | H | H | $—C(O)—NH—CH_3$ |
| H | $—(CH_2)_2OCH_2—$ | H | H | —C(O)—NH—isopropyl |
| H | $—(CH_2)_2OCH_2—$ | H | H | $—C(O)—N(CH_3)_2$ |
| H | $—(CH_2)_2OCH_2—$ | H | H | $—S(O)_2—CH_3$ |
| H | $—(CH_2)_2OCH_2—$ | H | $—CH_3$ | —C(O)—phenyl |
| H | $—(CH_2)_2OCH_2—$ | H | $—CH_3$ | $—C(O)—C_2H_5$ |
| H | $—(CH_2)_2OCH_2—$ | H | $—CH_3$ | —C(O)—NH—phenyl |
| H | $—(CH_2)_2OCH_2—$ | H | $—CH_3$ | $—C(O)—NH—CH_3$ |
| H | $—(CH_2)_2OCH_2—$ | H | $—CH_3$ | —C(O)—NH—isopropyl |
| H | $—(CH_2)_2OCH_2—$ | H | $—CH_3$ | $—C(O)—N(CH_3)_2$ |
| H | $—(CH_2)_2OCH_2—$ | H | $—CH_3$ | $—S(O)_2—CH_3$ |
| H | $—(CH_2)_2OCH_2—$ | $—CH_3$ | H | —C(O)—phenyl |
| H | $—(CH_2)_2OCH_2—$ | $—CH_3$ | H | $—C(O)—C_2H_5$ |
| H | $—(CH_2)_2OCH_2—$ | $—CH_3$ | H | —C(O)—NH—phenyl |
| H | $—(CH_2)_2OCH_2—$ | $—CH_3$ | H | $—C(O)—NH—CH_3$ |
| H | $—(CH_2)_2OCH_2—$ | $—CH_3$ | H | —C(O)—NH—isopropyl |
| H | $—(CH_2)_2OCH_2—$ | $—CH_3$ | H | $—C(O)—N(CH_3)_2$ |
| H | $—(CH_2)_2OCH_2—$ | $—CH_3$ | H | $—S(O)_2—CH_3$ |
| H | $—(CH_2)_2OCH_2—$ | $—CH_3$ | $—CH_3$ | —C(O)—phenyl |
| H | $—(CH_2)_2OCH_2—$ | $—CH_3$ | $—CH_3$ | $—C(O)—C_2H_5$ |
| H | $—(CH_2)_2OCH_2—$ | $—CH_3$ | $—CH_3$ | —C(O)—NH—phenyl |
| H | $—(CH_2)_2OCH_2—$ | $—CH_3$ | $—CH_3$ | $—C(O)—NH—CH_3$ |
| H | $—(CH_2)_2OCH_2—$ | $—CH_3$ | $—CH_3$ | —C(O)—NH—isopropyl |
| H | $—(CH_2)_2OCH_2—$ | $—CH_3$ | $—CH_3$ | $—C(O)—N(CH_3)_2$ |
| H | $—(CH_2)_2OCH_2—$ | $—CH_3$ | $—CH_3$ | $—S(O)_2—CH_3$ |
| $—CH_3$ | $—(CH_2)_3—$ | H | H | —C(O)—phenyl |
| $—CH_3$ | $—(CH_2)_3—$ | H | H | $—C(O)—C_2H_5$ |
| $—CH_3$ | $—(CH_2)_3—$ | H | H | —C(O)—NH—phenyl |
| $—CH_3$ | $—(CH_2)_3—$ | H | H | $—C(O)—NH—CH_3$ |
| $—CH_3$ | $—(CH_2)_3—$ | H | H | —C(O)—NH—isopropyl |
| $—CH_3$ | $—(CH_2)_3—$ | H | H | $—C(O)—N(CH_3)_2$ |
| $—CH_3$ | $—(CH_2)_3—$ | H | H | $—S(O)_2—CH_3$ |
| $—CH_3$ | $—(CH_2)_3—$ | H | $—CH_3$ | —C(O)—phenyl |
| $—CH_3$ | $—(CH_2)_3—$ | H | $—CH_3$ | $—C(O)—C_2H_5$ |
| $—CH_3$ | $—(CH_2)_3—$ | H | $—CH_3$ | —C(O)—NH—phenyl |
| $—CH_3$ | $—(CH_2)_3—$ | H | $—CH_3$ | $—C(O)—NH—CH_3$ |
| $—CH_3$ | $—(CH_2)_3—$ | H | $—CH_3$ | —C(O)—NH—isopropyl |
| $—CH_3$ | $—(CH_2)_3—$ | H | $—CH_3$ | $—C(O)—N(CH_3)_2$ |
| $—CH_3$ | $—(CH_2)_3—$ | H | $—CH_3$ | $—S(O)_2—CH_3$ |
| $—CH_3$ | $—(CH_2)_3—$ | $—CH_3$ | H | —C(O)—phenyl |
| $—CH_3$ | $—(CH_2)_3—$ | $—CH_3$ | H | $—C(O)—C_2H_5$ |
| $—CH_3$ | $—(CH_2)_3—$ | $—CH_3$ | H | —C(O)—NH—phenyl |
| $—CH_3$ | $—(CH_2)_3—$ | $—CH_3$ | H | $—C(O)—NH—CH_3$ |
| $—CH_3$ | $—(CH_2)_3—$ | $—CH_3$ | H | —C(O)—NH—isopropyl |
| $—CH_3$ | $—(CH_2)_3—$ | $—CH_3$ | H | $—C(O)—N(CH_3)_2$ |
| $—CH_3$ | $—(CH_2)_3—$ | $—CH_3$ | H | $—S(O)_2—CH_3$ |
| $—CH_3$ | $—(CH_2)_3—$ | $—CH_3$ | $—CH_3$ | —C(O)—phenyl |
| $—CH_3$ | $—(CH_2)_3—$ | $—CH_3$ | $—CH_3$ | $—C(O)—C_2H_5$ |
| $—CH_3$ | $—(CH_2)_3—$ | $—CH_3$ | $—CH_3$ | —C(O)—NH—phenyl |
| $—CH_3$ | $—(CH_2)_3—$ | $—CH_3$ | $—CH_3$ | $—C(O)—NH—CH_3$ |
| $—CH_3$ | $—(CH_2)_3—$ | $—CH_3$ | $—CH_3$ | —C(O)—NH—isopropyl |
| $—CH_3$ | $—(CH_2)_3—$ | $—CH_3$ | $—CH_3$ | $—C(O)—N(CH_3)_2$ |
| $—CH_3$ | $—(CH_2)_3—$ | $—CH_3$ | $—CH_3$ | $—S(O)_2—CH_3$ |
| $—CH_3$ | $—(CH_2)_4—$ | H | H | —C(O)—phenyl |
| $—CH_3$ | $—(CH_2)_4—$ | H | H | $—C(O)—C_2H_5$ |
| $—CH_3$ | $—(CH_2)_4—$ | H | H | —C(O)—NH—phenyl |
| $—CH_3$ | $—(CH_2)_4—$ | H | H | $—C(O)—NH—CH_3$ |
| $—CH_3$ | $—(CH_2)_4—$ | H | H | —C(O)—NH—isopropyl |
| $—CH_3$ | $—(CH_2)_4—$ | H | H | $—C(O)—N(CH_3)_2$ |
| $—CH_3$ | $—(CH_2)_4—$ | H | H | $—S(O)_2—CH_3$ |
| $—CH_3$ | $—(CH_2)_4—$ | H | $—CH_3$ | —C(O)—phenyl |
| $—CH_3$ | $—(CH_2)_4—$ | H | $—CH_3$ | $—C(O)—C_2H_5$ |
| $—CH_3$ | $—(CH_2)_4—$ | H | $—CH_3$ | —C(O)—NH—phenyl |
| $—CH_3$ | $—(CH_2)_4—$ | H | $—CH_3$ | $—C(O)—NH—CH_3$ |
| $—CH_3$ | $—(CH_2)_4—$ | H | $—CH_3$ | —C(O)—NH—isopropyl |
| $—CH_3$ | $—(CH_2)_4—$ | H | $—CH_3$ | $—C(O)—N(CH_3)_2$ |
| $—CH_3$ | $—(CH_2)_4—$ | H | $—CH_3$ | $—S(O)_2—CH_3$ |

| | | | | |
|---|---|---|---|---|
| $-CH_3$ | $-(CH_2)_4-$ | $-CH_3$ | H | $-C(O)-$phenyl |
| $-CH_3$ | $-(CH_2)_4-$ | $-CH_3$ | H | $-C(O)-C_2H_5$ |
| $-CH_3$ | $-(CH_2)_4-$ | $-CH_3$ | H | $-C(O)-NH-$phenyl |
| $-CH_3$ | $-(CH_2)_4-$ | $-CH_3$ | H | $-C(O)-NH-CH_3$ |
| $-CH_3$ | $-(CH_2)_4-$ | $-CH_3$ | H | $-C(O)-NH-$isopropyl |
| $-CH_3$ | $-(CH_2)_4-$ | $-CH_3$ | H | $-C(O)-N(CH_3)_2$ |
| $-CH_3$ | $-(CH_2)_4-$ | $-CH_3$ | H | $-S(O)_2-CH_3$ |
| $-CH_3$ | $-(CH_2)_4-$ | $-CH_3$ | $-CH_3$ | $-C(O)-$phenyl |
| $-CH_3$ | $-(CH_2)_4-$ | $-CH_3$ | $-CH_3$ | $-C(O)-C_2H_5$ |
| $-CH_3$ | $-(CH_2)_4-$ | $-CH_3$ | $-CH_3$ | $-C(O)-NH-$phenyl |
| $-CH_3$ | $-(CH_2)_4-$ | $-CH_3$ | $-CH_3$ | $-C(O)-NH-CH_3$ |
| $-CH_3$ | $-(CH_2)_4-$ | $-CH_3$ | $-CH_3$ | $-C(O)-NH-$isopropyl |
| $-CH_3$ | $-(CH_2)_4-$ | $-CH_3$ | $-CH_3$ | $-C(O)-N(CH_3)_2$ |
| $-CH_3$ | $-(CH_2)_4-$ | $-CH_3$ | $-CH_3$ | $-S(O)_2-CH_3$ |
| $-CH_3$ | $-CH_2C(CH_3)_2-$ | H | H | $-C(O)-$phenyl |
| $-CH_3$ | $-CH_2C(CH_3)_2-$ | H | H | $-C(O)-C_2H_5$ |
| $-CH_3$ | $-CH_2C(CH_3)_2-$ | H | H | $-C(O)-NH-$phenyl |
| $-CH_3$ | $-CH_2C(CH_3)_2-$ | H | H | $-C(O)-NH-CH_3$ |
| $-CH_3$ | $-CH_2C(CH_3)_2-$ | H | H | $-C(O)-NH-$isopropyl |
| $-CH_3$ | $-CH_2C(CH_3)_2-$ | H | H | $-C(O)-N(CH_3)_2$ |
| $-CH_3$ | $-CH_2C(CH_3)_2-$ | H | H | $-S(O)_2-CH_3$ |
| $-CH_3$ | $-CH_2C(CH_3)_2-$ | H | $-CH_3$ | $-C(O)-$phenyl |
| $-CH_3$ | $-CH_2C(CH_3)_2-$ | H | $-CH_3$ | $-C(O)-C_2H_5$ |
| $-CH_3$ | $-CH_2C(CH_3)_2-$ | H | $-CH_3$ | $-C(O)-NH-$phenyl |
| $-CH_3$ | $-CH_2C(CH_3)_2-$ | H | $-CH_3$ | $-C(O)-NH-CH_3$ |
| $-CH_3$ | $-CH_2C(CH_3)_2-$ | H | $-CH_3$ | $-C(O)-NH-$isopropyl |
| $-CH_3$ | $-CH_2C(CH_3)_2-$ | H | $-CH_3$ | $-C(O)-N(CH_3)_2$ |
| $-CH_3$ | $-CH_2C(CH_3)_2-$ | H | $-CH_3$ | $-S(O)_2-CH_3$ |
| $-CH_3$ | $-CH_2C(CH_3)_2-$ | $-CH_3$ | H | $-C(O)-$phenyl |
| $-CH_3$ | $-CH_2C(CH_3)_2-$ | $-CH_3$ | H | $-C(O)-C_2H_5$ |
| $-CH_3$ | $-CH_2C(CH_3)_2-$ | $-CH_3$ | H | $-C(O)-NH-$phenyl |
| $-CH_3$ | $-CH_2C(CH_3)_2-$ | $-CH_3$ | H | $-C(O)-NH-CH_3$ |
| $-CH_3$ | $-CH_2C(CH_3)_2-$ | $-CH_3$ | H | $-C(O)-NH-$isopropyl |
| $-CH_3$ | $-CH_2C(CH_3)_2-$ | $-CH_3$ | H | $-C(O)-N(CH_3)_2$ |
| $-CH_3$ | $-CH_2C(CH_3)_2-$ | $-CH_3$ | H | $-S(O)_2-CH_3$ |
| $-CH_3$ | $-CH_2C(CH_3)_2-$ | $-CH_3$ | $-CH_3$ | $-C(O)-$phenyl |
| $-CH_3$ | $-CH_2C(CH_3)_2-$ | $-CH_3$ | $-CH_3$ | $-C(O)-C_2H_5$ |
| $-CH_3$ | $-CH_2C(CH_3)_2-$ | $-CH_3$ | $-CH_3$ | $-C(O)-NH-$phenyl |
| $-CH_3$ | $-CH_2C(CH_3)_2-$ | $-CH_3$ | $-CH_3$ | $-C(O)-NH-CH_3$ |
| $-CH_3$ | $-CH_2C(CH_3)_2-$ | $-CH_3$ | $-CH_3$ | $-C(O)-NH-$isopropyl |
| $-CH_3$ | $-CH_2C(CH_3)_2-$ | $-CH_3$ | $-CH_3$ | $-C(O)-N(CH_3)_2$ |
| $-CH_3$ | $-CH_2C(CH_3)_2-$ | $-CH_3$ | $-CH_3$ | $-S(O)_2-CH_3$ |
| $-CH_3$ | $-CH_2C(CH_3)_2CH_2-$ | H | H | $-C(O)-$phenyl |
| $-CH_3$ | $-CH_2C(CH_3)_2CH_2-$ | H | H | $-C(O)-C_2H_5$ |
| $-CH_3$ | $-CH_2C(CH_3)_2CH_2-$ | H | H | $-C(O)-NH-$phenyl |
| $-CH_3$ | $-CH_2C(CH_3)_2CH_2-$ | H | H | $-C(O)-NH-CH_3$ |
| $-CH_3$ | $-CH_2C(CH_3)_2CH_2-$ | H | H | $-C(O)-NH-$isopropyl |
| $-CH_3$ | $-CH_2C(CH_3)_2CH_2-$ | H | H | $-C(O)-N(CH_3)_2$ |
| $-CH_3$ | $-CH_2C(CH_3)_2CH_2-$ | H | H | $-S(O)_2-CH_3$ |
| $-CH_3$ | $-CH_2C(CH_3)_2CH_2-$ | H | $-CH_3$ | $-C(O)-$phenyl |
| $-CH_3$ | $-CH_2C(CH_3)_2CH_2-$ | H | $-CH_3$ | $-C(O)-C_2H_5$ |
| $-CH_3$ | $-CH_2C(CH_3)_2CH_2-$ | H | $-CH_3$ | $-C(O)-NH-$phenyl |
| $-CH_3$ | $-CH_2C(CH_3)_2CH_2-$ | H | $-CH_3$ | $-C(O)-NH-CH_3$ |
| $-CH_3$ | $-CH_2C(CH_3)_2CH_2-$ | H | $-CH_3$ | $-C(O)-NH-$isopropyl |
| $-CH_3$ | $-CH_2C(CH_3)_2CH_2-$ | H | $-CH_3$ | $-C(O)-N(CH_3)_2$ |
| $-CH_3$ | $-CH_2C(CH_3)_2CH_2-$ | H | $-CH_3$ | $-S(O)_2-CH_3$ |
| $-CH_3$ | $-CH_2C(CH_3)_2CH_2-$ | $-CH_3$ | H | $-C(O)-$phenyl |
| $-CH_3$ | $-CH_2C(CH_3)_2CH_2-$ | $-CH_3$ | H | $-C(O)-C_2H_5$ |
| $-CH_3$ | $-CH_2C(CH_3)_2CH_2-$ | $-CH_3$ | H | $-C(O)-NH-$phenyl |
| $-CH_3$ | $-CH_2C(CH_3)_2CH_2-$ | $-CH_3$ | H | $-C(O)-NH-CH_3$ |
| $-CH_3$ | $-CH_2C(CH_3)_2CH_2-$ | $-CH_3$ | H | $-C(O)-NH-$isopropyl |
| $-CH_3$ | $-CH_2C(CH_3)_2CH_2-$ | $-CH_3$ | H | $-C(O)-N(CH_3)_2$ |
| $-CH_3$ | $-CH_2C(CH_3)_2CH_2-$ | $-CH_3$ | H | $-S(O)_2-CH_3$ |
| $-CH_3$ | $-CH_2C(CH_3)_2CH_2-$ | $-CH_3$ | $-CH_3$ | $-C(O)-$phenyl |
| $-CH_3$ | $-CH_2C(CH_3)_2CH_2-$ | $-CH_3$ | $-CH_3$ | $-C(O)-C_2H_5$ |
| $-CH_3$ | $-CH_2C(CH_3)_2CH_2-$ | $-CH_3$ | $-CH_3$ | $-C(O)-NH-$phenyl |
| $-CH_3$ | $-CH_2C(CH_3)_2CH_2-$ | $-CH_3$ | $-CH_3$ | $-C(O)-NH-CH_3$ |
| $-CH_3$ | $-CH_2C(CH_3)_2CH_2-$ | $-CH_3$ | $-CH_3$ | $-C(O)-NH-$isopropyl |
| $-CH_3$ | $-CH_2C(CH_3)_2CH_2-$ | $-CH_3$ | $-CH_3$ | $-C(O)-N(CH_3)_2$ |
| $-CH_3$ | $-CH_2C(CH_3)_2CH_2-$ | $-CH_3$ | $-CH_3$ | $-S(O)_2-CH_3$ |
| $-CH_3$ | $-(CH_2)_2OCH_2-$ | H | H | $-C(O)-$phenyl |
| $-CH_3$ | $-(CH_2)_2OCH_2-$ | H | H | $-C(O)-C_2H_5$ |
| $-CH_3$ | $-(CH_2)_2OCH_2-$ | H | H | $-C(O)-NH-$phenyl |
| $-CH_3$ | $-(CH_2)_2OCH_2-$ | H | H | $-C(O)-NH-CH_3$ |
| $-CH_3$ | $-(CH_2)_2OCH_2-$ | H | H | $-C(O)-NH-$isopropyl |
| $-CH_3$ | $-(CH_2)_2OCH_2-$ | H | H | $-C(O)-N(CH_3)_2$ |
| $-CH_3$ | $-(CH_2)_2OCH_2-$ | H | H | $-S(O)_2-CH_3$ |
| $-CH_3$ | $-(CH_2)_2OCH_2-$ | H | $-CH_3$ | $-C(O)-$phenyl |
| $-CH_3$ | $-(CH_2)_2OCH_2-$ | H | $-CH_3$ | $-C(O)-C_2H_5$ |
| $-CH_3$ | $-(CH_2)_2OCH_2-$ | H | $-CH_3$ | $-C(O)-NH-$phenyl |
| $-CH_3$ | $-(CH_2)_2OCH_2-$ | H | $-CH_3$ | $-C(O)-NH-CH_3$ |
| $-CH_3$ | $-(CH_2)_2OCH_2-$ | H | $-CH_3$ | $-C(O)-NH-$isopropyl |

| | | | | |
|---|---|---|---|---|
| —$CH_3$ | —$(CH_2)_2OCH_2$— | H | —$CH_3$ | —C(O)—$N(CH_3)_2$ |
| —$CH_3$ | —$(CH_2)_2OCH_2$— | H | —$CH_3$ | —$S(O)_2$—$CH_3$ |
| —$CH_3$ | —$(CH_2)_2OCH_2$— | —$CH_3$ | H | —C(O)—phenyl |
| —$CH_3$ | —$(CH_2)_2OCH_2$— | —$CH_3$ | H | —C(O)—$C_2H_5$ |
| —$CH_3$ | —$(CH_2)_2OCH_2$— | —$CH_3$ | H | —C(O)—NH—phenyl |
| —$CH_3$ | —$(CH_2)_2OCH_2$— | —$CH_3$ | H | —C(O)—NH—$CH_3$ |
| —$CH_3$ | —$(CH_2)_2OCH_2$— | —$CH_3$ | H | —C(O)—NH—isopropyl |
| —$CH_3$ | —$(CH_2)_2OCH_2$— | —$CH_3$ | H | —C(O)—$N(CH_3)_2$ |
| —$CH_3$ | —$(CH_2)_2OCH_2$— | —$CH_3$ | H | —$S(O)_2$—$CH_3$ |
| —$CH_3$ | —$(CH_2)_2OCH_2$— | —$CH_3$ | —$CH_3$ | —C(O)—phenyl |
| —$CH_3$ | —$(CH_2)_2OCH_2$— | —$CH_3$ | —$CH_3$ | —C(O)—$C_2H_5$ |
| —$CH_3$ | —$(CH_2)_2OCH_2$— | —$CH_3$ | —$CH_3$ | —C(O)—NH—phenyl |
| —$CH_3$ | —$(CH_2)_2OCH_2$— | —$CH_3$ | —$CH_3$ | —C(O)—NH—$CH_3$ |
| —$CH_3$ | —$(CH_2)_2OCH_2$— | —$CH_3$ | —$CH_3$ | —C(O)—NH—isopropyl |
| —$CH_3$ | —$(CH_2)_2OCH_2$— | —$CH_3$ | —$CH_3$ | —C(O)—$N(CH_3)_2$ |
| —$CH_3$ | —$(CH_2)_2OCH_2$— | —$CH_3$ | —$CH_3$ | —$S(O)_2$—$CH_3$ |
| —$(CH_2)_2CH_3$ | —$(CH_2)_3$— | H | H | —C(O)—phenyl |
| —$(CH_2)_2CH_3$ | —$(CH_2)_3$— | H | H | —C(O)—$C_2H_5$ |
| —$(CH_2)_2CH_3$ | —$(CH_2)_3$— | H | H | —C(O)—NH—phenyl |
| —$(CH_2)_2CH_3$ | —$(CH_2)_3$— | H | H | —C(O)—NH—$CH_3$ |
| —$(CH_2)_2CH_3$ | —$(CH_2)_3$— | H | H | —C(O)—NH—isopropyl |
| —$(CH_2)_2CH_3$ | —$(CH_2)_3$— | H | H | —C(O)—$N(CH_3)_2$ |
| —$(CH_2)_2CH_3$ | —$(CH_2)_3$— | H | H | —$S(O)_2$—$CH_3$ |
| —$(CH_2)_2CH_3$ | —$(CH_2)_3$— | H | —$CH_3$ | —C(O)—phenyl |
| —$(CH_2)_2CH_3$ | —$(CH_2)_3$— | H | —$CH_3$ | —C(O)—$C_2H_5$ |
| —$(CH_2)_2CH_3$ | —$(CH_2)_3$— | H | —$CH_3$ | —C(O)—NH—phenyl |
| —$(CH_2)_2CH_3$ | —$(CH_2)_3$— | H | —$CH_3$ | —C(O)—NH—$CH_3$ |
| —$(CH_2)_2CH_3$ | —$(CH_2)_3$— | H | —$CH_3$ | —C(O)—NH—isopropyl |
| —$(CH_2)_2CH_3$ | —$(CH_2)_3$— | H | —$CH_3$ | —C(O)—$N(CH_3)_2$ |
| —$(CH_2)_2CH_3$ | —$(CH_2)_3$— | H | —$CH_3$ | —$S(O)_2$—$CH_3$ |
| —$(CH_2)_2CH_3$ | —$(CH_2)_3$— | —$CH_3$ | H | —C(O)—phenyl |
| —$(CH_2)_2CH_3$ | —$(CH_2)_3$— | —$CH_3$ | H | —C(O)—$C_2H_5$ |
| —$(CH_2)_2CH_3$ | —$(CH_2)_3$— | —$CH_3$ | H | —C(O)—NH—phenyl |
| —$(CH_2)_2CH_3$ | —$(CH_2)_3$— | —$CH_3$ | H | —C(O)—NH—$CH_3$ |
| —$(CH_2)_2CH_3$ | —$(CH_2)_3$— | —$CH_3$ | H | —C(O)—NH—isopropyl |
| —$(CH_2)_2CH_3$ | —$(CH_2)_3$— | —$CH_3$ | H | —C(O)—$N(CH_3)_2$ |
| —$(CH_2)_2CH_3$ | —$(CH_2)_3$— | —$CH_3$ | H | —$S(O)_2$—$CH_3$ |
| —$(CH_2)_2CH_3$ | —$(CH_2)_3$— | —$CH_3$ | —$CH_3$ | —C(O)—phenyl |
| —$(CH_2)_2CH_3$ | —$(CH_2)_3$— | —$CH_3$ | —$CH_3$ | —C(O)—$C_2H_5$ |
| —$(CH_2)_2CH_3$ | —$(CH_2)_3$— | —$CH_3$ | —$CH_3$ | —C(O)—NH—phenyl |
| —$(CH_2)_2CH_3$ | —$(CH_2)_3$— | —$CH_3$ | —$CH_3$ | —C(O)—NH—$CH_3$ |
| —$(CH_2)_2CH_3$ | —$(CH_2)_3$— | —$CH_3$ | —$CH_3$ | —C(O)—NH—isopropyl |
| —$(CH_2)_2CH_3$ | —$(CH_2)_3$— | —$CH_3$ | —$CH_3$ | —C(O)—$N(CH_3)_2$ |
| —$(CH_2)_2CH_3$ | —$(CH_2)_3$— | —$CH_3$ | —$CH_3$ | —$S(O)_2$—$CH_3$ |
| —$(CH_2)_2CH_3$ | —$(CH_2)_4$— | H | H | —C(O)—phenyl |
| —$(CH_2)_2CH_3$ | —$(CH_2)_4$— | H | H | —C(O)—$C_2H_5$ |
| —$(CH_2)_2CH_3$ | —$(CH_2)_4$— | H | H | —C(O)—NH—phenyl |
| —$(CH_2)_2CH_3$ | —$(CH_2)_4$— | H | H | —C(O)—NH—$CH_3$ |
| —$(CH_2)_2CH_3$ | —$(CH_2)_4$— | H | H | —C(O)—NH—isopropyl |
| —$(CH_2)_2CH_3$ | —$(CH_2)_4$— | H | H | —C(O)—$N(CH_3)_2$ |
| —$(CH_2)_2CH_3$ | —$(CH_2)_4$— | H | H | —$S(O)_2$—$CH_3$ |
| —$(CH_2)_2CH_3$ | —$(CH_2)_4$— | H | —$CH_3$ | —C(O)—phenyl |
| —$(CH_2)_2CH_3$ | —$(CH_2)_4$— | H | —$CH_3$ | —C(O)—$C_2H_5$ |
| —$(CH_2)_2CH_3$ | —$(CH_2)_4$— | H | —$CH_3$ | —C(O)—NH—phenyl |
| —$(CH_2)_2CH_3$ | —$(CH_2)_4$— | H | —$CH_3$ | —C(O)—NH—$CH_3$ |
| —$(CH_2)_2CH_3$ | —$(CH_2)_4$— | H | —$CH_3$ | —C(O)—NH—isopropyl |
| —$(CH_2)_2CH_3$ | —$(CH_2)_4$— | H | —$CH_3$ | —C(O)—$N(CH_3)_2$ |
| —$(CH_2)_2CH_3$ | —$(CH_2)_4$— | H | —$CH_3$ | —$S(O)_2$—$CH_3$ |
| —$(CH_2)_2CH_3$ | —$(CH_2)_4$— | —$CH_3$ | H | —C(O)—phenyl |
| —$(CH_2)_2CH_3$ | —$(CH_2)_4$— | —$CH_3$ | H | —C(O)—$C_2H_5$ |
| —$(CH_2)_2CH_3$ | —$(CH_2)_4$— | —$CH_3$ | H | —C(O)—NH—phenyl |
| —$(CH_2)_2CH_3$ | —$(CH_2)_4$— | —$CH_3$ | H | —C(O)—NH—$CH_3$ |
| —$(CH_2)_2CH_3$ | —$(CH_2)_4$— | —$CH_3$ | H | —C(O)—NH—isopropyl |
| —$(CH_2)_2CH_3$ | —$(CH_2)_4$— | —$CH_3$ | H | —C(O)—$N(CH_3)_2$ |
| —$(CH_2)_2CH_3$ | —$(CH_2)_4$— | —$CH_3$ | H | —$S(O)_2$—$CH_3$ |
| —$(CH_2)_2CH_3$ | —$(CH_2)_4$— | —$CH_3$ | —$CH_3$ | —C(O)—phenyl |
| —$(CH_2)_2CH_3$ | —$(CH_2)_4$— | —$CH_3$ | —$CH_3$ | —C(O)—$C_2H_5$ |
| —$(CH_2)_2CH_3$ | —$(CH_2)_4$— | —$CH_3$ | —$CH_3$ | —C(O)—NH—phenyl |
| —$(CH_2)_2CH_3$ | —$(CH_2)_4$— | —$CH_3$ | —$CH_3$ | —C(O)—NH—$CH_3$ |
| —$(CH_2)_2CH_3$ | —$(CH_2)_4$— | —$CH_3$ | —$CH_3$ | —C(O)—NH—isopropyl |
| —$(CH_2)_2CH_3$ | —$(CH_2)_4$— | —$CH_3$ | —$CH_3$ | —C(O)—$N(CH_3)_2$ |
| —$(CH_2)_2CH_3$ | —$(CH_2)_4$— | —$CH_3$ | —$CH_3$ | —$S(O)_2$—$CH_3$ |
| —$(CH_2)_2CH_3$ | —$CH_2C(CH_3)_2$— | H | H | —C(O)—phenyl |
| —$(CH_2)_2CH_3$ | —$CH_2C(CH_3)_2$— | H | H | —C(O)—$C_2H_5$ |
| —$(CH_2)_2CH_3$ | —$CH_2C(CH_3)_2$— | H | H | —C(O)—NH—phenyl |
| —$(CH_2)_2CH_3$ | —$CH_2C(CH_3)_2$— | H | H | —C(O)—NH—$CH_3$ |
| —$(CH_2)_2CH_3$ | —$CH_2C(CH_3)_2$— | H | H | —C(O)—NH—isopropyl |
| —$(CH_2)_2CH_3$ | —$CH_2C(CH_3)_2$— | H | H | —C(O)—$N(CH_3)_2$ |
| —$(CH_2)_2CH_3$ | —$CH_2C(CH_3)_2$— | H | H | —$S(O)_2$—$CH_3$ |
| —$(CH_2)_2CH_3$ | —$CH_2C(CH_3)_2$— | H | —$CH_3$ | —C(O)—phenyl |
| —$(CH_2)_2CH_3$ | —$CH_2C(CH_3)_2$— | H | —$CH_3$ | —C(O)—$C_2H_5$ |
| —$(CH_2)_2CH_3$ | —$CH_2C(CH_3)_2$— | H | —$CH_3$ | —C(O)—NH—phenyl |

| | | | | |
|---|---|---|---|---|
| —$(CH_2)_2CH_3$ | —$CH_2C(CH_3)_2$— | H | —$CH_3$ | —C(O)—NH—$CH_3$ |
| —$(CH_2)_2CH_3$ | —$CH_2C(CH_3)_2$— | H | —$CH_3$ | —C(O)—NH—isopropyl |
| —$(CH_2)_2CH_3$ | —$CH_2C(CH_3)_2$— | H | —$CH_3$ | —C(O)—N$(CH_3)_2$ |
| —$(CH_2)_2CH_3$ | —$CH_2C(CH_3)_2$— | H | —$CH_3$ | —$S(O)_2$—$CH_3$ |
| —$(CH_2)_2CH_3$ | —$CH_2C(CH_3)_2$— | —$CH_3$ | H | —C(O)—phenyl |
| —$(CH_2)_2CH_3$ | —$CH_2C(CH_3)_2$— | —$CH_3$ | H | —C(O)—$C_2H_5$ |
| —$(CH_2)_2CH_3$ | —$CH_2C(CH_3)_2$— | —$CH_3$ | H | —C(O)—NH—phenyl |
| —$(CH_2)_2CH_3$ | —$CH_2C(CH_3)_2$— | —$CH_3$ | H | —C(O)—NH—$CH_3$ |
| —$(CH_2)_2CH_3$ | —$CH_2C(CH_3)_2$— | —$CH_3$ | H | —C(O)—NH—isopropyl |
| —$(CH_2)_2CH_3$ | —$CH_2C(CH_3)_2$— | —$CH_3$ | H | —C(O)—N$(CH_3)_2$ |
| —$(CH_2)_2CH_3$ | —$CH_2C(CH_3)_2$— | —$CH_3$ | H | —$S(O)_2$—$CH_3$ |
| —$(CH_2)_2CH_3$ | —$CH_2C(CH_3)_2$— | —$CH_3$ | —$CH_3$ | —C(O)—phenyl |
| —$(CH_2)_2CH_3$ | —$CH_2C(CH_3)_2$— | —$CH_3$ | —$CH_3$ | —C(O)—$C_2H_5$ |
| —$(CH_2)_2CH_3$ | —$CH_2C(CH_3)_2$— | —$CH_3$ | —$CH_3$ | —C(O)—NH—phenyl |
| —$(CH_2)_2CH_3$ | —$CH_2C(CH_3)_2$— | —$CH_3$ | —$CH_3$ | —C(O)—NH—$CH_3$ |
| —$(CH_2)_2CH_3$ | —$CH_2C(CH_3)_2$— | —$CH_3$ | —$CH_3$ | —C(O)—NH—isopropyl |
| —$(CH_2)_2CH_3$ | —$CH_2C(CH_3)_2$— | —$CH_3$ | —$CH_3$ | —C(O)—N$(CH_3)_2$ |
| —$(CH_2)_2CH_3$ | —$CH_2C(CH_3)_2$— | —$CH_3$ | —$CH_3$ | —$S(O)_2$—$CH_3$ |
| —$(CH_2)_2CH_3$ | —$CH_2C(CH_3)_2CH_2$— | H | H | —C(O)—phenyl |
| —$(CH_2)_2CH_3$ | —$CH_2C(CH_3)_2CH_2$— | H | H | —C(O)—$C_2H_5$ |
| —$(CH_2)_2CH_3$ | —$CH_2C(CH_3)_2CH_2$— | H | H | —C(O)—NH—phenyl |
| —$(CH_2)_2CH_3$ | —$CH_2C(CH_3)_2CH_2$— | H | H | —C(O)—NH—$CH_3$ |
| —$(CH_2)_2CH_3$ | —$CH_2C(CH_3)_2CH_2$— | H | H | —C(O)—NH—isopropyl |
| —$(CH_2)_2CH_3$ | —$CH_2C(CH_3)_2CH_2$— | H | H | —C(O)—N$(CH_3)_2$ |
| —$(CH_2)_2CH_3$ | —$CH_2C(CH_3)_2CH_2$— | H | H | —$S(O)_2$—$CH_3$ |
| —$(CH_2)_2CH_3$ | —$CH_2C(CH_3)_2CH_2$— | H | —$CH_3$ | —C(O)—phenyl |
| —$(CH_2)_2CH_3$ | —$CH_2C(CH_3)_2CH_2$— | H | —$CH_3$ | —C(O)—$C_2H_5$ |
| —$(CH_2)_2CH_3$ | —$CH_2C(CH_3)_2CH_2$— | H | —$CH_3$ | —C(O)—NH—phenyl |
| —$(CH_2)_2CH_3$ | —$CH_2C(CH_3)_2CH_2$— | H | —$CH_3$ | —C(O)—NH—$CH_3$ |
| —$(CH_2)_2CH_3$ | —$CH_2C(CH_3)_2CH_2$— | H | —$CH_3$ | —C(O)—NH—isopropyl |
| —$(CH_2)_2CH_3$ | —$CH_2C(CH_3)_2CH_2$— | H | —$CH_3$ | —C(O)—N$(CH_3)_2$ |
| —$(CH_2)_2CH_3$ | —$CH_2C(CH_3)_2CH_2$— | H | —$CH_3$ | —$S(O)_2$—$CH_3$ |
| —$(CH_2)_2CH_3$ | —$CH_2C(CH_3)_2CH_2$— | —$CH_3$ | H | —C(O)—phenyl |
| —$(CH_2)_2CH_3$ | —$CH_2C(CH_3)_2CH_2$— | —$CH_3$ | H | —C(O)—$C_2H_5$ |
| —$(CH_2)_2CH_3$ | —$CH_2C(CH_3)_2CH_2$— | —$CH_3$ | H | —C(O)—NH—phenyl |
| —$(CH_2)_2CH_3$ | —$CH_2C(CH_3)_2CH_2$— | —$CH_3$ | H | —C(O)—NH—$CH_3$ |
| —$(CH_2)_2CH_3$ | —$CH_2C(CH_3)_2CH_2$— | —$CH_3$ | H | —C(O)—NH—isopropyl |
| —$(CH_2)_2CH_3$ | —$CH_2C(CH_3)_2CH_2$— | —$CH_3$ | H | —C(O)—N$(CH_3)_2$ |
| —$(CH_2)_2CH_3$ | —$CH_2C(CH_3)_2CH_2$— | —$CH_3$ | H | —$S(O)_2$—$CH_3$ |
| —$(CH_2)_2CH_3$ | —$CH_2C(CH_3)_2CH_2$— | —$CH_3$ | —$CH_3$ | —C(O)—phenyl |
| —$(CH_2)_2CH_3$ | —$CH_2C(CH_3)_2CH_2$— | —$CH_3$ | —$CH_3$ | —C(O)—$C_2H_5$ |
| —$(CH_2)_2CH_3$ | —$CH_2C(CH_3)_2CH_2$— | —$CH_3$ | —$CH_3$ | —C(O)—NH—phenyl |
| —$(CH_2)_2CH_3$ | —$CH_2C(CH_3)_2CH_2$— | —$CH_3$ | —$CH_3$ | —C(O)—NH—$CH_3$ |
| —$(CH_2)_2CH_3$ | —$CH_2C(CH_3)_2CH_2$— | —$CH_3$ | —$CH_3$ | —C(O)—NH—isopropyl |
| —$(CH_2)_2CH_3$ | —$CH_2C(CH_3)_2CH_2$— | —$CH_3$ | —$CH_3$ | —C(O)—N$(CH_3)_2$ |
| —$(CH_2)_2CH_3$ | —$CH_2C(CH_3)_2CH_2$— | —$CH_3$ | —$CH_3$ | —$S(O)_2$—$CH_3$ |
| —$(CH_2)_2CH_3$ | —$(CH_2)_2OCH_2$— | H | H | —C(O)—phenyl |
| —$(CH_2)_2CH_3$ | —$(CH_2)_2OCH_2$— | H | H | —C(O)—$C_2H_5$ |
| —$(CH_2)_2CH_3$ | —$(CH_2)_2OCH_2$— | H | H | —C(O)—NH—phenyl |
| —$(CH_2)_2CH_3$ | —$(CH_2)_2OCH_2$— | H | H | —C(O)—NH—$CH_3$ |
| —$(CH_2)_2CH_3$ | —$(CH_2)_2OCH_2$— | H | H | —C(O)—NH—isopropyl |
| —$(CH_2)_2CH_3$ | —$(CH_2)_2OCH_2$— | H | H, | —C(O)—N$(CH_3)_2$ |
| —$(CH_2)_2CH_3$ | —$(CH_2)_2OCH_2$— | H | H | —$S(O)_2$—$CH_3$ |
| —$(CH_2)_2CH_3$ | —$(CH_2)_2OCH_2$— | H | —$CH_3$ | —C(O)—phenyl |
| —$(CH_2)_2CH_3$ | —$(CH_2)_2OCH_2$— | H | —$CH_3$ | —C(O)—$C_2H_5$ |
| —$(CH_2)_2CH_3$ | —$(CH_2)_2OCH_2$— | H | —$CH_3$ | —C(O)—NH—phenyl |
| —$(CH_2)_2CH_3$ | —$(CH_2)_2OCH_2$— | H | —$CH_3$ | —C(O)—NH—$CH_3$ |
| —$(CH_2)_2CH_3$ | —$(CH_2)_2OCH_2$— | H | —$CH_3$ | —C(O)—NH—isopropyl |
| —$(CH_2)_2CH_3$ | —$(CH_2)_2OCH_2$— | H | —$CH_3$ | —C(O)—N$(CH_3)_2$ |
| —$(CH_2)_2CH_3$ | —$(CH_2)_2OCH_2$— | H | —$CH_3$ | —$S(O)_2$—$CH_3$ |
| —$(CH_2)_2CH_3$ | —$(CH_2)_2OCH_2$— | —$CH_3$ | H | —C(O)—phenyl |
| —$(CH_2)_2CH_3$ | —$(CH_2)_2OCH_2$— | —$CH_3$ | H | —C(O)—$C_2H_5$ |
| —$(CH_2)_2CH_3$ | —$(CH_2)_2OCH_2$— | —$CH_3$ | H | —C(O)—NH—phenyl |
| —$(CH_2)_2CH_3$ | —$(CH_2)_2OCH_2$— | —$CH_3$ | H | —C(O)—NH—$CH_3$ |
| —$(CH_2)_2CH_3$ | —$(CH_2)_2OCH_2$— | —$CH_3$ | H | —C(O)—NH—isopropyl |
| —$(CH_2)_2CH_3$ | —$(CH_2)_2OCH_2$— | —$CH_3$ | H | —C(O)—N$(CH_3)_2$ |
| —$(CH_2)_2CH_3$ | —$(CH_2)_2OCH_2$— | —$CH_3$ | H | —$S(O)_2$—$CH_3$ |
| —$(CH_2)_2CH_3$ | —$(CH_2)_2OCH_2$— | —$CH_3$ | —$CH_3$ | —C(O)—phenyl |
| —$(CH_2)_2CH_3$ | —$(CH_2)_2OCH_2$— | —$CH_3$ | —$CH_3$ | —C(O)—$C_2H_5$ |
| —$(CH_2)_2CH_3$ | —$(CH_2)_2OCH_2$— | —$CH_3$ | —$CH_3$ | —C(O)—NH—phenyl |
| —$(CH_2)_2CH_3$ | —$(CH_2)_2OCH_2$— | —$CH_3$ | —$CH_3$ | —C(O)—NH—$CH_3$ |
| —$(CH_2)_2CH_3$ | —$(CH_2)_2OCH_2$— | —$CH_3$ | —$CH_3$ | —C(O)—NH—isopropyl |
| —$(CH_2)_2CH_3$ | —$(CH_2)_2OCH_2$— | —$CH_3$ | —$CH_3$ | —C(O)—N$(CH_3)_2$ |
| —$(CH_2)_2CH_3$ | —$(CH_2)_2OCH_2$— | —$CH_3$ | —$CH_3$ | —$S(O)_2$—$CH_3$ |
| —$CH_2OCH_2CH_3$ | —$(CH_2)_3$— | H | H | —C(O)—phenyl |
| —$CH_2OCH_2CH_3$ | —$(CH_2)_3$— | H | H | —C(O)—$C_2H_5$ |
| —$CH_2OCH_2CH_3$ | —$(CH_2)_3$— | H | H | —C(O)—NH—phenyl |
| —$CH_2OCH_2CH_3$ | —$(CH_2)_3$— | H | H | —C(O)—NH—$CH_3$ |
| —$CH_2OCH_2CH_3$ | —$(CH_2)_3$— | H | H | —C(O)—NH—isopropyl |
| —$CH_2OCH_2CH_3$ | —$(CH_2)_3$— | H | H | —C(O)—N$(CH_3)_2$ |
| —$CH_2OCH_2CH_3$ | —$(CH_2)_3$— | H | H | —$S(O)_2$—$CH_3$ |
| —$CH_2OCH_2CH_3$ | —$(CH_2)_3$— | H | —$CH_3$ | —C(O)—phenyl |

| | | | | |
|---|---|---|---|---|
| $-CH_2OCH_2CH_3$ | $-(CH_2)_3-$ | H | $-CH_3$ | $-C(O)-C_2H_5$ |
| $-CH_2OCH_2CH_3$ | $-(CH_2)_3-$ | H | $-CH_3$ | $-C(O)-NH-$phenyl |
| $-CH_2OCH_2CH_3$ | $-(CH_2)_3-$ | H | $-CH_3$ | $-C(O)-NH-CH_3$ |
| $-CH_2OCH_2CH_3$ | $-(CH_2)_3-$ | H | $-CH_3$ | $-C(O)-NH-$isopropyl |
| $-CH_2OCH_2CH_3$ | $-(CH_2)_3-$ | H | $-CH_3$ | $-C(O)-N(CH_3)_2$ |
| $-CH_2OCH_2CH_3$ | $-(CH_2)_3-$ | H | $-CH_3$ | $-S(O)_2-CH_3$ |
| $-CH_2OCH_2CH_3$ | $-(CH_2)_3-$ | $-CH_3$ | H | $-C(O)-$phenyl |
| $-CH_2OCH_2CH_3$ | $-(CH_2)_3-$ | $-CH_3$ | H | $-C(O)-C_2H_5$ |
| $-CH_2OCH_2CH_3$ | $-(CH_2)_3-$ | $-CH_3$ | H | $-C(O)-NH-$phenyl |
| $-CH_2OCH_2CH_3$ | $-(CH_2)_3-$ | $-CH_3$ | H | $-C(O)-NH-CH_3$ |
| $-CH_2OCH_2CH_3$ | $-(CH_2)_3-$ | $-CH_3$ | H | $-C(O)-NH-$isopropyl |
| $-CH_2OCH_2CH_3$ | $-(CH_2)_3-$ | $-CH_3$ | H | $-C(O)-N(CH_3)_2$ |
| $-CH_2OCH_2CH_3$ | $-(CH_2)_3-$ | $-CH_3$ | H | $-S(O)_2-CH_3$ |
| $-CH_2OCH_2CH_3$ | $-(CH_2)_3-$ | $-CH_3$ | $-CH_3$ | $-C(O)-$phenyl |
| $-CH_2OCH_2CH_3$ | $-(CH_2)_3-$ | $-CH_3$ | $-CH_3$ | $-C(O)-C_2H_5$ |
| $-CH_2OCH_2CH_3$ | $-(CH_2)_3-$ | $-CH_3$ | $-CH_3$ | $-C(O)-NH-$phenyl |
| $-CH_2OCH_2CH_3$ | $-(CH_2)_3-$ | $-CH_3$ | $-CH_3$ | $-C(O)-NH-CH_3$ |
| $-CH_2OCH_2CH_3$ | $-(CH_2)_3-$ | $-CH_3$ | $-CH_3$ | $-C(O)-NH-$isopropyl |
| $-CH_2OCH_2CH_3$ | $-(CH_2)_3-$ | $-CH_3$ | $-CH_3$ | $-C(O)-N(CH_3)_2$ |
| $-CH_2OCH_2CH_3$ | $-(CH_2)_3-$ | $-CH_3$ | $-CH_3$ | $-S(O)_2-CH_3$ |
| $-CH_2OCH_2CH_3$ | $-(CH_2)_4-$ | H | H | $-C(O)-$phenyl |
| $-CH_2OCH_2CH_3$ | $-(CH_2)_4-$ | H | H | $-C(O)-C_2H_5$ |
| $-CH_2OCH_2CH_3$ | $-(CH_2)_4-$ | H | H | $-C(O)-NH-$phenyl |
| $-CH_2OCH_2CH_3$ | $-(CH_2)_4-$ | H | H | $-C(O)-NH-CH_3$ |
| $-CH_2OCH_2CH_3$ | $-(CH_2)_4-$ | H | H | $-C(O)-NH-$isopropyl |
| $-CH_2OCH_2CH_3$ | $-(CH_2)_4-$ | H | H | $-C(O)-N(CH_3)_2$ |
| $-CH_2OCH_2CH_3$ | $-(CH_2)_4-$ | H | H | $-S(O)_2-CH_3$ |
| $-CH_2OCH_2CH_3$ | $-(CH_2)_4-$ | H | $-CH_3$ | $-C(O)-$phenyl |
| $-CH_2OCH_2CH_3$ | $-(CH_2)_4-$ | H | $-CH_3$ | $-C(O)-C_2H_5$ |
| $-CH_2OCH_2CH_3$ | $-(CH_2)_4-$ | H | $-CH_3$ | $-C(O)-NH-$phenyl |
| $-CH_2OCH_2CH_3$ | $-(CH_2)_4-$ | H | $-CH_3$ | $-C(O)-NH-CH_3$ |
| $-CH_2OCH_2CH_3$ | $-(CH_2)_4-$ | H | $-CH_3$ | $-C(O)-NH-$isopropyl |
| $-CH_2OCH_2CH_3$ | $-(CH_2)_4-$ | H | $-CH_3$ | $-C(O)-N(CH_3)_2$ |
| $-CH_2OCH_2CH_3$ | $-(CH_2)_4-$ | H | $-CH_3$ | $-S(O)_2-CH_3$ |
| $-CH_2OCH_2CH_3$ | $-(CH_2)_4-$ | $-CH_3$ | H | $-C(O)-$phenyl |
| $-CH_2OCH_2CH_3$ | $-(CH_2)_4-$ | $-CH_3$ | H | $-C(O)-C_2H_5$ |
| $-CH_2OCH_2CH_3$ | $-(CH_2)_4-$ | $-CH_3$ | H | $-C(O)-NH-$phenyl |
| $-CH_2OCH_2CH_3$ | $-(CH_2)_4-$ | $-CH_3$ | H | $-C(O)-NH-CH_3$ |
| $-CH_2OCH_2CH_3$ | $-(CH_2)_4-$ | $-CH_3$ | H | $-C(O)-NH-$isopropyl |
| $-CH_2OCH_2CH_3$ | $-(CH_2)_4-$ | $-CH_3$ | H | $-C(O)-N(CH_3)_2$ |
| $-CH_2OCH_2CH_3$ | $-(CH_2)_4-$ | $-CH_3$ | H | $-S(O)_2-CH_3$ |
| $-CH_2OCH_2CH_3$ | $-(CH_2)_4-$ | $-CH_3$ | $-CH_3$ | $-C(O)-$phenyl |
| $-CH_2OCH_2CH_3$ | $-(CH_2)_4-$ | $-CH_3$ | $-CH_3$ | $-C(O)-C_2H_5$ |
| $-CH_2OCH_2CH_3$ | $-(CH_2)_4-$ | $-CH_3$ | $-CH_3$ | $-C(O)-NH-$phenyl |
| $-CH_2OCH_2CH_3$ | $-(CH_2)_4-$ | $-CH_3$ | $-CH_3$ | $-C(O)-NH-CH_3$ |
| $-CH_2OCH_2CH_3$ | $-(CH_2)_4-$ | $-CH_3$ | $-CH_3$ | $-C(O)-NH-$isopropyl |
| $-CH_2OCH_2CH_3$ | $-(CH_2)_4-$ | $-CH_3$ | $-CH_3$ | $-C(O)-N(CH_3)_2$ |
| $-CH_2OCH_2CH_3$ | $-(CH_2)_4-$ | $-CH_3$ | $-CH_3$ | $-S(O)_2-CH_3$ |
| $-CH_2OCH_2CH_3$ | $-CH_2C(CH_3)_2-$ | H | H | $-C(O)-$phenyl |
| $-CH_2OCH_2CH_3$ | $-CH_2C(CH_3)_2-$ | H | H | $-C(O)-C_2H_5$ |
| $-CH_2OCH_2CH_3$ | $-CH_2C(CH_3)_2-$ | H | H | $-C(O)-NH-$phenyl |
| $-CH_2OCH_2CH_3$ | $-CH_2C(CH_3)_2-$ | H | H | $-C(O)-NH-CH_3$ |
| $-CH_2OCH_2CH_3$ | $-CH_2C(CH_3)_2-$ | H | H | $-C(O)-NH-$isopropyl |
| $-CH_2OCH_2CH_3$ | $-CH_2C(CH_3)_2-$ | H | H | $-C(O)-N(CH_3)_2$ |
| $-CH_2OCH_2CH_3$ | $-CH_2C(CH_3)_2-$ | H | H | $-S(O)_2-CH_3$ |
| $-CH_2OCH_2CH_3$ | $-CH_2C(CH_3)_2-$ | H | $-CH_3$ | $-C(O)-$phenyl |
| $-CH_2OCH_2CH_3$ | $-CH_2C(CH_3)_2-$ | H | $-CH_3$ | $-C(O)-C_2H_5$ |
| $-CH_2OCH_2CH_3$ | $-CH_2C(CH_3)_2-$ | H | $-CH_3$ | $-C(O)-NH-$phenyl |
| $-CH_2OCH_2CH_3$ | $-CH_2C(CH_3)_2-$ | H | $-CH_3$ | $-C(O)-NH-CH_3$ |
| $-CH_2OCH_2CH_3$ | $-CH_2C(CH_3)_2-$ | H | $-CH_3$ | $-C(O)-NH-$isopropyl |
| $-CH_2OCH_2CH_3$ | $-CH_2C(CH_3)_2-$ | H | $-CH_3$ | $-C(O)-N(CH_3)_2$ |
| $-CH_2OCH_2CH_3$ | $-CH_2C(CH_3)_2-$ | H | $-CH_3$ | $-S(O)_2-CH_3$ |
| $-CH_2OCH_2CH_3$ | $-CH_2C(CH_3)_2-$ | $-CH_3$ | H | $-C(O)-$phenyl |
| $-CH_2OCH_2CH_3$ | $-CH_2C(CH_3)_2-$ | $-CH_3$ | H | $-C(O)-C_2H_5$ |
| $-CH_2OCH_2CH_3$ | $-CH_2C(CH_3)_2-$ | $-CH_3$ | H | $-C(O)-NH-$phenyl |
| $-CH_2OCH_2CH_3$ | $-CH_2C(CH_3)_2-$ | $-CH_3$ | H | $-C(O)-NH-CH_3$ |
| $-CH_2OCH_2CH_3$ | $-CH_2C(CH_3)_2-$ | $-CH_3$ | H | $-C(O)-NH-$isopropyl |
| $-CH_2OCH_2CH_3$ | $-CH_2C(CH_3)_2-$ | $-CH_3$ | H | $-C(O)-N(CH_3)_2$ |
| $-CH_2OCH_2CH_3$ | $-CH_2C(CH_3)_2-$ | $-CH_3$ | H | $-S(O)_2-CH_3$ |
| $-CH_2OCH_2CH_3$ | $-CH_2C(CH_3)_2-$ | $-CH_3$ | $-CH_3$ | $-C(O)-$phenyl |
| $-CH_2OCH_2CH_3$ | $-CH_2C(CH_3)_2-$ | $-CH_3$ | $-CH_3$ | $-C(O)-C_2H_5$ |
| $-CH_2OCH_2CH_3$ | $-CH_2C(CH_3)_2-$ | $-CH_3$ | $-CH_3$ | $-C(O)-NH-$phenyl |
| $-CH_2OCH_2CH_3$ | $-CH_2C(CH_3)_2-$ | $-CH_3$ | $-CH_3$ | $-C(O)-NH-CH_3$ |
| $-CH_2OCH_2CH_3$ | $-CH_2C(CH_3)_2-$ | $-CH_3$ | $-CH_3$ | $-C(O)-NH-$isopropyl |
| $-CH_2OCH_2CH_3$ | $-CH_2C(CH_3)_2-$ | $-CH_3$ | $-CH_3$ | $-C(O)-N(CH_3)_2$ |
| $-CH_2OCH_2CH_3$ | $-CH_2C(CH_3)_2-$ | $-CH_3$ | $-CH_3$ | $-S(O)_2-CH_3$ |
| $-CH_2OCH_2CH_3$ | $-CH_2C(CH_3)_2CH_2-$ | H | H | $-C(O)-$phenyl |
| $-CH_2OCH_2CH_3$ | $-CH_2C(CH_3)_2CH_2-$ | H | H | $-C(O)-C_2H_5$ |
| $-CH_2OCH_2CH_3$ | $-CH_2C(CH_3)_2CH_2-$ | H | H | $-C(O)-NH-$phenyl |
| $-CH_2OCH_2CH_3$ | $-CH_2C(CH_3)_2CH_2-$ | H | H | $-C(O)-NH-CH_3$ |
| $-CH_2OCH_2CH_3$ | $-CH_2C(CH_3)_2CH_2-$ | H | H | $-C(O)-NH-$isopropyl |
| $-CH_2OCH_2CH_3$ | $-CH_2C(CH_3)_2CH_2-$ | H | H | $-C(O)-N(CH_3)_2$ |

| | | | | |
|---|---|---|---|---|
| $—CH_2OCH_2CH_3$ | $—CH_2C(CH_3)_2CH_2—$ | H | H | $—S(O)_2—CH_3$ |
| $—CH_2OCH_2CH_3$ | $—CH_2C(CH_3)_2CH_2—$ | H | $—CH_3$ | —C(O)—phenyl |
| $—CH_2OCH_2CH_3$ | $—CH_2C(CH_3)_2CH_2—$ | H | $—CH_3$ | $—C(O)—C_2H_5$ |
| $—CH_2OCH_2CH_3$ | $—CH_2C(CH_3)_2CH_2—$ | H | $—CH_3$ | —C(O)—NH—phenyl |
| $—CH_2OCH_2CH_3$ | $—CH_2C(CH_3)_2CH_2—$ | H | $—CH_3$ | $—C(O)—NH—CH_3$ |
| $—CH_2OCH_2CH_3$ | $—CH_2C(CH_3)_2CH_2—$ | H | $—CH_3$ | —C(O)—NH—isopropyl |
| $—CH_2OCH_2CH_3$ | $—CH_2C(CH_3)_2CH_2—$ | H | $—CH_3$ | $—C(O)—N(CH_3)_2$ |
| $—CH_2OCH_2CH_3$ | $—CH_2C(CH_3)_2CH_2—$ | H | $—CH_3$ | $—S(O)_2—CH_3$ |
| $—CH_2OCH_2CH_3$ | $—CH_2C(CH_3)_2CH_2—$ | $—CH_3$ | H | —C(O)—phenyl |
| $—CH_2OCH_2CH_3$ | $—CH_2C(CH_3)_2CH_2—$ | $—CH_3$ | H | $—C(O)—C_2H_5$ |
| $—CH_2OCH_2CH_3$ | $—CH_2C(CH_3)_2CH_2—$ | $—CH_3$ | H | —C(O)—NH—phenyl |
| $—CH_2OCH_2CH_3$ | $—CH_2C(CH_3)_2CH_2—$ | $—CH_3$ | H | $—C(O)—NH—CH_3$ |
| $—CH_2OCH_2CH_3$ | $—CH_2C(CH_3)_2CH_2—$ | $—CH_3$ | H | —C(O)—NH—isopropyl |
| $—CH_2OCH_2CH_3$ | $—CH_2C(CH_3)_2CH_2—$ | $—CH_3$ | H | $—C(O)—N(CH_3)_2$ |
| $—CH_2OCH_2CH_3$ | $—CH_2C(CH_3)_2CH_2—$ | $—CH_3$ | H | $—S(O)_2—CH_3$ |
| $—CH_2OCH_2CH_3$ | $—CH_2C(CH_3)_2CH_2—$ | $—CH_3$ | $—CH_3$ | —C(O)—phenyl |
| $—CH_2OCH_2CH_3$ | $—CH_2C(CH_3)_2CH_2—$ | $—CH_3$ | $—CH_3$ | $—C(O)—C_2H_5$ |
| $—CH_2OCH_2CH_3$ | $—CH_2C(CH_3)_2CH_2—$ | $—CH_3$ | $—CH_3$ | —C(O)—NH—phenyl |
| $—CH_2OCH_2CH_3$ | $—CH_2C(CH_3)_2CH_2—$ | $—CH_3$ | $—CH_3$ | $—C(O)—NH—CH_3$ |
| $—CH_2OCH_2CH_3$ | $—CH_2C(CH_3)_2CH_2—$ | $—CH_3$ | $—CH_3$ | —C(O)—NH—isopropyl |
| $—CH_2OCH_2CH_3$ | $—CH_2C(CH_3)_2CH_2—$ | $—CH_3$ | $—CH_3$ | $—C(O)—N(CH_3)_2$ |
| $—CH_2OCH_2CH_3$ | $—CH_2C(CH_3)_2CH_2—$ | $—CH_3$ | $—CH_3$ | $—S(O)_2—CH_3$ |
| $—CH_2OCH_2CH_3$ | $—(CH_2)_2OCH_2—$ | H | H | —C(O)—phenyl |
| $—CH_2OCH_2CH_3$ | $—(CH_2)_2OCH_2—$ | H | H | $—C(O)—C_2H_5$ |
| $—CH_2OCH_2CH_3$ | $—(CH_2)_2OCH_2—$ | H | H | —C(O)—NH—phenyl |
| $—CH_2OCH_2CH_3$ | $—(CH_2)_2OCH_2—$ | H | H | $—C(O)—NH—CH_3$ |
| $—CH_2OCH_2CH_3$ | $—(CH_2)_2OCH_2—$ | H | H | —C(O)—NH—isopropyl |
| $—CH_2OCH_2CH_3$ | $—(CH_2)_2OCH_2—$ | H | H | $—C(O)—N(CH_3)_2$ |
| $—CH_2OCH_2CH_3$ | $—(CH_2)_2OCH_2—$ | H | H | $—S(O)_2—CH_3$ |
| $—CH_2OCH_2CH_3$ | $—(CH_2)_2OCH_2—$ | H | $—CH_3$ | —C(O)—phenyl |
| $—CH_2OCH_2CH_3$ | $—(CH_2)_2OCH_2—$ | H | $—CH_3$ | $—C(O)—C_2H_5$ |
| $—CH_2OCH_2CH_3$ | $—(CH_2)_2OCH_2—$ | H | $—CH_3$ | —C(O)—NH—phenyl |
| $—CH_2OCH_2CH_3$ | $—(CH_2)_2OCH_2—$ | H | $—CH_3$ | $—C(O)—NH—CH_3$ |
| $—CH_2OCH_2CH_3$ | $—(CH_2)_2OCH_2—$ | H | $—CH_3$ | —C(O)—NH—isopropyl |
| $—CH_2OCH_2CH_3$ | $—(CH_2)_2OCH_2—$ | H | $—CH_3$ | $—C(O)—N(CH_3)_2$ |
| $—CH_2OCH_2CH_3$ | $—(CH_2)_2OCH_2—$ | H | $—CH_3$ | $—S(O)_2—CH_3$ |
| $—CH_2OCH_2CH_3$ | $—(CH_2)_2OCH_2—$ | $—CH_3$ | H | —C(O)—phenyl |
| $—CH_2OCH_2CH_3$ | $—(CH_2)_2OCH_2—$ | $—CH_3$ | H | $—C(O)—C_2H_5$ |
| $—CH_2OCH_2CH_3$ | $—(CH_2)_2OCH_2—$ | $—CH_3$ | H | —C(O)—NH—phenyl |
| $—CH_2OCH_2CH_3$ | $—(CH_2)_2OCH_2—$ | $—CH_3$ | H | $—C(O)—NH—CH_3$ |
| $—CH_2OCH_2CH_3$ | $—(CH_2)_2OCH_2—$ | $—CH_3$ | H | —C(O)—NH—isopropyl |
| $—CH_2OCH_2CH_3$ | $—(CH_2)_2OCH_2—$ | $—CH_3$ | H | $—C(O)—N(CH_3)_2$ |
| $—CH_2OCH_2CH_3$ | $—(CH_2)_2OCH_2—$ | $—CH_3$ | H | $—S(O)_2—CH_3$ |
| $—CH_2OCH_2CH_3$ | $—(CH_2)_2OCH_2—$ | $—CH_3$ | $—CH_3$ | —C(O)—phenyl |
| $—CH_2OCH_2CH_3$ | $—(CH_2)_2OCH_2—$ | $—CH_3$ | $—CH_3$ | $—C(O)—C_2H_5$ |
| $—CH_2OCH_2CH_3$ | $—(CH_2)_2OCH_2—$ | $—CH_3$ | $—CH_3$ | —C(O)—NH—phenyl |
| $—CH_2OCH_2CH_3$ | $—(CH_2)_2OCH_2—$ | $—CH_3$ | $—CH_3$ | $—C(O)—NH—CH_3$ |
| $—CH_2OCH_2CH_3$ | $—(CH_2)_2OCH_2—$ | $—CH_3$ | $—CH_3$ | —C(O)—NH—isopropyl |
| $—CH_2OCH_2CH_3$ | $—(CH_2)_2OCH_2—$ | $—CH_3$ | $—CH_3$ | $—C(O)—N(CH_3)_2$ |
| $—CH_2OCH_2CH_3$ | $—(CH_2)_2OCH_2—$ | $—CH_3$ | $—CH_3$ | $—S(O)_2—CH_3$ |
| $—(CH_2)_2OCH_3$ | $—(CH_2)_3—$ | H | H | —C(O)—phenyl |
| $—(CH_2)_2OCH_3$ | $—(CH_2)_3—$ | H | H | $—C(O)—C_2H_5$ |
| $—(CH_2)_2OCH_3$ | $—(CH_2)_3—$ | H | H | —C(O)—NH—phenyl |
| $—(CH_2)_2OCH_3$ | $—(CH_2)_3—$ | H | H | $—C(O)—NH—CH_3$ |
| $—(CH_2)_2OCH_3$ | $—(CH_2)_3—$ | H | H | —C(O)—NH—isopropyl |
| $—(CH_2)_2OCH_3$ | $—(CH_2)_3—$ | H | H | $—C(O)—N(CH_3)_2$ |
| $—(CH_2)_2OCH_3$ | $—(CH_2)_3—$ | H | H | $—S(O)_2—CH_3$ |
| $—(CH_2)_2OCH_3$ | $—(CH_2)_3—$ | H | $—CH_3$ | —C(O)—phenyl |
| $—(CH_2)_2OCH_3$ | $—(CH_2)_3—$ | H | $—CH_3$ | $—C(O)—C_2H_5$ |
| $—(CH_2)_2OCH_3$ | $—(CH_2)_3—$ | H | $—CH_3$ | —C(O)—NH—phenyl |
| $—(CH_2)_2OCH_3$ | $—(CH_2)_3—$ | H | $—CH_3$ | $—C(O)—NH—CH_3$ |
| $—(CH_2)_2OCH_3$ | $—(CH_2)_3—$ | H | $—CH_3$ | —C(O)—NH—isopropyl |
| $—(CH_2)_2OCH_3$ | $—(CH_2)_3—$ | H | $—CH_3$ | $—C(O)—N(CH_3)_2$ |
| $—(CH_2)_2OCH_3$ | $—(CH_2)_3—$ | H | $—CH_3$ | $—S(O)_2—CH_3$ |
| $—(CH_2)_2OCH_3$ | $—(CH_2)_3—$ | $—CH_3$ | H | —C(O)—phenyl |
| $—(CH_2)_2OCH_3$ | $—(CH_2)_3—$ | $—CH_3$ | H | $—C(O)—C_2H_5$ |
| $—(CH_2)_2OCH_3$ | $—(CH_2)_3—$ | $—CH_3$ | H | —C(O)—NH—phenyl |
| $—(CH_2)_2OCH_3$ | $—(CH_2)_3—$ | $—CH_3$ | H | $—C(O)—NH—CH_3$ |
| $—(CH_2)_2OCH_3$ | $—(CH_2)_3—$ | $—CH_3$ | H | —C(O)—NH—isopropyl |
| $—(CH_2)_2OCH_3$ | $—(CH_2)_3—$ | $—CH_3$ | H | $—C(O)—N(CH_3)_2$ |
| $—(CH_2)_2OCH_3$ | $—(CH_2)_3—$ | $—CH_3$ | H | $—S(O)_2—CH_3$ |
| $—(CH_2)_2OCH_3$ | $—(CH_2)_3—$ | $—CH_3$ | $—CH_3$ | —C(O)—phenyl |
| $—(CH_2)_2OCH_3$ | $—(CH_2)_3—$ | $—CH_3$ | $—CH_3$ | $—C(O)—C_2H_5$ |
| $—(CH_2)_2OCH_3$ | $—(CH_2)_3—$ | $—CH_3$ | $—CH_3$ | —C(O)—NH—phenyl |
| $—(CH_2)_2OCH_3$ | $—(CH_2)_3—$ | $—CH_3$ | $—CH_3$ | $—C(O)—NH—CH_3$ |
| $—(CH_2)_2OCH_3$ | $—(CH_2)_3—$ | $—CH_3$ | $—CH_3$ | —C(O)—NH—isopropyl |
| $—(CH_2)_2OCH_3$ | $—(CH_2)_3—$ | $—CH_3$ | $—CH_3$ | $—C(O)—N(CH_3)_2$ |
| $—(CH_2)_2OCH_3$ | $—(CH_2)_3—$ | $—CH_3$ | $—CH_3$ | $—S(O)_2—CH_3$ |
| $—(CH_2)_2OCH_3$ | $—(CH_2)_4—$ | H | H | —C(O)—phenyl |
| $—(CH_2)_2OCH_3$ | $—(CH_2)_4—$ | H | H | $—C(O)—C_2H_5$ |
| $—(CH_2)_2OCH_3$ | $—(CH_2)_4—$ | H | H | —C(O)—NH—phenyl |
| $—(CH_2)_2OCH_3$ | $—(CH_2)_4—$ | H | H | $—C(O)—NH—CH_3$ |

| | | | | |
|---|---|---|---|---|
| $-(CH_2)_2OCH_3$ | $-(CH_2)_4-$ | H | H | —C(O)—NH—isopropyl |
| $-(CH_2)_2OCH_3$ | $-(CH_2)_4-$ | H | H | $-C(O)-N(CH_3)_2$ |
| $-(CH_2)_2OCH_3$ | $-(CH_2)_4-$ | H | H | $-S(O)_2-CH_3$ |
| $-(CH_2)_2OCH_3$ | $-(CH_2)_4-$ | H | $-CH_3$ | —C(O)—phenyl |
| $-(CH_2)_2OCH_3$ | $-(CH_2)_4-$ | H | $-CH_3$ | $-C(O)-C_2H_5$ |
| $-(CH_2)_2OCH_3$ | $-(CH_2)_4-$ | H | $-CH_3$ | —C(O)—NH—phenyl |
| $-(CH_2)_2OCH_3$ | $-(CH_2)_4-$ | H | $-CH_3$ | $-C(O)-NH-CH_3$ |
| $-(CH_2)_2OCH_3$ | $-(CH_2)_4-$ | H | $-CH_3$ | —C(O)—NH—isopropyl |
| $-(CH_2)_2OCH_3$ | $-(CH_2)_4-$ | H | $-CH_3$ | $-C(O)-N(CH_3)_2$ |
| $-(CH_2)_2OCH_3$ | $-(CH_2)_4-$ | H | $-CH_3$ | $-S(O)_2-CH_3$ |
| $-(CH_2)_2OCH_3$ | $-(CH_2)_4-$ | $-CH_3$ | H | —C(O)—phenyl |
| $-(CH_2)_2OCH_3$ | $-(CH_2)_4-$ | $-CH_3$ | H | $-C(O)-C_2H_5$ |
| $-(CH_2)_2OCH_3$ | $-(CH_2)_4-$ | $-CH_3$ | H | —C(O)—NH—phenyl |
| $-(CH_2)_2OCH_3$ | $-(CH_2)_4-$ | $-CH_3$ | H | $-C(O)-NH-CH_3$ |
| $-(CH_2)_2OCH_3$ | $-(CH_2)_4-$ | $-CH_3$ | H | —C(O)—NH—isopropyl |
| $-(CH_2)_2OCH_3$ | $-(CH_2)_4-$ | $-CH_3$ | H | $-C(O)-N(CH_3)_2$ |
| $-(CH_2)_2OCH_3$ | $-(CH_2)_4-$ | $-CH_3$ | H | $-S(O)_2-CH_3$ |
| $-(CH_2)_2OCH_3$ | $-(CH_2)_4-$ | $-CH_3$ | $-CH_3$ | —C(O)—phenyl |
| $-(CH_2)_2OCH_3$ | $-(CH_2)_4-$ | $-CH_3$ | $-CH_3$ | $-C(O)-C_2H_5$ |
| $-(CH_2)_2OCH_3$ | $-(CH_2)_4-$ | $-CH_3$ | $-CH_3$ | —C(O)—NH—phenyl |
| $-(CH_2)_2OCH_3$ | $-(CH_2)_4-$ | $-CH_3$ | $-CH_3$ | $-C(O)-NH-CH_3$ |
| $-(CH_2)_2OCH_3$ | $-(CH_2)_4-$ | $-CH_3$ | $-CH_3$ | —C(O)—NH—isopropyl |
| $-(CH_2)_2OCH_3$ | $-(CH_2)_4-$ | $-CH_3$ | $-CH_3$ | $-C(O)-N(CH_3)_2$ |
| $-(CH_2)_2OCH_3$ | $-(CH_2)_4-$ | $-CH_3$ | $-CH_3$ | $-S(O)_2-CH_3$ |
| $-(CH_2)_2OCH_3$ | $-CH_2C(CH_3)_2-$ | H | H | —C(O)—phenyl |
| $-(CH_2)_2OCH_3$ | $-CH_2C(CH_3)_2-$ | H | H | $-C(O)-C_2H_5$ |
| $-(CH_2)_2OCH_3$ | $-CH_2C(CH_3)_2-$ | H | H | —C(O)—NH—phenyl |
| $-(CH_2)_2OCH_3$ | $-CH_2C(CH_3)_2-$ | H | H | $-C(O)-NH-CH_3$ |
| $-(CH_2)_2OCH_3$ | $-CH_2C(CH_3)_2-$ | H | H | —C(O)—NH—isopropyl |
| $-(CH_2)_2OCH_3$ | $-CH_2C(CH_3)_2-$ | H | H | $-C(O)-N(CH_3)_2$ |
| $-(CH_2)_2OCH_3$ | $-CH_2C(CH_3)_2-$ | H | H | $-S(O)_2-CH_3$ |
| $-(CH_2)_2OCH_3$ | $-CH_2C(CH_3)_2-$ | H | $-CH_3$ | —C(O)—phenyl |
| $-(CH_2)_2OCH_3$ | $-CH_2C(CH_3)_2-$ | H | $-CH_3$ | $-C(O)-C_2H_5$ |
| $-(CH_2)_2OCH_3$ | $-CH_2C(CH_3)_2-$ | H | $-CH_3$ | —C(O)—NH—phenyl |
| $-(CH_2)_2OCH_3$ | $-CH_2C(CH_3)_2-$ | H | $-CH_3$ | $-C(O)-NH-CH_3$ |
| $-(CH_2)_2OCH_3$ | $-CH_2C(CH_3)_2-$ | H | $-CH_3$ | —C(O)—NH—isopropyl |
| $-(CH_2)_2OCH_3$ | $-CH_2C(CH_3)_2-$ | H | $-CH_3$ | $-C(O)-N(CH_3)_2$ |
| $-(CH_2)_2OCH_3$ | $-CH_2C(CH_3)_2-$ | H | $-CH_3$ | $-S(O)_2-CH_3$ |
| $-(CH_2)_2OCH_3$ | $-CH_2C(CH_3)_2-$ | $-CH_3$ | H | —C(O)—phenyl |
| $-(CH_2)_2OCH_3$ | $-CH_2C(CH_3)_2-$ | $-CH_3$ | H | $-C(O)-C_2H_5$ |
| $-(CH_2)_2OCH_3$ | $-CH_2C(CH_3)_2-$ | $-CH_3$ | H | —C(O)—NH—phenyl |
| $-(CH_2)_2OCH_3$ | $-CH_2C(CH_3)_2-$ | $-CH_3$ | H | $-C(O)-NH-CH_3$ |
| $-(CH_2)_2OCH_3$ | $-CH_2C(CH_3)_2-$ | $-CH_3$ | H | —C(O)—NH—isopropyl |
| $-(CH_2)_2OCH_3$ | $-CH_2C(CH_3)_2-$ | $-CH_3$ | H | $-C(O)-N(CH_3)_2$ |
| $-(CH_2)_2OCH_3$ | $-CH_2C(CH_3)_2-$ | $-CH_3$ | H | $-S(O)_2-CH_3$ |
| $-(CH_2)_2OCH_3$ | $-CH_2C(CH_3)_2-$ | $-CH_3$ | $-CH_3$ | —C(O)—phenyl |
| $-(CH_2)_2OCH_3$ | $-CH_2C(CH_3)_2-$ | $-CH_3$ | $-CH_3$ | $-C(O)-C_2H_5$ |
| $-(CH_2)_2OCH_3$ | $-CH_2C(CH_3)_2-$ | $-CH_3$ | $-CH_3$ | —C(O)—NH—phenyl |
| $-(CH_2)_2OCH_3$ | $-CH_2C(CH_3)_2-$ | $-CH_3$ | $-CH_3$ | $-C(O)-NH-CH_3$ |
| $-(CH_2)_2OCH_3$ | $-CH_2C(CH_3)_2-$ | $-CH_3$ | $-CH_3$ | —C(O)—NH—isopropyl |
| $-(CH_2)_2OCH_3$ | $-CH_2C(CH_3)_2-$ | $-CH_3$ | $-CH_3$ | $-C(O)-N(CH_3)_2$ |
| $-(CH_2)_2OCH_3$ | $-CH_2C(CH_3)_2-$ | $-CH_3$ | $-CH_3$ | $-S(O)_2-CH_3$ |
| $-(CH_2)_2OCH_3$ | $-CH_2C(CH_3)_2CH_2-$ | H | H | —C(O)—phenyl |
| $-(CH_2)_2OCH_3$ | $-CH_2C(CH_3)_2CH_2-$ | H | H | $-C(O)-C_2H_5$ |
| $-(CH_2)_2OCH_3$ | $-CH_2C(CH_3)_2CH_2-$ | H | H | —C(O)—NH—phenyl |
| $-(CH_2)_2OCH_3$ | $-CH_2C(CH_3)_2CH_2-$ | H | H | $-C(O)-NH-CH_3$ |
| $-(CH_2)_2OCH_3$ | $-CH_2C(CH_3)_2CH_2-$ | H | H | —C(O)—NH—isopropyl |
| $-(CH_2)_2OCH_3$ | $-CH_2C(CH_3)_2CH_2-$ | H | H | $-C(O)-N(CH_3)_2$ |
| $-(CH_2)_2OCH_3$ | $-CH_2C(CH_3)_2CH_2-$ | H | H | $-S(O)_2-CH_3$ |
| $-(CH_2)_2OCH_3$ | $-CH_2C(CH_3)_2CH_2-$ | H | $-CH_3$ | —C(O)—phenyl |
| $-(CH_2)_2OCH_3$ | $-CH_2C(CH_3)_2CH_2-$ | H | $-CH_3$ | $-C(O)-C_2H_5$ |
| $-(CH_2)_2OCH_3$ | $-CH_2C(CH_3)_2CH_2-$ | H | $-CH_3$ | —C(O)—NH—phenyl |
| $-(CH_2)_2OCH_3$ | $-CH_2C(CH_3)_2CH_2-$ | H | $-CH_3$ | $-C(O)-NH-CH_3$ |
| $-(CH_2)_2OCH_3$ | $-CH_2C(CH_3)_2CH_2-$ | H | $-CH_3$ | —C(O)—NH—isopropyl |
| $-(CH_2)_2OCH_3$ | $-CH_2C(CH_3)_2CH_2-$ | H | $-CH_3$ | $-C(O)-N(CH_3)_2$ |
| $-(CH_2)_2OCH_3$ | $-CH_2C(CH_3)_2CH_2-$ | H | $-CH_3$ | $-S(O)_2-CH_3$ |
| $-(CH_2)_2OCH_3$ | $-CH_2C(CH_3)_2CH_2-$ | $-CH_3$ | H | —C(O)—phenyl |
| $-(CH_2)_2OCH_3$ | $-CH_2C(CH_3)_2CH_2-$ | $-CH_3$ | H | $-C(O)-C_2H_5$ |
| $-(CH_2)_2OCH_3$ | $-CH_2C(CH_3)_2CH_2-$ | $-CH_3$ | H | —C(O)—NH—phenyl |
| $-(CH_2)_2OCH_3$ | $-CH_2C(CH_3)_2CH_2-$ | $-CH_3$ | H | $-C(O)-NH-CH_3$ |
| $-(CH_2)_2OCH_3$ | $-CH_2C(CH_3)_2CH_2-$ | $-CH_3$ | H | —C(O)—NH—isopropyl |
| $-(CH_2)_2OCH_3$ | $-CH_2C(CH_3)_2CH_2-$ | $-CH_3$ | H | $-C(O)-N(CH_3)_2$ |
| $-(CH_2)_2OCH_3$ | $-CH_2C(CH_3)_2CH_2-$ | $-CH_3$ | H | $-S(O)_2-CH_3$ |
| $-(CH_2)_2OCH_3$ | $-CH_2C(CH_3)_2CH_2-$ | $-CH_3$ | $-CH_3$ | —C(O)—phenyl |
| $-(CH_2)_2OCH_3$ | $-CH_2C(CH_3)_2CH_2-$ | $-CH_3$ | $-CH_3$ | $-C(O)-C_2H_5$ |
| $-(CH_2)_2OCH_3$ | $-CH_2C(CH_3)_2CH_2-$ | $-CH_3$ | $-CH_3$ | —C(O)—NH—phenyl |
| $-(CH_2)_2OCH_3$ | $-CH_2C(CH_3)_2CH_2-$ | $-CH_3$ | $-CH_3$ | $-C(O)-NH-CH_3$ |
| $-(CH_2)_2OCH_3$ | $-CH_2C(CH_3)_2CH_2-$ | $-CH_3$ | $-CH_3$ | —C(O)—NH—isopropyl |
| $-(CH_2)_2OCH_3$ | $-CH_2C(CH_3)_2CH_2-$ | $-CH_3$ | $-CH_3$ | $-C(O)-N(CH_3)_2$ |
| $-(CH_2)_2OCH_3$ | $-CH_2C(CH_3)_2CH_2-$ | $-CH_3$ | $-CH_3$ | $-S(O)_2-CH_3$ |
| $-(CH_2)_2OCH_3$ | $-(CH_2)_2OCH_2-$ | H | H | —C(O)—phenyl |
| $-(CH_2)_2OCH_3$ | $-(CH_2)_2OCH_2-$ | H | H | $-C(O)-C_2H_5$ |

| | | | | |
|---|---|---|---|---|
| $-(CH_2)_2OCH_3$ | $-(CH_2)_2OCH_2-$ | H | H | —C(O)—NH—phenyl |
| $-(CH_2)_2OCH_3$ | $-(CH_2)_2OCH_2-$ | H | H | $-C(O)-NH-CH_3$ |
| $-(CH_2)_2OCH_3$ | $-(CH_2)_2OCH_2-$ | H | H | —C(O)—NH—isopropyl |
| $-(CH_2)_2OCH_3$ | $-(CH_2)_2OCH_2-$ | H | H | $-C(O)-N(CH_3)_2$ |
| $-(CH_2)_2OCH_3$ | $-(CH_2)_2OCH_2-$ | H | H | $-S(O)_2-CH_3$ |
| $-(CH_2)_2OCH_3$ | $-(CH_2)_2OCH_2-$ | H | $-CH_3$ | —C(O)—phenyl |
| $-(CH_2)_2OCH_3$ | $-(CH_2)_2OCH_2-$ | H | $-CH_3$ | $-C(O)-C_2H_5$ |
| $-(CH_2)_2OCH_3$ | $-(CH_2)_2OCH_2-$ | H | $-CH_3$ | —C(O)—NH—phenyl |
| $-(CH_2)_2OCH_3$ | $-(CH_2)_2OCH_2-$ | H | $-CH_3$ | $-C(O)-NH-CH_3$ |
| $-(CH_2)_2OCH_3$ | $-(CH_2)_2OCH_2-$ | H | $-CH_3$ | —C(O)—NH—isopropyl |
| $-(CH_2)_2OCH_3$ | $-(CH_2)_2OCH_2-$ | H | $-CH_3$ | $-C(O)-N(CH_3)_2$ |
| $-(CH_2)_2OCH_3$ | $-(CH_2)_2OCH_2-$ | H | $-CH_3$ | $-S(O)_2-CH_3$ |
| $-(CH_2)_2OCH_3$ | $-(CH_2)_2OCH_2-$ | $-CH_3$ | H | —C(O)—phenyl |
| $-(CH_2)_2OCH_3$ | $-(CH_2)_2OCH_2-$ | $-CH_3$ | H | $-C(O)-C_2H_5$ |
| $-(CH_2)_2OCH_3$ | $-(CH_2)_2OCH_2-$ | $-CH_3$ | H | —C(O)—NH—phenyl |
| $-(CH_2)_2OCH_3$ | $-(CH_2)_2OCH_2-$ | $-CH_3$ | H | $-C(O)-NH-CH_3$ |
| $-(CH_2)_2OCH_3$ | $-(CH_2)_2OCH_2-$ | $-CH_3$ | H | —C(O)—NH—isopropyl |
| $-(CH_2)_2OCH_3$ | $-(CH_2)_2OCH_2-$ | $-CH_3$ | H | $-C(O)-N(CH_3)_2$ |
| $-(CH_2)_2OCH_3$ | $-(CH_2)_2OCH_2-$ | $-CH_3$ | H | $-S(O)_2-CH_3$ |
| $-(CH_2)_2OCH_3$ | $-(CH_2)_2OCH_2-$ | $-CH_3$ | $-CH_3$ | —C(O)—phenyl |
| $-(CH_2)_2OCH_3$ | $-(CH_2)_2OCH_2-$ | $-CH_3$ | $-CH_3$ | $-C(O)-C_2H_5$ |
| $-(CH_2)_2OCH_3$ | $-(CH_2)_2OCH_2-$ | $-CH_3$ | $-CH_3$ | —C(O)—NH—phenyl |
| $-(CH_2)_2OCH_3$ | $-(CH_2)_2OCH_2-$ | $-CH_3$ | $-CH_3$ | $-C(O)-NH-CH_3$ |
| $-(CH_2)_2OCH_3$ | $-(CH_2)_2OCH_2-$ | $-CH_3$ | $-CH_3$ | —C(O)—NH—isopropyl |
| $-(CH_2)_2OCH_3$ | $-(CH_2)_2OCH_2-$ | $-CH_3$ | $-CH_3$ | $-C(O)-N(CH_3)_2$ |
| $-(CH_2)_2OCH_3$ | $-(CH_2)_2OCH_2-$ | $-CH_3$ | $-CH_3$ | $-S(O)_2-CH_3$ |

Exemplary Compounds Table 2

Certain exemplary compounds, including some of those described above in the Examples, have the following Formulas (III-2, IV-6, IV-7, IV-8, IV-9, IV-10, V-2, VI-2, and VII-2), wherein X, $R_2$, $R_{1-1}$, and $R_{1-2}$ are defined immediately below in the table. In this table, for each ring system, each row represents one specific compound.

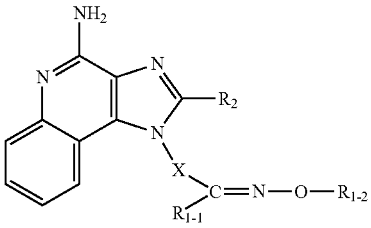

IV-6

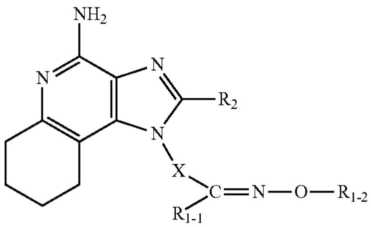

V-2

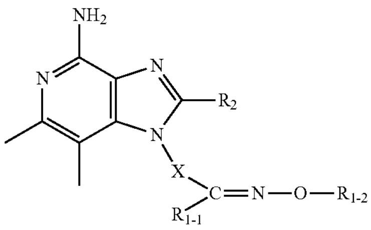

III-2

-continued

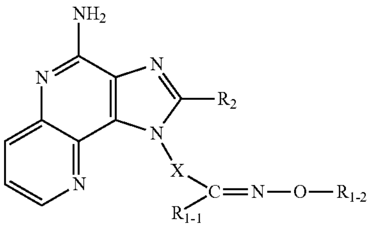

VI-2

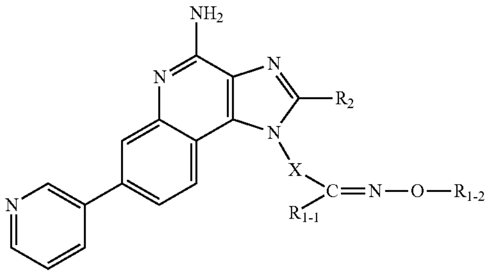

IV-7

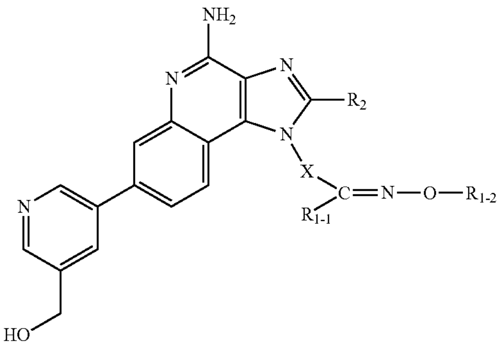

IV-8

-continued

IV-9

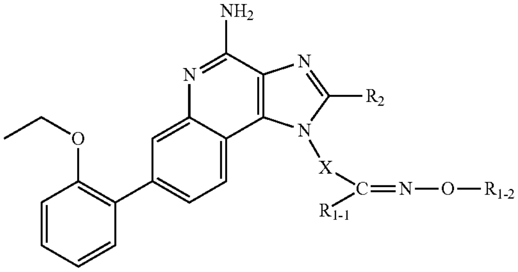

IV-10

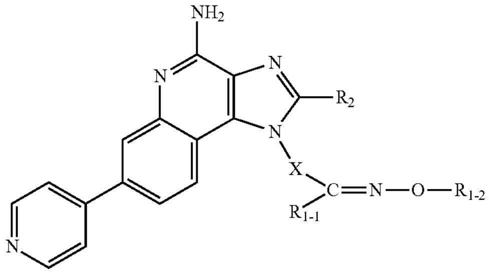

VII-2

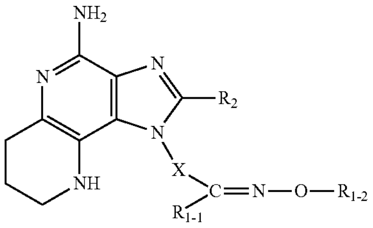

| $R_2$ | X | $R_{1-1}$ | $R_{1-2}$ |
|---|---|---|---|
| H | $—(CH_2)_3—$ | H | H |
| H | $—(CH_2)_3—$ | H | $—CH_3$ |
| H | $—(CH_2)_3—$ | $—CH_3$ | H |
| H | $—(CH_2)_3—$ | $—CH_3$ | $—CH_3$ |
| H | $—(CH_2)_4—$ | H | H |
| H | $—(CH_2)_4—$ | H | $—CH_3$ |
| H | $—(CH_2)_4—$ | $—CH_3$ | H |
| H | $—(CH_2)_4—$ | $—CH_3$ | $—CH_3$ |
| H | $—CH_2C(CH_3)_2—$ | H | H |
| H | $—CH_2C(CH_3)_2—$ | H | $—CH_3$ |
| H | $—CH_2C(CH_3)_2—$ | $—CH_3$ | H |
| H | $—CH_2C(CH_3)_2—$ | $—CH_3$ | $—CH_3$ |
| H | $—CH_2C(CH_3)_2CH_2—$ | H | H |
| H | $—CH_2C(CH_3)_2CH_2—$ | H | $—CH_3$ |
| H | $—CH_2C(CH_3)_2CH_2—$ | $—CH_3$ | H |
| H | $—CH_2C(CH_3)_2CH_2—$ | $—CH_3$ | $—CH_3$ |
| H | $—(CH_2)_2OCH_2—$ | H | H |
| H | $—(CH_2)_2OCH_2—$ | H | $—CH_3$ |
| H | $—(CH_2)_2OCH_2—$ | $—CH_3$ | H |
| H | $—(CH_2)_2OCH_2—$ | $—CH_3$ | $—CH_3$ |
| $—CH_3$ | $—(CH_2)_3—$ | H | H |
| $—CH_3$ | $—(CH_2)_3—$ | H | $—CH_3$ |
| $—CH_3$ | $—(CH_2)_3—$ | $—CH_3$ | H |
| $—CH_3$ | $—(CH_2)_3—$ | $—CH_3$ | $—CH_3$ |
| $—CH_3$ | $—(CH_2)_4—$ | H | H |
| $—CH_3$ | $—(CH_2)_4—$ | H | $—CH_3$ |
| $—CH_3$ | $—(CH_2)_4—$ | $—CH_3$ | H |
| $—CH_3$ | $—(CH_2)_4—$ | $—CH_3$ | $—CH_3$ |
| $—CH_3$ | $—CH_2C(CH_3)_2—$ | H | H |
| $—CH_3$ | $—CH_2C(CH_3)_2—$ | H | $—CH_3$ |
| $—CH_3$ | $—CH_2C(CH_3)_2—$ | $—CH_3$ | H |
| $—CH_3$ | $—CH_2C(CH_3)_2—$ | $—CH_3$ | $—CH_3$ |
| $—CH_3$ | $—CH_2C(CH_3)_2CH_2—$ | H | H |
| $—CH_3$ | $—CH_2C(CH_3)_2CH_2—$ | H | $—CH_3$ |
| $—CH_3$ | $—CH_2C(CH_3)_2CH_2—$ | $—CH_3$ | H |
| $—CH_3$ | $—CH_2C(CH_3)_2CH_2—$ | $—CH_3$ | $—CH_3$ |
| $—CH_3$ | $—(CH_2)_2OCH_2—$ | H | H |
| $—CH_3$ | $—(CH_2)_2OCH_2—$ | H | $—CH_3$ |
| $—CH_3$ | $—(CH_2)_2OCH_2—$ | $—CH_3$ | H |
| $—CH_3$ | $—(CH_2)_2OCH_2—$ | $—CH_3$ | $—CH_3$ |
| $—(CH_2)_2CH_3$ | $—(CH_2)_3—$ | H | H |
| $—(CH_2)_2CH_3$ | $—(CH_2)_3—$ | H | $—CH_3$ |
| $—(CH_2)_2CH_3$ | $—(CH_2)_3—$ | $—CH_3$ | H |
| $—(CH_2)_2CH_3$ | $—(CH_2)_3—$ | $—CH_3$ | $—CH_3$ |
| $—(CH_2)_2CH_3$ | $—(CH_2)_4—$ | H | H |
| $—(CH_2)_2CH_3$ | $—(CH_2)_4—$ | H | $—CH_3$ |
| $—(CH_2)_2CH_3$ | $—(CH_2)_4—$ | $—CH_3$ | H |
| $—(CH_2)_2CH_3$ | $—(CH_2)_4—$ | $—CH_3$ | $—CH_3$ |
| $—(CH_2)_2CH_3$ | $—CH_2C(CH_3)_2—$ | H | H |
| $—(CH_2)_2CH_3$ | $—CH_2C(CH_3)_2—$ | H | $—CH_3$ |
| $—(CH_2)_2CH_3$ | $—CH_2C(CH_3)_2—$ | $—CH_3$ | H |
| $—(CH_2)_2CH_3$ | $—CH_2C(CH_3)_2—$ | $—CH_3$ | $—CH_3$ |
| $—(CH_2)_2CH_3$ | $—CH_2C(CH_3)_2CH_2—$ | H | H |
| $—(CH_2)_2CH_3$ | $—CH_2C(CH_3)_2CH_2—$ | H | $—CH_3$ |
| $—(CH_2)_2CH_3$ | $—CH_2C(CH_3)_2CH_2—$ | $—CH_3$ | H |
| $—(CH_2)_2CH_3$ | $—CH_2C(CH_3)_2CH_2—$ | $—CH_3$ | $—CH_3$ |
| $—(CH_2)_2CH_3$ | $—(CH_2)_2OCH_2—$ | H | H |
| $—(CH_2)_2CH_3$ | $—(CH_2)_2OCH_2—$ | H | $—CH_3$ |
| $—(CH_2)_2CH_3$ | $—(CH_2)_2OCH_2—$ | $—CH_3$ | H |
| $—(CH_2)_2CH_3$ | $—(CH_2)_2OCH_2—$ | $—CH_3$ | $—CH_3$ |
| $—CH_2OCH_2CH_3$ | $—(CH_2)_3—$ | H | H |
| $—CH_2OCH_2CH_3$ | $—(CH_2)_3—$ | H | $—CH_3$ |
| $—CH_2OCH_2CH_3$ | $—(CH_2)_3—$ | $—CH_3$ | H |
| $—CH_2OCH_2CH_3$ | $—(CH_2)_3—$ | $—CH_3$ | $—CH_3$ |
| $—CH_2OCH_2CH_3$ | $—(CH_2)_4—$ | H | H |
| $—CH_2OCH_2CH_3$ | $—(CH_2)_4—$ | H | $—CH_3$ |
| $—CH_2OCH_2CH_3$ | $—(CH_2)_4—$ | $—CH_3$ | H |
| $—CH_2OCH_2CH_3$ | $—(CH_2)_4—$ | $—CH_3$ | $—CH_3$ |
| $—CH_2OCH_2CH_3$ | $—CH_2C(CH_3)_2—$ | H | H |
| $—CH_2OCH_2CH_3$ | $—CH_2C(CH_3)_2—$ | H | $—CH_3$ |
| $—CH_2OCH_2CH_3$ | $—CH_2C(CH_3)_2—$ | $—CH_3$ | H |
| $—CH_2OCH_2CH_3$ | $—CH_2C(CH_3)_2—$ | $—CH_3$ | $—CH_3$ |
| $—CH_2OCH_2CH_3$ | $—CH_2C(CH_3)_2CH_2—$ | H | H |
| $—CH_2OCH_2CH_3$ | $—CH_2C(CH_3)_2CH_2—$ | H | $—CH_3$ |
| $—CH_2OCH_2CH_3$ | $—CH_2C(CH_3)_2CH_2—$ | $—CH_3$ | H |
| $—CH_2OCH_2CH_3$ | $—CH_2C(CH_3)_2CH_2—$ | $—CH_3$ | $—CH_3$ |
| $—CH_2OCH_2CH_3$ | $—(CH_2)_2OCH_2—$ | H | H |
| $—CH_2OCH_2CH_3$ | $—(CH_2)_2OCH_2—$ | H | $—CH_3$ |
| $—CH_2OCH_2CH_3$ | $—(CH_2)_2OCH_2—$ | $—CH_3$ | H |
| $—CH_2OCH_2CH_3$ | $—(CH_2)_2OCH_2—$ | $—CH_3$ | $—CH_3$ |
| $—(CH_2)_2OCH_3$ | $—(CH_2)_3—$ | H | H |
| $—(CH_2)_2OCH_3$ | $—(CH_2)_3—$ | H | $—CH_3$ |
| $—(CH_2)_2OCH_3$ | $—(CH_2)_3—$ | $—CH_3$ | H |
| $—(CH_2)_2OCH_3$ | $—(CH_2)_3—$ | $—CH_3$ | $—CH_3$ |
| $—(CH_2)_2OCH_3$ | $—(CH_2)_4—$ | H | H |
| $—(CH_2)_2OCH_3$ | $—(CH_2)_4—$ | H | $—CH_3$ |
| $—(CH_2)_2OCH_3$ | $—(CH_2)_4—$ | $—CH_3$ | H |
| $—(CH_2)_2OCH_3$ | $—(CH_2)_4—$ | $—CH_3$ | $—CH_3$ |
| $—(CH_2)_2OCH_3$ | $—CH_2C(CH_3)_2—$ | H | H |
| $—(CH_2)_2OCH_3$ | $—CH_2C(CH_3)_2—$ | H | $—CH_3$ |
| $—(CH_2)_2OCH_3$ | $—CH_2C(CH_3)_2—$ | $—CH_3$ | H |
| $—(CH_2)_2OCH_3$ | $—CH_2C(CH_3)_2—$ | $—CH_3$ | $—CH_3$ |
| $—(CH_2)_2OCH_3$ | $—CH_2C(CH_3)_2CH_2—$ | H | H |
| $—(CH_2)_2OCH_3$ | $—CH_2C(CH_3)_2CH_2—$ | H | $—CH_3$ |
| $—(CH_2)_2OCH_3$ | $—CH_2C(CH_3)_2CH_2—$ | $—CH_3$ | H |
| $—(CH_2)_2OCH_3$ | $—CH_2C(CH_3)_2CH_2—$ | $—CH_3$ | $—CH_3$ |
| $—(CH_2)_2OCH_3$ | $—(CH_2)_2OCH_2—$ | H | H |
| $—(CH_2)_2OCH_3$ | $—(CH_2)_2OCH_2—$ | H | $—CH_3$ |
| $—(CH_2)_2OCH_3$ | $—(CH_2)_2OCH_2—$ | $—CH_3$ | H |
| $—(CH_2)_2OCH_3$ | $—(CH_2)_2OCH_2—$ | $—CH_3$ | $—CH_3$ |

Cytokine Induction in Human Cells

Compounds of the invention have been found to induce cytokine biosynthesis when tested using the method described below.

An in vitro human blood cell system is used to assess cytokine induction. Activity is based on the measurement of interferon and tumor necrosis factor (α) (IFN and TNF, respectively) secreted into culture media as described by Testerman et. al. in "Cytokine Induction by the Immunomodulators Imquimod and S-27609", *Journal of Leukocyte Biology,* 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4\times10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30-0.014 μM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

Certain compounds of the invention may modulate cytokine biosynthesis by inhibiting production of tumor necrosis factor α (TNF-α) when tested using the method described below.

TNF-α Inhibition in Mouse Cells

The mouse macrophage cell line Raw 264.7 is used to assess the ability of compounds to inhibit tumor necrosis factor-α(TNF-α) production upon stimulation by lipopolysaccharide (LPS).

Single Concentration Assay

Blood Cell Preparation for Culture

Raw cells (ATCC) are harvested by gentle scraping and then counted. The cell suspension is brought to $3\times10^5$ cells/mL in RPMI with 10% fetal bovine serum (FBS). Cell suspension (100 μL) is added to 96-well flat bottom sterile tissues culture plates (Becton Dickinson Labware, Lincoln Park, N.J.). The final concentration of cells is $3\times10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 μM. LPS (Lipopolysaccaride from *Salmonella typhimurium*, Sigma-Aldrich) is diluted with colorless RPMI to the $EC_{70}$ concentration as measured by a dose response assay.

Incubation

A solution of test compound (1 μl) is added to each well. The plates are mixed on a microtiter plate shaker for 1 minute and then placed in an incubator. Twenty minutes later the solution of LPS (1 μL, $EC_{70}$ concentration ~10 ng/mL) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay

Blood Cell Preparation for Culture

Raw cells (ATCC) are harvested by gentle scraping and then counted. The cell suspension is brought to $4\times10^5$ cells/mL in RPMI with 10% FBS. Cell suspension (250 μL) is added to 48-well flat bottom sterile tissues culture plates (Costar, Cambridge, Mass.). The final concentration of cells is $1\times10^5$ cells/well. The plates are incubated for 3 hours. Prior to the addition of test compound the medium is replaced with colorless RPMI medium with 3% PBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 μM. LPS (Lipopolysaccaride from *Salmonella typhimurium*, Sigma-Aldrich) is diluted with colorless RPMI to the $EC_{70}$ concentration as measured by dose response assay.

Incubation

A solution of test compound (200 μl) is added to each well. The plates are mixed on a microtiter plate shaker for 1 minute and then placed in an incubator. Twenty minutes later the solution of LPS (200 μL, $EC_{70}$ concentration ~10 ng/mL) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from, Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula (II):

II

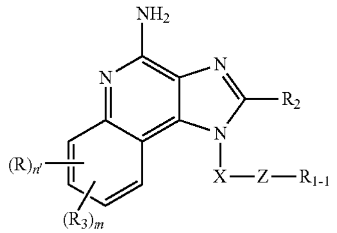

wherein:

Z is $—C(=N—O—R_{1-2})—$

X is:

$—CH(R_9)—$, or $—CH(R_9)$-alkylene-;

$R_{1-1}$ is selected from the group consisting of:

hydrogen, alkyl, and aryl;

$R_{1-2}$ is selected from the group consisting of:

hydrogen, alkyl, heterocyclyl, aryl, heteroaryl, and alkyl, heterocyclyl, aryl, or heteroaryl, substituted by one or more substituents selected from the group consisting of:

halogen, cyano, alkyl, hydroxy, hydroxyalkyl, alkoxy, dialkylamino, heterocyclyl, aryl, and heteroaryl;

R is selected from the group consisting of:

halogen, hydroxy, alkyl, alkenyl, haloalkyl, alkoxy, alkylthio, and $—N(R_9)_2$;

$R_2$ is selected from the group consisting of:

hydrogen;

alkyl;

alkoxyalkyl; and hydroxyalkyl;

$R_3$ is selected from the group consisting of:

aryl, heteroaryl, and aryl and heteroaryl substituted by one or more of the groups selected from halogen, hydroxyl, alkoxy, hydroxyalkyl, cyano, dialkylamino, heterocyclyl, $—C(O)NH_2$, $—NHS(O)_2$-alkyl, —C(O)NH-alkyl, —NHC(O)-alkyl, —C(O)NH-heterocyclyl, and

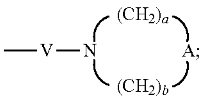

$R_6$ is selected from the group consisting of =O and =S;

$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;

$R_9$ is selected from the group consisting of hydrogen and alkyl;

A is selected from the group consisting of —O—, —C(O)—, $—S(O)_{0-2}—$, and $—CH_2—$;

V is selected from the group consisting of $—C(R_6)—$, $—O—C(R_6)—$, $—N(R_8)—C(R_6)—$, and $—S(O)_2—$;

a and b are each independently integers from 1 to 6 with the proviso that a+b is ≤7;

n' is an integer from 0 to 4; and m is 0 or 1; with the proviso that when m is 1, then n' is 0 or 1;

or a pharmaceutically acceptable salt thereof.

2. The compound or salt of claim 1 wherein m is 0.

3. The compound or salt of claim 1 wherein n' is 0.

4. The compound or salt of claim 2 wherein m and n' are both 0.

5. The compound or salt of claim 1, wherein $R_3$ is selected from the group consisting of pyridin-3-yl, pyridin-4-yl, 5-(hydroxymethyl)pyridin-3-yl, and 2-ethoxyphenyl.

6. The compound or salt of claim 1 wherein $R_2$ is selected from the group consisting of $C_{1-4}$ alkyl, and $C_{1-4}$ alkylenyl-$O—C_{1-4}$ alkyl.

7. The compound or salt of claim 1 wherein X is selected from the group consisting of $—(CH_2)_{1-6}—$, $—CH_2C(CH_3)_2—$, and $—CH_2C(CH_3)_2CH_2—$.

8. The compound or salt of claim 1 wherein $R_{1-1}$ is selected from the group consisting of hydrogen, $C_{1-4}$ alkyl, and phenyl.

9. The compound or salt of claim 1 wherein $R_{1-2}$ is selected from the group consisting of hydrogen, $C_{1-4}$ alkyl, benzyl, and pyridin-2-ylmethyl.

10. A pharmaceutical composition comprising a therapeutically effective amount of a compound or salt of claim 1 in combination with a pharmaceutically acceptable carrier.

11. A method of inducing cytokine biosynthesis in an animal comprising administering an effective amount of a compound or salt of claim 1 to the animal, wherein the cytokine induced is selected interferon or tumor necrosis factor alpha.

12. A compound of the Formula (IV):

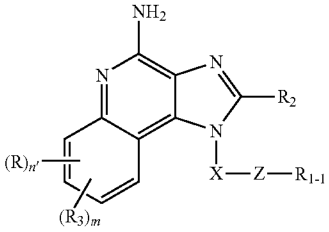

IV wherein:

Z is —C(=N—O—$R_{1-2}$)—

X is —CH($R_9$)— or —CH($R_9$)-alkylene-;

$R_{1-1}$ is selected from the group consisting of:
- hydrogen,
- alkyl, and
- aryl;

$R_{1-2}$ is selected from the group consisting of:
- hydrogen,
- alkyl,
- aryl, and
- alkyl substituted by one or more substituents selected from the group consisting of aryl and heteroaryl;

R is selected from the group consisting of:
- halogen,
- hydroxy,
- alkyl,
- alkenyl,
- haloalkyl,
- alkoxy,
- alkylthio, and
- —N($R_9$)$_2$;

$R_2$ is selected from the group consisting of:
- hydrogen,
- alkyl,
- alkoxyalkyl, and
- hydroxyalkyl;

$R_3$ is selected from the group consisting of:
- halogen,
- aryl,
- heteroaryl, and
- aryl and heteroaryl substituted by one or more of the groups selected from hydroxyl, —C(O)$NH_2$, —NHS(O)$_2$-alkyl, —C(O)NH-alkyl, —C(O)NH-heterocyclyl;

$R_9$ is selected from the group consisting of hydrogen and alkyl;

n' is 0 or 1; and m is 0 or 1;

or a pharmaceutically acceptable salt thereof.

13. A compound selected from the group consisting of:

5-(4-amino-7-phenyl-2-propyl-1H-imidazo[4,5-c]quinolin-1-yl)pentan-2-one-O-methyloximine;

4-(4-amino-2-butyl-1H-imidazo[4,5-c]quinolin-1-yl)-1-phenylbutan-1-one-oxime;

4-(4-amino-2-butyl-1H-imidazo[4,5-c]quinolin-1-yl)-1-phenylbutan-1-one-O-methyloxime;

5-(4-amino-2-methyl-1H-imidazo[4,5-c]quinolin-1-yl) pentan-2-one-oxime;

5-(4-amino-2-methyl-1H-imidazo[4,5-c]quinolin-1-yl) pentan-2-one-O-benzyloxime;

5-(4-amino-2-methyl-1H-imidazo[4,5-c]quinolin-1-yl) pentan-2-one-O-methyloxime;

5-(4-amino-2-butyl-1H-imidazo[4,5-c]quinolin-1-yl)pentan-2-one-O-methyloxime;

5-(4-amino-2-ethoxymethyl-1H-imidazo[4,5-c]quinolin-1-yl)pentan-2-one-oxime;

5-(4-amino-2-ethoxymethyl-1H-imidazo[4,5-c]quinolin-1-yl)pentan-2-one-O-methyloxime hydrochloride;

5-(4-amino-2-ethoxymethyl-1H-imidazo[4,5-c]quinolin-1-yl)pentan-2-one-O-benzyloxime hydrochloride;

1-(4-amino-2-propyl-1H-imidazo[4,5-c]quinolin-1-yl)-6-methylheptan-4-one-oxime;

1-(4-amino-2-propyl-1H-imidazo[4,5-c]quinolin-1-yl)decan-4-one-oxime;

5-(4-amino-2-methyl-1H-imidazo[4,5-c]quinolin-1-yl)-4,4-dimethylpentan-2-one-O-methyloxime;

5-(4-amino-2-propyl-1H-imidazo[4,5-c]quinolin-1-yl)-4,4-dimethylpentan-2-one-O-methyloxime;

5-(4-amino-1H-imidazo-[4,5-c]quinolin-1-yl)-4,4-dimethylpentan-2-one-O-methyloxime;

(1E,Z)-4-(4-amino-2-butyl-1H-imidazo[4,5-c]quinolin-1-yl)butanal-O-methyloxime;

4-(4-amino-2-methyl-1H-imidazo[4,5-c]quinolin-1-yl) butanal-O-methyloxime;

1-[4-amino-2-(ethoxymethyl)-1H-imidazo[4,5-c]quinolin-1-yl]butan-2-one-O-methyloxime;

or a pharmaceutically acceptable salt thereof.

* * * * *

UNITED STATES PATENT AND TRADEMARK OFFICE

CERTIFICATE OF CORRECTION

PATENT NO. : 8,778,963 B2
APPLICATION NO. : 10/595895
DATED : July 15, 2014
INVENTOR(S) : Larry Krepski It is certified that error appears in the above-identified patent and that said Letters Patent is hereby corrected as shown below:

IN THE SPECIFICATION:

Column 1
Line 33, Delete "tetrahydronaphthyridinamine" and insert -- tetrahydronaphthyridin-4-amine --, therefor.

Column 4
Line 28, Delete "$R_{1-1}$," and insert -- $R_{1-1}$ --, therefor.

Column 5
Line 44, After "n" insert -- = --.

Column 11
Line 25, Delete "—C(R)—," and insert -- -C($R_6$)-, --, therefor.

Column 12
Line 24, Delete "—C($R_4$)—," and insert -- —C($R_6$)—, --, therefor.
Line 24, Delete "-C($R_6$N" and insert -- -C($R_6$)-N --, therefor.
Line 61, Delete "$R_{1-4}$" and insert -- $R_{1-1}$ --, therefor.

Column 13
Line 54, Delete "-N($R_9$)-" and insert -- -N($R_8$)- --, therefor.

Column 15
Line 2, After "$R_4$," insert -- -X'-$R_4$, --.

Column 17
Line 41, Delete "-N($R_9$)" and insert -- -N($R_8$)- --, therefor.

Signed and Sealed this
Thirtieth Day of December, 2014

Michelle K. Lee

Michelle K. Lee
*Deputy Director of the United States Patent and Trademark Office*

Column 18
Line 28, Delete "-N($R_9$)-," and insert -- -N($R_8$)-, --, therefor.

Column 20
Line 14, Delete "-C(O)-," and insert -- -C($R_6$)-, --, therefor.

Column 28
Line 8, Delete "-C(R)-" and insert -- -C($R_6$)- --, therefor.
Line 47, Delete "$R_{1-4}$" and insert -- $R_{1-1}$ --, therefor.

Column 29
Line 64, Before "aryl," insert -- alkyl, --.

Column 30
Line 28, Delete "-N($R_9$)-," and insert -- -N($R_8$)-, --, therefor.

Column 33
Line 46, Delete "-C(O)-" and insert -- -C($R_6$)- --, therefor.

Column 34
Line 5, Delete "-N($R_9$)-," and insert -- -N($R_8$)-, --, therefor.
Line 58, Delete "-N($R_9$)-." and insert -- -N($R_8$)-. --, therefor.
Line 66, Delete "-N($R_9$)-" and insert -- -N($R_8$)- --, therefor.

Column 35
Line 4,

Delete " 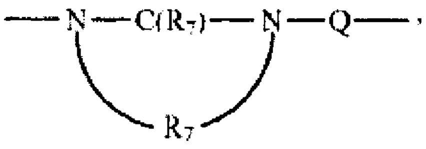 " and insert -- 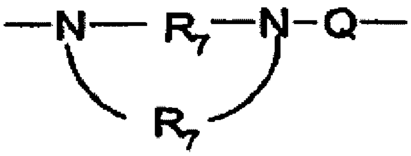 , --, therefor.

Column 40
Line 15, Delete "animated" and insert -- aminated --, therefor.
Line 18, Delete "amiuating" and insert -- aminating --, therefor.
Line 21, Delete "animating" and insert -- aminating --, therefor.
Line 35, Delete "$NH_2OR_{1-2}$—HCl" and insert -- $NH_2OR_{1-2}$•HCl --, therefor
Line 58, Delete "quinolinamine" and insert -- quinolin-4-amine --, therefor.

Column 43
Line 61, Delete "nitro methane" and insert -- nitromethane --, therefor.

Column 44
Line 51, Delete "XX." and insert -- XXI. --, therefor.
Line 58, Delete "animated" and insert -- aminated --, therefor.
Line 58, Delete "XXII" and insert -- XXIII --, therefor.

Column 50
Line 40, Delete "animated" and insert -- aminated --, therefor.
Line 42, Delete "animation" and insert -- amination --, therefor.

Column 49-50
Line 50,

Delete " 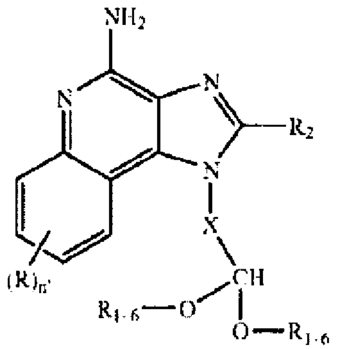 XXIa " and insert -- 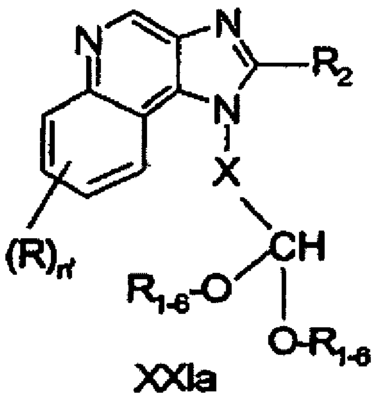 XXIa --, therefor.

Column 51
Line 25, Delete "XXX." and insert -- XXXI. --, therefor.
Line 44, Delete "XI" and insert -- XXXI --, therefor.
Line 59, Delete "XXXI." and insert -- XXXIII. --, therefor.

Column 52
Line 21, Delete "XXXII" and insert -- XXXIII --, therefor.
Line 24, Delete "XIV." and insert -- XXXIV. --, therefor.
Line 46, Delete "XVI" and insert -- XXXVI --, therefor.
Line 49, Delete "XXXI." and insert -- XXXVII. --, therefor.
Line 57, Delete "XXXVX" and insert -- XXXVII --, therefor.
Line 58, Delete "pyridin-amine" and insert -- pyridin-4-amine --, therefor.

Column 55
Line 61, Delete "(I)" and insert -- (IV) --, therefor.

Column 56
Line 1, Delete "pyridamine" and insert -- pyridin-4-amine --, therefor.

Column 58
Line 65, Delete "naphthyridin-amines" and insert -- naphthyridin-4-amines --, therefor.

Column 59
Line 62, Delete "LVII" and insert -- LVIII --, therefor.
Line 62, Delete "animated" and insert -- aminated --, therefor.

Column 62
Line 58, Delete "animated" and insert -- aminated --, therefor.

Column 63
Line 58-59, Delete "animated" and insert -- aminated --, therefor.
Line 66, Delete "LXI" and insert -- LXIV --, therefor.
Line 67, Delete "[4,5-c)]" and insert -- [4,5-c] --, therefor.

Column 64
Line 58, Delete "-tetraydro-" and insert -- -tetrahydro- --, therefor.

Column 65-66
Line 1 (structure),

Delete " 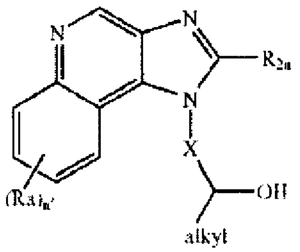 LXIII " and insert -- 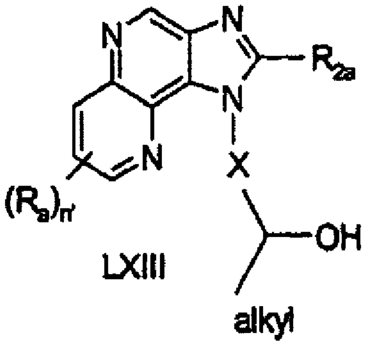 LXIII --, therefor.

Column 65
Line 62, Delete "of" and insert -- or --, therefor.

Column 69
Line 48, Delete "LXXI" and insert -- LXXXII --, therefor.
Line 51, Delete "LXXIII." and insert -- LXXXIII. --, therefor.
Line 52, Delete "LXXII" and insert -- LXXXII --, therefor.
Line 62, Delete "LXXIII" and insert -- LXXXIII --, therefor.

Column 74
Line 44, Delete "picomavirus" and insert -- picornavirus --, therefor.
Line 48, Delete "papillomavirises," and insert -- papillomaviruses, --, therefor.
Line 49-50, Delete "hepadnavinis" and insert -- hepadnavirus --, therefor.

Column 75
Line 36, Delete "papirloma" and insert -- papilloma --, therefor.

Column 77
Line 64, Delete “string,” and insert -- stirring, --, therefor.

Column 79
Line 54, Delete “methyloxine” and insert -- methyloxime --, therefor.

Column 80
Line 19, Delete “naphthyridin-yl)” and insert -- naphthyridin-4-yl) --, therefor.

Column 83
Line 45, Delete “triethylanmine” and insert -- triethylamine --, therefor.

Column 84
Line 25, Delete “dichlorometlane” and insert -- dichloromethane --, therefor.

Column 87
Line 7, Delete “(2 mL)” and insert -- (2 mL/L) --, therefor.

Column 88
Line 26, Delete “methoxymethanesulfonamide” and insert -- methoxy-methanesulfonamide --, therefor.

Column 89
Line 2, Delete “56.28;” and insert -- 56.28, --, therefor.

Column 102
Line 30, Delete “naphthyrdin” and insert -- naphthyridin --, therefor.

Column 105
Line 64, Delete “BPFC” and insert -- HPFC --, therefor.

Column 106
Line 29, Delete “hydroxylamnine” and insert -- hydroxylamine --, therefor.

Column 107
Line 23, Delete “$H_2O$.” and insert -- $H_2O$ --, therefor.
Line 59, Delete “nitroquinolin-ylamino)” and insert -- nitroquinolin-4-ylamino) --, therefor.

Column 109
Line 59, Delete “M” and insert -- (M --, therefor.

Column 110
Line 10, Delete “methyloximie” and insert -- methyloxime --, therefor.

Column 111
Line 66, Delete "H." and insert -- H, --, therefor.

Column 117
Line 67, Delete "$(M+M)^+$;" and insert -- $(M+H)^+$; --, therefor.

Column 118
Line 36, Delete "nitro methane" and insert -- nitromethane --, therefor.

Column 120
Line 1, Delete "$(M+M)^+$;" and insert -- $(M+H)^+$; --, therefor.

Column 121
Line 31, Delete "N-[2,2-" and insert -- $N^4$-[2,2- --, therefor.

Column 122
Line 33, Delete "-4(4-" and insert -- -4-(4- --, therefor.

Column 127
Line 63, Delete "Pair" and insert -- Parr --, therefor.

Column 129
Line 65, Delete "methyl-" and insert -- methyl-4- --, therefor.

Column 130
Line 16, Delete "(BPFC)" and insert -- (HPFC) --, therefor.
Line 25, Delete "animated." and insert -- aminated. --, therefor.
Line 34, Delete "H." and insert -- H, --, therefor.
Line 65-66, Delete "animated" and insert -- aminated --, therefor.

Column 131
Line 63, Delete "-1N-" and insert -- -N'- --, therefor.

Column 132
Line 2, Delete "$O_2$." and insert -- $O_2$* --, therefor.

Column 137
Line 18-24,

Delete " 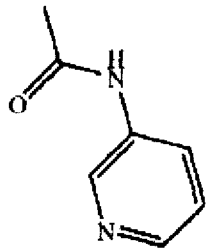 " and insert -- 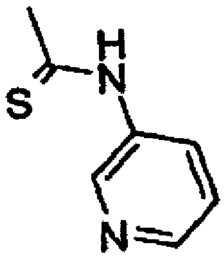 --, therefor.

Column 138
Line 57, Delete "each:" and insert -- each --, therefor.

Column 143
Line 2, Delete "BPFC" and insert -- HPFC --, therefor.

Column 144
Line 5, Delete "a," and insert -- a --, therefor.

Column 172
Line 66, Delete "Imquimod" and insert -- Imiquimod --, therefor.

Column 174
Line 47, Delete "PBS." and insert -- FBS. --, therefor.